United States Patent
Yamamoto et al.

[11] Patent Number: 6,040,331
[45] Date of Patent: Mar. 21, 2000

[54] NERVE CELL PROTECTIVE AGENTS

[75] Inventors: Ichiro Yamamoto; Manabu Itoh; Masato Shimojo; Yasunobu Yumiya; Takafumi Mukaihira; Yasushige Akada, all of Tokyo, Japan

[73] Assignee: Mochida Pharmaceutical Co., Ltd., Tokyo, Japan

[21] Appl. No.: 09/011,260

[22] PCT Filed: May 29, 1997

[86] PCT No.: PCT/JP97/01828

§ 371 Date: Jan. 30, 1998

§ 102(e) Date: Jan. 30, 1998

[87] PCT Pub. No.: WO97/45410

PCT Pub. Date: Dec. 4, 1997

[30] Foreign Application Priority Data

May 30, 1996 [JP] Japan .................................. 8-158985
Nov. 28, 1996 [JP] Japan .................................. 8-332764

[51] Int. Cl.[7] ........................ A61K 31/40; A61K 31/425; C07D 209/90; C07D 417/00; C07D 403/00
[52] U.S. Cl. .................. 514/411; 514/228.2; 514/232.8; 514/254; 514/323; 514/365; 544/60; 544/142; 544/372; 546/200; 548/181; 548/438
[58] Field of Search ............... 514/228.2, 232.8, 514/254, 323, 365, 411; 548/181, 438; 546/200; 544/60, 142, 372

[56] References Cited

U.S. PATENT DOCUMENTS

| 4,853,406 | 8/1989 | Rosentreter et al. ............ 514/411 |
| 5,021,438 | 6/1991 | Junge et al. .................... 514/373 |
| 5,039,820 | 8/1991 | Kress et al. .................... 548/436 |
| 5,496,843 | 3/1996 | Nagata et al. .................. 514/411 |
| 5,643,920 | 7/1997 | Mochizuki et al. ............. 514/294 |
| 5,712,312 | 1/1998 | Langlois et al. ............... 514/585 |
| 5,849,781 | 12/1998 | Langlois et al. ............... 514/411 |

FOREIGN PATENT DOCUMENTS

| 5062896 | 10/1996 | Australia . |
| 0737670A1 | 10/1996 | European Pat. Off. . |
| 60-156670A | 8/1985 | Japan . |
| 63-501361A | 5/1988 | Japan . |
| 63-310866A | 12/1988 | Japan . |
| 2-204479A | 8/1990 | Japan . |
| 4-211652A | 8/1992 | Japan . |
| 7-188166A | 7/1995 | Japan . |
| 8-291121A | 11/1996 | Japan . |

OTHER PUBLICATIONS

Cecil et al., Textbook of Medicine, 20th Edition, vol. 2, pp. 1992–1996, 1996.
Bode–Greuel et al., Stroke, vol. 21, No. 12, IV–164–166 (Dec. 1990).

*Primary Examiner*—Mukund J. Shah
*Assistant Examiner*—Brenda Coleman
*Attorney, Agent, or Firm*—Birch, Stewart, Kolasch & Birch, LLP

[57] ABSTRACT

The invention provides novel benzindole derivatives, processes for producing them, as well as a neuroprotective agent, an agent to prevent or treat diseases involving the degeneration, retraction or death of neurons, and an analgesic, each containing the benzindole derivatives as an active ingredient.

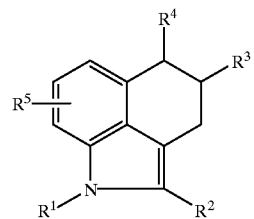

(I)

13 Claims, No Drawings

NERVE CELL PROTECTIVE AGENTS

This application is a national phase under 35 U.S.C. §371 of prior PCT International Application No. PCT/JP 97/01828 which has an International filing date of May 29, 1997 which designated the United States of America, the entire contents of which are hereby incorporated by reference.

TECHNICAL FIELD

This invention relates to novel benzindole derivatives, processes for producing them, pharmaceuticals containing them, in particular, neuroprotective agents and prophylactics or therapeutics of those diseases which involve the degeneration, retraction and death of neurons, as well as analgesics.

BACKGROUND ART

Cerebrovascular disorders and neurodegenerative diseases rank as major diseases in middle-aged to elderly persons and their onset is triggered by dysfunction, retraction, degeneration, decrease, necrosis and so forth of neurons in general or specific regions due to ischemia, trauma, aging or etiology which is in most cases unknown for the cause. Drugs currently used against these diseases are nosotropic ones which are called cerebral metabolism activators, cerebral circulation modifiers or neurotransmitting function improvers. The mechanism of action of these drugs remains unknown in many points and they have only proved to be unsatisfactory in clinical therapeutic efficacy.

Cerebral infarctions such as cerebral thrombosis and embolism are classified as cerebrovascular disorders and their onset is triggered by the brain becoming ischemic due to the stenosis of blood vessels, brain thrombi or brain emboli. For the treatment of cerebral infarctions in an acute phase, anti-edema agents such as mannitol which improve post-ischemic cerebral edema, thrombolytic agents such as urokinase which remove occlusive thrombi, microcirculation modifiers such as ozagrel or cerebral metabolism activators such as citicoline. However, these therapeutics are only nosotropic and their efficacy is by no means satisfactory. In the chronic phase of cerebral infarctions, cerebral metabolism activators such as idebenone and bifemelane, cerebral circulation modifiers such as nicardipine and indeloxazine or neurotransmitting function modifiers such as aniracetam and lisuride are used against dyskinesia such as paralysis, affective disorders such as depression, subjective symptoms such as numbness or consciousness disorders such as delirium and although some of them have been found to be effective in achieving transient improvements in mental conditions, they are generally held to have little efficacy.

A recent finding about cerebral damages due to ischemia is that in addition to the mechanism of tissue necrosis due to energy insufficiency caused by the abolishment of oxygen and nutrient supply to the brain, the mechanism by which glutamic acid which plays the role of a principal neurotransmitter at normal time is released excessively to impair neurons in a positive manner is important (a theory called "excitoneurotoxicity"). In addition, the death of neurons caused by glutamic acid is known to include an immediate disorder due to a rapid elevation of intracellular $Ca^{2+}$ and a delayed neuronal death that occurs several days after transient cerebral ischemia in gerbils as demonstrated by Kirino et al. in Brain Res., 239, pp. 57–69, 1982. Apoptosis which has recently gained interest as a mechanism for the death of cells has also been shown to be involved in this delayed neuronal death and other death cases of neurons in ischemic neuronal damages (Nitatori et al., J. Neurosci., 15, pp. 1001–1011, 1995).

Under the circumstances and from the viewpoint of the neurotoxicity of glutamic acid, active efforts have been made to develop drugs that relieve the toxicity of glutamic acid. Briefly, glutamic acid receptor blocking compounds such as dizocilpine, selphotel and YM90K and glutamic acid release suppressing lifarizine and BW619C89 have been demonstrated to be effective in experiments with cerebral ischemic animal models and their clinical efficacy is now under review. However, these drugs have encountered the difficulty that their side effects such as hallucination and hypotension become a dose limiting factor, making it impossible to administer sufficient doses to exhibit a neuroprotective effect.

Parkinson's disease which is a neurodegenerative disease is dyskinesia that involves selective degeneration of dopaminergic neurons in nigrostriatal pathway and a marked improvement in symptoms can be effected by a therapy for supplementing a neurotransmitter using L-dopa. However, it is held that the treatment with L-dopa cannot arrest but rather precipitates the progress of the disorders in dopaminergic neurons and no complete curing has been established. Recently, a report has been made to the effect that a neurotrophic factor which has a protective action on dopaminergic neurons was effective in animal models of Parkinson's disease; however, the experiment relied upon the administration of a protein into the brain and lacks clinical feasibility. In addition, it has been pointed out that apoptosis is involved in the death of dopaminergic neurons in Parkinson's disease.

With a view to treating dementia of Alzheimer's type which is a neurodegenerative disease characterized by pathological changes such as the deposition of amyloid senile plaques, the neurofibrillary tangle formation and the atrophy of the cerebrum, the aforementioned drugs administered in the chronic phase of cerebral infarctions are similarly used today and although some of them have been found to be effective in achieving transient improvements in metal conditions, they are generally held to have little efficacy. By analogy from Parkinson's disease and based on the hypothesis that supplementation of acetylcholine might be effective against dementia of Alzheimer's type, acetylcholine esterase inhibitors, acetylcholine agonists and the like have been developed worldwide. However, excepting the only approved case of tetrahydroaminoacridine, there is no drug that was truly established to have clinical efficacy. Thus, as in the case of Parkinson's disease, no method capable of achieving complete curing of dementia of Alzheimer's type has been established and there is no perspective for its possibility. Again, it has been pointed out that apoptosis is involved in the mechanism of neuronal death in dementia of Alzheimer's type.

Accordingly, in addition to the diseases described above, the following may be mentioned as diseases that involve the degeneration, retraction and death of neurons: various diseases accompanying cerebrovascular disorders including cerebral hemorrhages such as hypertensive intracerebral hemorrhage and subarachnoid hemorrhage, transient cerebral ischemic attacks, cerebroarteriosclerosis and their sequela, or neurodegenerative diseases such as amyotrophic lateral sclerosis, Down's syndrome, Huntington chorea and spinal cerebellar degeneration, as well as brain damages at the time of revivification after cardiac arrest, brain dysfunction prior to or after brain surgery, disorders of the nervous system due to hypoxia, hypoglycemia, brain or spinal damage, intoxication with drugs or gases, diabetes mellitus, administration of anti-cancer agents, alcohol and the like, senile dementia and dysmensia. A key to complete curing which is common to these diseases would be to control the neuronal deaths including apoptosis. In other words, compounds capable of controlling neuronal deaths including apoptosis are believed to be very important and useful not only in the treatment/prevention of cerebrovascular disorders, various neurodegenerative diseases or various other diseases that involve the degeneration, retraction and death of neurons but also in improving the pathological conditions and symptoms of these diseases; however, no compounds having the desired action have been disclosed in the prior art.

Under these circumstances, compounds that are highly safe and which suppress neuronal deaths including apoptosis, namely, those compounds which have a neuroprotective action are expected to provide for complete curing of cerebrovascular disorders, various neurodegenerative diseases or various other diseases that involve the degeneration, retraction and death of neurons and in view of their extreme utility, a strong need exists to formulate them as pharmaceuticals.

As benzindole derivatives, Unexamined Published Japanese Patent Application (kokai) No. 310866/1988 discloses polyhydrobenz[c,d]indolesulfonamide derivatives having a platelet aggregating action and it teaches that they can be used in the treatment of thrombosis, thromboembolism and ischemia; Unexamined Published Japanese Patent Application (kohyo) No. 501361/1988 provides a disclosure to the effect that tricyclic compounds having an indole structure providing a dopaminergic action can be used against hypertension and cardiac dysfunction; however, neither patent gives a description of other aspects such as actions on neuronal deaths and a neuroprotective action. Unexamined Published Japanese Patent Application No. 156670/1985 discloses 1,3,4,5-tetrahydrobenz[c,d]indole derivatives having high affinity for serotonin receptors (particularly those of 5-$HT_1$ type) and teaches that they are useful in the control of CNS diseases (in particular, anxiety, stress, insomnia and depression) or the treatment of cardiovascular and gastrointestinal diseases; again, there is no disclosure about the suppression of neuronal deaths or a neuroprotective action. As for BAY-R-1531 which is one of the compounds disclosed in the latter patent, Bode et al. reported in Stroke, 21, IV-164 to IV-166, 1990 that it was effective for damage to the hippocampus of gerbils after brain ischemia. However, it was also reported that the protective effect of the compound was only recognized at a by far higher dose than the one that caused altered patterns of behavior due to a serotonin-like action. In other words, the prior art of interest teaches a different structure than the compounds of the present invention and it has no disclosure about the action of suppressing neuronal deaths including apoptosis; in addition, if administered at a dose that shows a protective effect in models of neuronal death, the compound develops side effects due to a serotonin receptor agonist action, thus having clinical problems.

So-called "nonsteroid antiinflammatory drugs" are frequently used today as analgesics but they have no practical efficacy against strong pains such as cancer pain and the one associated with herpes zoster. Potent analgesics that are best known today are narcotic analgesics such as morphine; however, these drugs have the problem of causing tolerance and physical or mental dependence and their use is limited. Hence, there still is a strong need for analgesics that are effective and feature high safety.

Further, those compounds which have a capability of centrally lessening the pains accompanying various diseases are believed to be very important not only in the treatment of pains from various diseases of the nervous system caused by various physical or mental abnormalities but also for the purpose of improving the pathological conditions or symptoms of such diseases. Specific examples of the pains include those associated with cancers, diabetic neuropathy, herpes zoster, arthritis, rheumatism, as well as medical or dental surgery. No analgesic compounds like those of the subject application which have a capability of centrally alleviating the pains from various diseases have been disclosed in the prior art.

The benzindole derivatives disclosed in Unexamined Published Japanese Application No. 204479/1990 are agonists for receptors having high affinity for 5-hydroxytryptamine (of $5HT_1$-type) and which mediate the regulation of the central circulatory system to control unilateral headache. However, this patent makes no disclosure of the action of centrally alleviating the pains from various diseases as is achieved by the compounds of the present invention.

DISCLOSURE OF INVENTION

An object of the present invention is to provide compounds that act directly upon nerve cells and which are capable of suppressing neuronal deaths including apoptosis, namely, those compounds which have a neuroprotective action, cause less side effects and feature high safety. Another object of the invention is to provide compounds having an analgesic action.

Yet another object of the invention is to provide processes for producing these compounds, intermediates useful for producing them, as well as medicines and pharmaceutical compositions that contain them. The invention is particularly intended to provide neuroprotective agents, preventives or therapeutics of various diseases that involve the degeneration, retraction or death of neurons, and analgesics that overcome at least one of the aforementioned problems in the prior art.

The present inventors made intensive efforts to search for the compounds of interest which act directly upon nerve cells to be capable of suppressing neuronal deaths. As a result, they found that compounds having a specified benzindole skeleton were capable of suppressing the death of neurons under culture, that they were extremely effective in models of cerebral ischemia, that they had an analgesic action and further that they caused less side effects and featured high safety; the present invention has been accomplished on the basis of these findings.

According to its first aspect, the present invention provides compounds represented by the following formula (I) or salts thereof or medicines containing said compounds or salts thereof as an active ingredient:

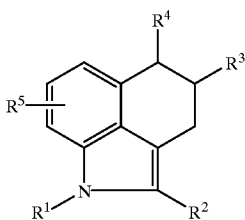

(I)

where $R^1$ represents a hydrogen atom or a straight-chained, branched or cyclic alkyl group having 1–4 carbon atoms which may be substituted by any group selected from the group consisting of one carboxyl group, one alkoxycarbonyl group having 1–4 carbon atoms and one hydroxyl group; $R^2$ represents a phenyl group which may be mono- or disubstituted by any group selected from the group consisting of a halogen atom, an alkyl group having 1–4 carbon atoms which may be substituted by one hydroxyl group, an alkoxyl group having 1–4 carbon atoms which may be substituted by one hydroxyl group, an optionally protected hydroxyl group, an alkylthio group having 1–4 carbon atoms, an alkylsulfinyl group having 1–4 carbon atoms, an alkylsulfonyl group having 1–4 carbon atoms, a nitro group, an optionally protected amino group, an acetylamino group, a cyano group, an optionally protected carboxyl group, an alkoxycarbonyl group having 1–4 carbon atoms, a carbamoyl group and a trifluoromethyl group; either one of $R^3$ and $R^4$ represents a hydrogen atom and the other represents a group represented by the following formula (II):

(II)

(where $R^6$ and $R^7$ each represent a hydrogen atom, a phenyl group, a benzyl group, an alkyl group having 1–4 carbon atoms which may be monosubstituted by any group selected from the group consisting of one hydroxyl group, one amino group, one carboxyl group, one carbamoyl group and one alkoxycarbonyl group having 1–4 carbon atoms, a formyl group, an alkanoyl group having 1–4 carbon atoms which may be monosubstituted by an amino group, or a benzoyl group which may be monosubstituted by an amino group; $R^6$ and $R^7$ may form a pyrrolidine, thiazolidine, piperidine, morpholine, thiomorpholine or piperazine ring together with the nitrogen atom to which they are bound, provided that the 4-position of the piperidine ring may be monosubstituted by any group selected from the group consisting of a hydroxyl group, a carboxyl group and an alkoxycarbonyl group having 1–4 carbon atoms and that the nitrogen atom at the 4-position of the piperazine ring where a hydrogen atom is substituted may be substituted by any group selected from the group consisting of an oxalo group, an alkoxyoxalyl group having 1–4 carbon atoms, an alkanoyl group having 1–4 carbon atoms which may be substituted by one hydroxyl group and an alkyl group having 1–4 carbon atoms); $R^5$ represents a hydrogen atom, a halogen atom, an alkyl group having 1–4 carbon atoms, an optionally protected hydroxyl group, an alkylthio group having 1–4 carbon atoms, an alkylsulfinyl group having 1–4 carbon atoms, an alkylsulfonyl group having 1–4 carbon atoms, a cyano group, a nitro group or an alkoxyl group having 1–4 carbon atoms which may be monosubstituted by a group selected from the group consisting of one carboxyl group, one alkoxycarbonyl group having 1–4 carbon atoms and one hydroxyl group.

The preferred substituents in the compounds represented by the above formula (I) or the preferred combinations thereof are set forth below but the present invention is by no means limited to these examples.

$R^1$ is preferably a hydrogen atom or a straight-chained alkyl group having 1–4 carbon atoms.

$R^2$ is preferably a phenyl group which may be mono- or disubstituted by any group selected from the group consisting of a halogen atom, an alkyl group having 1–4 carbon atoms which may be substituted by one hydroxyl group, an alkoxyl group having 1–4 carbon atoms which may be substituted by one hydroxyl group, a nitro group, an optionally protected amino group, a cyano group and a trifluoromethyl group and, more preferably, $R^2$ is a phenyl group which may be monosubstituted by a halogen atom.

Either one of $R^3$ and $R^4$ is a hydrogen atom and the other is represented by the above formula (II), provided that $R^3$ and $R^4$ are not the same group. In one case, $R^3$ is a hydrogen atom and $R^4$ is represented by the above formula (II) and, in the other case, $R^3$ is represented by the above formula (II) and $R^4$ is a hydrogen atom; preferably, $R^3$ is a hydrogen atom and $R^4$ is represented by the above formula (II).

Preferably, $R^6$ in the above formula (II) is a hydrogen atom, a phenyl group, a benzyl group or an alkyl group having 1–4 carbon atoms which may be substituted by one hydroxyl group and $R^7$ is a hydrogen atom or an alkyl group having 1–4 carbon atoms; more preferably, $R^6$ is a hydrogen atom or an alkyl group having 1–4 carbon atoms which may be substituted by one hydroxyl group and $R^7$ is a hydrogen atom or an alkyl group having 1–4 carbon atoms.

When $R^6$ and $R^7$ form a ring together with the nitrogen atom to which they are bound, they preferably form a pyrrolidine, piperidine, morpholine or piperazine ring and, more preferably, they form a morpholine ring.

$R^5$ is preferably a hydrogen atom, a halogen atom, an alkyl group having 1–4 carbon atoms, an optionally protected hydroxyl group, a nitro group or an alkoxyl group having 1–4 carbon atoms; more preferably, $R^5$ is a hydrogen atom, a halogen atom, an alkyl group having 1–4 carbon atoms or an optionally protected hydroxyl group.

The preferred combinations of the substituents are such that $R^1$ is a hydrogen atom or a straight-chained alkyl group having 1–4 carbon atoms, $R^2$ is a phenyl group which may be monosubstituted by a halogen atom, $R^3$ is a hydrogen atom, $R^4$ is represented by the above formula (II) (where $R^6$ is a hydrogen atom or an alkyl group having 1–4 carbon atoms which may be substituted by one hydroxyl group and $R^7$ is a hydrogen atom or an alkyl group having 1–4 carbon atoms, provided that $R^6$ and $R^7$ may form a morpholine group together with the nitrogen atom to which they are bound) and $R^5$ is a hydrogen atom, a halogen atom, an alkyl group having 1–4 carbon atoms or an optionally protected hydroxyl group.

According to its second aspect, the present invention provides compounds or salts thereof which are useful for the synthesis of the compounds of the above formula (I) or salts thereof and which are represented by the following formula (III):

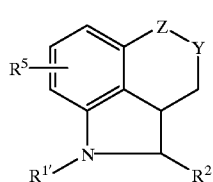

(III)

where $R^{1'}$ represents a hydrogen atom, a formyl group, an alkanoyl group having 1–4 carbon atoms, a benzoyl group or a straight-chained, branched or cyclic alkyl group having 1–4 carbon atoms which may be substituted by any group selected from the group consisting of one carboxyl group, one alkoxycarbonyl group having 1–4 carbon atoms and one hydroxyl group; $R^2$ represents a phenyl group which may be mono- or disubstituted by any group selected from the group consisting of a halogen atom, an alkyl group having 1–4 carbon atoms which may be substituted by one hydroxyl group, an alkoxyl group having 1–4 carbon atoms which may be substituted by one hydroxyl group, an optionally protected hydroxyl group, an alkylthio group having 1–4 carbon atoms, an alkylsulfinyl group having 1–4 carbon atoms, an alkylsulfonyl group having 1–4 carbon atoms, a nitro group, an optionally protected amino group, an acetylamino group, a cyano group, an optionally protected carboxyl group, an alkoxycarbonyl group having 1–4 carbon atoms, a carbamoyl group and a trifluoromethyl group; $R^5$ represents a hydrogen atom, a halogen atom, an alkyl group having 1–4 carbon atoms, an optionally protected hydroxyl group, an alkylthio group having 1–4 carbon atoms, an alkylsulfinyl group having 1–4 carbon atoms, an alkylsulfonyl group having 1–4 carbon atoms, a cyano group, a nitro group or an alkoxyl group having 1–4 carbon atoms which may be substituted by a group selected from the group consisting of one carboxyl group, one alkoxycarbonyl group having 1–4 carbon atoms and one hydroxyl group; Y and Z each represent a methylene group or a carbonyl group, provided that they are not the same.

According to its third aspect, the present invention provides processes (1 and 2) for producing said derivative compounds of the above formula (I)

(Process 1)

In this process, a compound represented by the following formula (III) or a salt thereof:

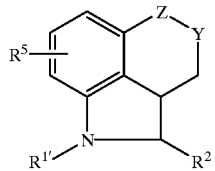

(III)

(where $R^{1'}$ represents a hydrogen atom, a formyl group, an alkanoyl group having 1–4 carbon atoms, a benzoyl group or a straight-chained, branched or cyclic alkyl group having 1–4 carbon atoms which may be substituted by any group selected from the group consisting of one carboxyl group, one alkoxycarbonyl group having 1–4 carbon atoms and one hydroxyl group; $R^2$ represents a phenyl group which may be mono- or disubstituted by any group selected from the group consisting of a halogen atom, an alkyl group having 1–4 carbon atoms which may be substituted by one hydroxyl group, an alkoxyl group having 1–4 carbon atoms which may be substituted by one hydroxyl group, an optionally protected hydroxyl group, an alkylthio group having 1–4 carbon atoms, an alkylsulfinyl group having 1–4 carbon atoms, an alkylsulfonyl group having 1–4 carbon atoms, a nitro group, an optionally protected amino group, an acetylamino group, a cyano group, an optionally protected carboxyl group, an alkoxycarbonyl group having 1– 4 carbon atoms, a carbamoyl group and a trifluoromethyl group; $R^5$ represents a hydrogen atom, a halogen atom, an alkyl group having 1–4 carbon atoms, an optionally protected hydroxyl group, an alkylthio group having 1–4 carbon atoms, an alkylsulfinyl group having 1–4 carbon atoms, an alkylsulfonyl group having 1–4 carbon atoms, a cyano group, a nitro group or an alkoxyl group having 1–4 carbon atoms which may be substituted by a group selected from the group consisting of one carboxyl group, one alkoxycarbonyl group having 1–4 carbon atoms and one hydroxyl group; Y and Z each represent a methylene group or a carbonyl group, provided that they are not the same), after removing the acyl group at 1-position as required, is dehydrogenated with a suitable oxidizing reagent to prepare a compound represented by the following formula (IV) or a salt thereof:

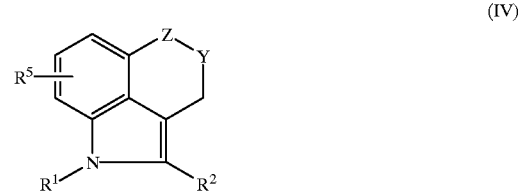

(IV)

(where $R^1$, $R^2$, $R^5$, Y and Z have the same meanings as defined above) and said compound or salt thereof is reacted under reducing conditions with an amine derivative represented by the following formula (V) or a salt thereof:

$HNR^6R^7$ (V)

(where $R^6$ and $R^7$ have the same meanings as defined above) so as to produce the compound represented by the following formula (I) or a salt thereof:

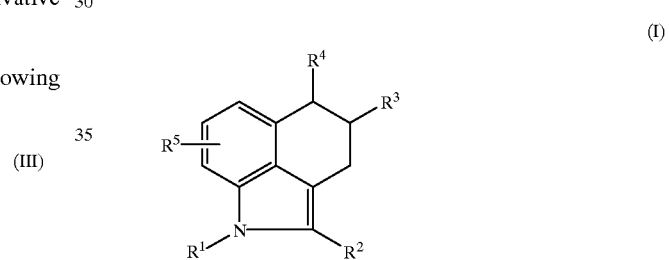

(I)

(where $R^1$, $R^2$, $R^3$, $R^4$, $R^5$ and $R^6$ or $R^7$ in the formula (II) set forth in the definitions of $R^3$ and $R^4$ have the same meanings as defined above).

(Process 2)

In this process, a compound represented by the following formula (III) or a salt thereof:

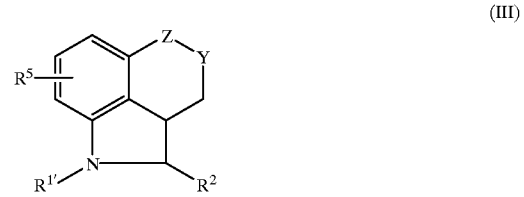

(III)

(where $R^{1'}$ represents a hydrogen atom, a formyl group, an alkanoyl group having 1–4 carbon atoms, a benzoyl group or a straight-chained, branched or cyclic alkyl group having 1–4 carbon atoms which may be substituted by any group selected from the group consisting of one carboxyl group, one alkoxycarbonyl group having 1–4 carbon atoms and one hydroxyl group; $R^2$ represents a phenyl group which may be mono- or disubstituted by any group selected from the group consisting of a halogen atom, an alkyl group having 1–4 carbon atoms which may be substituted by one hydroxyl group, an alkoxyl group having 1–4 carbon atoms which may be substituted by one hydroxyl group, an optionally protected hydroxyl group, an alkylthio group having 1–4 carbon atoms, an alkylsulfinyl group having 1–4 carbon atoms, an alkylsulfonyl group having 1–4 carbon atoms, a nitro group, an optionally protected amino group, an acetylamino group, a cyano group, an optionally protected carboxyl group, an alkoxycarbonyl group having 1–4 carbon atoms, a carbamoyl group and a trifluoromethyl group; $R^5$ represents a hydrogen atom, a halogen atom, an alkyl group having 1–4 carbon atoms, an optionally protected hydroxyl group, an alkylthio group having 1–4 carbon atoms, an alkylsulfinyl group having 1–4 carbon atoms, an alkylsulfonyl group having 1–4 carbon atoms, a cyano group, a nitro group or an alkoxyl group having 1–4 carbon atoms which may be substituted by a group selected from the group consisting of one carboxyl group, one alkoxycarbonyl group having 1–4 carbon atoms and one hydroxyl group; Y and Z each represent a methylene group or a carbonyl group, provided that they are not the same) is reduced to prepare a hydroxy form, which is reacted with a halogenating agent to prepare a compound represented by the following formula (VI) or a salt thereof:

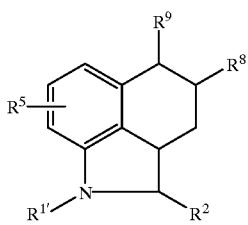

(VI)

(where $R^{1'}$, $R^2$ and $R^5$ have the same meanings as defined above; $R^8$ and $R^9$ each represent a hydrogen atom or a halogen atom, provided that they are not the same) and said compound or salt thereof is reacted with an amine derivative represented by the following formula (V) or a salt thereof:

HNR$^6$R$^7$ (V)

(where $R^6$ and $R^7$ have the same meanings as defined above) so as to prepare a compound represented by the following formula (VII) or a salt thereof:

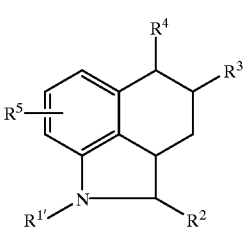

(VII)

(where $R^{1'}$, $R^2$, $R^3$, $R^4$, $R^5$ and $R^6$ or $R^7$ in the formula (II) set forth in the definitions of $R^3$ and $R^4$ have the same meanings as defined above) and, after removing the acyl group at 1-position as required, said compound or salt thereof is dehydrogenated with a suitable oxidizing reagent to produce the compound represented by the following formula (I) or a salt thereof:

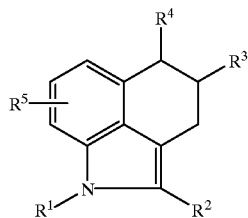

(I)

(where $R^1$, $R^2$ $R^3$, $R^4$, $R^5$ and $R^6$ or $R^7$ in the formula (II) set forth in the definitions of $R^3$ and $R^4$ have the same meanings as defined above).

According to its fourth aspect, the present invention provides neuroprotective agents containing at least one of the compounds of the above formula (I) or salts thereof as an active ingredient.

According to its fifth aspect, the present invention provides preventives or therapeutics of diseases involving the degeneration, retraction or death of neurons which contain one of the compounds of the above formula (I) or salts thereof as an active ingredient.

According to its sixth aspect, the present invention provides analgesics containing at least one of the compounds of the above formula (I) or salts thereof as an active ingredient.

The term "neuroprotective agents" as used herein means those drugs which act directly upon neurons including brain neurons to exhibit a capability of suppressing neuronal deaths including apoptosis. The term "analgesics" means those drugs which can centrally alleviate the pains associated with various diseases.

BEST MODE FOR CARRYING OUT THE INVENTION

The present invention will now be described below in detail.

Unless otherwise specified, the alkyl group, the alkoxy group and any other alkyl moieties that appear in the invention shall embrace all kinds such as those which have straight chains or branches or which are cyclic. Similarly, unless otherwise noted, the propyl group and the butyl group shall embrace all kinds such as n-propyl group, i-propyl group, c-propyl group, n-butyl group and i-butyl group.

The position numbers for the benzindole derivatives, which are the compounds of the invention, are as noted in the following diagram, which shows that the position at which $R^1$ is bound is 1-position, the position at which $R^2$ is bound is 2-position, the position at which $R^3$ is bound is 4-position, the position at which $R^4$ is bound is 5-position and that $R^5$ is bound at any of 6-, 7- and 8 -positions:

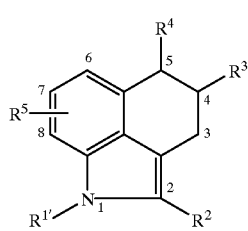

(I)

The compounds of the invention are represented by the following formula (I):

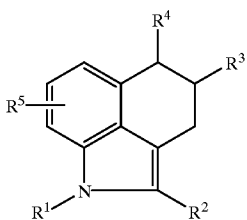

(I)

In the formula (I), $R^1$ represents a hydrogen atom or a straight-chained, branched or cyclic alkyl group having 1–4 carbon atoms which may be substituted by any group selected from the group consisting of one carboxyl group, one alkoxycarbonyl group having 1–4 carbon atoms and one hydroxyl group. The term "alkoxycarbonyl group having 1–4 carbon atoms" refers to a methoxycarbonyl group, an ethoxycarbonyl group, a propoxycarbonyl group or a butoxycarbonyl group; the term "straight-chained, branched or cyclic alkyl group having 1–4 carbon atoms" refers to a methyl group, an ethyl group, a n-propyl group, an i-propyl group, a c-propyl group, a n-butyl group, an i-butyl group or the like. Preferably, $R^1$ represents a hydrogen atom, a methyl group, an ethyl group, a n-propyl group, an i-propyl group, a c-propyl group, a n-butyl group, a carboxymethyl group, a 1-carboxyethyl group, a 2-carboxyethyl group, a 3-carboxypropyl group, a 4-carboxybutyl group, a methoxycarbonylmethyl group, an ethoxycarbonylmethyl group, a butoxycarbonylmethyl group, a 1-methoxycarbonylethyl group, a 2-methoxycarbonylethyl group, a 4-methoxycarbonyl-n-butyl group, a 2-hydroxyethyl group, a 2-hydroxypropyl group, a 3-hydroxypropyl group or the like.

More preferably, $R^1$ represents a hydrogen atom, a methyl group, an ethyl group, a n-propyl group or a n-butyl group.

$R^2$ represents a phenyl group which may be mono- or disubstituted by any group selected from the group consisting of a halogen atom, an alkyl group having 1–4 carbon atoms which may be substituted by one hydroxyl group, an alkoxyl group having 1–4 carbon atoms which may be substituted by one hydroxyl group, an optionally protected hydroxyl group, an alkylthio group having 1–4 carbon atoms, an alkylsulfinyl group having 1–4 carbon atoms, an alkylsulfonyl group having 1–4 carbon atoms, a nitro group, an optionally protected amino group, an acetylamino group, a cyano group, an optionally protected carboxyl group, an alkoxycarbonyl group having 1–4 carbon atoms, a carbamoyl group and a trifluoromethyl group. The term "halogen atom" refers to a fluorine atom, a chlorine atom, a bromine atom or an iodine atom; the term "alkyl group having 1–4 carbon atoms which may be substituted by one hydroxyl group" means a methyl group, an ethyl group, a n-propyl group, a n-butyl group, a hydroxymethyl group, a 2-hydroxyethyl group, a 2-hydroxypropyl group, a 3-hydroxypropyl group or the like; the term "alkoxyl group having 1–4 carbon atoms which may be substituted by one hydroxyl group" refers to a methoxy group, an ethoxy group, a propoxy group, a butoxy group, a 2-hydroxyethyloxy group, a 2-hydroxypropyloxy group, a 3-hydroxypropyloxy group or the like; the term "alkylthio group having 1–4 carbon atoms" refers to a methylthio group, an ethylthio group, a propylthio group, a butylthio group or the like; the term "alkylsulfinyl group having 1–4 carbon atoms" refers to a methylsulfinyl group, an ethylsulfinyl group, a propylsulfinyl group, a butylsulfinyl group or the like; the term "alkylsulfonyl group having 1–4 carbon atoms" refers to a methylsulfonyl group, an ethylsulfonyl group, a propylsulfonyl group, a butylsulfonyl group or the like; the term "alkoxycarbonyl group having 1–4 carbon atoms" refers to a methoxycarbonyl group, an ethoxycarbonyl group, a butoxycarbonyl group or the like; the term "phenyl group which may be mono- or disubstituted by any selected group" refers to an unsubstituted phenyl group, a 2-substituted phenyl group, a 3-substituted phenyl group, a 4-substituted phenyl group, a 2, 3-disubstituted phenyl group, a 2,4-disubstituted phenyl group, a 2,5-disubstituted phenyl group, a 2,6-disubstituted phenyl group, a 3,4-disubstituted phenyl group or a 3,5-disubstituted phenyl group. In the case of a disubstituted phenyl group, the respective substituents may be the same or different.

Preferably, $R^2$ represents an unsubstituted phenyl group, a 2-fluorophenyl group, a 3-fluorophenyl group, a 4-fluorophenyl group, a 2,3-difluorophenyl group, a 2,4-difluorophenyl group, a 2,6-difluorophenyl group, a 3,4-difluorophenyl group, a 2-chlorophenyl group, a 3-chlorophenyl group, a 4-chlorophenyl group, a 2,3-dichlorophenyl group, a 2,4-dichlorophenyl group, a 2,6-dichlorophenyl group, a 3,4-dichlorophenyl group, a 2-bromophenyl group, a 3-bromophenyl group, a 4-bromophenyl group, a 2-iodophenyl group, a 3-iodophenyl group, a 4-iodophenyl group, a 2-fluoro-4-chlorophenyl group, a 2-chloro-4-fluorophenyl group, a 2-chloro-6-fluorophenyl group, a 2-methylphenyl group, a 3-methylphenyl group, a 4-methylphenyl group, a 2,4-dimethylphenyl group, a 4-ethylphenyl group, a 4-propylphenyl group, a 4-butylphenyl group, a 2-hydroxymethyl phenyl group, a 3-hydroxymethylphenyl group, a 4-hydroxymethylphenyl group, a 4-(2-hydroxyethyl)phenyl group, a 4-(2-hydroxypropyl)phenyl group, a 4-(3-hydroxypropyl)phenyl group, a 2-methoxyphenyl group, a 3-methoxyphenyl group, a 4-methoxyphenyl group, a 2,4-dimethoxyphenyl group, a 3,4-dimethoxyphenyl group, a 4-ethoxyphenyl group, a 4-butoxyphenyl group, a hydroxyethyloxy)phenyl group, a 3-(2-hydroxyethyloxy)phenyl group, a 4-(2-hydroxyethyloxy)phenyl group, a 4-(2-hydroxypropyloxy) phenyl group, a 4-(3-hydroxypropyloxy)phenyl group, a 2-hydroxyphenyl group, a 3-hydroxyphenyl group, a 4-hydroxyphenyl group, a 2,4-dihydroxyphenyl group, a 2-methylthiophenyl group, a 3-methylthiophenyl group, a 4-methylthiophenyl group, a 2-ethylthiophenyl group, a 4-ethylthiophenyl group, a 2-propylthiophenyl group, a 4-propylthiophenyl group, a 2-butylthiophenyl group, a 4-butylthiophenyl group, a 2-methylsulfinylphenyl group, a 3-methylsulfinylphenyl group, a 4-methylsulfinylphenyl group, a 2-ethylsulfinylphenyl group, a 4-ethylsulfinylphenyl group, a 2-propylsulfinylphenyl group, a 4-propylsulfinylphenyl group, a 2-butylsulfinylphenyl group, a 4-butylsulfinylphenyl group, a 2-methylsulfonylphenyl group, a 3-methylsulfonylphenyl group, a 4-methylsulfonylphenyl group, a 2-ethylsulfonylphenyl group, a 4-ethylsulfonylphenyl group, a 2-propylsulfonylphenyl group, a 4-propylsulfonylphenyl group, a 2-butylsulfonylphenyl group, a 4-butylsulfonylphenyl group, a 2-nitrophenyl group, a 3-nitrophenyl group, a 4-nitrophenyl group, a 3,4 -dinitrophenyl group, a 2-chloro-4-nitrophenyl group, a 2-aminophenyl group, a 3-aminophenyl group, a 4-aminophenyl group, a 3,4-diaminophenyl group, a 2-acetylaminophenyl group, a 3-acetylaminophenyl group, a 4-acetylaminophenyl group, a 2-cyanophenyl group, a 3-cyanophenyl group, a 4-cyanophenyl group, a 2-carboxyphenyl group, a 3-carboxyphenyl group, a 4-carboxyphenyl group, a 2-methoxycarbonylphenyl group, a 3-methoxycarbonylphenyl group, a 4-methoxycarbonylphenyl group, a 2-carbamoylphenyl group, a 3-carbamoylphenyl group, a 4-carbamoylphenyl group, a 2-trifluoromethylphenyl group, a 3-trifluoromethylphenyl group, a 4-trifluoromethylphenyl group, a 2,5-bis(trifluoromethyl)phenyl group or the like.

More preferably, $R^2$ represents an unsubstituted phenyl group, a 2-fluorophenyl group, a 3-fluorophenyl group, a 4-fluorophenyl group, a 2,3-difluorophenyl group, a 2,4-difluorophenyl group, a 2,6-difluorophenyl group, a 3,4-difluorophenyl group, a 2-chlorophenyl group, a 3-chlorophenyl group, a 4-chlorophenyl group, a 2,3-dichlorophenyl group, a 2,4-dichlorophenyl group, a 2,6-dichlorophenyl group, a 3,4-dichlorophenyl group, a 2-bromophenyl group, a 3-bromophenyl group, a 4-bromophenyl group, a 2-iodophenyl, a 3-iodophenyl group, a 4-iodophenyl group, a 2-fluoro-4-chlorophenyl group, a 2-chloro-4-fluorophenyl group, a 2-chloro-6-fluorophenyl group, a 2-methylphenyl group, a 3-methylphenyl group, a 4-methylphenyl group, a 2,4-dimethylphenyl group, a 4-ethylphenyl group, a 4-propylphenyl group, a 4-butylphenyl group, a 2-hydroxymethylphenyl group, a 3-hydroxymethylphenyl group, a 4-hydroxymethylphenyl group, a 4-(2-hydroxyethyl)phenyl group, a 4-(2-hydroxypropyl)phenyl group, a 4-(3-hydroxypropyl)phenyl group, a 2-methoxyphenyl group, a 3-methoxyphenyl group, a 4-methoxyphenyl group, a 2,4-dimethoxyphenyl group, a 3,4-dimethoxyphenyl group, a 4-ethoxyphenyl group, a 4-butoxyphenyl group, a 2-nitrophenyl group, a 3-nitrophenyl group, a 4-nitrophenyl group, a 2,4-dinitrophenyl group, a 2-chloro-4-nitrophenyl group, a 2-aminophenyl group, a 3-aminophenyl group, a 4-aminophenyl group, a 2-cyanophenyl group, a 3-cyanophenyl group, a 4-cyanophenyl group, a 2-trifluoromethylphenyl group, a 3-trifluoromethylphenyl group, a 4-trifluoromethylphenyl group, a 2,5-bis(trifluoromethyl)phenyl group or the like.

Even more preferably, $R^2$ represents an unsubstituted phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group or the like.

Either one of $R^3$ and $R^4$ represents a hydrogen atom and the other is a group represented by the following formula (II):

$$—NR^6R^7 \qquad (II)$$

Preferably, $R^3$ represents a hydrogen atom and $R^4$ is represented by the formula (II).

$R^6$ and $R^7$ each represent a hydrogen atom, a phenyl group, a benzyl group, an alkyl group having 1–4 carbon atoms which may be monosubstituted by any group selected from the group consisting of one hydroxyl group, one amino group, one carboxyl group, one carbamoyl group and one alkoxycarbonyl group having 1–4 carbon atoms, a formyl group, an alkanoyl group having 1–4 carbon atoms which may be monosubstituted by an amino group, or a benzoyl group which may be monosubstituted by an amino group. The term "alkyl group having 1–4 carbon atoms which may be monosubstituted by any group selected from the group consisting of one hydroxyl group, one amino group, one carboxyl group, one carbamoyl group and one alkoxycarbonyl group having 1–4 carbon atoms" refers to a methyl group, an ethyl group, a n-propyl group, a n-butyl group, a 2-aminoethyl group, a 3-aminopropyl group, a carboxymethyl group, a 1-carboxyethyl group, a 2-carboxyethyl group, a 4-carboxy-n-butyl group, a carbamoylmethyl group, a 1-carbamoylethyl group, a 2-carbamoylethyl group, a 4-carbamoyl-n-butyl group, a methoxycarbonylmethyl group, an ethoxycarbonylmethyl group, a 1-methoxycarbonylethyl group, a 2-methoxycarbonylethyl group, a 4-methoxycarbonyl-n-butyl group, a 2-hydroxyethyl group, a 2-hydroxypropyl group, a 3-hydroxypropyl group, a 2-hydroxybutyl group, a 3-hydroxybutyl group, a 4-hydroxybutyl group or the like; the term "alkanoyl group having 1–4 carbon atoms which may be monosubstituted by an amino group" refers to an acetyl group, a propanoyl group, a butanoyl group, an aminoacetyl group, a 3-aminopropanoyl group, a 4-aminobutanoyl group or the like; the term "benzoyl group which may be monosubstituted by an amino group" refers to a benzoyl group, a 2-aminobenzoyl group, a 3-aminobenzoyl group or a 4-aminobenzoyl group.

Preferably, $R^6$ and $R^7$ each represent a hydrogen atom, a phenyl group, a benzyl group, a methyl group, an ethyl group, a n-propyl group, a n-butyl group, a 2-aminoethyl group, a 3-aminopropyl group, a carboxymethyl group, a 1-carboxyethyl group, a 2-carboxyethyl group, a 4-carboxy-n-butyl group, a carbamoylmethyl group, a 1-carbamoylethyl group, 2-carbamoylethyl group, a 4-carbamoyl-n-butyl group, a methoxycarbonylmethyl group, an ethoxycarbonylmethyl group, a 2-methoxycarbonylethyl group, a 1-methoxycarbonylethyl group, a 2-methoxycarbonylethyl group, a 4-methoxycarbonyl-n-butyl group, a 2-hydroxyethyl group, a 2-hydroxypropyl group, a 3-hydroxypropyl group, a 2-hydroxybutyl group, a 3-hydroxybutyl group, a 4-hydroxybutyl group, a formyl group, an acetyl group, a propanoyl group, a butanoyl group, an aminoacetyl group, a 3-aminopropanoyl group, a 4-aminobutanoyl group, a benzoyl group, a 2-aminobenzoyl group, a 3-aminobenzoyl group, a 4-aminobenzoyl group or the like.

The preferred combinations of $R^6$ and $R^7$ are such that $R^6$ is a hydrogen atom, a phenyl group, a benzyl group, a methyl group, an ethyl group, a n-propyl group, a n-butyl group, a 2-hydroxyethyl group, a 2-hydroxypropyl group, a 3-hydroxypropyl group, a 2-hydroxybutyl group, a 3-hydroxybutyl group, a 4-hydroxybutyl group or the like, with $R^7$ being a hydrogen atom, a methyl group, an ethyl group, a n-propyl group or a n-butyl group.

The more preferred combinations of $R^6$ and $R^7$ are such that $R^6$ is a hydrogen atom, a methyl group, an ethyl group, a n-propyl group, a n-butyl group, a 2-hydroxyethyl group, a 2-hydroxypropyl group, a 3-hydroxypropyl group, a 2-hydroxybutyl group, a 3-hydroxybutyl group, a 4-hydroxybutyl group or the like, with $R^7$ being a hydrogen atom, a methyl group, an ethyl group, a n-propyl group or a n-butyl group, $R^6$ and $R^7$ may form a pyrrolidine, thiazolidine, piperidine, morpholine, thiomorpholine or piperazine ring together with the nitrogen atom to which they are bound; the 4-position of the piperidine ring may be monosubstituted by any group selected from the group consisting of a hydroxyl group, a carboxyl group and an alkoxycarbonyl group having 1–4 carbon atoms, and the nitrogen atom at the 4-position of the piperazine ring where a hydrogen atom is substituted may be substituted by any group selected from the group consisting of an oxalo group, an alkoxyoxalyl group having 1–4 carbon atoms, an alkanoyl group having 1–4 carbon atoms which may be substituted by one hydroxyl group and an alkyl group having 1–4 carbon atoms. The term "alkoxycarbonyl group having 1–4 carbon atoms" refers to a methoxycarbonyl group, an ethoxycarbonyl group, a butoxycarbonyl group or the like; the term "alkoxyoxalyl group having 1–4 carbon atoms" refers to a methoxalyl group, an ethoxalyl group, a butoxyoxalyl group or the like; the term "alkanoyl group having 1–4 carbon atoms which may be substituted by one hydroxyl group" refers to an acetyl group, a propanoyl group, a butanoyl group, a hydroxyacetyl group, a 3-hydroxypropanoyl group, a 4-hydroxybutanoyl group or the like; and the term "alkyl group having 1–4 carbon atoms" refers to a methyl group, an ethyl group, a propyl group or a butyl group.

Preferred examples that may be represented include a pyrrolidinyl group, a thiazolidinyl group, a piperidinyl group, a 4-hydroxypiperidinyl group, a 4-carboxypiperidinyl group, a 4-methoxycarbonylpiperidinyl group, a 4-ethoxycarbonylpiperidinyl group, a 4-butoxycarbonylpiperidinyl group, a morpholinyl group, a thiomorpholinyl group, a piperazinyl group, a 4-oxalylpiperazinyl group, a 4-methoxalylpiperazinyl group, a 4-ethoxalylpiperazinyl group, a 4-butoxyoxalylpiperazinyl group, a 4-acetylpiperazinyl group, a 4-propanoylpiperazinyl group, a 4-butanoylpiperazinyl group, a 4-hydroxyacetylpiperazinyl group, a 4-(3-hydroxypropanoyl) piperazinyl group, a 4-(4-hydroxybutanoyl)piperazinyl group, a 4-methylpiperazinyl group, a 4-ethylpiperazinyl group, a 4-propylpiperazinyl group, a 4-butylpiperazinyl group and the like.

More preferred examples that may be represented include a pyrrolidinyl group, a piperidinyl group, a morpholinyl group and a piperazinyl group.

An even more preferred example that may be represented is a morpholinyl group.

$R^5$ represents a hydrogen atom, a halogen atom, an alkyl group having 1–4 carbon atoms, an optionally protected hydroxyl group, an alkylthio group having 1–4 carbon atoms, an alkylsulfinyl group having 1–4 carbon atoms, an alkylsulfonyl group having 1–4 carbon atoms, a cyano group, a nitro group or an alkoxyl group having 1–4 carbon atoms which may be substituted by a group selected from the group consisting of one carboxyl group, one alkoxycarbonyl group having 1–4 carbon atoms and one hydroxyl group. The term "halogen atom" refers to a fluorine atom, a chlorine atom, a bromine atom or an iodine atom; the term "alkyl group having 1–4 carbon atoms" refers to a methyl group, an ethyl group, a propyl group or a butyl group; the term "alkylthio group having 1–4 carbon atoms" refers to a methylthio group, an ethylthio group, a propylthio group, a butylthio group or the like; the term "alkylsulfinyl group having 1–4 carbon atoms" refers to a methylsulfinyl group, an ethylsulfinyl group, a propylsulfinyl group, a butylsulfinyl group or the like; the term "alkylsulfonyl group having 1–4 carbon atoms" refers to a methylsulfonyl group, an ethylsulfonyl group, a propylsulfonyl group, a butylsulfonyl group or the like; the term "alkoxyl group having 1–4 carbon atoms which may be substituted by a group selected from the group consisting of one carboxyl group, one alkoxycarbonyl group having 1–4 carbon atoms and one hydroxyl group" refers to a methoxy group, an ethoxy group, a propoxy group, a butoxy group, a carboxymethyloxy group, a 1-carboxyethyloxy group, a 2-carboxyethyloxy group, a 3-carboxypropyloxy group, a methoxycarbonylmethyloxy group, an ethoxycarbonylmethyloxy group, a 1-methoxycarbonylethyloxy group, a 2-methoxycarbonylethyloxy group, a 3-methoxycarbonylpropyloxy group, a 2-hydroxyethyloxy group, a 2-hydroxypropyloxy group, a 3-hydroxypropyloxy group or the like.

Preferably, $R^5$ represents a hydrogen atom, a fluorine atom, a chlorine atom, a bromine atom, an iodine atom, a methyl group, an ethyl group, a propyl group, a butyl group, a hydroxyl group, a methylthio group, an ethylthio group, a propylthio group, a butylthio group, a methylsulfinyl group, an ethylsulfinyl group, a propylsulfinyl group, a butylsulfinyl group, a methylsulfonyl group, an ethylsulfonyl group, a propylsulfonyl group, a butylsulfonyl group, a cyano group, a nitro group, a methoxy group, an ethoxy group, a propoxy group, a butoxy group, a carboxymethyloxy group, a 1-carboxyethyloxy group, a 2-carboxyethyloxy group, a 3-carboxypropyloxy group, a methoxycarbonylmethyloxy group, an ethoxycarbonylmethyloxy group, a 1-methoxycarbonylethyloxy group, a 2-methoxycarbonylethyloxy group, a 3-methoxycarbonylpropyloxy group, a 2-hydroxyethyloxy group, a 2-hydroxypropyloxy group, a 3-hydroxypropyloxy group or the like.

More preferably, $R^5$ represents a hydrogen atom, a fluorine atom, a chlorine atom, a bromine atom, an iodine atom, a methyl group, an ethyl group, a propyl group, a butyl group, a hydroxyl group, a nitro group, a methoxy group, an ethoxy group, a propoxy group, a butoxy group or the like.

Even more preferably, $R^5$ represents a hydrogen atom, a fluorine atom, a chlorine atom, a bromine atom, an iodine atom, a methyl group, an ethyl group, a propyl group, a butyl group, a hydroxyl group or the like.

The preferred combinations of the substituents are such that $R^1$ is a hydrogen atom, a methyl group, an ethyl group, a n-propyl group or a n-but yl group, $R^2$ is an unsubstituted phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group or a 4-iodophenyl group, $R^3$ is a hydrogen atom, $R^4$ is represented by the above formula (II) (where $R^6$ is a hydrogen atom, a methyl group, an ethyl group, a propyl group, a butyl group, a 2-hydroxyethyl group, a 2-hydroxypropyl group, a 3-hydroxypropyl group, a 2-hydroxybutyl group, a 3-hydroxybutyl group, a 4-hydroxybutyl group or the like and $R^7$ is a hydrogen atom, a methyl group, an ethyl group, a propyl group or a butyl group, provided that if $R^6$ and $R^7$ form any ring together with the nitrogen atom to which they are bound, the ring is a morpholine ring), and $R^5$ is a hydrogen atom, a fluorine atom, a chlorine atom, a bromine atom, an iodine atom, a methyl group, an ethyl group, a propyl group, a butyl group or a hydroxyl group.

Throughout the specification, the number of carbon atoms indicated for the alkoxycarbonyl group, alkanoyl group or alkoxyoxalyl group refers to that of carbon atoms in the corresponding alkoxy, alkyl or alkoxy portion, respectively.

Aside from the protective groups specifically mentioned herein for the optionally protected substituents, the following may be mentioned: protective groups for the hydroxyl group include alkyl-type protective groups such as a methyl group, a t-butyl group, a benzyl group, a trityl group and a methoxymethyl group, silyl-type protective groups such as a trimethylsilyl group and a t-butyldimethylsilyl group, acyl-type protective groups such as a formyl group, an acetyl group and a benzoyl group, and carbonate-type protective groups such as a methoxycarbonyl group and a benzyloxycarbonyl group; protective groups for the carboxyl group include ester-type protective groups such as a methyl group, an ethyl group, a t-butyl group, a benzyl group and a methoxymethyl group; protective groups for the amino group include alkyl-type protective groups such as a benzyl group, a trityl group and a methoxymethyl group, acyl-type protective groups such as a formyl group, an acetyl group and a benzoyl group, and carbamate-type protective groups such as a t-butoxycarbonyl group and a benzyloxycarbonyl group.

Subsequently, we will describe stereoisomers of the compounds of the invention.

The compounds of the invention which are represented by the above formula (I) have an asymmetric center at either 4- or 5-position and, hence, occur as two types of enantiomer; it should, however, be noted that optically pure compounds and a mixture of these enantiomers are also included within the scope of the invention. If intermediates for the compounds of the invention have two or more asymmetric centers, they can occur as two or more types of diastereomer and it should be noted that diastereomerically pure compounds and a mixture of these diastereomers are also included within the scope of the invention.

The compounds of the invention can form salts with inorganic or organic acids. Examples of these salts include inorganic acid salts such as hydrochlorides, hydrobromides, phosphates and sulfates, organic acid salts such as acetates, oxalates, citrates, tartrates, maleates, alginates, methanesulfonates, p-toluenesulfonates and salicylates, and acidic amino acid salts such as glutamates and aspartates. Depending on the types of the substituents used, the compounds of the invention may form salts with inorganic or organic bases. Examples of these salts include inorganic metal salts such as sodium salts, potassium salts, magnesium salts and calcium salts, organic base salts such as ammonium salts, triethylammonium salts and pyridinium salts, and basic amino acid salts such as arginine salts, lysine salts and histidine salts. These salts can be obtained in the usual manner, for example, by mixing an equivalent amount of a compound of the invention with a solution containing desired acid or base and then recovering the desired salt by filtration or collecting it after distilling off the solvent. It should also be noted that the compounds of the invention or salts thereof can form solvates with solvents such as water, ethanol and glycerol.

Processes for producing the compounds of the invention will now be described, with particular reference being made to the respective reaction steps. The definitions of $R^1$, $R^{1'}$, $R^2$, $R^3$, $R^4$, $R^5$, $R^6$, $R^7$, $R^8$, $R^9$, Y and Z in the compounds represented by the formulae (I), (II), (III), (IV), (V), (VI) and (VII) which appear in the following reaction schemes and relevant explanation are respectively the same as already discussed above.

The compounds of the invention which are represented by the formula (I) and salts thereof can be produced from compounds represented by the formula (III) in accordance with the process set forth below as Reaction Scheme 1 or slight modifications thereof.

Reaction Scheme 1

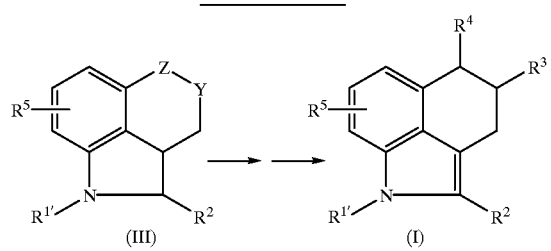

The compounds of the invention which are represented by the formula (I) can be produced from compounds of the formula (III) (as prepared by the process to be described below) in accordance with Process 1 or 2 set forth in Reaction Scheme 2. Among the intermediates obtained in Reaction Scheme 2, the compounds having two or more asymmetric centers can occur as two or more types of diastereomer; it should, however, be noted that diastereomerically pure isomers alone or a mixture of these diastereomers may be subjected to a reaction of interest.

Reaction Scheme 2

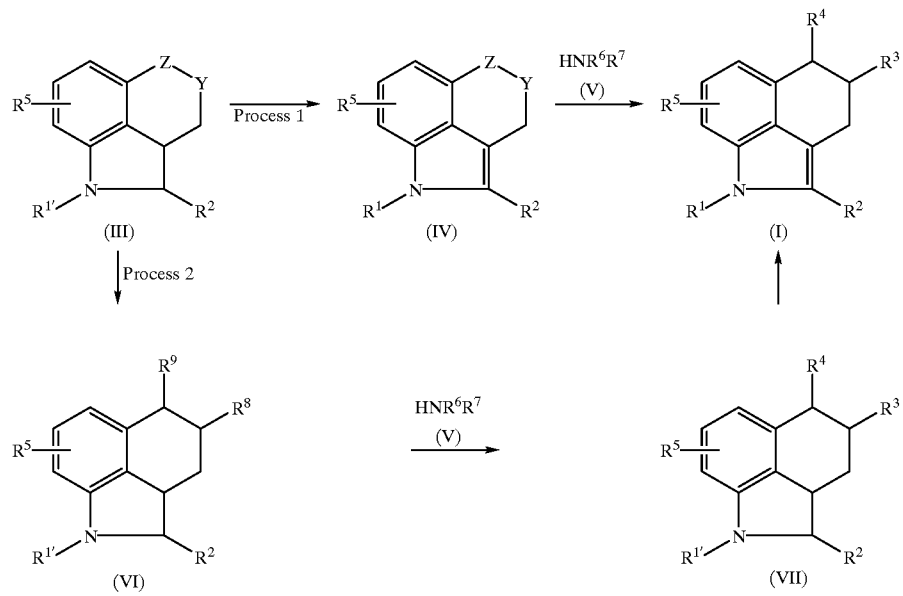

(Process 1)

To produce the compounds of the invention which are represented by the formula (I), tricyclic compounds represented by the formula (III) are optionally subjected to remove the acyl group at 1-position and, thereafter, the indoline portion is dehydrogenated with a suitable oxidizing reagent to prepare indole derivatives represented by the formula (IV), which are then reacted with amine derivatives of the formula (V) under reducing conditions.

From a compound represented by the formula (III) where Y is a carbonyl group and Z is a methylene group, is produced a compound of the formula (I) where $R^3$ is represented by the formula (II):

and $R^4$ is a hydrogen atom; on the other hand, from a compound represented by the formula (III) where Z is a carbonyl group and Y is a methylene group, is produced a compound of the formula (I) where $R^4$ is represented by the formula (II) and $R^3$ is a hydrogen atom.

The indoline portion of a tricyclic compound represented by the formula (III) where $R^1$ is an alkyl group may be dehydrogenated by the reaction with a quinone-type oxidizing reagent such as chloranil, o-chloranil or dichlorodicyanobenzoquinone (DDQ), preferably o-chloranil, in an ether-type solvent such as diethyl ether or tetrahydrofuran (THF), preferably using tetrahydrofuran (THF) as a solvent at a temperature ranging from the one obtained by cooling with ice to the one where the reaction mixture refluxes, preferably at a temperature ranging from the one obtained by cooling with ice to room temperature; by this procedure, indole derivatives of the formula (IV) can be prepared.

The dehydrogenation reaction can also be accomplished by oxidation with ammonium cerium(IV) nitrate in acetonitrile or by oxidation with manganese dioxide in a halogenated hydrocarbon-type solvent such as methylene chloride or chloroform, an ether-type solvent such as petroleum ether or diethyl ether or a solvent inert to the reaction such as acetone or acetonitrile, preferably in methylene chloride.

The oxidation with ammonium cerium(IV) nitrate can be performed at a temperature ranging from −20° C. to room temperature, preferably at a temperature ranging from the one obtained by cooling with ice to room temperature. The oxidation with manganese oxide can be accomplished at a temperature ranging from −20° C. to room temperature, preferably at room temperature.

A tricyclic compound of the formula (III) where $R^{1'}$ is an acyl group such as a formyl group, an acetyl group or a benzoyl group can be derivated to an indole derivative of the formula (IV) by first removing the acyl group in an alcoholic solvent such as ethanol or methanol or a solvent inert to the reaction condition such as dimethylimidazolidone (DMI) under acidic conditions, for example, in the presence of 6 N HCl to conc. HCl at a temperature ranging from room temperature to the one where the reaction mixture refluxes, preferably in a mixture of ethanol and hydrochloric acid with heating to reflux, then alkylating the 1-position of the resulting compound as required, and thereafter dehydrogenating the compound by one of the methods already described above.

The alkylation may be performed using a n alkylating agent such as an alkyl halide typified by methyl iodide or bromoacetic acid ester or an alkylsulfuric acid typified by dimethylsulfuric acid in the presence of a suitable base such as an organic base (e.g. triethylamine or pyridine) or an inorganic base (e.g. potassium carbonate or sodium hydride).

The thus obtained indole derivative represented by the formula (IV) where $R^1$ is hydrogen may, if necessary, be alkylated at 1-position by performing reaction in a solvent inert to the reaction such as dimethylformamide (DMF) or dimethylimidazolidone (DMI) in the presence of sodium hydride or, alternatively, in an ether-type solvent such as diethyl ether or tetrahydrofuran (THF) in the presence of a disilazide-type base such as sodium hexamethyl disilazide using the aforementioned alkylating agent such as an alkyl halide or alkylsulfuric acid at a temperature ranging from −20° C. to the one where the reaction mixture refluxes, preferably at a temperature ranging from the one obtained by cooling with ice to room temperature.

Conversion from the compound represented by the formula (IV) to the compound represented by the formula (I) can be accomplished by reductive amination with a substituted amine represented by the formula (V) and a reducing agent such as sodium borohydride or sodium cyanoborohydride, preferably sodium cyanoborohydride, in an alcoholic solvent such as methanol or ethanol or a mixture of an alcoholic solvent and a halogenated hydrocarbon-type solvent such as methylene chloride or chloroform or a polar solvent such as dimethylformamide (DMF) or dimethylimidazolidone (DMI), preferably in a mixture of methanol and methylene chloride, at a temperature ranging from the one obtained by cooling with ice to the one where the reaction mixture refluxes, preferably at a temperature ranging from room temperature to the one where reflux occurs.

The same reaction may also be performed by first forming imine or its tautomeric form enamine in the presence of an acidic catalyst such as hydrochloric acid, p-toluenesulfonic acid or titanium tetrachloride and then performing either reduction with a hydride-type reducing agent typified by sodium cyanoborohydride, sodium borohydride or lithium aluminum hydride or hydrogenation in ethyl acetate or an alcoholic solvent in the presence of a metal catalyst such as palladium or platinum oxide.

If an ammonium salt such as ammonium acetate or ammonium formate, preferably ammonium acetate, is used in place of the substituted amine represented by the formula (V), one can also synthesize a compound represented by the formula (I) where $R^3$ or $R^4$ is represented by the formula (II) in which the substituents $R^6$ and $R^7$ are both hydrogen.

Alternatively, the compound represented by the formula (IV) may be reacted with hydroxylamine or a salt thereof by heating to reflux in a halogenated hydrocarbon-type solvent such as methylene chloride or chloroform or an alcoholic solvent such as methanol or ethanol in the presence of a base such as pyridine or triethylamine, preferably, in the presence of pyridine in methanol to give an oxime form which, in turn, is hydrogenated in an alcoholic solvent in the presence of a metal catalyst such as palladium or reduced with a zinc powder in an acetic acid solvent or with a tin powder in hydrochloric acid, thereby producing a compound of the formula (I) where $R^3$ or $R^4$ is represented by the formula (II) in which the substituents $R^6$ and $R^7$ are both hydrogen.

The compound represented by the formula (I) can also be synthesized by reducing and the following halogenating the compound of the formula (IV) in accordance with the methods described in Process 2 and by then reacting the product with a compound of the formula (V).

(Process 2)

Another way to produce the compound of the invention which is represented by the formula (I) is as follows: the compound represented by the formula (III) is reduced to give a hydroxyl form, which is halogenated to give a compound of the formula (VI) which, in turn, is reacted with a compound of the formula (V) to give an amine derivative of the formula (VII) and, after the acyl group at 1-position is removed as required, the indoline portion of the product is dehydrogenated to yield the target compound.

From a compound represented by the formula (III) where Y is a carbonyl group and Z is a methylene group, is produced a compound of the formula (I) where $R^3$ is represented by the formula (II) and $R^4$ is a hydrogen atom; on the other hand, from a compound represented by the formula (III) where Z is a carbonyl group and Y is a methylene group, is produced a compound of the formula (I) where $R^4$ is represented by the formula (II) and $R^3$ is a hydrogen atom.

The ketone portion of the compound represented by the formula (III) can be reduced by, for example, reaction with sodium cyanoborohydride or sodium borohydride in either an alcoholic solvent such as methanol or ethanol or a mixture of an alcoholic solvent and a halogenated hydrocarbon-type solvent such as methylene chloride or chloroform or by reaction with lithium aluminum hydride in an ether-type solvent such as diethyl ether or tetrahydrofuran (THF); such reduction may preferably be performed in methanol using sodium borohydride at a temperature ranging from –20° C. to room temperature, preferably at a temperature ranging from the one obtained by cooling with ice to room temperature.

The thus obtained hydroxyl form may be halogenated with a halogenating agent such as a phosphorus halide reagent or a thionyl halide reagent, preferably brominated with phosphorus tribromide, in a halogenated hydrocarbon-type solvent such as methylene chloride or chloroform, an aromatic hydrocarbon-type solvent such as toluene or a mixture of these solvents at a temperature ranging from –20° C. to the one where the reaction mixture refluxes, preferably at a temperature ranging from the one obtained by cooling with ice to room temperature, whereby aforementioned hydroxyl form is converted to a compound of the formula (VI) where $R^8$ or $R^9$ is a halogen.

To introduce an amino group into the compound represented by the formula (VI), it may be reacted with a substituted amine of the formula (V) in a halogenated hydrocarbon-type solvent such as methylene chloride or chloroform, an ether-type solvent such as tetrahydrofuran (THF) or dioxane or a solvent inert to the reaction such as dimethylimidazolidone (DMI) in the presence or absence of an organic base such as pyridine or triethylamine or an inorganic base such as sodium hydroxide, potassium hydroxide or potassium carbonate at a temperature ranging from the one obtained by cooling with ice to the one where the reaction mixture refluxes, preferably at a temperature ranging from room temperature to the one where heating to reflux occurs; as a result of this procedure, one can produce an amino derivative represented by the formula (VII). From a compound represented by the formula (VI) where $R^8$ is a halogen and $R^9$ is a hydrogen atom, is produced a compound of the formula (VII) where $R^3$ is represented by the formula (II) and $R^4$ is a hydrogen atom; on the other hand, from a compound represented by the formula (VI) where $R^9$ is a halogen and $R^8$ is a hydrogen atom, is produced a compound of the formula (VII) where $R^4$ is represented by the formula (II) and $R^3$ is a hydrogen atom.

Conversion from th e tricyclic compound of the formula (III) to the amino derivative of the formula (VII) can be accomplished directly by, for example, performing the reductive amination reaction described in Process 1. From a compound represented by the formula (III) where Y is a carbonyl group and Z is a methylene group, is produced a compound of the formula (VII) where $R^3$ is represented by the formula (II) and $R^4$ is a hydrogen atom; from a compound represented by the formula (III) where Z is a carbonyl group and Y is a methylene group, is produced a compound of the formula (VII) where $R^4$ is represented by the formula (II) and $R^3$ is a hydrogen atom.

Conversion from the tricyclic compound of the formula (III) to the amino derivative of the formula (VII) can also be accomplished by other methods such as the reductive amination reaction and the reduction after conversion to imine or its tautomeric form enamine as described in Process 1. If $R^1$ in the tricyclic compound of the formula (III) is an acyl group such as a formyl group, an acetyl group or a benzoyl group, before conversion to the amino derivative the acyl group may be removed by the aforementioned method and, if necessary, the 1-position of the resulting compound is alkylated. From a compound represented by the formula (III) where Y is a carbonyl group and Z is a methylene group, is produced a compound of the formula (VII) where $R^3$ is represented by the formula (II) and $R^4$ is a hydrogen atom; on the other hand, from a compound represented by the formula (III) where Z is a carbonyl group and Y is a methylene group, is produced a compound of the formula (VII) where $R^4$ is represented by the formula (II) and $R^3$ is a hydrogen atom.

Among the amino derivatives represented by the formula (VII), a compound in which $R^1$ is hydrogen or an alkyl group can directly be converted to the compound of the formula (I) by performing dehydrogenation in accordance with one of the methods described in Process 1.

Among the amino derivatives represented by the formula (VII), a compound in which $R^{1'}$ is an acyl group such as a formyl group, an acetyl group or a benzoyl group may be derivated to the compound of the formula (I) by first performing deacylation in accordance with the method described in Process 1, optionally alkylating the 1-position of the resulting compound and then dehydrogenating the indoline portion in accordance with one of the methods described in Process 1. Alkylation of the 1-position may be performed directly by using the aforementioned alkyl halide, alkylsulfuric acid or the like; alternatively, it may be performed by the reductive amination reaction with an aldehyde typified by formaldehyde or acetaldehyde in the presence of sodium cyanoborohydride.

Among the thus produced compounds of the formula (I), one in which $R^3$ or $R^4$ is represented by the formula (II) where at least either one of the substituents $R^6$ and $R^7$ is a hydrogen atom may be alkylated by the aforementioned direct alkylation or reductive amination reaction; alternatively, it may be acylated using an organic acid typified by formic acid, acetic acid or benzoic acid, an amino acid or activated derivatives thereof. The thus obtained N-acyl form may be converted to a N-alkyl form by a known method of reduction, for example, reduction with lithium aluminum hydride in an ether-type solvent such as diethyl ether or tetrahydrofuran (THF) or reduction with borane-methyl sulfide complex in tetrahydrofuran (THF). Among the compounds represented by the formula (I), one in which $R^3$ or $R^4$ is represented by the formula (II) where the substituents $R^6$ and $R^7$ form a piperazino group together with the nitrogen atom to which they are bound may be subjected to acylation of the nitrogen atom at 4-position of piperazine ring by the aforementioned method. Among the compounds represented by the formula (I), one in which $R^1$ is a hydrogen atom and $R^3$ or $R^4$ is represented by the formula (II) where the substituents $R^6$ and $R^7$ form a morpholine ring, a piperidine ring or a 4-position acylated piperazine ring together with the nitrogen atom to which they are bound may be alkylated at 1-position by the aforementioned method.

We next describe the processes for producing the compounds of the formula (III) which are intermediates for the synthesis of the compounds of the invention represented by the formula (I).

(Intermediate Preparing Process 1)

The compound represented by the formula (III) where Y is a methylene group and Z is a carbonyl group, that is the compound represented by the formula (III-b):

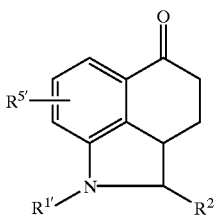

(III-b)

(where $R^{1'}$ and $R^2$ have the same meanings as defined above and $R^{5'}$ represents a hydrogen atom, a halogen atom, an alkyl group having 1–4 carbon atoms, an optionally protected hydroxyl group, an alkylthio group having 1–4 carbon atoms, an alkylsulfinyl group having 1–4 carbon atoms, an alkylsulfonyl group having 1–4 carbon atoms or an alkoxyl group having 1–4 carbon atoms which may be substituted by a group selected from the group consisting of one carboxyl group, one alkoxycarbonyl group having 1–4 carbon atoms and one hydroxyl group) is prepared in accordance with the following Reaction Scheme 3:

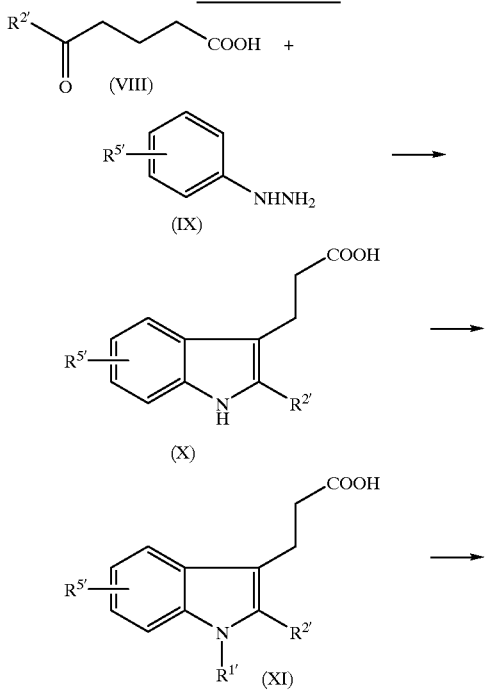

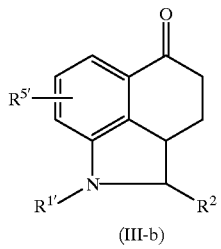

(III-b)

A benzoylbutyric acid derivative represented by the formula (VIII) (where $R^{2'}$ represents a phenyl group which may be mono- or disubstituted by any group selected from the group consisting of a hydrogen atom, a halogen atom, an alkyl group having 1–4 carbon atoms, an alkoxyl group having 1–4 carbon atoms, an alkylthio group having 1–4 carbon atoms, an alkylsulfinyl group having 1–4 carbon atoms, an alkylsulfonyl group having 1–4 carbon atoms, a nitro group, an acetylamino group, a cyano group and a trifluoromethyl group) which is either commercially available or synthesized by one of the known methods or the methods to be described below and a hydrazine derivative represented by the formula (IX) (where $R^{5'}$ has the same meaning as defined above) or a salt thereof which are either commercially available or synthesized by any known method are subjected to Fischer's indole synthesis reaction; namely, the compound of the formula (VIII) and the compound of the formula (IX) are heated to reflux in acetic acid in the presence or absence of an acid catalyst such as sulfuric acid, hydrochloric acid or hydrobromic acid, thereby synthesizing an indolepropionic acid derivative represented by the formula (X) (where $R^{2'}$ and $R^{5'}$ have the same meanings as defined above).

By reducing the compound of the formula (X) with a HCl—Zn powder in a dimethylimidazolidone (DMI) solvent to reflux, one can obtain an indoline derivative of the formula (XI) (where $R^{1'}$, $R^{2'}$ and $R^{5'}$ have the same meanings as defined above). This reaction may also be performed in the presence of mercury(II) chloride or the like. If desired, the zinc powder may be replaced by a Zn—Cu couple or a Zn—Hg amalgam or the like. If an alcoholic solvent is used, the reduction product can be obtained as an ester, which may be hydrolyzed by any known method to give an indoline derivative of the formula (XI).

Reduction of the indole derivative of the formula (X) to the indoline derivative of the formula (XI) can also be accomplished using sodium cyanoborohydride in an organic acid typified by acetic acid or trifluoroacetic acid at a temperature ranging from the one obtained by cooling with ice to room temperature; if the reaction time is prolonged, one can synthesize a compound in which the 1-position is substituted by an alkyl group corresponding to the organic acid used as the solvent.

The thus obtained indoline derivative of the formula (XI) has asymmetric centers at 2- and 3-positions, so it occurs as a mixture of diastereomers; however, the both isomers turn to the same compound upon oxidation to indole and, hence, they may be subjected to subsequent reactions either individually or as a mixture of them.

The 1-position of an indoline derivative represented by the formula (XI) where $R^{1'}$ is hydrogen may be protected, as required, with suitable protective groups, preferably acyl-type protective groups such as formyl, acetyl and benzoyl by the methods described in the Overview in "Protective Groups in Organic Synthesis", 2nd Ed., compiled by T. W.

Green and P. G. M. Wuts, published by John Wiley and Sons, 1991 and this yields indoline derivatives represented by the formula (XI) where $R^{1'}$ is an acyl group. By alkylation of the 1-position of the indoline derivative by the aforementioned method, one can synthesize a compound represented by the formula (XI) where $R^{1'}$ is an alkyl group.

The ring closure of the indoline derivative represented by the formula (XI) can be accomplished by an intramolecular Friedel-Crafts reaction. Namely, the compound represented by the formula (XI) is reacted with a halogenating agent such as a phosphorus halide reagent or a thionyl halide reagent at a temperature ranging from the one obtained by cooling with ice to the one at which the reaction mixture refluxes to produce an acid halide, preferably reacted with thionyl chloride at a temperature ranging from the one obtained by cooling with ice to room temperature to produce an acid chloride, which in turn is subjected to intramolecular ring closure in a halogenated hydrocarbon-type solvent such as methylene chloride, chloroform or dichloroethane, an aromatic hydrocarbon-type solvent such as nitrobenzene or dichlorobenzene or a solvent inert to the reaction such as carbon disulfide in the presence of a Lewis acid catalyst typified by aluminum chloride, zinc chloride or tin chloride, preferably in the presence of aluminum chloride at a temperature ranging from the one obtained by cooling with ice to the one where the reaction mixture refluxes.

Alternatively, following the reaction with the aforementioned halogenating reagent, preferably thionyl chloride in a halogenated hydrocarbon-type solvent such as methylene chloride or dichloroethane, the resulting acid halide is not isolated but directly subjected to reaction in the presence of the aforementioned Lewis acid, preferably aluminum chloride at a temperature ranging from the one obtained by cooling with ice to the one at which the reaction mixture refluxes.

And furthermore, another method of implementing the ring closure of the compound represented by the formula (XI) is by performing the reaction with polyphosphoric acid, a polyphosphoric acid ester, trifluoroacetic anhydride or trifluoromethanesulfonic acid, preferably trifluoromethanesulfonic acid and trifluoroacetic anhydride in a halogenated hydrocarbon-type solvent such as methylene chloride or chloroform, preferably in chloroform, at a temperature ranging from the one obtained by cooling with ice to the one where the reaction mixture refluxes, preferably at a temperature ranging from the one obtained by cooling with ice to room temperature.

The thus obtained ring closure product may optionally be subjected to conversion of a substituent by one of the aforementioned methods, the methods to be described below or the like, thereby yielding the compound represented by the formula (III-b).

Thus produced 5-keto compound of the formula (III-b) where $R^{5'}$ is a hydrogen atom may be reacted with an electrophilic reagent to introduce various substituents in the 6- or 8-position. Reactions that may be carried out for this purpose include halogenation in a halogenated hydrocarbon-type solvent such as methylene chloride or chloroform using an N-halogeno compound typified by N-chlorosuccinimide (NCS) or N-bromosuccinimide (NBS) at a reaction temperature ranging from the one obtained by cooling with ice to the one where the reaction mixture refluxes, and nitration using a nitrating agent typified by a mixture of nitric acid and sulfuric acid, acetyl nitrate prepared from nitric acid and acetic anhydride or nitronium tetrafluoroborate in sulfolane at a reaction temperature ranging from the one obtained by cooling with ice to room temperature.

(Intermediate Preparing Process 2)

The compound represented by the formula (III) where Y is a methylen group and Z is a carbonyl group, that is the compound represented by the formula (III-c):

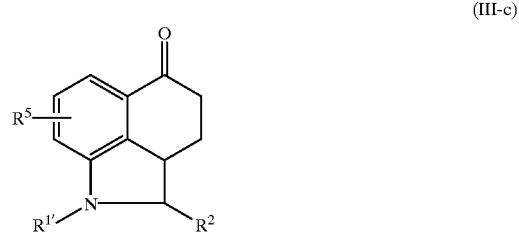

(III-c)

(where $R^{1'}$, $R^2$ and $R^5$ have the same meanings as defined above) and the intermediate represented by the formula (IV) where Y is a methylene group and Z is a carbonyl group, that is the compound represented by the formula (IV-b):

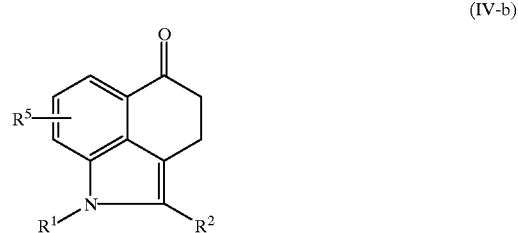

(IV-b)

(where $R^1$, $R^2$ and $R^5$ have the same meanings as defined above) can also be prepared in accordance with the following Reaction Scheme 4:

Reaction Scheme 4

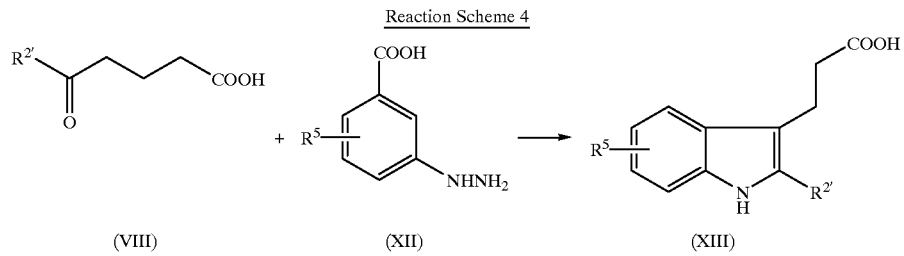

(VIII)  (XII)  (XIII)

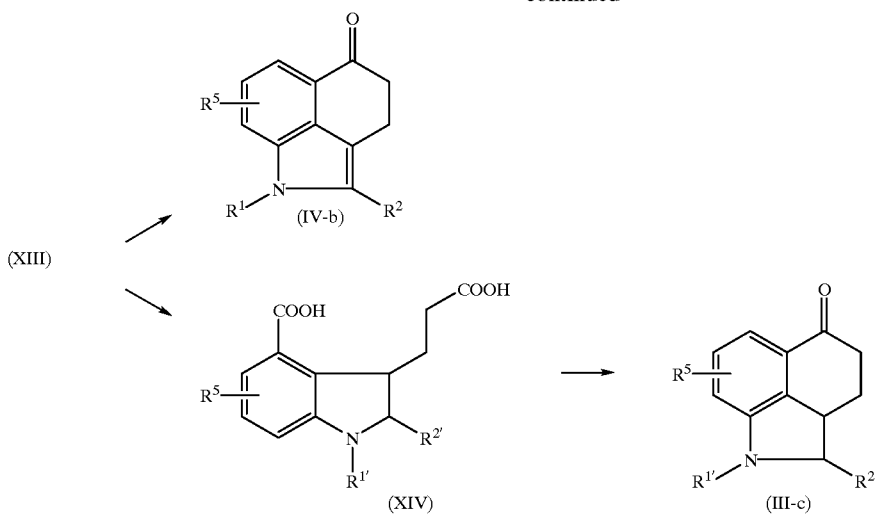

The compound represented by the formula (IV-b) can be prepared by such a method of an intramolecular condensation-decarboxylation reaction of a dicarboxylic acid derivative represented by the formula (XIII) (where $R^{2\prime}$ and $R^5$ have the same meanings as defined above) which is prepared from a hydrazine derivative represented by the formula (XII) (where $R^5$ has the same meaning as defined above) which is synthesized from a 3-aminobenzoic acid derivative by a known process and a benzoylbutylic acid derivative of the formula (VIII) through the aforementioned Fischer's indole synthesis reaction.

The intramolecular condensation-decarboxylation reaction may be carried out in accordance with a known documented method such as heating to reflux in acetic anhydride in the presence of sodium acetate described in G. S. Ponticello et al., The Journal of Organic Chemistry, 45, 4236–4238, 1980 and, if necessary, conversion of a substituent may be performed by one of the aforementioned methods or the methods to be described below, thereby yielding the compound represented by the formula (IV-b).

The indole portion of the dicarboxylic acid derivative represented by the formula (XIII) is reduced in accordance with one of the methods described in the aforementioned Process 2 and acylation or alkylation is performed as required to form an indoline derivative of the formula (XIV) (where $R^1$, $R^{2\prime}$ and $R^5$ have the same meanings as defined above), followed by the aforementioned intramolecular condensation-decarboxylation reaction and, if necessary, conversion of a substituent may be performed by one of the aforementioned methods, the methods to be described below or the like, thereby yielding the compound represented by the formula (III-c).

(Intermediate Preparing Process 3)

The compound represented by the formula (III) where Z is a methylene group and Y is a carbonyl group, that is the compound represented by the formula (III-d):

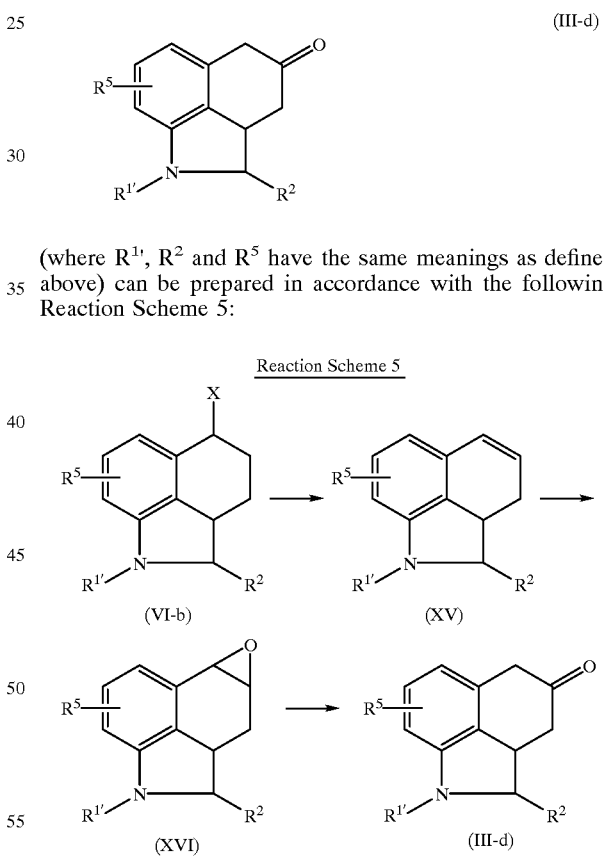

(where $R^{1\prime}$, $R^2$ and $R^5$ have the same meanings as defined above) can be prepared in accordance with the following Reaction Scheme 5:

The 4-keto form represented by the formula (III-d) can be prepared by such a method that a compound represented by the formula (VI-b) (where $R^{1\prime}$, $R^2$ and $R^5$ have the same meanings as defined above and X represents a hydroxyl group or a halogen atom), which is synthesized from the compound represented by the formula (III-c) in accordance with the Process 2, is converted to a compound represented by the formula (XV) (where $R^{1\prime}$, $R^2$ and $R^5$ have the same meanings as defined above) which, in turn, is epoxidized to a compound represented by the formula (XVI) (where $R^{1\prime}$, $R^2$ and $R^5$ have the same meanings as defined above) which, in turn, is isomerized to 4-keto form.

A compound of the formula (VI-b) where X is a halogen is converted to the compound of the formula (XV) by reactions under a suitable basic condition, for example, the reaction with an organic base such as triethylamine, 1,5-diazabicyclo[4.3.0]non-5-ene (DBN) or 1,8-diazabicyclo[5.4.0]-7-undecene (DBU) in a halogenated hydrocarbon-type solvent such as methylene chloride or chloroform or an ether-type solvent such as diethyl ether or tetrahydrofuran (THF) or the reaction with an inorganic base such as potassium carbonate, potassium hydroxide or sodium hydroxide in an alcoholic solvent such as methanol or ethanol or a solvent inert to the reaction such as dimethylimidazolidone (DMI), preferably by heating to reflux in dimethylimidazolidone (DMI) in the presence of potassium hydroxide.

The compound of the formula (XV) may alternatively be prepared by another method in which a compound of the formula (VI-b) where X is a hydroxyl group is reacted with a sulfonyl chloride such as methanesulfonyl chloride or toluenesulfonyl chloride, preferably methanesulfonyl chloride, in a halogenated hydrocarbon-type solvent such as methylene chloride or chloroform, an ether-type solvent such as diethyl ether or tetrahydrofuran (THF) or an aromatic hydrocarbon-type solvent such as benzene or toluene, preferably in methylene chloride in the presence of the aforementioned organic base, preferably triethylamine at a temperature ranging from −20° C. to the one where the reaction mixture refluxes, preferably at a temperature ranging from the one obtained by cooling with ice to room temperature.

Conversion from the compound of the formula (VI-b) where X is a hydroxyl group to the compound of the formula (XV) can also be performed in the presence of an acidic catalyst such as sulfuric acid or p-toluenesulfonic acid or, alternatively, by heating in an aromatic hydrocarbon-type solvent such as benzene or toluene in the presence of a strong acidic resin typified by Amberlyst 15E.

Conversion from the compound of the formula (XV) to the epoxy form of the formula (XVI) can be accomplished by performing reaction using an organic peroxide such as m-chloroperbenzoic acid or peracetic acid or an inorganic peroxide such as hydrogen peroxide, preferably m-chloroperbenzoic acid in a halogenated hydrocarbon-type solvent such as methylene chloride or chloroform at a temperature ranging from −20° C. to the one where the reaction mixture refluxes, preferably at a temperature ranging from the one obtained by cooling with ice to room temperature.

Conversion from the epoxy form of the formula (XVI) to the 4-keto form of the formula (III-d) can be accomplished by performing reaction using a metal halide such as zinc(II) iodide or magnesium bromide, preferably magnesium bromide in an ether-type solvent such as diethyl ether or tetrahydrofuran (THF), a halogenated hydrocarbon-type solvent such as methylene chloride or chloroform or an aromatic hydrocarbon-type solvent such as benzene or toluene or mixtures thereof at a temperature ranging from the one obtained by cooling with ice to the one where the reaction mixture refluxes, preferably by heating to reflux.

The benzoylbutyric acid derivative of the formula (VIII) which is the starting material in the Reaction Schemes 3 and 4 is prepared in accordance with the following Reaction Scheme 6:

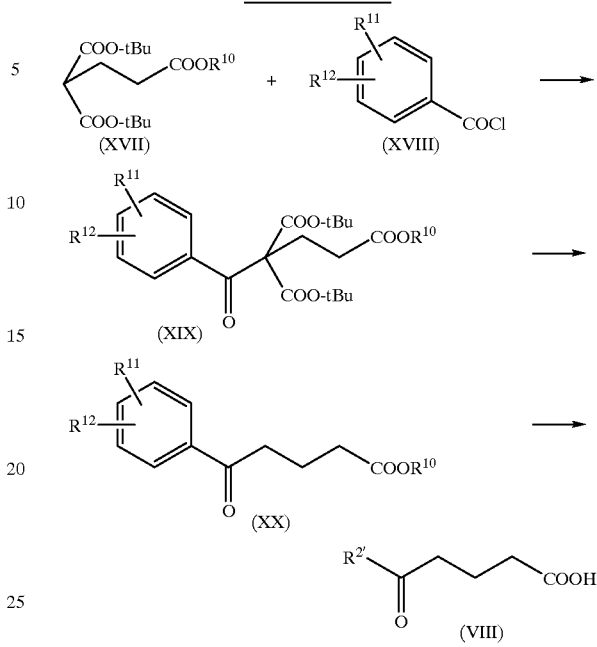

Reaction Scheme 6

A triester represented by the formula (XVII) (where $R^{10}$ represents a methyl group or an ethyl group) which is prepared by the reaction between an acrylic acid ester and a t-butyl malonate and a benzoyl chloride derivative which is either commercially available or prepared by a known method and which is represented by the formula (XVIII) (where $R^{11}$ and $R^{12}$ which may be the same or different represent a hydrogen atom, a halogen atom, an alkyl group having 1–4 carbon atoms, an alkoxyl group having 1–4 carbon atoms, an alkylthio group having 1–4 carbon atoms, an alkylsulfinyl group having 1–4 carbon atoms, an alkylsulfonyl group having 1–4 carbon atoms, a nitro group, an acetylamino group, a cyano group or a trifluoromethyl group) are reacted in acetonitrile in the presence of diisopropylethylamine and lithium chloride at a temperature ranging from the one obtained by cooling with ice to the one where the reaction mixture refluxes, preferably at room temperature to yield a benzoyl derivative represented by the formula (XIX) (where $R^{10}$, $R^{11}$ and $R^{12}$ have the same meanings as defined above). Conversion from the compound represented by the formula (XIX) to a benzoylbutyric acid ester of the formula (XX) (where $R^{10}$, $R^{11}$ and $R^{12}$ have the same meanings as defined above) can be accomplished by heating to reflux in an aromatic hydrocarbon-type solvent such as benzene or toluene in the presence of an acid catalyst such as p-toluenesulfonic acid or acetic acid, preferably in toluene in the presence of a p-toluenesulfonic acid catalyst. The thus obtained compound of the formula (XX) can be hydrolyzed by a known method, for example, in an alcoholic solvent such as methanol or ethanol in the presence of an aqueous solution of lithium hydroxide, sodium hydroxide or the like at a temperature ranging from room temperature to the one where the reaction mixture refluxes, thereby yielding the benzoylbutyric acid derivative of the formula (VIII).

Thus, the benzoylbutyric acid derivative of the formula (VIII) can be easily produced from either commercially available or known benzoyl chloride derivatives and, hence, a variety of such derivatives can be synthesized.

In addition, the process just described above enables the synthesis of trisubstituted benzoylbutyric acid derivatives from either commercially available or known benzoyl chloride derivatives and examples of the derivatives that can be synthesized include: 4-(4-bromo-3,5-dimethoxybenzoyl) butyric acid, 4-(2-chloro-3,5-dinitrobenzoyl)butyric acid, 4-(4-chloro-3,5-dinitrobenzoyl)butyric acid, 4-(3,5-dibromo-2-methoxybenzoyl)butyric acid, 4-(3,5-dichloro-2-methoxybenzoyl)butyric acid, 4-(3,5-dichloro-4-methoxybenzoyl)butyric acid, 4-(3,5-dimethoxy-4-methylbenzoyl)butyric acid, 4-(3,5-dinitro-2-methoxybenzoyl)butyric acid, 4-(3,5-dinitro-2-methylbenzoyl)butyric acid, 4-(3,5-dinitro-4-methylbenzoyl)butyric acid, 4-(2,3,4-trimethoxybenzoyl) butyric acid, 4-(2,4,6-trimethoxybenzoyl)butyric acid, 4-(3,4,5-trimethoxybenzoyl)butyric acid, 4-(2,3,5-trichlorobenzoyl)butyric acid, 4-(2,4,6-trichlorobenzoyl) butyric acid, 4-(2,3,4-trifluorobenzoyl)butyric acid, 4-(2,3,6-trifluorobenzoyl)butyric acid, 4-(2,4,5-trifluorobenzoyl) butyric acid, 4-(2,4,6-trifluorobenzoyl)butyric acid, 4-(3,4,5-trifluorobenzoyl)butyric acid, 4-(2,4,6-trimethylbenzoyl) butyric acid, and so forth.

The substituents on the compounds synthesized by the processes described above may optionally be converted to other substituents at various stages of the processes in accordance with the aforementioned methods or the methods to be described below.

(Conversion from halogen atoms)

Halogen atoms on the aromatic ring can be replaced by a hydrogen atom by hydrogenation under a suitable reducing condition as in an alcoholic solvent or a mixture thereof with a halogenated hydrocarbon-type solvent or a polar solvent such as dimethyl sulfoxide (DMSO) or dimethylformamide (DMF) in the presence of a metal catalyst such as palladium. If a carbonyl group is present in the molecule, selective reduction can be effected in the presence of potassium hydroxide; if an amino group is present in the molecule at the benzyl position, selective reduction can be effected by addition of hydrochloric acid.

Halogen atoms on the aromatic ring can also be converted to a cyano group by heating with copper(I) cyanide, potassium cyanide or sodium cyanide in a polar aprotic solvent such as dimethyl sulfoxide (DMSO), dimethylformamide (DMF) or dimethylimidazolidone (DMI). Transition metal complexes can be used as the catalyst and they include palladium complexes typified by palladium acetate and nickel complexes typified by tetrakistriphenylphosphine nickel. The cyano group obtained by this conversion can further be converted to a carboxyl group or a carboxyamido group by hydrolysis under a suitable alkaline condition using sodium hydroxide, potassium hydroxide or the like, or under a suitable acidic condition using sulfuric acid, hydrochloric acid or the like.

(Conversion from a carboxyl group)

A carboxyl group can be derivated to an alkoxycarbonyl group by an esterification reaction involving dehydration using an alcohol in the presence of a mineral acid such as sulfuric acid or hydrochloric acid or by an O-alkylation reaction using an alkylating agent such as trimethylsilyldiazomethane, diazomethane or an alkylsulfuric acid; alternatively, the carboxyl group can be converted to a substituted carbamoyl group by reaction with a primary amine or a secondary amine in the presence of a suitable dehydrative condensing agent typified by dicyclohexylcarbodiimide (DCC). Further, an alkoxycarbonyl group can be converted to a hydroxymethyl group by reduction with lithium aluminum hydride in an ether-type solvent typified by tetrahydrofuran (THF) or to a carbamoyl group by heating in aqueous ammonia or a solution of ammonia in ethanol.

(Conversion from an alkylthio group)

An alkylthio group can be converted to an alkylsulfinyl group and an alkylsulfonyl group by oxidation with a suitable oxidizing reagent such as m-chloroperbenzoic acid in methylene chloride. An equivalent amount of the oxidizing reagent permits conversion to an alkylsulfinyl group whereas an excess of the oxidizing reagent permits conversion to an alkylsulfonyl group.

(Conversion from a nitro group)

A nitro group can be converted to an amino group under a suitable reducing condition, for example, by hydrogenation in an alcoholic solvent in the presence of a metal catalyst such as palladium. If a carbonyl group is present in the molecule, selective reduction can be effected in the presence of potassium hydroxide. The amino group thus obtained may in turn be acylated using an organic acid typified by formic acid or acetic acid, an amino acid typified by glycine, or activated derivatives thereof.

(Conversion from an alkoxyl group)

An alkoxyl group can be converted to a hydroxyl group by the methods described in the Overview in "Protective Groups in Organic Synthesis", 2nd Ed., 1991, for example, by treatment with aluminum chloride in an aromatic hydrocarbon-type solvent such as toluene or benzene. The hydroxyl group may in turn be alkylated with a suitable alkylating agent, for example, a halide such as ethyl iodide or a bromoacetic acid ester.

If reactive groups such as a hydroxyl group, an amino group and a carboxyl group are contained as substituents in the compounds synthesized by the processes described above, these groups may optionally be protected as appropriate in various reaction steps and, thereafter, the protective groups may be removed at suitable stages. The methods of introducing and removing the protective groups are appropriately selected depending upon the type of the group to be protected or the protective group used and exemplary methods are described in the Overview in "Protective Groups in Organic Synthesis", 2nd Ed., 1991. If desired, the above-mentioned reactive groups may be alkylated, amidated, esterified and otherwise treated in accordance with the aforementioned methods.

Substituents such as a nitro group, a cyano group, an alkoxycarbonyl group and an amido group on the intermediates may optionally be reduced in accordance with the aforementioned methods or by known methods.

As already noted, the compounds of the invention which are represented by the formula (I) have an asymmetric center in either 4- or 5-position and, hence, occur in two types of optical isomers. The respective optical isomers can be obtained by asymmetric synthesis or optical resolution.

Examples of asymmetric synthesis include the following: a method in which the compound represented by the formula (IV) is reacted with an optically active benzylamine typified by (−)-α-methylbenzylamine and thereafter the α-methylbenzyl group is removed by reduction, as described in Eugene Farkas et al., The Journal of Organic Chemistry, 50, 1110–1112, 1985; a method in which the compound represented by the formula (IV) is converted to an oxime form in accordance with the method described in Process 1 and thereafter asymmetric reduction is performed with a rhodium catalyst; and a method in which the compound represented by the formula (III) is converted to an optically active hydroxyl form under the action of optically active substances including an organoboron such as diisopinocanphenylboron chloride, an organo aluminum reagent and baker's yeast, and the resulting hydroxyl form is converted to the compound of the formula (I) in accordance with Process 2.

Optical resolution can be effected using optically active acids such as L-(+)-R-tartaric acid, (−)-dibenzoyltartaric acid, (+)-camphoric acid, (+)-10-camphorsulfonic acid and (−)-mandelic acid.

The isomers can also be separated by high-performance liquid chromatography (HPLC) using a chiral column for optical resolution such as "CHIRAL CELL OD" of DAICEL CHEMICAL INDUSTRIES, LTD.

Experiments

On the pages that follow, the present invention is described specifically with reference to experiments, which are by no means intended to limit the invention.

Pharmacological Experiment 1: Naturally occurring neuronal Death Suppressing Action The action of compounds to suppress the naturally occurring death of neurons was evaluated in terms of their effectiveness in suppressing or inhibiting the naturally occurring death of neurons as induced by exposing cultured neurons to serum-free cultivation conditions. An experiment was run by a method adapted from the method of Shimojo et al., Neurosci. Lett., 151, 170, 1993. Specifically, neurons were isolated from the cerebrum of embryonic day 16 rats in the usual manner, suspended in a DMEM/F12 medium containing 1% fetal bovine serum, seeded onto a polylysine-coated culture plate at a density of $5 \times 10^4$ cells per square centimeter and cultivated at 37° C. in 95% air+5% $CO_2$. After one day of culture, the medium was replaced with a serum-free medium containing a compound to be tested and the cultivation was continued for 3 more days. Subsequently, the cells were fixed with 1% glutaraldehyde and their number was determined by calorimetric quantification using Crystal Violet (Anal. Biochem., 182, 16–19, 1989). The percent suppression of neuronal death by the test compound was determined by the following formula:

$$100 \times (ODtest - ODcontrol)/(ODnormal - ODcontrol) \ (\%)$$

where ODtest is the number of cells (absorbance) in the group of addition of test compound after serum removal, ODcontrol is the number of cells (absorbance) in a control group after serum removal, and ODnormal is the number of cells (absorbance) in a control (normal) group without serum removal.

The death of neurons from cultivation under the serum-free condition which occurred in the above-described experimental system was also suppressed by other reagents such as actinomycin D (RNA synthesis inhibitor), cycloheximide (protein biosynthesis inhibitor) and aurin tricarboxylic acid (endonuclease inhibitor). Hence, the neuronal death which occurred in the experimental system of interest was shown to be apoptosis. The results of evaluation of typical compounds encompassed by the invention are shown in Table 1.

TABLE 1

Natural Neurocyte Death Suppressing Action

| Compound of Example | Concentration (μg/ml) | Suppression of Naturally Occurring Neuronal Death (%) |
|---|---|---|
| 81 | 1.0 | 51 |
| 87 | 3.0 | 84 |
| 96 | 1.0 | 37 |
| 99 | 0.3 | 59 |
| 103 | 0.3 | 56 |
| 121 | 3.0 | 72 |
| 124 | 3.0 | 23 |

TABLE 1-continued

Natural Neurocyte Death Suppressing Action

| Compound of Example | Concentration (μg/ml) | Suppression of Naturally Occurring Neuronal Death (%) |
|---|---|---|
| 130 | 1.0 | 76 |
| 148 | 1.0 | 65 |
| 151 | 3.0 | 98 |
| 153 | 1.0 | 100 |
| 174 | 0.3 | 64 |
| 185 | 0.3 | 100 |
| 216 | 1.0 | 75 |
| 223 | 3.0 | 81 |
| 244 | 3.0 | 57 |

As the above results show, each of the tested compounds of the invention exhibited a marked action to suppress the death of neuron s under the serum-free condition which occurred as apoptosis.

Pharmacological Experiment 2: Veratrine-Induced Neuronal Death Suppressing Action The action of compounds to suppress the death of neurons induced by veratrine was evaluated in terms of their effectiveness in suppressing the neuronal death as induced by direct addition of veratrine. An experiment was run by a method adapted from the method of Powells et al., J. Pharmacol. Exp. Therapeutics, 255, 1117, 1987. Specifically, neurons were isolated from the cerebrum of embryonic day 16 rats in the usual manner, suspended in a MEM medium containing 10% fetal bovine serum, seeded onto a polylysine-coated culture plate at a density of $2.5 \times 10^5$ cells per square centimeter and cultivated at 37° C. in 95% air+5% $CO_2$. Starting on the fifth day of cultivation, treatment was conducted with 10 μM of cytosine arabinoside for 2 days and the cultivation was continued until the 12th day, when a test was run as follows. The cells were treated with a buffer solution containing veratrine (0.35 mM) and a test compound, replaced in a serum-containing medium and cultivated for another 24 h. Subsequently, the number of viable cells was determined by calorimetric quantification using 3-(4,5-dimethylthiazol-2-yl)-2,5-diphenyltetrazolium bromide (MTT). The percent suppression of neuronal death by the test compound was determined by the following formula:

$$100 \times (ODtest - ODcontrol)/(ODnormal - ODcontrol) \ (\%)$$

where ODtest is the number of cells (absorbance) in the group of addition of veratrine+test compound, ODcontrol is the number of cells (absorbance) in a control group of addition of veratrine, and ODnormal is the number of cells (absorbance) in a control (normal) group without addition of veratrine.

In addition, $IC_{50}$ values indicating the effectiveness in achieving 50% suppression of neuronal death were calculated by the probit method on the basis of the result from more than one concentration. The $IC_{50}$ values of typical compounds encompassed by the invention are shown in Table 2.

TABLE 2

Veratrine-Induced Neuronal Death Suppressing Action

| Compound of Example | IC$_{50}$ (μg/ml) |
|---|---|
| 81 | 3.2 |
| 90 | 0.7 |
| 95 | 3.1 |
| 107 | 0.33 |
| 110 | 1.8 |
| 113 | 0.7 |
| 150 | 1.2 |
| 171 | 1.9 |
| 174 | 3.4 |
| 184 | 0.8 |
| 225 | 2.2 |
| 239 | 2.2 |

As the above results show, each of the compounds of the invention exhibited a marked action to suppress the death of neurons as induced by veratrine which would cause the overloading of Ca$^{2+}$ for excessive excitation of neurons.

Pharmacological Experiment 3A: Effectiveness in Gerbil Model of Delayed Neuronal Death The action of compounds to suppress the death of neurons in vivo was studied by a method adapted from the method of Kirino al., Brain Res., 239, 57, 1982. Specifically, the cervical part of a gerbil under anesthesia by halothane inhalation was incised along the median line to expose the carotid artery on both sides, which were occuluded with clips for 4 min and thereafter brought back to patency. After suturing the incised part, the anesthetization was turned off and the animal was brought back to keeping under normal condition. Three days after loading of cerebral ischemia, the gerbil was anesthetized by administering pentobarbital, fixed by transcardiac formalin perfusion and had the brain isolated. A coronary slice including the fimbria hippocampi was prepared from the isolated brain and stained with Cresyl Violet. The pyramidal cells in the hippocampus CA1 region were examined under an optical microscope and the degree of damage was rated by the following scores: 0, no damage; 1, slight damage; 2, moderate damage; 3, significant damage; 4, total damage. Each test compound was administered through the carotid arteries 5 min before ischemia. The results of evaluation of typical compounds encompassed by the invention are shown in Tables 3-1 and 3-2.

TABLE 3-1

Effectiveness in Gerbil Model of Delayed Neuronal Death

| Experimental Group | Dose (mg/kg) | No. of cases | Score of damage to hippocampus CA1 |
|---|---|---|---|
| Non-ischemic group | | 5 | 0 ± 0 |
| Ischemic control group | | 18 | 2.9 ± 0.3 |
| Group which was both ischemic and administered with the compound of Example 81 | 10 | 4 | 0.1 ± 0.1 |
| Group which was both ischemic and administered with the compound of Example 86 | 5 | 4 | 1.8 ± 0.1 |
| Group which was both ischemic and administered with the compound of Example 87 | 2 | 5 | 1.9 ± 0.6 |
| Group which was both ischemic and administered with the compound of Example 107 | 10 | 4 | 0.5 ± 0.5 |
| Group which was both ischemic and administered with the compound of Example 130 | 5 | 4 | 1.9 ± 0.1 |

Mean ± standard error

TABLE 3-2

Effectiveness in Gerbil Model of Delayed Neuronal Death

| Experimental Group | Dose (mg/kg) | No. of cases | Score of damage to hippocampus CA1 |
|---|---|---|---|
| Non-ischemic group | | 5 | 0 ± 0 |
| Ischemic control group | | 4 | 3.5 ± 0.4 |
| Group which was both ischemic and administered with the compound of Example 232 | 10 | 5 | 2.5 ± 0.7 |
| Group which was both ischemic and administered with the compound of Example 240 | 10 | 5 | 2.1 ± 0.5 |

Mean ± standard error

As the above results show, each of the compounds of the invention exhibited a marked effect in suppressing delayed neuronal death. Thus, the compounds of the invention also proved to be very effective in the in vivo model for which the involvement of the apoptosis of neurons was pointed out.

Pharmacological Experiment 3B: Effectiveness in Gerbil Model of Delayed Neuronal Death The action of compounds to suppress the death of neurons in vivo was studied by the method of Murase et al., Neurosci. Lett., 149, 229, 1993 which was adapted from the method of Kirino et al., Brain Res., 239, 57, 1982. Specifically, the cervical part of a gerbil under anesthesia by halothane inhalation was incised along the median line to expose the carotid artery on both sides, which were occuluded with clips for 3 min and thereafter brought back to patency. After suturing the incised part, the anesthetization was turned off and the animal was brought back to keeping under normal condition. Seven days after loading of cerebral ischemia, the gerbil was anesthetized by administering pentobarbital, fixed by transcardiac formalin perfusion and had the brain isolated. A coronary slice including the fimbria hippocampi was prepared from the isolated brain and stained with Cresyl Violet. The pyramidal cells in the hippocampus CA1 region were counted under an optical microscope. Each test compound was administered through the carotid arteries 5 min before ischemia. The results of evaluation of typical compounds encompassed by the invention are shown in Table 3-3.

TABLE 3-3

Effectiveness in Gerbil Model of Delayed Neuronal Death

| Experimental Group | Dose (mg/kg) | No. of cases | Pyramidal cell count in hippocampus CA1 (cells/mm) |
|---|---|---|---|
| Non-ischemic group | | 5 | 249 ± 10 |
| Ischemic control group | | 8 | 58 ± 22 |
| Group which was both ischemic and administered with the compound of Example 247 | 2.5 | 8 | 96 ± 31 |
| Group which was both ischemic and administered with the compound of Example 247 | 10 | 8 | 83 ± 35 |
| Group which was both ischemic and administered with the compound of Example 248 | 2.5 | 8 | 87 ± 29 |
| Group which was both ischemic and administered with the compound of Example 248 | 10 | 8 | 206 ± 14** |

Mean ± standard error;
**p < 0.01 vs ischemic control group

As is clear from the above results, when the compounds of the invention were resolved optically, the greater activity was recognized in the (−)-isoform.

Pharmacological Experiment 4: Effectiveness in Rat Model of Permanent Occlusion of Middle Cerebral Artery The therapeutic effect of compounds against cerebral infarction was studied in accordance with the method of Tamura et al., J. Cereb. Blood Flow Metab., 1, 53, 1981.

Specifically, a hole was made transorbitally in part of the cranial bone of a rat under anesthesia by halothane inhalation to expose the origin of the middle cerebral artery. Then, using a bipolar coagulator, the middle cerebral arteries were burnt to coagulate for permanent occlusion. The operative site was sutured and after the anesthetization was turned off, the animal was brought back to keeping under normal condition. Twenty-four hours after loading of cerebral ischemia, the rat was decapitated and the brain was isolated. The isolated brain was cut at a predetermined site to prepare five coronary slices. The infarct area of each section was rendered visible by staining with 2,3,5-triphenyltetrazolium chloride (TTC) and quantitated with an image analyzer. A test compound was administered through the tail vein 10 min after the occlusion of the middle cerebral arteries and comparison was made with a control group administered with a solvent alone. The results are shown in Table 4.

TABLE 4

Effectiveness in Rat Model of Permanent Occlusion of Middle Cerebral Arteries

| Experimental Group | No. of cases | Weight of infarction (%) |
|---|---|---|
| Control group | 20 | 14.7 ± 0.8 |
| Group administered with 10 mg/kg of the compound of Example 81 | 10 | 9.3 ± 1.5** |

Mean ± standard error;
**p < 0.01 vs control group

As the above results show, the compound of the invention proved to be very effective in the stroke model for reducing the infarct size.

Pharmacological Experiment 5: Effectiveness in Formalin Induced Paw Pain Test

The effectiveness of compounds in a formalin induced pain test was studied in accordance with the method of Shibata et al., Pain, 38, 347, 1989.

Specifically, the left hind paw of a mouse was injected subcutaneously with 25 μl of a 0.5% formalin solution and the duration of time for which the mouse licked and bit the treated foot starting just after the injection was measured with a stopwatch; the measured times were integrated for every 5 minutes and recorded. The formalin induction caused a characteristic biphase pain reaction; the pain recognized within 10 min after the induction was categorized as a first-phase pain reaction and the pain recognized from 10 min to 45 min as a second-phase reaction. The test compounds were administered orally 30 min before the injection of formalin. The percent suppression of the formalin induced pain reaction by each test compound was determined by the following formula:

$$100 \times (PRcontrol - PRtest)/(PRcontrol) \, (\%)$$

where PRtest is the time (sec) of pain reaction in a group administered with both formalin and the test compound and PRcontrol is the time (sec) of pain reaction in a control group subjected to formalin induction.

A group of mice administered subcutaneously with 10 mg/kg of pentazocine in the experimental system showed 61% and 40% suppression of the first- and second-phase pain reactions, respectively. Table 5 shows the results of evaluation of typical compounds encompassed by the invention.

TABLE 5

Effectiveness in Formalin Induced Paw Pain Test in Mouse

| Compound of Example | Dose (mg/kg) | Suppression of pain reaction (%) First phase | Suppression of pain reaction (%) Second phase |
|---|---|---|---|
| 232 | 200 | 51 | 100 |
| 237 | 100 | 63 | 97 |

As the above result shows, the compounds of the invention had an outstanding analgesic effect in the pain model.

Pharmacological Experiment 6: Acute Toxicity Test

The acute toxicity of compounds of the invention was studied on mice (ICR weighing 20–25 g; each group consisting of 3 animals); the compounds of Examples 81 and 86 were administered intraperitoneally, each in an amount of 100 mg/kg and upon 7-day observation, no case of death was found. From this result, one may safely conclude that the compounds of the invention are safe drugs.

As is clear from the foregoing experimental results, the compounds of the invention showed marked activities in both in vitro and in vivo models. In case of compounds having asymmetric carbon, the (−)-isoform had the stronger activity, indicating that an isomer having the same absolute configuration as said isoform possessed the stronger activity. In addition, the compounds of the invention suppressed the death of neurons caused by glutamic acid but did not show any action on the serotonin system. Even in the in vivo test and at doses where their efficacy was manifested, the compounds did not show any spasm causing action or any abnormalities in general symptoms, nor did they have any effects on the circulatory system.

Thus, the compounds of the invention were found to act directly upon neurons to suppress neuronal deaths extensively ranging from acute excitation death to delayed apoptosis; it was also shown that the in vitro effectiveness of the compounds was high enough to suppress the death of neurons caused by various factors. Further, the compounds of the invention showed an outstanding neuroprotective action from in vivo peripheral administration and were effective not only in the model of cerebral infarction but also in the model of delayed neuronal death; it was thus shown that the compounds had a wide spectrum of actions to be effective against various diseased states. In addition, the compounds of the invention were found to exhibit a marked analgesic effect in the pain model. Briefly, the compounds of the invention showed the action of alleviating the pains associated with various diseases and, hence, were found to be effective against the pains from various diseases of the nervous system caused by various physical and mental abnormalities.

On the other hand, the compounds of the invention are substantially free from the action on the circulatory system and the development of undesired symptoms in nerves, which are common side effects of the existing compounds having similar activities. Therefore, the compounds of the invention are candidates for drugs of less side effects that need not be administered directly into the cerebral ventricles or pulp chamber but can be administered safely for a prolonged period with a view to treating various diseases that involve the degeneration, retraction or death of neurons or as analgesics to alleviate the pains associated with such diseases.

The pharmaceutical compositions of the invention contain compounds that act directly upon neurons to be capable of directly suppressing their death; hence, unlike the heretofore used nosotropic drugs such as cerebral metabolism activators and cerebral circulation modifiers, the compositions directly prevent or otherwise control the dysfunction, degeneration or necrosis of neurons in general or specific regions due to ischemia, trauma, aging or etiology which is unknown for the cause, whereby they can be used in the treatment of cerebrovascular disorders, various neurodegenerative diseases or various other diseases that involve the degeneration, retraction or death of neurons. Specifically, cerebrovascular disorders include, but are not limited to, various diseases accompanying cerebrovascular disorders such as cerebral infarctions such as cerebral thrombosis and embolism, cerebral hemorrhages such as hypertensive intracerebral hemorrhage and subarachnoid hemorrhage, transient cerebral ischemic attacks, cerebroarteriosclerosis and their sequela; neurodegenerative diseases include, but are not limited to, dementia of Alzheimer's type, Parkinson's disease, amyotrophic lateral sclerosis (ALS), Down's syndrome, Huntington chorea and spinal cerebellar degeneration; and various other diseases that involve the degeneration, retraction or death of the neurons include, but are not limited to, brain disorders at the time of revivification after cardiac arrest, brain dysfunction prior to or after brain surgery, disorders of the nervous system due to hypoxia, hypoglycemia, brain or spinal damage, intoxication with drugs or gases, diabetes mellitus, administration of anticancer agents, alcohol and the like, senile dementia and hysmnesia.

Patients suffering from cerebrovascular disorders, various neurodegenerative diseases or various other diseases which involve the degeneration, retraction or death of neurons manifest various symptoms due to the damage of neurons in these diseases, as exemplified by volition derangements such as reduced volition, reduced reactivity and abulia, affective disorders such as depression, anxiety, irritation, incontinence of emotions, disposition to anger and amimia, subjective symptoms such as headache, vertigo, numbness and susurrus aurium, personality disorders such as aggressiveness, animus and opposition, behavioral disorders such as restlessness/excitedness, tachylogia and wandering, consciousness disorders such as delirium, complaint of general malaise, somnipathy, as well as mental dysfunctions that cannot be cured by existing therapeutics such as impaired ability to write names, impaired orientation, reduced thinking power and reduced judgment, dyskinesia, objective sensory disorders, unilateral paralysis, dystonia and parareflexia. The pharmaceutical compositions of the invention are effective against the symptoms mentioned above.

If desired, the pharmaceutical compositions of the invention can be administered to the human body when transplanting a nervous tissue and neurons or, alternatively, the nervous tissue and neurons to be transplanted may be treated with the compounds or pharmaceutical compositions of the invention for such purposes as preserving them or maintaining vital force.

In addition, the pharmaceutical compositions of the invention contain compounds having the action of centrally alleviating the pains from various diseases and, hence, can be used as therapeutics effective against pains from various diseases of the nervous system caused by various physical or mental abnormalities. Specific examples of such pains include, but are not limited to, those associated with cancers, diabetic neuropathy, herpes zoster, arthritis, rheumatism, as well as medical or dental surgery.

Further in addition, the pharmaceutical compositions of the invention can also be used against neuropathy associated with epilepsy, schizophrenia, depression, anxiety syndrome, AIDS, rabies, measles, Japanese B encephalitis, subacute sclerosing panencephalitis and infections such as tetanus, as well as diseases including mitochondrial myopathy, Leber's syndrome, Wernicke's syndrome, Rett's syndrome, homocysteinemia, hyperprolinemia, hydroxybutylamino acidouria, lead encephalopathy and insufficiency of sulfite oxidase.

The medicines of the invention are administered in various forms of drugs as pharmaceutical compositions containing the compounds represented by the formula (I) set forth above or salts thereof.

If the compounds of the invention are to be used as drugs, they can be prepared in various forms by any known procedures of pharmaceutical formulation. The compounds of the invention may be combined appropriately with suitable vehicles or media commonly employed in drugs, such as sterile water, physiological saline, vegetable oils (e.g., sesame oil, soybean oil and olive oil), organic solvents (e.g., ethanol, propylene glycol and macrogol 400), and optionally with excipients (e.g., lactose, sucrose, mannitol, crystalline cellulose and silicic acid), coloring agents, emulsifying agents, suspending agents (e.g., gum arabic), surfactants (e.g., polyoxyethylene hardened castor oil-type surfactants and polyethylene glycol-type surfactants), solubilizers (e.g., cholesterol and triethanolamine), stabilizers (e.g., sugar and sugar alcohol) or preservatives (e.g., parabens, benzyl alcohol and benzalkonium chloride) so as to formulate pharmaceutical preparations such as injections, nasal inhalants, transcutaneous inhalants and oral drugs, preferably injections or oral drugs, for effective administration to the human body. Speaking of injections, they can be provided as preparations such as freeze-dried products and solutions for injection.

The drugs of the invention can be administered by various methods including intra-arterial injection, intravenous injection, intramuscular injection, subcutaneous injection, intraventricular injection, intrathecal injection and peroral administration. Alternatively, they may be confined in an osmotic pump or the like and retained in the human body for continuous administration. In addition, the compounds of the invention may be confined in liposome forming substances (Unexamined Published Japanese Patent Application (kokai) No. 243022/1985 or 85920/1989) and thereafter administered as liposomes. If desired, a catheter may be implanted in a cerebral ventricle or pulp chamber for direct administration therefrom. It has been reported that injection of hypertonic solutions of mannitol, urea and so forth through the carotid arteries causes a transient increase in the passage through a blood brain barrier (Proc. Natl. Acad. Sci. USA, 76, 481–485, 1979) and that substances such as alkylglycerol have the action of enhancing the transfer of other drugs into the brain (Angew. Chem., 23, 257–328, 1984), and these techniques may also be employed to administer the drugs of the invention.

The drugs of the invention may be used at clinical situations and the following is an exemplary case of this, in which a cerebral stroke such as cerebral infarction occurs and after a differential diagnosis of the disease is successfully made, administration of a suitable drug is commenced at the earliest possible time either at the site of first aid, within an ambulance or in an intensive care unit. In this situation, it is usual that the patient has lost consciousness, so the drug is administered intravenously. In addition, in order to attain an effective concentration, an appropriate dose of the drug is at first administered within a short time and, thereafter, in order to maintain the effective concentration, the drug is administered by intravenous infusion in a sustained manner. Concurrently, therapeutics of cerebral edema (e.g., mannitol, concentrated glycerin or fructose, and furosemide) may also be applied against elevation of the intracranial pressure or various hypotensives (e.g., nifedipine and nicardipine hydrochloride) be applied for the control of blood pressure. Thereafter, for a period ranging from several days to several weeks, the appropriate amount of the drug is administered either in divided portions per day or by intravenous infusion in a sustained manner depending upon the state of the patient. In the case of cerebral thrombosis and the like, the drugs of the invention may be used in combination with antiplatelet drugs (e.g., ticlopidine hydrochloride and aspirin) or anticoagulants (e.g., warfarin) for preventing recurrence.

When used as drugs, the compounds of the invention should be administered in sufficient amounts to treat the disease of interest but they may be adjusted as appropriate for the dosage form, method of administration, the frequency of administration per day, the severity of the disease, body weight and age.

When used as drugs, the compounds of the invention are administered in daily doses of 0.001–500 mg/kg, preferably 0.01–100 mg/kg.

EXAMPLES

The following examples are provided for the purpose of further illustrating the present invention but are in no way to be taken as limiting.

NMR spectra were obtained with JEOL JNM-EX270 FT-NMR (product of JEOL Ltd.) or JEOL JNM-LA300 FT-NMR (product of JEOL Ltd.); IR spectra with HORIBA FT-200 (product of Horiba Ltd.); m.p. with Mettler FP80 or FP90 (each produced by Mettler Instruments AG); high-performance liquid chromatography with SHIMADZU LC-10A (product of Shimadzu Corporation); and preparative high-performance liquid chromatography with Waters Delta Prep 4000 (product of Waters Associates, Inc.). In the following examples, the absolute yield is followed by parentheses in which the relative yield is indicated in terms of percentage.

Example 1

Synthesis of 1-benzoyl-2-phenyl-1,2,2a,3,4,5-hexahydrobenz[cd]indol-5-one (Step 1) Synthesis of 2-phenylindole-3-propionic acid Phenylhydrazine hydrochloride (50 g) and benzoylbutyric acid (55.4 g) were suspended in acetic acid (500 ml), followed by heating to reflux for 1.5 hours. After allowing the suspension to cool, the insoluble matter was filtered off and the filtrate was concentrated under reduced pressure. Water was added to the residue, the mixture was extracted with ethyl acetate, and the organic layer was washed with water and saturated aqueous solution of sodium chloride, and thereafter dried over anhydrous sodium sulfate. The solvent was distilled off under reduced pressure and the residue was crystallized from an ether/hexane mixed solvent, followed by washing with a methylene chloride/hexane mixed solvent to yield 69 g (90%) of the titled compound as pale brown crystals.

(Step 2) Synthesis of 2-phenyl-2,3-dihydroindole-3-propionic acid

Zinc powder (96.2 g) was suspended in water (80 ml); following the addition of conc. hydrochloric acid (80 ml), a solution (200 ml) of the compound (39 g) obtained in step 1 in dimethylimidazolidone (DMI) was added and the mixture was heated to reflux for 1.5 hours. In the meantime, 60 ml of hydrochloric acid was added in five portions at 15-minute intervals. After allowing the mixture to cool, the zinc was filtered off and water was added to the filtrate, followed by extraction with five portions of ethyl acetate. The organic layers were combined, washed four times with water and once with saturated aqueous solution of sodium chloride, dried over anhydrous sodium sulfate and the solvent was thereafter distilled off under reduced pressure. The residue was purified by silica gel column chromatography (methylene chloride–methylene chloride/ethyl acetate= 19:1) to yield 25 g (64%) of the titled compound as crystals.

(Step 3) Synthesis of 1-benzoyl-2-phenyl-2,3-dihydroindole-3-propionic acid

A portion (30 g) of the compound obtained in step 2 and triethylamine (15.6 ml) were dissolved in chloroform (1000 ml) and benzoyl chloride (14.4 ml) was added under cooling with ice. After stirring at room temperature for 30 minutes, water was added to the reaction mixture and the organic layer was separated, and then the aqueous layer was extracted with methylene chloride. The organic layers were combined, washed with saturated aqueous solution of sodium chloride, dried over anhydrous sodium sulfate and the solvent was thereafter distilled off under reduced pressure. The residue was purified by silica gel column chromatography (methylene chloride–methylene chloride/methanol=97:3) to yield 30 g (72%) of the titled compound as an oil.

(Step 4) Synthesis of 1-benzoyl-2-phenyl-1,2,2a,3,4,5-hexahydrobenz[cd]indol-5-one Thionyl chloride (40.7 ml) was added under cooling with ice to the compound (30 g) obtained in step 3 and after stirring at room temperature for 15 minutes, the excess thionyl chloride was distilled off under reduced pressure. The residue was dissolved in carbon disulfide (50 ml) and the resulting solution was slowly added dropwise to a suspension (350 ml) of aluminum chloride (48.6 g) in carbon disulfide. After heating to reflux for 1 hour, the mixture was allowed to cool and poured onto ice after addition of ethyl acetate. Following extraction with ethyl acetate, the organic layer was washed with saturated aqueous solution of sodium chloride, dried over anhydrous sodium sulfate and the solvent was thereafter distilled off under reduced pressure. The residue was purified by silica gel column chromatography (methylene chloride) to yield 15 g (53%) of the titled compound as crystals.

Example 2

Synthesis of 1-acetyl-6-methoxy-2-phenyl-1,2,2a,3,4,5-hexahydrobenz[cd]indol-5-one (Step 1) Synthesis of 1-acetyl-5-methoxy-2-phenyl-2,3-dihydroindole-3-propionic acid 5-methoxy-2-phenyl-2,3-dihydroindole-3-propionic acid (10.2 g) synthesized as in Example 1, steps 1 and 2, was dissolved in anhydrous methylene chloride (80 ml). Pyridine (2.77 ml), then acetic anhydride (3.24 ml) were added to the solution under cooling with ice, and the mixture was stirred for 30 minutes at room temperature. The reaction mixture was poured into ice water. The organic layer of the mixture was separated, washed with 1N hydrochloric acid, water and saturated aqueous solution of sodium chloride successively and dried over anhydrous sodium sulfate. Then, the solvent was distilled off under reduced pressure to yield 11.5 g (99%) of the titled compound as a crude rubber-like product.

(Step 2) Synthesis of 1-acetyl-6-methoxy-2-phenyl-1,2,2a,3,4,5-hexahydrobenz[cd]indol-5-one A portion (5.0 g) of the compound obtained in step 1 was dissolved in anhydrous chloroform (150 ml) and to the solution were added trifluoromethanesulfonic acid (1.3 ml) and trifluoroacetic anhydride (2.08 ml) under cooling with ice. The mixture was stirred overnight at room temperature. The reaction mixture was poured into ice water and the organic layer was separated. The aqueous layer was extracted with methylene chloride. The organic layers were combined, washed with water, saturated aqueous solution of sodium hydrogencarbonate and saturated aqueous solution of sodium chloride and dried over anhydrous sodium sulfate. The solvent was distilled off under reduced pressure and the residue was purified by silica gel column chromatography (methylene chloride/ethyl acetate=19:1), and further crystallized from an ether/hexane mixed solvent to yield 2.52 g (53%) of the titled compound as a yellow powder.

Example 3

Synthesis of 1-formyl-8-methyl-2-phenyl-1,2,2a,3,4,5-hexahydrobenz[cd]indol-5-one (Step 1) Synthesis of 1-formyl-7-methyl-2-phenyl-2,3-dihydroindole-3-propionic acid 7-methyl-2-phenyl-2,3-dihydroindole-3-propionic acid (13.47 g) synthesized as in Example 1, steps 1 and 2 was dissolved in formic acid (50 ml) and to the solution was added acetic anhydride (4.53 ml) under cooling with ice. The mixture was stirred for 3 days at room temperature. After adding water, the reaction mixture was extracted twice with ethyl acetate. The organic layers were combined, washed with water and saturated aqueous solution of sodium chloride successively and dried over anhydrous sodium sulfate. The solvent was distilled off under reduced pressure and the residue was crystallized from an ether/hexane mixed solvent to yield 13.07 g (97%) of the titled compound as pale brown crystals.

(Step 2) Synthesis of 1-formyl-8-methyl-2-phenyl-1,2,2a,3,4,5-hexahydrobenz[cd]indol-5-one A portion (1.0 g) of the compound obtained in step 1 was dissolved in anhydrous methylene chloride (10 ml) and to the solution was added thionyl chloride (0.26 ml) under cooling with ice. The mixture was stirred for 1 hour. Thionyl chloride (0.12 ml) was further added, and the mixture was stirred for additional 30 minutes under cooling with ice. After adding aluminum chloride (1.94 g), the reaction mixture was stirred for 45 minutes at room temperature. The reaction mixture was poured into ice water, followed by addition of methylene chloride. The insoluble matter was filtered through Celite pad. The filtrate was separated, and the organic layer was washed with water and saturated aqueous solution of sodium chloride and dried over anhydrous sodium sulfate. The solvent was distilled off under reduced pressure and the residue was purified by silica gel column chromatography (hexane/ethyl acetate=1:4) to yield 0.45 g (48%) of the titled compound as colorless needles.

Example 4

Synthesis of 1-acetyl-7-chloro-2-phenyl-1,2,2a,3,4,5-hexahydrobenz[cd]indol-5-one (Step 1) Synthesis of ethyl 6-chloro-2-phenyl-2,3-dihydroindole-3-propionate 6-chloro-2-phenylindole-3-propionic acid (19.5 g) synthesized as in Example 1, step 1 was suspended in ethanol (200 ml), and to the suspension were added zinc powder (42.5 g), then conc. hydrochloric acid (50 ml). The mixture was heated to reflux for 3 hours. In the meantime, two portions (50 ml and 20 ml) of conc. hydrochloric acid were further added 1 hour and 2 hours later respectively. After allowing the mixture to cool, the zinc was filtered off and the filtrate was diluted with water, adjusted to about pH 4 with potassium carbonate and extracted three times with ethyl acetate. The organic layers were combined, washed with saturated aqueous solution of sodium chloride and dried over anhydrous sodium sulfate. The solvent was distilled off under reduced pressure and the residue was purified by silica gel column chromatography (hexane/ethyl acetate=9:1) to yield 4.2 g (20%) of the titled compound as a pale yellow syrup.

(Step 2) Synthesis of 6-chloro-2-phenyl-2,3-dihydroindole-3-propionic acid

A portion (4.2 g) of the compound obtained in step 1 was suspended in a mixed solvent of methanol (20 ml) and water (10 ml), and to the suspension was added lithium hydroxide monohydrate (1.07 g). The mixture was heated to reflux for 30 minutes and allowed to cool. The mixture was diluted with water and adjusted to pH 4 with conc. hydrochloric acid and extracted three times with ethyl acetate. The organic layers were combined, washed with saturated aqueous solution of sodium chloride and dried over anhydrous sodium sulfate. The solvent was distilled off under reduced pressure and the residue was crystallized from an ether/hexane mixed solvent to yield 2.55 g (66%) of the titled compound as pale yellow crystals.

(Step 3) Synthesis of 1-acetyl-7-chloro-2-phenyl-1,2,2a,3,4,5-hexahydrobenz[cd]indol-5-one The procedure of Example 3 was repeated using the compound obtained in step 2 to yield the titled compound.

The following compounds were obtained according to the procedure of one of Examples 1 to 4:

Example 5

1-acetyl-2-phenyl-1,2,2a,3,4,5-hexahydrobenz[cd]indol-5-one

Example 6

1-acetyl-6-fluoro-2-phenyl-1,2,2a,3,4,5-hexahydrobenz[cd]indol-5-one

Example 7

1-acetyl-7-fluoro-2-phenyl-1,2,2a,3,4,5-hexahydrobenz[cd]indol-5-one

Example 8

1-formyl-8-fluoro-2-phenyl-1,2,2a,3,4,5-hexahydrobenz[cd]indol-5-one

Example 9
8-bromo-1-formyl-2-phenyl-1,2,2a,3,4,5-hexahydrobenz[cd]indol-5-one

Example 10
1-benzoyl-6-methyl-2-phenyl-1,2,2a,3,4,5-hexahydrobenz[cd]indol-5-one

Example 11
1-benzoyl-7-methyl-2-phenyl-1,2,2a,3,4,5-hexahydrobenz[cd]indol-5-one

Example 12
1-acetyl-2-(4-chlorophenyl)-1,2,2a,3,4,5-hexahydrobenz[cd]indol-5-one

Example 13
1-acetyl-2-(3-chlorophenyl)-1,2,2a,3,4,5-hexahydrobenz[cd]indol-5-one

Example 14
1-acetyl-2-(2-chlorophenyl)-1,2,2a,3,4,5-hexahydrobenz[cd]indol-5-one

Example 15
1-acetyl-2-(4-trifluoromethylphenyl)-1,2,2a,3,4,5-hexahydrobenz[cd]indol-5-one

Example 16
Synthesis of 1-benzoyl-6-bromo-2-phenyl-1,2,2a,3,4,5-hexahydrobenz[cd]indol-5-one A portion (2.0 g) of the compound obtained in Example 1 was dissolved in anhydrous methylene chloride (20 ml) and to the solution was added N-bromosuccinimide (NBS; 1.01 g). The mixture was stirred for 3 days at room temperature. After adding water, the reaction mixture was extracted three times with methylene chloride. The organic layers were combined, washed with saturated aqueous solution of sodium chloride and dried over anhydrous sodium sulfate. The solvent was distilled off under reduced pressure and the residue was purified by silica gel column chromatography (methylene chloride/hexane/ethyl acetate=5:5:1) and further crystallized from an ether/hexane mixed solvent to yield 2.02 g (83%) of the titled compound as pale yellow crystals.

The following compound was synthesized according to the procedure of Example 16.

Example 17
1-acetyl-6-bromo-2-phenyl-1,2,2a,3,4,5-hexahydrobenz[cd]indol-5-one

Example 18
Synthesis of 1-acetyl-6-chloro-2-phenyl-1,2,2a,3,4,5-hexahydrobenz[cd]indol-5-one A portion (2.0 g) of the compound obtained in Example 5 was dissolved in anhydrous methylene chloride (20 ml) and to the solution was added N-chlorosuccinimide (NCS; 1.10 g). The mixture was stirred for 11 days at room temperature. After adding water, the reaction mixture was extracted three times with methylene chloride. The organic layers were combined, washed with saturated aqueous solution of sodium chloride and dried over anhydrous sodium sulfate. The solvent was distilled off under reduced pressure and the residue was purified by silica gel column chromatography (methylene chloride/hexane/ethyl acetate 10:10:1) and further crystallized from an ether/hexane mixed solvent to yield 2.00 g (89%) of the titled compound as pale yellow crystals.

Example 19
Synthesis of 1-acetyl-6-nitro-2-phenyl-1,2,2a,3,4,5-hexahydrobenz[cd]indol-5-one A portion (5.0 g) of the compound obtained in Example 5 was dissolved in sulfolane (10 ml). To the solution was added dropwise a solution of nitronium tetrafluoroborate in sulfolane (0.5 M; 37.8 ml), followed by stirring for 1 hour at room temperature. After further adding a solution of nitronium tetrafluoroborate in sulfolane (0.5 M; 37.8 ml), the mixture was stirred for further 20 hours at room temperature. After adding ethyl acetate, the reaction mixture was washed five times with water and once with saturated aqueous solution of sodium chloride and dried over anhydrous sodium sulfate. The solvent was distilled off under reduced pressure and the residue was purified by silica gel column chromatography (methylene chloride) and further crystallized from an ether/hexane mixed solvent to yield 1.40 g (24%) of the titled compound as yellow crystals.

Example 20
Synthesis of 1-acetyl-6-cyano-2-phenyl-1,2,2a,3,4,5-hexahydrobenz[cd]indol-5-one A portion (4.40 g) of the compound obtained in Example 17 was suspended in dimethylformamide (DMF; 40 ml) and to the suspension was added copper (I) cyanide (4.26 g). The mixture was heated to reflux for 15 minutes. Methylene chloride and an aqueous solution (400 ml) of ethylene diamine (3.18 ml) were added to the reaction mixture and the precipitated insoluble matter was filtered off. The aqueous layer of the filtrate was separted and extracted twice with methylene chloride. The organic layers were combined, washed with saturated aqueous solution of sodium chloride and dried over anhydrous sodium sulfate. The solvent was distilled off under reduced pressure and the residue was crystallized from ether to yield 3.40 g (90%) of the titled compound as pale brown crystals.

The following compound was synthesized according to the procedure of Example 20.

Example 21
1-formyl-8-cyano-2-phenyl-1,2,2a,3,4,5-hexahydrobenz[cd]indol-5-one

Example 22
Synthesis of 2-phenyl-1,2,2a,3,4,5-hexahydrobenz[cd]indol-5-one

A portion (4.25 g) of the compound obtained in Example 1 was dissolved in ethanol (40 ml). To the solution was added conc. hydrochloric acid (40 ml) and the resulting mixture was heated to reflux for 2 hours. After allowing to cool, the mixture was diluted with water, adjusted to pH 9 with potassium carbonate and extracted three times with ethyl acetate. The organic layers were combined, washed with saturated aqueous solution of sodium chloride and dried over anhydrous sodium sulfate. Then, the solvent was distilled off under reduced pressure and the residue was crystallized from an ether/hexane mixed solvent to yield 3.33 g (92%) of the titled compound as crystals.

The following compounds were synthesized according to the procedure of Example 22.

Example 23
6-fluoro-2-phenyl-1,2,2a,3,4,5-hexahydrobenz[cd]indol-5-one

Example 24
7-fluoro-2-phenyl-1,2,2a,3,4,5-hexahydrobenz[cd]indol-5-one

Example 25
8-fluoro-2-phenyl-1,2,2a,3,4,5-hexahydrobenz[cd]indol-5-one

Example 26
6-chloro-2-phenyl-1,2,2a,3,4,5-hexahydrobenz[cd]indol-5-one

Example 27
7-chloro-2-phenyl-1,2,2a,3,4,5-hexahydrobenz[cd]indol-5-one

Example 28
6-bromo-2-phenyl-1,2,2a,3,4,5-hexahydrobenz[cd]indol-5-one

Example 29
8-bromo-2-phenyl-1,2,2a,3,4,5-hexahydrobenz[cd]indol-5-one

Example 30
6-methyl-2-phenyl-1,2,2a,3,4,5-hexahydrobenz[cd]indol-5-one

Example 31
7-methyl-2-phenyl-1,2,2a,3,4,5-hexahydrobenz[cd]indol-5-one

Example 32
8-methyl-2-phenyl-1,2,2a,3,4,5-hexahydrobenz[cd]indol-5-one

Example 33
6-methoxy-2-phenyl-1,2,2a,3,4,5-hexahydrobenz[cd]indol-5-one

Example 34
6-nitro-2-phenyl-1,2,2a,3,4,5-hexahydrobenz[cd]indol-5-one

Example 35
6-cyano-2-phenyl-1,2,2a,3,4,5-hexahydrobenz[cd]indol-5-one

Example 36
8-cyano-2-phenyl-1,2,2a,3,4,5-hexahydrobenz[cd]indol-5-one

Example 37
2-(4-chlorophenyl)-1,2,2a,3,4,5-hexahydrobenz[cd]indol-5-one

Example 38
2-(3-chlorophenyl)-1,2,2a,3,4,5-hexahydrobenz[cd]indol-5-one

Example 39
2-(2-chlorophenyl)-1,2,2a,3,4,5-hexahydrobenz[cd]indol-5-one

Example 40
2-(4-trifluoromethylphenyl)-1,2,2a,3,4,5-hexahydrobenz[cd]indol-5-one

Example 41
Synthesis of 2-phenyl-1,3,4,5-tetrahydrobenz[cd]indol-5-one

A portion (3.3 g) of the compound obtained in Example 22 was dissolved in anhydrous tetrahydrofuran (THF; 400 ml) and to the solution was added o-chloranil (3.6 g). The resulting mixture was stirred for 30 minutes at room temperature. After adding 1N aqueous solution of sodium hydroxide, the reaction mixture was extracted twice with ethyl acetate. The organic layers were combined, washed twice with 1N aqueous solution of sodium hydroxide and once with saturated aqueous solution of sodium chloride and dried over anhydrous sodium sulfate. Then, the solvent was distilled off under reduced pressure and the residue was purified by silica gel column chromatography (methylene chloride) and further crystallized from an ether/hexane mixed solvent to yield 2.3 g (70%) of the titled compound as crystals.

The following compounds were synthesized in the same manner.

Example 42
6-fluoro-2-phenyl-1,3,4,5-tetrahydrobenz[cd]indol-5-one

Example 43
7-fluoro-2-phenyl-1,3,4,5-tetrahydrobenz[cd]indol-5-one

Example 44
8-fluoro-2-phenyl-1,3,4,5-tetrahydrobenz[cd]indol-5-one

Example 45
6-chloro-2-phenyl-1,3,4,5-tetrahydrobenz[cd]indol-5-one

Example 46
7-chloro-2-phenyl-1,3,4,5-tetrahydrobenz[cd]indol-5-one

Example 47
6-bromo-2-phenyl-1,3,4,5-tetrahydrobenz[cd]indol-5-one

Example 48
8-bromo-2-phenyl-1,3,4,5-tetrahydrobenz[cd]indol-5-one

Example 49
6-methyl-2-phenyl-1,3,4,5-tetrahydrobenz[cd]indol-5-one

Example 50
7-methyl-2-phenyl-1,3,4,5-tetrahydrobenz[cd]indol-5-one

Example 51
8-methyl-2-phenyl-1,3,4,5-tetrahydrobenz[cd]indol-5-one

Example 52
6-methoxy-2-phenyl-1,3,4,5-tetrahydrobenz[cd]indol-5-one

Example 53
2-(4-chlorophenyl)-1,3,4,5-tetrahydrobenz[cd]indol-5-one

Example 54
2-(3-chlorophenyl)-1,3,4,5-tetrahexahydrobenz[cd]indol-5-one

Example 55
2-(2-chlorophenyl)-1,3,4,5-tetrahydrobenz[cd]indol-5-one

Example 56
2-(4-trifluoromethylphenyl)-1,3,4,5-tetrahydrobenz[cd]indol-5-one

Example 57
Synthesis of 6-nitro-2-phenyl-1,3,4,5-tetrahydrobenz[cd]indol-5-one A portion (1.05 g) of the compound obtained in Example 34 was dissolved in anhydrous acetonitrile (30 ml) and to the solution was added ammonium cerium (IV) nitrate (3.91 g).

The resulting mixture was stirred for 15 minutes at room temperature. After adding water to the reaction mixture, the precipitated crystals were washed with water, methanol and ether successively to yield 1.0 g (96%) of the titled compound as yellow crystals.

The following compounds were synthesized according to the procedure of Example 57.

Example 58
6-cyano-2-phenyl-1,3,4,5-tetrahydrobenz[cd]indol-5-one

Example 59
8-cyano-2-phenyl-1,3,4,5-tetrahydrobenz[cd]indol-5-one

Example 60
Synthesis of 8-chloro-2-phenyl-1,3,4,5-tetrahydrobenz[cd]indol-5-one
(Step 1) Synthesis of benzoylbutyric acid (5-carboxy-2-chlorophenyl)hydrazone (5-carboxy-2-chlorophenyl)hydrazine hydrochloride (46 g) and benzoylbutyric acid (39.6 g) were suspended in water (500 ml) and the suspension was heated to reflux for 1 hour and allowed to cool. The crystals precipitated were collected by filtration, washed with methanol and ether, and air-dried to yield 62.4 g (84%) of the titled compound as pale brown crystals.
(Step 2) Synthesis of 4-carboxy-7-chloro-2-phenylindole-3-propionic acid A portion (62 g) of the compound obtained in step 1 was suspended in acetic acid (300 ml) and to the suspension was added dropwise a solution of sulfuric acid (23 ml) in acetic acid (50 ml) for 30 minutes under reflux. The mixture was refluxed for additional 1 hour and allowed to cool. Then, the crystals precipitated were collected by filtration, washed with acetic acid and water, dried and washed with hexane to yield 25.6 g (43%) of the titled compound as pale brown crystals.
(Step 3) Synthesis of 8-chloro-2-phenyl-1,3,4,5-tetrahydrobenz[cd]indol-5-one A portion (25.5 g) of the compound obtained in step 2 was suspended in acetic anhydride (300 ml) and to the suspension was added sodium acetate (1.52 g). The mixture was heated to reflux for 8 hours and allowed to cool. Then, the crystals precipitated were collected by filtration and washed with acetic anhydride, water and ethyl acetate successively. The resulting residue was purified by silica gel column chromatography (hexane/methylene chloride=2:1) and further washed with ethyl acetate and ether successively to yield 9.90 g (47%) of the titled compound as yellow crystals.

The following compounds were synthesized according to the procedure of Example 60.

Example 61
8-chloro-2-(4-fluorophenyl)-1,3,4,5-tetrahydrobenz[cd]indol-5-one

Example 62
8-chloro-2-(4-chlorophenyl)-1,3,4,5-tetrahydrobenz[cd]indol-5-one

Example 63
2-(4-bromophenyl)-8-chloro-1,3,4,5-tetrahydrobenz[cd]indol-5-one

Example 64
8-chloro-2-(4-methoxyphenyl)-1,3,4,5-tetrahydrobenz[cd]indol-5-one

Example 65
8-chloro-2-(4-methylphenyl)-1,3,4,5-tetrahydrobenz[cd]indol-5-one

Example 66
8-chloro-2-(4-nitrophenyl)-1,3,4,5-tetrahydrobenz[cd]indol-5-one

Example 67
7-methoxy-2-phenyl-1,3,4,5-tetrahydrobenz[cd]indol-5-one

Example 68
8-methoxy-2-phenyl-1,3,4,5-tetrahydrobenz[cd]indol-5-one

Example 69
Synthesis of 2-phenyl-1,3,4,5-tetrahydrobenz[cd]indol-5-one

A portion (2.4 g) of the compound obtained in Example 60 was dissolved in a solution of potassium hydroxide (3 g) in methanol (150 ml) and to the solution was added 10% palladium-carbon (500 mg). The mixture was stirred for 30 minutes at room temperature under a hydrogen atmosphere. The catalyst was filtered off and the filtrate was concentrated under reduced pressure. The residue was dissolved in ethyl acetate, washed with water and saturated aqueous solution of sodium chloride and dried over anhydrous sodium sulfate. The solvent was distilled off under reduced pressure and the residue was purified by silica gel column chromatography (ethyl acetate/hexane=10:1–2:1) to yield 700 mg (39%) of the titled compound.

The following compounds were synthesized according to the procedure of Example 69.

Example 70
2-(4-fluorophenyl)-1,3,4,5-tetrahydrobenz[cd]indol-5-one

Example 71
2-(4-methoxyphenyl)-1,3,4,5-tetrahydrobenz[cd]indol-5-one

Example 72
2-(4-methylphenyl)-1,3,4,5-tetrahydrobenz[cd]indol-5-one

Example 73
2-(4-aminophenyl)-8-chloro-1,3,4,5-tetrahydrobenz[cd]indol-5-one

Example 74
2-(4-aminophenyl)-1,3,4,5-tetrahydrobenz[cd]indol-5-one

Example 75
Synthesis of 8-hydroxy-2-phenyl-1,3,4,5-tetrahydrobenz[cd]indol-5-one A portion (2.10 g) of the compound obtained in Example 68 was suspended in 1,2-dichloroethane (200 ml) and to the suspension was added aluminum chloride (5.05 g). The mixture was heated to reflux for 30 minutes. The reaction mixture was poured into ice water and the insoluble matter was filtered off. The filtrate was extracted three times with ethyl acetate. The organic layer was washed with water and saturated aqueous solution of sodium chloride and dried over anhydrous sodium sulfate. The solvent was distilled off under reduced pressure and the residue was purified by silica gel column chromatography (methylene chloride/ethyl acetate=9:1–1:1) to yield 1.39 g (70%) of the titled compound as a yellowish brown powder.

Example 76
Synthesis of 8-(methoxycarbonylmethyl)oxy-2-phenyl-1,3,4,5-tetrahydrobenz[cd]indol-5-one A portion (1.09 g) of the compound obtained in Example 75 was dissolved in dimethylsulfoxide (20 ml) and to the solution were added potassium carbonate (1.14 g) and methyl bromoacetate (0.43 ml). The mixture was stirred for 1 hour at room temperature. After adding water, the reaction mixture was extracted three times with ethyl acetate. The organic layer was washed with water and saturated aqueous solution of sodium chloride and dried over anhydrous sodium sulfate. The solvent was distilled off under reduced pressure and the residue was crystallized from ether to yield 1.18 g (85%) of the titled compound as a yellowish brown powder.

Example 77

Synthesis of 8-chloro-2-(4-chlorophenyl)-1-methyl-1,3,4,5-tetrahydrobenz[cd]indol-5-one A portion (300 mg) of the compound obtained in Example 62 was dissolved in anhydrous dimethylformamide (DMF; 10 ml) and to the solution was added sodium hydride (60% dispersion in oil; 39 mg) under cooling with ice. The mixture was stirred for 20 minutes at room temperature. After adding methyl iodide (1.3 g), the reaction mixture was stirred for 1.5 hours at room temperature. Water was added to the reaction mixture, followed by extraction with ether. The organic layer was washed with water and saturated aqueous solution of sodium chloride and dried over anhydrous sodium sulfate. The solvent was distilled off under reduced pressure and the residue was purified by silica gel column chromatography (hexane-ethyl acetate/hexane=1:30) to yield 240 mg (77%) of the titled compound as a yellow powder.

The following compound was synthesized according to the procedure of Example 77.

Example 78

1-methyl-2-phenyl-1,3,4,5-tetrahydrobenz[cd]indol-5-one

Example 79

Synthesis of 1-methoxycarbonylmethyl-2-phenyl-1,3,4,5-tetrahydrobenz[cd]indol-5-one A solution of the compound (1.37 g) obtained in Example 41 in anhydrous dimethylformamide (DMF; 60 ml) was added to a suspension of sodium hydride (60% dispersion in oil; 0.30 g) in DMF(10 ml) at room temperature. After stirring for 15 minutes, a solution of methyl bromoacetate (0.72 ml) in DMF (10 ml) was added to the reaction mixture. The reaction mixture was stirred for 10 minutes at room temperature, followed by addition of water and extraction with three portions of ethyl acetate. The organic layer was washed with water and saturated aqueous solution of sodium chloride and dried over anhydrous sodium sulfate. The solvent was distilled off under reduced pressure and the residue was crystallized from ethyl acetate to yield 1.58 g (90%) of the titled compound as a yellow powder.

Example 80

Synthesis of 2-[4-(N-acetylamino)phenyl]-1,3,4,5-tetrahydrobenz[cd]indol-5-one

A portion (400 mg) of the compound obtained in Example 74 was dissolved in a mixed solvent of methylene chloride (30 ml) and dimethylformamide (DMF; 5 ml) and to the solution were added triethylamine (234 μl) and acetyl chloride (108 μl) under cooling with water. The mixture was stirred for 1 hour at room temperature. Acetyl chloride (11 μl) was further added and the mixture was stirred for additional 1 hour at room temperature. Hexane was added to the reaction mixture. The crystals were collected by filtration, washed with water and ethanol successively and dried to yield 369 mg (80%) of the titled compound as a yellow powder.

Example 81

Synthesis of 5-amino-2-phenyl-1,3,4,5-tetrahydrobenz[cd]indole

A portion (2.3 g) of the compound obtained in Example 41 was dissolved in a mixed solvent of methylene chloride (450 ml) and methanol (450 ml) and to the solution were added ammonium acetate (7.12 g) and sodium cyanoborohydride (0.76 g). The mixture was stirred for 3 days at room temperature. Water was added to the reaction mixture, followed by extraction with ethyl acetate. The organic layer was washed with water and saturated aqueous solution of sodium chloride and dried over anhydrous sodium sulfate. The solvent was distilled off under reduced pressure and the residue was purified by silica gel column chromatography (ethyl acetate–ethyl acetate/methanol=9:1) to yield 1.2 g (52%) of the titled compound as pale brown crystals.

The following compounds were synthesized according to the procedure of Example 81.

Example 82

5-amino-7-fluoro-2-phenyl-1,3,4,5-tetrahydrobenz[cd]indole

Example 83

5-amino-8-fluoro-2-phenyl-1,3,4,5-tetrahydrobenz[cd]indole

Example 84

5-amino-6-chloro-2-phenyl-1,3,4,5-tetrahydrobenz[cd]indole

Example 85

5-amino-7-chloro-2-phenyl-1,3,4,5-tetrahydrobenz[cd]indole

Example 86

5-amino-8-chloro-2-phenyl-1,3,4,5-tetrahydrobenz[cd]indole

Example 87

5-amino-6-bromo-2-phenyl-1,3,4,5-tetrahydrobenz[cd]indole

Example 88

5-amino-8-bromo-2-phenyl-1,3,4,5-tetrahydrobenz[cd]indole

Example 89

5-amino-7-methoxy-2-phenyl-1,3,4,5-tetrahydrobenz[cd]indole

Example 90

5-amino-6-nitro-2-phenyl-1,3,4,5-tetrahydrobenz[cd]indole

Example 91

5-amino-6-cyano-2-phenyl-1,3,4,5-tetrahydrobenz[cd]indole

Example 92

5-amino-8-cyano-2-phenyl-1,3,4,5-tetrahydrobenz[cd]indole

Example 93

5-amino-2-(4-aminophenyl)-1,3,4,5-tetrahydrobenz[cd]indole

Example 94

2-(4-acetylaminophenyl)-5-amino-1,3,4,5-tetrahydrobenz[cd]indole

Example 95
5-amino-2-(4-fluorophenyl)-1,3,4,5-tetrahydrobenz[cd]indole

Example 96
5-amino-2-(4-chlorophenyl)-1,3,4,5-tetrahydrobenz[cd]indole

Example 97
5-amino-2-(3-chlorophenyl)-1,3,4,5-tetrahexahydrobenz[cd]indole

Example 98
5-amino-2-(2-chlorophenyl)-1,3,4,5-tetrahydrobenz[cd]indole

Example 99
5-amino-2-(4-methylphenyl)-1,3,4,5-tetrahydrobenz[cd]indole

Example 100
5-amino-2-(4-methoxyphenyl)-1,3,4,5-tetrahydrobenz[cd]indole

Example 101
5-amino-2-(4-trifluoromethylphenyl)-1,3,4,5-tetrahydrobenz[cd]indole

Example 102
5-amino-2-(4-aminophenyl)-8-chloro-1,3,4,5-tetrahydrobenz[cd]indole

Example 103
5-amino-8-chloro-2-(4-chlorophenyl)-1,3,4,5-tetrahydrobenz[cd]indole

Example 104
5-amino-2-(4-bromophenyl)-8-chloro-1,3,4,5-tetrahydrobenz[cd]indole

Example 105
5-amino-8-chloro-2-(4-nitrophenyl)-1,3,4,5-tetrahydrobenz[cd]indole

Example 106
5-amino-8-chloro-2-(4-chlorophenyl)-1-methyl-1,3,4,5-tetrahydrobenz[cd]indole

Example 107
5-amino-1-methyl-2-phenyl-1,3,4,5-tetrahydrobenz[cd]indole

Example 108
Synthesis of 5-amino-2-phenyl-1,2,2a,3,4,5-hexahydrobenz[cd]indole 5-amino-1-benzoyl-2-phenyl-1,2,2a,3,4,5-hexahydrobenz[cd]indole (350 mg) obtained by aminating the compound (500 mg) obtained in Example 1 according to the procedure of Example 81 was suspended in 10% hydrogen chloride in methanol (10 ml) and to the suspension was added conc. hydrochloric acid (10 ml). The mixture was heated to reflux for 3 hours. After adding water, the reaction mixture was washed with ethyl acetate and the aqueous layer was made basic with sodium carbonate and extracted with ethyl acetate. The organic layer was washed with saturated aqueous solution of sodium chloride and dried over anhydrous sodium sulfate. The solvent was distilled off under reduced pressure and the residue was purified by silica gel column chromatography (methylene chloride/methanol= 99:1–19:1) to yield 200 mg (81%) of the titled compound.

Example 109
Synthesis of 5-amino-6-fluoro-2-phenyl-1,3,4,5-tetrahydrobenz[cd]indole A portion (0.36 g) of the compound obtained in Example 42 was suspended in anhydrous methanol (5 ml) and to the suspension were added pyridine (0.44 ml) and hydroxylamine hydrochloride (0.19 g). The mixture was heated to reflux for 15 minutes and allowed to cool. The reaction mixture was poured into water and extracted twice with ethyl acetate. The organic layers were combined, washed with 1N hydrochloric acid, water and saturated aqueous solution of sodium chloride successively and dried over anhydrous sodium sulfate. The solvent was distilled off under reduced pressure and the resulting residue was dissolved in acetic acid (10 ml) and to the solution was added zinc powder (0.86 g). The mixture was stirred overnight at room temperature. The zinc powder was filtered off. The filtrate was poured into water, made basic with potassium carbonate and extracted twice with ethyl acetate. The organic layers were combined, washed with saturated aqueous solution of sodium hydrogencarbonate, water and saturated aqueous solution of sodium chloride successively and dried over anhydrous sodium sulfate. The solvent was distilled off under reduced pressure and the residue was purified by silica gel column chromatography (methylene chloride-methylene chloride/methanol=20:1) and further crystallized from ether to yield 0.27 g (60%) of the titled compound as yellowish brown crystals.

The following compounds were synthesized according to the procedure of Example 109.

Example 110
5-amino-6-methoxy-2-phenyl-1,3,4,5-tetrahydrobenz[cd]indole

Example 111
5-amino-8-methoxy-2-phenyl-1,3,4,5-tetrahydrobenz[cd]indole

Example 112
5-amino-6-methyl-2-phenyl-1,3,4,5-tetrahydrobenz[cd]indole

Example 113
5-amino-7-methyl-2-phenyl-1,3,4,5-tetrahydrobenz[cd]indole

Example 114
Synthesis of 5-amino-8-methyl-2-phenyl-1,3,4,5-tetrahydrobenz[cd]indole A portion (0.22 g) of the compound obtained in Example 51 was suspended in anhydrous methanol (3 ml) and to the suspension were added pyridine (0.27 ml) and hydroxylamine hydrochloride (0.12 g). The mixture was heated to reflux for 10 minutes. The solvent was distilled off under reduced pressure and to the residue was added methylene chloride. The mixture was washed with 1N hydrochloric acid, water and saturated aqueous solution of sodium chloride successively and dried over anhydrous sodium sulfate. The solvent was distilled off under reduced pressure and the resulting residue was suspended in methanol (5 ml) and to the suspension was added 10% palladium-carbon (0.02 g). The mixture was stirred for 2 days at room temperature under a hydrogen atmosphere. The catalyst was filtered off and the residue obtained by concentrating the filtrate under reduced pressure was crystallized from ether to yield 0.12 g (54%) of the titled compound as pale yellow crystals.

Example 115
Synthesis of 5-amino-1-methoxycarbonylmethyl-2-phenyl-1,3,4,5-tetrahydrobenz[cd]indole A portion (1.53 g) of the compound obtained in Example 79 was aminated according to the procedure of Example 81 to yield 0.82 g (53%) of the titled compound as pale yellow crystals.

Example 116
Synthesis of 5-amino-1-carboxymethyl-2-phenyl-1,3,4,5-tetrahydrobenz[cd]indole A portion (198 mg) of the compound obtained in Example 115 was dissolved in methanol (5 ml) and to the solution was added an aqueous solution (5 ml) of lithium hydroxide monohydrate (52 mg). The mixture was heated to reflux for 10 minutes.

After allowing to cool, the reaction mixture was diluted with water and adjusted to pH 7 with dilute hydrochloric acid. The crystals precipitated were collected by filtration and subjected to azeotropical distillation with ethanol to yield 142 mg (76%) of the titled compound as pale brown crystals.

Example 117
Synthesis of 5-amino-1-(2-hydroxyethyl)-2-phenyl-1,3,4,5-tetrahydrobenz[cd]indole Lithium aluminum hydride (35 mg) was suspended in anhydrous tetrahydrofuran (THF; 1 ml) and to the suspension was added a solution of the compound (197 mg) obtained in Example 115 in anhydrous THF (7 ml) at room temperature. The mixture was stirred for 5 minutes. To the reaction mixture were slowly added water, then 1N aqueous solution of sodium hydroxide, followed by extraction with two portions of ethyl acetate. The organic layer was washed with water and saturated aqueous solution of sodium chloride successively and dried over anhydrous sodium sulfate. The solvent was distilled off under reduced pressure and the residue was crystallized from ether to yield 149 mg (83%) of the titled compound as pale yellow crystals.

Example 118
Synthesis of 5-amino-8-(methoxycarbonylmethyl)oxy-2-phenyl-1,3,4,5-tetrahydrobenz[cd]indole A portion (1.00 g) of the compound obtained in Example 76 was aminated according to the procedure of Example 81 to yield 0.51 g (51%) of the titled compound as yellow crystals.

Example 119
Synthesis of 5-amino-8-(carboxymethyl)oxy-2-phenyl-1,3,4,5-tetrahydrobenz[cd]indole A portion (153 mg) of the compound obtained in Example 118 was hydrolyzed according to the procedure of Example 116 to yield 136 mg (93%) of the titled compound as yellow crystals.

Example 120
Synthesis of 5-amino-8-(2-hydroxyethyl)oxy-2-phenyl-1,3,4,5-tetrahydrobenz[cd]indole A portion (160 mg) of the compound obtained in Example 118 was reduced according to the procedure of Example 117 to yield 132 mg (90%) of the titled compound as yellow crystals.

Example 121
Synthesis of 5-(N,N-dimethylamino)2-phenyl-1,3,4,5-tetrahydrobenz[cd]indole A portion (400 mg) of the compound obtained in Example 81 was dissolved in acetonitrile (15 ml) and to the solution were added formalin (37% aqueous solution; 0.66 ml), acetic acid (0.5 ml) and sodium cyanoborohydride (155 mg). The mixture was stirred for 10 minutes at room temperature. To the reaction mixture was added 1N aqueous solution of sodium hydroxide, followed by extraction with ethyl acetate. The organic layer was washed with saturated aqueous solution of sodium chloride and dried over anhydrous sodium sulfate. Then, the solvent was distilled off under reduced pressure and the residue was purified by silica gel column chromatography (methylene chloride/methanol=49:1) to yield 50 mg (11%) of the titled compound as yellowish brown crystals.

Example 122
Synthesis of 5-[N-(2-hydroxyethyl)amino]-2-phenyl-1,3,4,5-tetrahydrobenz[cd]indole A portion (0.20 g) of the compound obtained in Example 41 and 2-aminoethanol (0.49 ml) were suspended in a mixed solvent of methanol (3 ml) and methylene chloride (2 ml) and to the suspension was added sodium cyanoborohydride (61 mg). The mixture was stirred for 13 hours at room temperature and heated to reflux for further 8 hours. The reaction mixture was concentrated under reduced pressure. Water was added to the residue, followed by extraction with three portions of methylene chloride. The organic layers were combined, washed with saturated aqueous solution of sodium chloride and dried over anhydrous sodium sulfate. Then, the solvent was distilled off under reduced pressure and the residue was purified by silica gel column chromatography (methylene chloride/methanol=19:1) and further crystallized from ether to yield 75 mg (32%) of the titled compound as yellowish brown crystals.

Example 123
Synthesis of 5-[N-(2-aminoethyl)amino]-2-phenyl-1,3,4,5-tetrahydrobenz[cd]indole dihydrochloride A portion (0.20 g) of the compound obtained in Example 41 and ethylenediamine (0.54 ml) were suspended in a mixed solvent of methanol (3 ml) and methylene chloride (3 ml) and to the suspension was added sodium cyanoborohydride (61 mg). The mixture was stirred for 13 hours at room temperature and heated to reflux for further 20 hours. The reaction mixture was concentrated under reduced pressure. Water was added to the residue, followed by extraction with three portions of methylene chloride. The organic layers were combined, washed with saturated aqueous solution of sodium chloride and dried over anhydrous sodium sulfate. Then, the solvent was distilled off under reduced pressure and the residue was purified by silica gel column chromatography (methylene chloride/methanol=19:1–9:1–4:1). The resulting brown foam was dissolved in a solution (3 ml) of 10% hydrochloric acid in methanol and the solution was concentrated. The concentrate was crystallized from ether to yield 93 mg (32%) of the titled compound as brown crystals.

Example 124
Synthesis of 5-(N-acetylamino)-2-phenyl-1,3,4,5-tetrahydrobenz[cd]indole A portion (70 mg) of the compound obtained in Example 81 was dissolved in anhydrous methylene chloride (10 ml) and to the solution were added pyridine (22 mg) and acetic anhydride (29 mg). The mixture was stirred for 20 minutes at room temperature. To the reaction mixture was added water, followed by extraction with methylene chloride. The organic layer was washed with water and saturated aqueous solution of sodium chloride and dried over anhydrous sodium sulfate. Then, the solvent was distilled off under reduced pressure and the residue was purified by silica gel column chromatography (ethyl acetate/hexane=1:2–1:1–2:1) to yield 50 mg (61%) of the titled compound as a pale brown powder.

Example 125
Synthesis of 5-(N-benzoylamino)-2-phenyl-1,3,4,5-tetrahydrobenz[cd]indole A portion (70 mg) of the compound obtained in Example 81 was dissolved in anhydrous methylene chloride (15 ml) and to the solution were added triethylamine (69 μl) and benzoyl chloride (29 μl). The mixture was stirred for 1 hour at room temperature. To the reaction mixture was added water, followed by extraction with methylene chloride. The organic layer was washed with 1N aqueous solution of sodium hydroxide, water and saturated aqueous solution of sodium chloride and dried over anhydrous sodium sulfate. Then, the solvent was distilled off under reduced pressure to yield 90 mg (91%) of the titled compound.

Example 126
Synthesis of 5-[N-(N-t-butoxycarbonylglycyl)amino]-2-phenyl-1,3,4,5-tetrahydrobenz[cd]indole A portion (200 mg) of the compound obtained in Example 81 and N-t-butoxycarbonylglycine (170 mg) were suspended in methylene chloride (15 ml) and to the suspension was added dichlorohexylcarbodiimide (216 mg) under cooling with ice. The mixture was stirred for 1 hour at room temperature. To the reaction mixture was added water, followed by extraction with ethyl acetate. The organic layer was washed with water and saturated aqueous solution of sodium chloride and dried over anhydrous sodium sulfate. Then, the solvent was distilled off under reduced pressure to yield the titled compound (470 mg) as a crude yellow solid. The compound was used in the subsequent reaction without further purification.

Example 127
Synthesis of 5-(N-glycylamino)-2-phenyl-1,3,4,5-tetrahydrobenz[cd]indole A portion (470 mg) of the crude compound obtained in Example 126 was suspended in methylene chloride (4 ml) and to the suspension was added trifluoroacetic acid (4 ml). The mixture was stirred for 1 hour at room temperature. The reaction mixture was made basic with saturated aqueous solution of sodium hydrogencarbonate and extracted with ethyl acetate. The organic layer was washed with water and saturated aqueous solution of sodium chloride and dried over anhydrous sodium sulfate. Then, the solvent was distilled off under reduced pressure. The residue was purified by silica gel column chromatography (ethyl acetate-ethyl acetate/methanol=9:1) to yield 100 mg (41%) of the titled compound.

Example 128
Synthesis of 5-[N-(2-nitrobenzoyl)amino]-2-phenyl-1,3,4,5-tetrahydrobenz[cd]indole A portion (200 mg) of the compound obtained in Example 81 was suspended in methylene chloride (10 ml) and to the suspension were added 2-nitrobenzoyl chloride (0.18 ml) and triethylamine (0.11 ml) under cooling with ice. The mixture was stirred for 30 minutes at room temperature. n-Hexane was added to the reaction mixture, and the crystals were collected by filtration and washed with water and n-hexane successively to yield 260 mg (81%) of the titled compound as brown crystals.

Example 129
Synthesis of 5-[N-(2-aminobenzoyl)amino]-2-phenyl-1,3,4,5-tetrahydrobenz[cd]indole A portion (250 mg) of the compound obtained in Example 128 was suspended in methanol (50 ml) and to the suspension was added 10% palladium-carbon (25 mg). The mixture was stirred for 3.5 hours at room temperature under a hydrogen atmosphere. Ethyl acetate was added to the reaction mixture, the catalyst was filtered off and the filtrate was concentrated under reduced pressure. The residue was crystallized from ether to yield 134 mg (58%) of the titled compound.

Example 130
Synthesis of 5-(N-methylamino)-2-phenyl-1,3,4,5-tetrahydrobenz[cd]indole A portion (100 mg) of the compound obtained in Example 81 was suspended in tetrahydrofuran (THF; 3 ml) and to the suspension was added a solution (1M; 0.5 ml) of an acid anhydride prepared from acetic anhydride and formic acid in THF at −20° C. The mixture was stirred for 20 minutes. The solid obtained by concentrating the reaction mixture was suspended in THF (3 ml) and to the suspension was added a solution of borane-methyl sulfide complex in THF (10M; 100 μl). The mixture was heated to reflux for 1 hour and allowed to cool. 3N solution (10 ml) of hydrochloric acid in methanol was added to the reaction mixture, followed by stirring for 1 hour at room temperature. The reaction mixture was made basic with 3N aqueous solution of sodium hydroxide and extracted with ethyl acetate. The organic layer was washed with saturated aqueous solution of sodium chloride and dried over anhydrous sodium sulfate. Then, the solvent was distilled off under reduced pressure to yield 90 mg (85%) of the titled compound.

Example 131
Synthesis of 1-ethyl-2-phenyl-1,2,2a,3,4,5-hexahydrobenz[cd]indol-5-one (Step 1) Synthesis of 4-carboxy-2-phenylindole-3-propionic acid 5-carboxy-7-chloro-2-(4-chlorophenyl)indole-3-propionic acid (4.0 g) synthesized by the procedure of Example 60, steps 1 and 2 was dissolved in 2N aqueous solution of sodium hydroxide (30 ml) and to the solution was added 10% palladium-carbon (0.4 g). The mixture was stirred for 5 days at room temperature under a hydrogen atmosphere. The catalyst was filtered off. The filtrate was acidified with hydrochloric acid and extracted twice with ethyl acetate. The organic layers were combined, washed with saturated aqueous solution of sodium chloride and dried over anhydrous sodium sulfate. The solvent was distilled off under reduced pressure and the residue was washed with an ether/hexane mixed solvent to yield 3.05 g (93%) of the titled compound.

(Step 2) Synthesis of 4-carboxy-1-ethyl-2-phenyl-2,3-dihyroindole-3-propionic acid A portion (2.69 g) of the compound obtained in step 1 was suspended in acetic acid (100 ml) and to the suspension was added in 6 portions sodium cyanoborohydride (16.4 g) at 10-minute intervals under cooling with water. At the end of addition, the mixture was stirred for 30 minutes. Water was added to the mixture, followed by extraction with ethyl acetate. The organic layer was washed with water and saturated aqueous solution of sodium chloride and dried over anhydrous sodium sulfate. The solvent was distilled off under reduced pressure and the residue was crystallized from ether to yield 1.56 g (53%) of the titled compound as pale yellow crystals.

(Step 3) Synthesis of 1-ethyl-2-phenyl-1,2,2a,3,4,5-hexahydrobenz[cd] indol-5-one The procedure of Example 60, step 3 was repeated using the compound (0.68 g) obtained in step 2 to yield 0.36 g (81%) of the titled compound.

Example 132
Synthesis of 1-benzoyl-5-bromo-2-phenyl-1,2,2a,3,4,5-hexahydrobenz[cd]indole A portion (5 g) of the compound obtained in Example 1 was dissolved in a mixed solvent of methylene chloride (40 ml) and methanol (40 ml) and to the solution was added sodium borohydride (540 mg) at room temperature. The mixture was stirred for 1 hour at room temperature. Water was added to the reaction mixture, followed by extraction with ethyl acetate. The organic layer was washed with saturated aqueous solution of sodium chloride and dried over anhydrous sodium sulfate. Then, the solvent was distilled off under reduced pressure and the residue (2 g) was dissolved in a mixed solvent of toluene (16 ml) and methylene chloride (16 ml). After adding phosphorus tribromide (0.2 ml) under cooling with ice, the mixture was stirred for 1 hour at room temperature. Water was added to the reaction mixture, followed by extraction with ethyl acetate.

The organic layer was washed with saturated aqueous solution of sodium chloride and dried over anhydrous sodium sulfate. The solvent was distilled off under reduced pressure to yield the titled compound (2.3 g) as a crude yellow solid. The compound was used in the subsequent reaction without further purification.

The following compound was synthesized according to the procedure of Example 132.

Example 133
5-bromo-1-ethyl-2-phenyl-1,2,2a,3,4,5-hexahydrobenz[cd]indole

Example 134
Synthesis of 1-benzoyl-5-morpholino-2-phenyl-1,2,2a,3,4,5-hexahydrobenz[cd]indole A portion (600 mg) of the compound obtained in Example 132 was dissolved in anhydrous methylene chloride (10 ml) and to the solution was added morpholine (0.25 ml). The mixture was stirred overnight at room temperature. Water was added to the reaction mixture, followed by extraction with ethyl acetate. The organic layer was washed with saturated aqueous solution of sodium chloride and dried over anhydrous sodium sulfate. The solvent was distilled off under reduced pressure. The residue was purified by silica gel column chromatography (ethyl acetate/hexane= 1:19–1:3) to yield 560 mg (92%) of the titled compound.

The following compounds were synthesized according to the procedure of Example 134.

Example 135
1-benzoyl-5-(N-phenylamino)-2-phenyl-1,2,2a,3,4,5-hexahydrobenz[cd]indole Example 136
1-benzoyl-5-(N-benzylamino)-2-phenyl-1,2,2a,3,4,5-hexahydrobenz[cd]indole Example 137
1-benzoyl-2-phenyl-5-piperidino-1,2,2a,3,4,5-hexahydrobenz[cd]indole Example 138
5-(4-acetylpiperadinyl)-1-benzoyl-2-phenyl-1,2,2a,3,4,5-hexahydrobenz[cd]indole Example 139
1-acetyl-5-[N-(ethoxycarbonylmethyl)amino]-2-phenyl-1,2,2a,3,4,5-hexahydrobenz[cd]indole Example 140
1-ethyl-5-morpholino-2-phenyl-1,2,2a,3,4,5-hexahydrobenz[cd]indole Example 141
Synthesis of 5-morpholino-2-phenyl-1,2,2a,3,4,5-hexahydrobenz[cd]indole A portion (0.56 g) of the compound obtained in Example 134 was dissolved in a solution (15 ml) of 10% hydrochloric acid in methanol and to the solution was added 6N hyrdochloric acid (15 ml). The mixture was heated to reflux for 3 hours and allowed to cool. The reaction mixture was diluted with water, adjusted to pH 9 with potassium carbonate and extracted three times with ethyl acetate. The organic layers were combined, washed with saturated aqueous solution of sodium chloride and dried over anhydrous sodium sulfate. The solvent was distilled off under reduced pressure and the residue was crystallized from an ether/hexane mixed solvent to yield 0.38 g (90%) of the titled compound.

The following compounds were synthesized according to the procedure of Example 141.

Example 142
2-phenyl-5-(N-phenylamino)-1,2,2a,3,4,5-hexahydrobenz[cd]indole

Example 143
5-(N-benzylamino)-2-phenyl-1,2,2a,3,4,5-hexahydrobenz[cd]indole

Example 144
2-phenyl-5-piperidino-1,2,2a,3,4,5-hexahydrobenz[cd]indole

Example 145
2-phenyl-5-piperadinyl-1,2,2a,3,4,5-hexahydrobenz[cd]indole

Example 146
5-[N-(methoxycarbonylmethyl)amino]-2-phenyl-1,2,2a,3,4,5-hexahydrobenz[cd]indole A portion (0.70 g) of the compound obtained in Example 139 was dissolved in methanol (15 ml) and to the solution was added 6N hyrdochloric acid (15 ml). The mixture was heated to reflux for 1 hour and allowed to cool. The reaction mixture was diluted with water, adjusted to pH 9 with sodium carbonate and extracted three times with ethyl acetate. The organic layers were combined, washed with saturated aqueous solution of sodium chloride and dried over anhydrous sodium sulfate. Then, the solvent was distilled off under reduced pressure and the residue was purified by silica gel column chromatography (ethyl acetate/hexane= 1:9–1:4) to yield 0.38 g (64%) of the titled compound.

Example 147
Synthesis of 5-(N,N-dipropylamino)-2-phenyl-1,2,2a,3,4,5-hexahydrobenz[cd]indole The crude 1-benzoyl-5-(N,N-dipropylamino)-2-phenyl-1,2,2a,3,4,5-hexahydrobenz[cd]indole obtained by aminating the compound (0.50 g) obtained in Example 132 according to the procedure of Example 134 was hydrolyzed by the procedure of Example 141 to yield 0.32 g (80%) of the titled compound.

Example 148
Synthesis of 5-morpholino-2-phenyl-1,3,4,5-tetrahydrobenz[cd]indole The procedure of Example 41 was repeated using the compound (157 mg) obtained in Example 141 to yield 106 mg (68%) of the titled compound.

The following compounds were synthesized according to the procedure of Example 148.

Example 149
2-phenyl-5-(N-phenylamino)-1,3,4,5-tetrahydrobenz[cd]indole

Example 150
5-(N,N-dipropylamino)-2-phenyl-1,3,4,5-tetrahydrobenz[cd]indole

Example 151
2-phenyl-5-piperidino-1,3,4,5-tetrahydrobenz[cd]indole

Example 152
2-phenyl-5-piperadinyl-1,3,4,5-tetrahydrobenz[cd]indole

Example 153
Synthesis of 5-(N-benzylamino)-2-phenyl-1,3,4,5-tetrahydrobenz[cd]indole A portion (180 mg) of the compound obtained in Example 143 was dissolved in methylene chloride (10 ml) and to the solution was added active manganese dioxide (400 mg). The mixture was stirred for 15 minutes at room temperature. The manganese dioxide was filtered off and the filtrate was concentrated under reduced pressure. The residue was purified by silica gel column chromatography (acetone/hexane=1:4) to yield 60 mg (34%) of the titled compound.

The following compound was synthesized according to the procedure of Example 153.

Example 154
1-ethyl-5-morpholino-2-phenyl-1,3,4,5-tetrahydrobenz[cd]indole

Example 155
5-[N-(methoxycarbonylmethyl)amino]-2-phenyl-1,3,4,5-tetrahydrobenz[cd]indole A portion (360 mg) of the compound obtained in Example 146 was dissolved in chloroform (60 ml) and to the solution was added active manganese dioxide (1.44 g). The mixture was heated to reflux for 2 hours. The manganese dioxide was filtered off and the filtrate was washed with a methylene chloride/methanol mixed solvent and concentrated under reduced pressure. The residue was purified by silica gel column chromatography (hexane/ethyl acetate=6:1) to yield 190 mg (53%) of the titled compound.

Example 156
5-[N-(carboxymethyl)amino]-2-phenyl-1,3,4,5-tetrahydrobenz[cd]indole A portion (120 mg) of the compound obtained in Example 155 was hydrolyzed according to the procedure of Example 116 to yield 80 mg (70%) of the titled compound as pale yellow crystals.

Example 157
Synthesis of 5-(4-methoxalylpiperadinyl)-2-phenyl-1,3,4,5-tetrahydrobenz[cd]indole A portion (0.60 g) of the compound obtained in Example 152 was dissolved in anhydrous methylene chloride (100 ml) and to the solution were added triethylamine (0.26 ml) and methyl oxalyl chloride (0.17 ml). The mixture was stirred for 30 minutes at room temperature. Water was added to the reaction mixture, followed by extraction with ethyl acetate. The organic layer was washed with saturated aqueous solution of sodium chloride and dried over anhydrous sodium sulfate. The solvent was distilled off under reduced pressure and the residue was purified by silica gel column chromatography (ethyl acetate/hexane=1:1) to yield 0.50 g (66%) of the titled compound.

Example 158
Synthesis of 5-(4-oxalopiperadinyl)-2-phenyl-1,3,4,5-tetrahydrobenz[cd]indole A portion (0.17 g) of the compound obtained in Example 157 was dissolved in ethanol/water (4:1) (80 ml) and to the solution was added potassium butoxide (t-BuOK; 48 mg). The mixture was heated to reflux for 30 minutes. The reaction mixture was adjusted to pH 5 by addition of 1N hydrochloric acid. Thereafter, the solvent was distilled off under reduced pressure. The residue was crystallized from ethanol and water to yield 0.12 g (73%) of the titled compound.

Example 159
Synthesis of 5-(4-hydroxyacetylpiperadinyl)-2-phenyl-1,3,4,5-tetrahydrobenz[cd]indole To a suspension of the compound (100 mg) obtained in Example 157 in anhydrous tetrahydrofuran (THF; 20 ml) was added lithium borohydride (5.5 mg) under cooling with ice. The mixture was stirred for 5 minutes. After adding another lithium borohydride (5.5 mg), the mixture was stirred for further 5 minutes. Water was added to the reaction mixture, followed by extraction with methylene chloride. The organic layer was washed with saturated aqueous solution of sodium chloride and dried over anhydrous sodium sulfate. The solvent was distilled off under reduced pressure and the residue was purified by silica gel column chromatography (ethyl acetate/methylene chloride=1:1) to yield 45 mg (48%) of the titled compound.

Example 160
Synthesis of 1-methyl-5-morpholino-2-phenyl-1,3,4,5-tetrahydrobenz[cd]indole The procedure of Example 77 was repeated using the compound (42 mg) obtained in Example 148 to yield 9.8 mg (23%) of the titled compound as white crystals.

Example 161
Synthesis of 1-acetyl-5-bromo-2-phenyl-1,2,2a,3,4,5-hexahydrobenz[cd]indole The procedure of Example 132 was repeated using the compound (5.00 g) obtained in Example 5 to yield 5.69 g (94%) of the titled compound as orange crystals.

Example 162
Synthesis of 1-acetyl-2-phenyl-1,2,2a,3-tetrahydrobenz[cd]indole A portion (5.60 g) of the compound obtained in Example 161 was dissolved in dimethylimidazolidone (DMI; 100 ml) and to the solution was added potassium hydroxide powder (1.46 g). The mixture was heated for 1 hour at 110° C. and allowed to cool. The reaction mixture was diluted with water and extracted three times with ethyl acetate. The organic layers were combined, washed with water and saturated aqueous solution of sodium chloride successively and dried over anhydrous sodium sulfate. Then, the solvent was distilled off under reduced pressure and the residue was crystallized from ether to yield 3.70 g (86%) of the titled compound as white crystals.

Example 163
Synthesis of 1-acetyl-4.5-ethoxy-2-phenyl-1,2,2a,3,4,5-hexahydrobenz[cd]indole A portion (3.70 g) of the compound obtained in Example 162 was dissolved in methylene chloride (400 ml) and to the solution was added m-chloroperbenzoic acid (6.96 g). The mixture was stirred for 1.5 hours at room temperature. The reaction mixture was diluted with water, stirred with sodium sulfite (5 g) for 30 minutes at room temperature and extracted three times with methylene chloride. The organic layers were combined, washed with saturated aqueous solution of sodium hydrogencarbonate and saturated aqueous solution of sodium chloride successively and dried over anhydrous sodium sulfate. Then, the solvent was distilled off under reduced pressure. The residue was crystallized from ether to yield 3.32 g (85%) of the titled compound as white crystals.

Example 164
Synthesis of 1-acetyl-2-phenyl-1,2,2a,3,4,5-hexahydrobenz[cd]indol-4-one To a solution of magnesium bromide in ether (1400 ml) prepared from magnesium (7.00 g) and bromine (6.60 ml) was added a solution of the compound (3.32 g) obtained in Example 163 in benzene (80 ml) and the mixture was stirred for 19 hours at room temperature. The reaction mixture was concentrated under reduced pressure. Thereafter, the residue was suspended in toluene (500 ml) and the suspension was heated to reflux for 1.5 hours and allowed to cool. The reaction mixture was diluted with water and extracted twice with ethyl acetate. The organic layers were combined, washed with saturated aqueous solution of sodium chloride and dried over anhydrous sodium sulfate. Then, the solvent was distilled off under reduced pressure. The residue was crystallized from ether to yield 2.50 g (74%) of the titled compound as pale brown crystals.

Example 165
Synthesis of 2-phenyl-1,2,2a,3,4,5-hexahydrobenz[cd]indol-4-one

The procedure of Example 22 was repeated using the compound (2.47 g) obtained in Example 164 to yield 1.41 g (67%) of the titled compound as white crystals.

Example 166
Synthesis of 4-amino-2-phenyl-1,2,2a,3,4,5-hexahydrobenz[cd]indole The procedure of Example 81 was repeated using the compound (1.23 g) obtained in Example 165 to yield 0.85 g (69%) of the titled compound as red crystals.

Example 167
Synthesis of 4-amino-2-phenyl-1,3,4,5-tetrahydrobenz[cd]indole

A portion (0.83 g) of the compound obtained in Example 166 was dissolved in methylene chloride (80 ml) and to the solution was added active manganese dioxide (1.66 g). The mixture was heated to reflux for 28 hours. The manganese dioxide was filtered off and the filtrate was concentrated under reduced pressure. The residue was purified by silica gel column chromatography (methylene chloride/methanol=7:1) to yield 240 mg (29%) of the titled compound.

Example 168
Synthesis of 5-amino-8-chloro-2-(4-cyano-phenyl)-1,3,4,5-tetrahydrobenz[cd]indole A portion (2.66 g) of the compound obtained in Example 104 was dissolved in anhydrous dimethylformamide (DMF; 27 ml) and to the solution were added potassium cyanide (718 mg), palladium acetate (248 mg) and triphenylphosphine (580 mg). The mixture was stirred for 2.5 hours at 80° C. and allowed to cool. Water was added to the reaction mixture, followed by extraction with five portions of ethyl acetate. The organic layers were combined, washed three times with water and dried over anhydrous sodium sulfate. The solvent was distilled off under reduced pressure and the residue was purified by silica gel column chromatography (methylene chloride/methanol=19:1–9:1) to yield 2.20 g (82%) of the titled compound as a brown solid.

Example 169
Synthesis of 5-amino-2-(4-carbamoylphenyl)-8-chloro-1,3,4,5-tetrahydrobenz[cd]indole A portion (1.0 g) of the compound obtained in Example 168 was dissolved in acetic acid (30 ml) and to the solution was added 50% sulfuric acid (60 ml). The mixture was stirred for 2 hours at 120° C. and allowed to cool. The reaction mixture was neutralized with 6N aqueous solution of sodium hydroxide and the insoluble matter was filtered off. The filtrate was extracted three times with ethyl acetate, washed with saturated aqueous solution of sodium chloride and dried over anhydrous sodium sulfate. The solvent was distilled off under reduced pressure and the residue was crystallized from ether to yield 170 mg (17%) of the titled compound.

Example 170
Synthesis of 5-amino-2-(4-carboxyphenyl)-8-chloro-1,3,4 5-tetrahydrobenz[cd]indole hydrochloride A portion (0.93 g) of the compound obtained in Example 168 was dissolved in acetic acid (25 ml) and to the solution was added 50% sulfuric acid (50 ml). The mixture was heated to reflux for 7 hours and allowed to cool. The reaction mixture was neutralized with 6N aqueous solution of sodium hydroxide and the crystals precipitated were filtered off. The crystals were suspended in methanol, and the insoluble matter was filtered off after addition of a solution of 10% hydrochloric acid in methanol. The filtrate was distilled off under reduced pressure. The residue was crystallized from ether to yield 195 mg (18%) of the titled compound.

Example 171
Synthesis of 5-amino-8-chloro-2-(4-methoxycarbonylphenyl)-1,3,4,5-tetrahydrobenz[cd]indole A portion (460 mg) of the crude compound obtained in Example 170 was dissolved in anhydrous methanol (20 ml) and to the solution was added conc. sulfuric acid (1 ml). The mixture was heated to reflux for 1.5 hours and allowed to cool. After addition of water, the reaction mixture was neutralized with 1N aqueous solution of sodium hydroxide and extracted twice with ethyl acetate. The organic layers were combined, washed with saturated aqueous solution of sodium chloride and dried over anhydrous sodium sulfate. The solvent was distilled off under reduced pressure and the residue was purified by silica gel column chromatography (methylene chloride/methanol=10:1) and further crystallized from ether to yield 170 mg (26%) of the titled compound as a brown solid.

Example 172
Synthesis of 5-amino-8-chloro-2-(4-hydroxymethylphenyl)-1,3,4,5-tetrahydrobenz[cd]indole A portion (170 mg) of the compound obtained in Example 171 was dissolved in anhydrous tetrahydrofuran (10 ml) and to the solution was added lithium aluminum hydride (76 mg). The mixture was stirred for 1 hour at room temperature. To the reaction mixture were added water-containing ether, then water and ethyl acetate, under cooling with ice. The insoluble matter was filtered off, followed by phase separation of the filtrate. The aqueous layer was extracted three times with ethyl acetate. The organic layers were combined, washed with water and saturated aqueous solution of sodium chloride and dried over anhydrous sodium sulfate. The solvent was distilled off under reduced pressure and the residue was purified by silica gel column chromatography (methylene chloride/methanol=2:1) to yield 109 mg (70%) of the titled compound as brown crystals.

Example 173
Synthesis of 5-amino-2-(4-hydroxyphenyl)-1,3,4,5-tetrahydrobenz[cd]indole A portion (120 mg) of the compound obtained in Example 100 was dissolved in anhydrous toluene (50 ml) and to the solution was added aluminum chloride (1.15 g). The mixture was stirred overnight at room temperature. The reaction mixture was poured into water, neutralized with saturated aqueous solution of sodium hydrogencarbonate. The insoluble matter was filtered off, and the filtrate was extracted with three portions of ethyl acetate. The organic layers were washed with saturated aqueous solution of sodium chloride and dried over anhydrous sodium sulfate. The solvent was distilled off under reduced pressure and the crystals produced were washed with ethyl acetate to yield 90 mg (79%) of the titled compound.

Example 174
Synthesis of 5-amino-6-hydroxy-2-phenyl-1,3,4,5-tetrahydrobenz[cd]indole A portion (106 mg) of the compound obtained in Example 110 was dissolved in anhydrous methylene chloride (20 ml) and to the solution was added aluminum chloride (1.02 g). The mixture was heated to reflux for 38 hours. The reaction mixture was poured into ice water, neutralized with saturated aqueous solution of sodium hydrogencarbonate. The insoluble matter was filtered off, followed by phase separation of the filtrate. The organic layer was washed with water and saturated aqueous solution of sodium chloride and dried over anhydrous sodium sulfate. The solvent was distilled off under reduced pressure and the residue was crystallized from an ether/hexane mixed solvent to yield 48 mg (47%) of the titled compound as brown crystals.

Examples 175 and 176
Syntheses of (+)-5-amino-2-phenyl-1,3,4,5-tetrahydrobenz[cd]indole (Example 175) and (−)-5-amino-2-phenyl-1,3,4,5-tetrahydrobenz[cd]indole (Example 176)

A portion (100 mg) of the compound obtained in Example 81 was separated by high-performance liquid chromatography (Daicel Chemical Industries, Ltd., chiral cell OD; 20 mm×250 mm; eluent: ethanol/hexane=1:19) to yield (+)-5-amino-2-phenyl-1,3,4,5-tetrahydrobenz[cd]indole (36 mg) as the component for the retention time of 30 minutes and (−)-5-amino-2-phenyl-1,3,4,5-tetrahydrobenz[cd] indole (22 mg) as the component for the retention time of 37 minutes, respectively.

(+)-5-amino-2-phenyl-1,3,4,5-tetrahydrobenz[cd]indole (Example 175)
Specific rotation: $[\alpha]_D$ +125= (25° C., c0.1, methanol)
(−)-5-amino-2-phenyl-1,3,4,5-tetrahydrobenz[cd]indole (Example 176)
Specific rotation: $[\alpha]_D$=125° (25° C., c0.1, methanol)

Examples 177
Preparation of 5-amino-2-phenyl-1,3,4,5-tetrahydrobenz [cd]indole hydrochloride A portion (1.0 g) of the compound obtained in Example 81 was suspended in ethanol (10 ml) and to the suspension was added a solution (2.5 ml) of 20% hydrochloric acid in ethanol. The mixture was stirred for 10 minutes at room temperature. The reaction mixture was concentrated under reduced pressure. The crystals obtained were washed with ether and ether/methanol to yield 0.87 g (76%) of the titled compound as pale brown crystals.

The following hydrochlorides were prepared according to the procedure of Example 177.

Example 178
5-amino-1-methyl-2-phenyl-1,3,4,5-tetrahydrobenz[cd] indole hydrochloride

Example 179
5-amino-8-chloro-2-(4-chlorophenyl)-1,3,4,5-tetrahydrobenz[cd]indole hydrochloride

Example 180
5-amino-8-chloro-2-(4-chlorophenyl)-1-methyl-1,3,4,5-tetrahydrobenz[cd]indole hydrochloride

Example 181
5-(N,N-dimethylamino)-2-phenyl-1,3,4,5-tetrahydrobenz [cd]indole hydrochloride

Example 182
Synthesis of 8-chloro-2-(2-methoxyphenyl)-1,3,4,5-tetrahydrobenz[cd]indol-5-one The procedure of Example 60, steps 1 to 3 was repeated using (5-carboxy-2-chlorophenyl)hydrazine hydrochloride (24.1 g) and (2-methoxybenzoyl)butyric acid (16 g) to yield 2.45 g (12%) of the titled compound as a yellow powder.

Example 183
Synthesis of 5-amino-8-chloro-2-(2-methoxyphenyl)-1,3,4,5-tetrahydrobenz[cd]indole A portion (2.34 g) of the compound obtained in Example 182 was aminated according to the procedure of Example 81 to yield 1.67 g (71%) of the titled compound as pale brown crystals.

Example 184
Synthesis of 5-amino-2-(2-methoxyphenyl)-1,3,4,5-tetrahydrobenz[cd]indole A portion (1.45 g) of the compound obtained in Example 183 was dissolved in methanol (50 ml) and 1N hydrochloric acid (50 ml) and to the solution was added 10% palladium-carbon (1.45 g). The mixture was stirred overnight at room temperature under a hydrogen atmosphere. The reaction mixture was neutralized with potassium carbonate, the catalyst and the inorganic salt were filtered off and washed with methylene chloride. The filtrate and the washed liquid were combined, washed with saturated aqueous solution of sodium chloride and dried over anhydrous sodium sulfate. Then, the solvent was distilled off under reduced pressure. The residue was crystallized from ether to yield 0.93 g (72%) of the titled compound as a pale yellow powder.

Example 185
Synthesis of 5-amino-2-(2-hydroxyphenyl)-1,3,4,5-tetrahydrobenz[cd]indole A portion (200 mg) of the compound obtained in Example 184 was demethylated according to the procedure of Example 174 to yield 60 mg (32%) of the titled compound as a brown powder.

Example 186
Synthesis of 1-acetyl-2-(2-fluorophenyl)-1,2,2a,3,4,5-hexahydrobenz[cd]indol-5-one The procedure of Example 1, steps 1 and 2 was repeated using phenylhydrazine hydrochloride (17.9 g) and (2-fluorobenzoyl)butyric acid (15.1 g) to synthesize 2-(2-fluorophenyl)-2,3-dihydroindole-3-propionic acid, which was reacted according the procedures of Example 2, step 1 and Example 3, step 2 to yield 4.8 g (total yield: 22%) of the titled compound as white crystals.

Example 187
Synthesis of 1-acetyl-5-bromo-2-phenyl-1,2,2a,3,4,5-hexahydrobenz[cd]indole The procedure of Example 132 was repeated using the compound (20.0 g) obtained in Example 5 to yield 21.7 g (89%) of the titled compound.

The following compounds were synthesized in the same manner.

Example 188
1-acetyl-5-bromo-2-(2-chlorophenyl)-1,2,2a,3,4,5-hexahydrobenz[cd]indole

Example 189
1-acetyl-5-bromo-2-(2-fluorophenyl)-1,2,2a,3,4,5-hexahydrobenz[cd]indole

Example 190
Synthesis of 1-acetyl-2-phenyl-5-pyrrolidino-1,2,2a,3,4,5-hexahydrobenz[cd]indole The compound (500 mg) obtained in Example 187 and pyrrolidine (0.24 ml) were subjected to amination according to the procedure of Example 134 to yield 370 mg (76%) of the titled compound as a white powder.

The following compounds were synthesized in the same manner.

Example 191
1-acetyl-2-(2-chlorophenyl)-5-morpholino-1,2,2a,3,4,5-hexahydrobenz[cd]indole

Example 192
1-acetyl-2-(2-fluorophenyl)-5-morpholino-1,2,2a,3,4,5-hexahydrobenz[cd]indole

Example 193
1-acetyl-5-(4-hydroxypiperidino-2-phenyl-1,2,2a,3,4,5-hexahydrobenz[cd]indole

Example 194
1-acetyl-5-(4-ethoxycarbonylpiperidino)-2-phenyl-1,2,2a,3,4,5-hexahydrobenz[cd]indole

Example 195
1-acetyl-2-(2-chlorophenyl)-5-[N,N-bis(2-hydroxyethyl)]amino-1,2,2a,3,4,5-hexahydrobenz[cd]indole

Example 196
1-acetyl-2-(2-fluorophenyl)-5-[N,N-bis(2-hydroxyethyl)]amino-1,2,2a,3,4,5-hexahydrobenz[cd]indole

Example 197
1-acetyl-5-[N-(ethoxycarbonylmethyl)-N-methyl]amino-2-phenyl-1,2,2a,3,4,5-hexahydrobenz[cd]indole

Example 198
1-acetyl-2-(2-fluorophenyl)-5-[N-(methoxycarbonylmethyl)]amino-1,2,2a,3,4,5-hexahydrobenz[cd]indole

Example 199
Synthesis of 2-phenyl-5-pyrrolidino-1,2,2a,3,4,5-hexahydrobenz[cd]indole A portion (350 mg) of the compound obtained in Example 190 was hydrolyzed according to the procedure of Example 141 to yield 250 mg (81%) of the titled compound as pale brown crystals.

The following compounds were synthesized in the same manner.

Example 200
2-(2-chlorophenyl)-5-morpholino-1,2,2a,3,4,5-hexahydrobenz[cd]indole

Example 201
2-(2-fluorophenyl)-5-morpholino-1,2,2a,3,4,5-hexahydrobenz[cd]indole

Example 202
5-(4-hydroxypiperidino)-2-phenyl-1,2,2a,3,4,5-hexahydrobenz[cd]indole

Example 203
2-(2-chlorophenyl)-5-[N,N-bis(2-hydroxyethyl)]amino-1,2,2a,3,4,5-hexahydrobenz[cd]indole

Example 204
2-(2-fluorophenyl)-5-[N,N-bis(2-hydroxyethyl)]amino-1,2,2a,3,4,5-hexahydrobenz[cd]indole

Example 205
2-(2-fluorophenyl)-5-[N-(methoxycarbonylmethyl)]amino-1,2,2a,3,4,5-hexahydrobenz[cd]indole

Example 206
Synthesis of 5-[N-(ethoxycarbonylmethyl)]-amino-2-phenyl-1,2,2a,3,4,5-hexahydrobenz[cd]indole A portion (4.47 g) of the compound obtained in Example 139 was dissolved in ethanol (100 ml) and to the solution was added 6N hydrochloric acid (100 ml). The mixture was heated to reflux for 1 hour and allowed to cool. The reaction mixture was diluted with water, neutralized with potassium carbonate and extracted three times with ethyl acetate. The organic layers were combined, washed with saturated aqueous solution of sodium chloride and dried over anhydrous sodium sulfate. The solvent was distilled off under reduced pressure to yield 2.54 g (57%) of the titled compound as a brown rubber-like product.

The following compounds were synthesized in the same manner.

Example 207
5-(4-ethoxycarbonylpiperidino)-2-phenyl-1,2,2a,3,4,5-hexahydrobenz[cd]indole

Example 208
5-[N-(ethoxycarbonylmethyl)-N-methyl]amino-2-phenyl-1,2,2a,3,4,5-hexahydrobenz[cd]indole

Example 209
Synthesis of 2-(2-chlorophenyl)-5-morpholino-1,3,4,5-tetrahydrobenz[cd]indole A portion (740 mg) of the compound obtained in Example 200 was dehydrogenated by the procedure of Example 41 to yield 360 mg (49%) of the titled compound as pale yellow crystals.

The following compounds were synthesized in the same manner.

Example 210
2-(2-fluorophenyl)-5-morpholino-1,3,4,5-tetrahydrobenz[cd]indole

Example 211
5-(4-ethoxycarbonylpiperidino)-2-phenyl-1,3,4,5-tetrahydrobenz[cd]indole

Example 212
2-(2-chlorophenyl)-5-[N,N-bis(2-hydroxyethyl)]amino-1,3,4,5-tetrahydrobenz[cd]indole

Example 213
2-(2-fluorophenyl)-5-[N,N-bis(2-hydroxyethyl)]amino-1,3,4,5-tetrahydrobenz[cd]indole

Example 214
5-[N-(ethoxycarbonylmethyl)-N-methyl]amino-2-phenyl-1,3,4,5-tetrahydrobenz[cd]indole

Example 215
Synthesis of 2-phenyl-5-pyrrolidino-1,3,4,5-tetrahydrobenz[cd]indole A portion (230 mg, of the compound obtained in Example 199 was dehydrogenated by the procedure of Example 155 to yield 100 mg (44%) of the titled compound as a pale brown powder.

The following compounds were synthesized in the same manner.

Example 216
5-(4-hydroxypiperidino)-2-phenyl-1,3,4,5-tetrahydrobenz[cd]indole

Example 217
5-[N-(ethoxycarbonylmethyl)]amino-2-phenyl-1,3,4,5-tetrahydrobenz[cd]indole

Example 218
2-(2-fluorophenyl)-5-[N-(methoxycarbonylmethyl)]amino-1,3,4,5-tetrahydrobenz[cd]indole

Example 219
Synthesis of 5-[N-(carbamoylmethyl)]amino-2-phenyl-1,3,4,5-tetrahydrobenz[cd]indole hydrochloride A portion (200 mg) of the compound obtained in Example 217 was dissolved in a solution of ammonia in ethanol (2.0 M; 1.5 ml) and the solution was stirred overnight at room temperature. The solvent was distilled off under reduced pressure and the residue was purified by silica gel column chromatography (ethyl acetate/hexane=1:4). The conversion of the resulting compound (110 mg) to the hydrochloride according to the procedure of Example 177 provided 100 mg (49%) of the titled compound as a pale green powder.

Example 220
Synthesis of 2-(2-chlorophenyl)-1-methyl-5-morpholino-1,3,4,5-tetrahydrobenz[cd]indole A portion (160 mg) of the compound obtained in Example 209 was methylated according to the procedure of Example 77 to yield 140 mg (84%) of the titled compound as an oil.

The following compounds were synthesized in the same manner.

Example 221
2-(2-fluorophenyl)-1-methyl-5-morpholino-1,3,4,5-tetrahydrobenz[cd]indole

Example 222
5-[N-(ethoxycarbonylmethyl)]amino-1-methyl-2-phenyl-1,3,4,5-tetrahydrobenz[cd]indole

Example 223
Synthesis of 5-[N-(carboxymethyl)]amino-1-methyl-2-phenyl-1,3,4,5-tetrahydrobenz[cd]indole hydrochloride A portion (160 mg) of the compound obtained in Example 222 was hydrolyzed according to the procedure of Example 116, followed by conversion to the hydrochloride according to the procedure of Example 177 to yield 110 mg (67%) of the titled compound as a colorless powder.

Example 224
Synthesis of 5-(4-carboxypiperidino)-2-phenyl-1,3,4,5-tetrahydrobenz[cd]indole A portion (100 mg) of the compound obtained in Example 211 was hydrolyzed by the procedure of Example 116 to yield 62 mg (67%) of the titled compound as a pale brown powder.

Example 225
Synthesis of 5-(4-methoxycarbonylpiperidino)-2-phenyl-1,3,4,5-tetrahydrobenz[cd]indole hydrochloride A portion (70 mg) of the compound obtained in Example 224 was dissolved in a solution of 10% hydrochloric acid in methanol. The solution was heated to reflux for 1 hour and allowed to cool. The solvent was distilled off under reduced pressure and the residue was crystallized from ether to yield 50 mg (69%) of the titled compound.

Examples 226 and 227
Syntheses of (+)-5-morpholino-2-phenyl-1,3,4,5-tetrahydrobenz[cd]indole (Example 226) and (−)-5-morpholino-2-phenyl-1,3,4,5-tetrahydrobenz[cd]indole (Example 227)

A portion (200 mg) of the compound obtained in Example 148 was separated by high-performance liquid chromatography (Daicel Chemical Industries, Ltd., chiral cell OD; 20 mm×250 mm; eluent: isopropanol/hexane=1:4) to yield (+)-5-morpholino-2-phenyl-1,3,4,5-tetrahydrobenz[cd]indole (75 mg) as the component for the retention time of 11.5 minutes and (−)-5-morpholino-2-phenyl-1,3,4,5-tetrahydrobenz[cd]indole (62 mg) as the component for the retention time of 14.5 minutes, respectively.

(+)-5-morpholino-2-phenyl-1,3,4,5-tetrahydrobenz[cd]indole (Example 226)

Specific rotation: $[\alpha]_D$ +36° (27° C., c1.0, chloroform)

(−)-5-morpholino-2-phenyl-1,3,4,5-tetrahydrobenz[cd]indole (Example 227)

Specific rotation: $[\alpha]_D$ −37° (27° C., c1.0, chloroform)

Examples 228 and 229
Syntheses of (+)-2-(2-fluorophenyl)-5-morpholino-1,3,4,5-tetrahydrobenz[cd]indole (Example 228) and (−)-2-(2-fluorophenyl)-5-morpholino-1,3,4,5-tetrahydrobenz[cd]indole (Example 229)

A portion (200 mg) of the compound obtained in Example 210 was separated by high-performance liquid chromatography (Daicel Chemical Industries, Ltd., chiral cell OD; 20 mm×250 mm; eluent: isopropanol/hexane=1:9) to yield (+)-

2-(2-fluorophenyl)-5-morpholino-1,3,4,5-tetrahydrobenz[cd]indole (60 mg) as the component for the retention time of 13.5 minutes and (−)-2-(2-fluorophenyl)-5-morpholino-1,3,4,5-tetrahydrobenz[cd]indole (50 mg) as the component for the retention time of 19 minutes, respectively.

(+)-2-(2-fluorophenyl)-5-morpholino-1,3,4,5-tetrahydrobenz[cd]indole (Example 228)

Specific rotation: $[\alpha]_D$ +34° (24° C., c1.0, chloroform)

(−)-2-(2-fluorophenyl)-5-morpholino-1,3,4,5-tetrahydrobenz[cd]indole (Example 229)

Specific rotation: $[\alpha]_D$ −34° (25° C., c1.0, chloroform)

Example 230

Synthesis of (+)-1-methyl-5-morpholino-2-phenyl-1,3,4,5-tetrahydrobenz[cd]indole A portion (55 mg) of the compound obtained in Example 226 was dissolved in anhydrous tetrahydrofuran (2 ml) and to the solution was added sodium hexamethyldisilazide (1.0 M tetrahydrofuran solution; 0.52 ml) under cooling with ice. After stirring for 30 minutes, methyl iodide (32.3 μl) was added to the mixture, followed by stirring for 15 minutes. After adding further sodium hexamethyldisilazide (1.0 M tetrahydrofuran solution; 0.35 ml), the mixture was stirred for 30 minutes. Then, methyl iodide (21.5 μl) was added and the mixture was stirred for additional 15 minutes. Water was added to the reaction mixture, followed by extraction with two portions of ethyl acetate. The organic layers were combined, washed with water and saturated aqueous solution of sodium chloride and dried over anhydrous sodium sulfate. The solvent was distilled off under reduced pressure and the residue was purified by preparative TLC (ethyl acetate/hexane=1:2) to yield 35 mg (61%) of the titled compound as a pale yellow solid. Specific rotation: $[\alpha]_D$ +21° (25° C., c0.75, chloroform)

The following compound was synthesized according to the procedure of Example 230.

Example 231

(−)-1-methyl-5-morpholino-2-phenyl-1,3,4,5-tetrahydrobenz[cd]indole

Specific rotation: $[\alpha]_D$ −20° (26° C., c0.75, chloroform)

Example 232

Preparation of 2-(2-fluorophenyl)-5-morpholino-1,3,4,5-tetrahydrobenz[cd]indole hydrochloride The procedure of Example 177 was repeated using the compound (200 mg) obtained in Example 210 to yield 182 mg (82%) of the titled compound.

Example 233

Preparation of 2-(2-fluorophenyl)-5-morpholino-1,3,4,5-tetrahydrobenz[cd]indole oxalate A portion (200 mg) of the compound obtained in Example 210 was dissolved in methanol (5 ml) and to the solution was added oxalic acid (54 mg). The mixture was stirred for 10 minutes at room temperature. The solvent was distilled off under reduced pressure and the crystals precipitated were washed with ether to yield 231 mg (91%) of the titled compound.

Example 234

Synthesis of 5-amino-8-methoxy-2-phenyl-1,3,4,5-tetrahydrobenz[cd]indole hydrochloride The procedure of Example 177 was repeated using the compound (39 mg) obtained in Example 111 to yield 23 mg (52%) of the titled compound.

The following hydrochlorides were prepared in the same manner.

Example 235

5-amino-2-(2-hydroxyphenyl)-1,3,4,5-tetrahydrobenz[cd]indole hydrochloride

Example 236

5-morpholino-2-phenyl-1,3,4,5-tetrahydrobenz[cd]indole hydrochloride

Example 237

1-methyl-5-morpholino-2-phenyl-1,3,4,5-tetrahydrobenz[cd]indole hydrochloride

Example 238

2-(2-chlorophenyl)-5-morpholino-1,3,4,5-tetrahydrobenz[cd]indole hydrochloride

Example 239

2-(2-chlorophenyl)-1-methyl-5-morpholino-1,3,4,5-tetrahydrobenz[cd]indole hydrochloride Example 240

2-(2-fluorophenyl)-1-methyl-5-morpholino-1,3,4,5-tetrahydrobenz[cd]indole hydrochloride Example 241

2-(2-chlorophenyl)-5-[N,N-bis(2-hydroxyethyl)]amino-1,3,4,5-tetrahydrobenz[cd]indole hydrochloride Example 242

2-(2-fluorophenyl)-5-[N,N-bis(2-hydroxyethyl)]amino-1,3,4,5-tetrahydrobenz[cd]indole hydrochloride Example 243

2-(2-fluorophenyl)-5-[N-(methoxycarbonylmethyl)]amino-1,3,4,5-tetrahydrobenz[cd]indole hydrochloride Example 244

5-[N-(ethoxycarbonylmethyl)]amino-1-methyl-2-phenyl-1,3,4,5-tetrahydrobenz[cd]indole hydrochloride Example 245

5-[N-(ethoxycarbonylmethyl)]amino-2-phenyl-1,3,4,5-tetrahydrobenz[cd]indole hydrochloride Example 246

5-[N-(ethoxycarbonylmethyl)-N-methyl]amino-2-phenyl-1,3,4,5-tetrahydrobenz[cd]indole hydrochloride Example 247

(+)-2-(2-fluorophenyl)-5-morpholino-1,3,4,5-tetrahydrobenz[cd]indole hydrochloride Specific rotation: $[\alpha]_D$ +206° (26° C., c1.0, methanol)

Example 248

(−)-2-(2-fluorophenyl)-5-morpholino-1,3,4,5-tetrahydrobenz[cd]indole hydrochloride Specific rotation: $[\alpha]_D$ −208° (26° C., c1.0, methanol)

Example 249

Synthesis of 1-acetyl-2-(2-fluorophenyl)-1,2,2a,3-tetrahydrobenz[cd]indole

The procedure of Example 162 was repeated using the compound (1.00 g) obtained in Example 189 to yield 0.42 g (54%) of the titled compound as yellow crystals.

Example 250

Synthesis of 1-acetyl-4,5-epoxy-2-(2-fluorophenyl)-1,2,2a,3,4,5-hexahydrobenz[cd]indole The procedure of Example 163 was repeated using the compound (0.70 g) obtained in Example 249 to yield 0.61 g (83%) of the titled compound as pale yellow crystals.

Example 251
Synthesis of 1-acetyl-2-(2-fluorophenyl)-1,2,2a,3,4,5-hexahydrobenz[cd]indol-4-one A portion (0.53 g) of the compound obtained in Example 250 was dissolved in anhydrous toluene (100 ml) and to the solution was added magnesium bromide etherate (5.54 g). The mixture was heated to reflux for 4 hours and allowed to cool. The reaction mixture was diluted with water and extracted twice with ethyl acetate. The organic layers were combined, washed with saturated aqueous solution of sodium chloride and dried over anhydrous sodium sulfate. Then, the solvent was distilled off under reduced pressure to yield 0.55 g of the titled compound as a crude yellow solid. The compound was used in the subsequent reaction without further purification.

Example 252
Synthesis of 2-(2-fluorophenyl)-1,2,2a,3,4,5-hexahydrobenz[cd]indol-4-one The procedure of Example 22 was repeated using the compound (0.55 g) obtained in Example 251 to yield 0.34 g (74%) of the titled compound as pale brown crystals.

Example 253
Synthesis of 2-(2-fluorophenyl)-4-morpholino-1,2,2a,3,4,5-hexahydrobenz[cd]indole (Step 1) Synthesis of 2-(2-fluorophenyl)-4-morpholino-1,2,2a,3-tetrahydrobenz[cd]indole Morpholine (0.51 ml) was dissolved in an anhydrous chloroform (5 ml) and to the solution was added dropwise a solution of titanium tetrachloride (98 µl) in anhydrous chloroform (2 ml) under cooling with ice, followed by addition of the compound (0.34 g) obtained in Example 252. The mixture was heated to reflux for 30 minutes and allowed to cool. The reaction mixture was diluted with saturated aqueous solution of sodium hydrogencarbonate and extracted twice with methylene chloride. The organic layers were combined, washed twice with water and once with saturated aqueous solution of sodium chloride successively and dried over anhydrous sodium sulfate. Then, the solvent was distilled off under reduced pressure to yield 0.42 g of the titled compound as a crude brown oil. The compound was used in the subsequent reaction without further purification.

(Step 2) Synthesis of 2-(2-fluorophenyl)-4-morpholino-1,2,2a,3,4,5-hexahydrobenz[cd]indole A portion (0.42 g) of the compound obtained in step 1 was dissolved in ethyl acetate (5 ml) and to the solution was added platinum (IV) oxide (0.05 g). The mixture was stirred overnight at room temperature under a hydrogen atmosphere. The reaction mixture was diluted with ethyl acetate and the catalyst was filtered off. The filtrate was concentrated under reduced pressure. The residue was purified by silica gel column chromatography (ethyl acetate/hexane=1:1) to yield 0.15 g (35%) of the titled compound.

Example 254
Synthesis of 2-(2-fluorophenyl)-4-morpholino-1,3,4,5-tetrahydrobenz[cd]indole The procedure of Example 41 was repeated using the compound (0.15 g) obtained in Example 253 to yield 64 mg (43%) of the titled compound.

Example 255
Preparation of 2-(2-fluorophenyl)-4-morpholino-1,3,4,5-tetrahydrobenz[cd]indole hydrochloride The procedure of Example 225 was repeated using the compound (64 mg) obtained in Example 254 to yield 64 mg (90%) of the titled compound.

Example 256
Synthesis of 5-hydroxy-2-phenyl-1,3,4,5-tetrahydrobenz[cd]indole The procedure of Example 132 was repeated using the compound (0.50 g) obtained in Example 41 to yield 0.48 g (95%) of the titled compound.

Example 257
Synthesis of 5-morpholino-2-phenyl-1,3,4,5-tetrahydrobenz[cd]indole A portion (0.47 g) of the compound obtained in Example 256 was suspended in anhydrous methylene chloride (15 ml) and to the suspension was added dropwise a solution of thionyl chloride (0.15 ml) in anhydrous methylene chloride (5 ml) under cooling with ice. After stirring for 30 minutes, a solution (10 ml) of morpholine (1.65 ml) in anhydrous methylene chloride was added dropwise and the mixture was stirred for 3 hours. Water was added to the reaction mixture, followed by extraction with methylene chloride. The organic layer was washed with water and saturated aqueous solution of sodium chloride and dried over anhydrous sodium sulfate. The solvent was distilled off under reduced pressure. The residue was washed with diethyl ether and methanol to yield 0.38 g (63%) of the titled compound as pale yellow crystals.

Physical data of the compounds of Examples 1 to 257 were shown in Table 6.

In the Table, Ex. No. 1-1 refers to Example 1, step 1.

TABLE 6

| Example No. | IR (cm$^{-1}$) | NMR (ppm) (non-mark: 300 MHz, 20° C.; *: 270 MHz, 20° C.; **: 270 MHz, 80° C.) | mp (° C.) |
|---|---|---|---|
| 1-1 | KBr: 3431, 1707, 1458, 1306, 1209, 746 | CDCl$_3$*: 8.05(1H, s), 7.64(1H, d, J=7.9Hz), 7.56–7.46(4H, m), 7.41–7.37(2H, m), 7.23–7.12(2H, m), 3.26(2H, t, J=8.3Hz), 2.74(2H, t, J=8.1Hz) | 155.5–157.8 |
| 1-2 | KBr: 3373, 1697, 1485, 1228, 750, 702 | CDCl$_3$: 7.37–7.24(5H, m), 7.10(1H, dd, J=7.5, 7.5Hz), 7.08(1H, d, J=7.5Hz), 6.76(1H, dd, J=7.5, 7.3Hz), 6.67(1H, d, J=7.7Hz), 4.51 (1H, d, J=6.8Hz), 3.28(1H, dt, J=6.5, 6.5Hz), 2.48–2.42(2H, m), 2.16–2.08(2H, m) | 119.2–120.5 |
| 1-3 | KBr: 1730, 1632, 1477, 1398, 766 | DMSO-d$_6$**: 7.50–7.16(11H, m), 7.09–7.03(1H, m), 6.96–6.93(2H, m), 5.18(1H, d, J=2.0Hz), 3.10–3.00 (1H, m), 2.37(2H, t, J=7.8Hz), 2.13–1.89(2H, m) | 194.4–198.0 |
| 1-4 | KBr: 1674, 1637, 1464, 1377, 1331 | DMSO-d$_6$**: 7.53–7.17(12H, m), 6.99(1H, d, J=7.9Hz), 5.31(1H, d, J=9.6Hz), 3.62–3.49(1H, m), 2.64–2.57(2H, m), 2.23–2.08(2H, m) | 183.8–185.5 |
| 2-1 | KBr: 1728, 1651, 1614, 1591, 1489, 1402, 1277 | CDCl$_3$*: 8.3–8.2(1H, m), 7.35–7.2 (3H, m), 7.2–7.0(2H, m), 6.9–6.8 (1H, m), 6.7–6.65(1H, m), 5.0–4.95 (1H, m), 3.78(3H, s), 3.2–3.05(1H, m), 2.6–2.4(2H, m), 2.2–1.95(5H, m) | Oil |
| 2-2 | KBr: 1682, 1647, 1477, 1454, 1383, 1329, 1273 | CDCl$_3$: 8.4–8.3(1H, m), 7.47–7.35 (5H, m), 6.85(1H, d, J=9.0Hz), 4.97 (1H, d, J=8.6Hz), 3.94(3H, s), 3.45–3.35(1H, m), 2.76(1H, ddd, J=18.0, 4.4, 2.0Hz), 2.46(1H, ddd, J=18.0, 13.6, 5.4Hz), 2.34–2.25(1H, m), 2.13–1.97(1H, m), 1.79(3H, s) | 195.6–198.0 |
| 3-1 | KBr: 1728, 1664, 1628, 1608, 1591, 1352 | CDCl$_3$*: 9.07(0.8H, brs), 8.96 (0.2H, brs), 7.3–6.95(8H, m), 5.83 (0.2H, d, J=8.9Hz), 5.49(0.8H, s), 3.85–3.7(0.2H, m), 3.18(0.8H, t, J=6.8Hz), 2.55–2.4(4H, m), 2.35–2.25(0.8H, m), 2.2–1.9(2H, m), 1.55–1.4(0.2H, m) | — |

TABLE 6-continued

| Example No. | IR (cm⁻¹) | NMR (ppm) (non-mark: 300 MHz, 20° C.; *: 270 MHz, 20° C.; **: 270 MHz, 80° C.) | mp (° C.) |
|---|---|---|---|
| 3-2 | KBr: 1666, 1612, 1591, 1421, 1313, 714 | DMSO-d₆**: 8.80(1H, brs), 7.5–7.3 (6H, m), 7.24(1H, d, J=7.9Hz), 5.10 (1H, d, J=9.6Hz), 3.54–3.44(1H, m), 2.60–2.55(2H, m), 2.52(3H, s), 2.24–2.15(1H, m), 2.09–1.93(1H, m) | 174.0–175.2 |
| 4-1 | Neat: 1728, 1606, 1483, 1452, 1182, 702 | CDCl₃: 7.36–7.27(5H, m), 6.97(1H, d, J=7.9Hz), 6.70(1H, dd, J=7.9, 1.8Hz), 6.62(1H, d, J=1.8Hz), 4.53 (1H, dd, J=6.3, 1.9Hz), 4.24–4.17 (1H, br), 4.08(2H, q, J=7.2Hz), 3.24–3.18(1H, m), 2.42–2.36(2H, m), 2.12–2.04(2H, m), 1.21(3H, t, J=7.2Hz) | Oil |
| 4-2 | KBr: 3365, 1699, 1606, 1485, 706 | CDCl₃: 7.39–7.27(5H, m), 6.96(1H, d, J=7.7Hz), 6.70(1H, dd, J=7.8, 1.9Hz), 6.63(1H, d, J=1.8Hz), 4.53 (1H, d, J=6.2Hz), 3.26–3.20(1H, m), 2.47–2.37(2H, m), 2.13–2.05(2H, m) | 109.2–113.5 |
| 4-3 | KBr: 1697, 1662, 1454, 1381, 1346, 1308 | CDCl₃: 8.40–8.28(1H, m), 7.55(1H, d, J=1.8Hz), 7.49–7.37(5H, m), 5.03 (1H, d, J=9.0Hz), 3.47–3.38(1H, m), 2.83–2.75(1H, m), 2.53–2.33(2H, m), 2.14–2.00(1H, m), 1.81(3H, s) | 141.4–147.9 |
| 5 | KBr: 1684, 1660, 1462, 1379, 1327 | CDCl₃: 8.39–8.26(1H, m), 7.59(1H, d, J=7.6Hz), 7.48–7.35(6H, m), 5.02 (1H, d, J=9.0Hz), 3.51–3.43(1H, m), 2.82–2.74(1H, m), 2.54–2.34(2H, m), 2.21–2.03(1H, m), 1.83(3H, s) | 189.5–192.0 |
| 6 | KBr: 1680, 1668, 1473, 1456, 1381, 1329, 837 | CDCl₃*: 8.4–8.2(1H, m), 7.5–7.3 (5H, m), 7.02(1H, ddd, J=10.9, 8.9, 1.0Hz), 5.03(1H, d, J=8.9Hz), 3.44 (1H, ddd, J=12.5, 8.6, 4.4Hz), 2.79 (1H, ddd, J=17.9, 4.2, 2.2Hz), 2.47 (1H, ddd, J=18.0, 13.4, 4.8Hz), 2.40–2.27(1H, m), 2.2–2.0(1H, m), 1.80(3H, s) | 202.6–203.5 |
| 7 | KBr: 1699, 1662, 1601, 1470, 1385, 1365, 1319, 706 | CDCl₃*: 8.2–8.0(1H, m), 7.50–7.36 (5H, m), 7.23(1H, dd, J=8.6, 2.3Hz), 3.50–3.40(1H, m), 2.79(1H, ddd, J=17.8, 4.0, 2.3Hz), 2.46(1H, ddd, J=17.8, 13.5, 5.0HZ), 2.43–2.32 (1H, m), 2.20–1.98(1H, m) | 170.8–172.0 |
| 8 | KBr: 1674, 1620, 1462, 1346, 1329, 1259, 1207, 698 | CDCl₃: 9.22(1H, brs), 7.59(1H, dd, J=8.6, 4.3Hz), 7.50–7.30(5H, m), 7.19(1H, ddd, J=33.4, 8.6, 0.9Hz), 5.12(1H, d, J=9.5Hz), 3.6–3.4(1H, m), 2.80(1H, ddd, J=17.7, 4.0, 2.2Hz), 2.49(1H, ddd, J=17.6, 13.5, 4.9Hz), 2.45–2.35(1H, m), 2.17–2.00(1H, m) | 164.5–165.9 |
| 9 | KBr: 1684, 1668, 1578, 1396, 1290, 1117 | CDCl₃: 10.01(1H, s), 7.57(1H, dd, J=8.3, 1.0Hz), 7.45–7.31(6H, m), 5.14(1H, d, J=9.4Hz), 3.49–3.39 (1H, m), 2.85–2.76(1H, m), 2.55–2.37(2H, m), 2.16–2.02(1H, m) | 178.3–181.7 |
| 10 | KBr: 1676, 1649, 1633, 1473, 1383, 1329, 702 | DMSO-d₆**: 7.5–7.1(10H, m), 7.00 (1H, d, J=7.9Hz), 6.93(1H, d, J=8.2Hz), 5.26(1H, d, J=9.6Hz), 3.55–3.45(1H, m), 2.60–2.50(2H, m), 2.50(3H, s), 2.15–2.00(2H, m) | 153.7–155.6 |
| 11 | KBr: 1676, 1647, 1606, 1365, 1342, 700 | DMSO-d₆**: 7.47–7.13(11H, m), 6.88(1H, s), 5.9(1H, d, J=9.6Hz), 3.49(1H, ddd, J=10.7, 10.7, 5.2Hz), 2.59–2.50(2H, m), 2.22(3H, s), 2.20–1.98(2H, m) | 171.2–172.4 |
| 12 | KBr: 1686, 1591, 1464, 1383, 1321 | CDCl₃*: 8.4–8.2(1H, m), 7.59(1H, d, J=7.6Hz), 7.47–7.34(5H, m), 5.00 (1H, d, J=8.9Hz), 3.48–3.36(1H, m), 2.85–2.74(1H, m), 2.48(1H, ddd, J=17.9, 13.4, 4.7Hz), 2.43–2.31(1H, m), 2.18–2.00(1H, m) | 92.7–102.8 |
| 13 | KBr: 3367, 3167, 1689, 1456, 1161 | CDCl₃*: 8.4–8.2(1H, m), 7.59(1H, dd, J=7.9, 0.7Hz), 7.44–7.30(5H, m), 5.00(1H, d, J=8.9Hz), 3.44(1H, ddd, J=12.5, 8.7, 4.1Hz), 2.79(1H, ddd, J=17.8, 4.1, 2.1Hz), 2.49(1H, ddd, J=18.2, 13.1, 4.5Hz), 2.44–2.29 (1H, m), 2.20–2.02(1H, m), 1.89 (3H, brs) | 180.1–183.1 |
| 14 | KBr: 2945, 1695, 1655, 1458, 1383 | CDCl₃*: 8.40–8.28(0.7H, m), 7.92–7.88(0.3H, m), 7.61–6.77(6H, m), 6.10(0.3H, d, J=9.6Hz), 5.75(0.7H, d, J=8.6Hz), 4.15–4.05(0.3H, m), 3.52–3.42(0.7H, m), 2.85–2.06(4H, m), 1.82(3H, brs) | 157.9–161.5 |
| 15 | KBr: 1686, 1587, 1458, 1381, 1321 | CDCl₃: 8.41–8.23(1H, m), 8.02(2H, d, J=8.6Hz), 7.61(1H, d, J=7.7Hz), 7.50(2H, d, J=8.3Hz), 7.40(1H, dd, J=7.9, 7.9Hz), 5.09(1H, d, J=9.0Hz), 3.49–3.40(1H, m), 2.84–2.77(1H, m), 2.56–2.34(2H, m), 2.20–2.06(1H, m), 1.90(3H, brs) | 237.7 (Dec.) |
| 16 | KBr: 1689, 1657, 1450, 1323, 700 | DMSO-d₆**: 7.54–7.03(12H, m), 5.33(1H, d, J=9.2Hz), 3.64–3.52(1H, m), 2.65–2.59(2H, m), 2.14–2.09(2H, m) | 120.9–124.2 |
| 17 | KBr: 1687, 1664, 1454, 1379, 1344, 1311 | CDCl₃: 8.20(1H, d, J=8.1Hz), 7.57 (1H, d, J=8.6Hz), 7.48–7.37(5H, m), 5.01(1H, d, J=8.8Hz), 3.51–3.38 (1H, m), 2.87–2.79(1H, m), 2.56–2.44(1H, m), 2.38–2.29(1H, m), 2.17–2.01(1H, m), 1.81(3H, s) | 195.5–197.4 |
| 18 | KBr: 1691, 1674, 1670, 1452, 1381, 1321 | CDCl₃: 8.28(1H, d, J=7.5Hz), 7.49–7.32(6H, m), 5.02(1H, d, J=8.8Hz), 3.48–3.39(1H, m), 2.86–2.78(1H, m), 2.56–2.43(1H, m), 2.37–2.29 (1H, m), 2.15–2.01(1H, m), 1.81 (3H, s) | 151.1–155.4 |
| 19 | KBr: 1693, 1682, 1525, 1327, 1311 | CDCl₃*: 8.35(1H, d, J=8.3Hz), 7.53 (1H, dd, J=8.6, 0.7Hz), 7.49–7.39 (5H, m), 5.09(1H, d, J=9.2Hz), 3.52–3.42(1H, m), 2.90–2.81(1H, m), 2.61–2.48(1H, m), 2.43–2.34 (1H, m), 2.25–2.09(1H, m), 1.84 (3H, s) | 180.1–182.4 |
| 20 | KBr: 2220, 1684, 1446, 1373, 1325, 1309 | CDCl₃*: 8.37(1H, d, J=8.3Hz), 7.70 (1H, dd, J=8.3, 0.7Hz), 7.51–7.38 (5H, m), 5.09(1H, d, J=8.9Hz), 3.52–3.43(1H, m), 2.92–2.83(1H, m), 2.59–2.36(2H, m), 2.22–2.07 (1H, m), 1.84(3H, s) | 212.7–215.0 |
| 21 | KBr: 2222, 1687, 1618, 1443, 1311, 1292 | CDCl₃: 9.90–9.65(1H, brs), 7.64–7.61(2H, m), 7.48–7.34(5H, m), 5.16(1H, d, J=9.4Hz), 3.54–3.40 (1H, m), 2.91–2.82(1H, m), 2.60–2.39(2H, m), 2.18–2.02(1H, m) | 223.5–226.2 |
| 22 | KBr: 3340, 1674, 1601, 1468, 1279 | CDCl₃: 7.58–7.54(2H, m), 7.44–7.35 (3H, m), 7.26(1H, d, J=7.9Hz), 7.18 (1H, dd, J=7.8, 7.5Hz), 6.83(1H, d, J=7.3Hz), 4.72(1H, d, J=11.0Hz), 4.29(1H, brs), 3.35–3.22(1H, m), 2.80–2.70(1H, m), 2.55–2.42(1H, m), 2.35–2.25(1H, m), 2.17–2.05 (1H, m) | 158.2–171.8 |
| 23 | KBr: 3358, 2947, 1678, 1603, 1470, 1223, 716 | CDCl₃: 7.55(2H, d, J=7.0Hz), 7.45–7.32(3H, m), 6.83(1H, dd, J=11.0, 8.4Hz), 6.75(1H, dd, J=8.3, 3.8Hz), 4.72(1H, d, J=9.7Hz), 4.18(1H, brs), 3.25(1H, ddd, J=11.6, 11.6, 4.6Hz), 2.74(1H, ddd, J=17.5, 4.0, 2.5Hz), 2.47(1H, ddd, J=17.6, 13.9, 4.9Hz), 2.32–2.22(1H, m), 2.15–1.99 (1H, m) | 203.5–204.8 |

TABLE 6-continued

| Example No. | IR (cm$^{-1}$) | NMR (ppm) (non-mark: 300 MHz, 20° C.; *: 270 MHz, 20° C.; **: 270 MHz, 80° C.) | mp (° C.) |
|---|---|---|---|
| 24 | KBr: 3325, 1678, 1626, 1610, 1483, 1371, 1117 | CDCl$_3$*: 7.53(2H, d, J=7.6Hz), 7.46–7.35(3H, m), 6.87(1H, dd, J=9.6, 2.0Hz), 6.52(1H, dd, J=9.6, 2.0Hz), 4.75(1H, dd, J=10.9, 3.0Hz), 4.37(1H, brs), 3.30–3.15 (1H, m), 2.74(1H, ddd, J=17.5, 4.1, 2.5Hz), 2.46(1H, ddd, J=17.5, 13.9, 4.6Hz), 2.35–2.25(1H, m), 2.15–1.97 (1H, m) | 182.8–183.5 |
| 25 | KBr: 3332, 1672, 1626, 1612, 1250, 1192, 802 | CDCl$_3$: 7.58(2H, d, J=8.0Hz), 7.46–7.33(3H, m), 7.27(1H, dd, J=8.4, 4.2Hz), 6.96(1H, dd, J=10.5, 8.6Hz), 4.77(1H, dd, J=11.2, 2.9Hz), 4.4–4.3(1H, br), 3.32(1H, ddd, J=11.6, 11.6, 4.8Hz), 2.73(1H, ddd, J=17.6, 4.0, 2.4Hz), 2.47(1H, ddd, J=17.6, 13.8, 4.8Hz), 2.35–2.27 1H, m), 2.15–2.00(1H, m) | 124.0–124.8 |
| 26 | KBr: 3292, 1682, 1595, 1452, 1269 | CDCl$_3$: 7.56–7.52(2H, m), 7.45–7.33 (3H, m), 7.14(1H, dd, J=8.2, 0.8Hz), 6.73(1H, d, J=8.1Hz), 4.71 (1H, dd, J=11.2, 3.5Hz), 4.32–4.25 (1H, br), 3.32–3.22(1H, m), 2.82–2.74(1H, m), 2.55–2.43(1H, m), 2.29–2.21(1H, m), 2.14–1.99(1H, m) | 166.9–169.5 |
| 27 | KBr: 3379, 1672, 1601, 752, 706 | CDCl$_3$: 7.53(2H, d, J=6.6Hz), 7.45–7.35(3H, m), 7.20(1H, d, J=1.5Hz), 6.76(1H, d, J=1.7Hz), 4.74(1H, dd, J=10.8, 2.9Hz), 4.40–4.32(1H, br), 3.28–3.19(1H, m), 2.79–2.70(1H, m), 2.54–2.27(2H, m), 2.13–1.99 (1H, m) | 212.5–214.3 |
| 28 | KBr: 3359, 1684, 1591, 1450, 1271, 700 | CDCl$_3$: 7.54(2H, d, J=7.0Hz), 7.44–7.34(4H, m), 6.66(1H, d, J=8.1Hz), 4.72(1H, d, J=11.2Hz), 4.38–4.20 (1H, br), 3.34–3.23(1H, m), 2.84–2.76(1H, m), 2.57–2.43(1H, m), 2.30–2.22(1H, m), 2.16–2.00(1H, m) | 187.0 (Dec.) |
| 29 | KBr: 3342, 1676, 1612, 1593, 800 | CDCl$_3$: 7.59–7.55(2H, m), 7.46–7.29 (4H, m), 7.12(1H, d, J=8.4Hz), 4.78 (1H, dd, J=11.0, 2.9Hz), 4.55–4.44 (1H, br), 3.43–3.33(1H, m), 2.77–2.69(1H, m), 2.52–2.27(2H, m), 2.17–2.03(1H, m) | 173.2–176.5 |
| 30 | KBr: 3305, 1662, 1595, 1473, 1269, 818, 700 | CDCl$_3$*: 7.55(2H, d, J=7.6Hz), 7.45–7.3(3H, m), 6.93(1H, d, J=7.9Hz), 6.74(1H, d, J=7.6Hz), 4.66(1H, d, J=11.2Hz), 4.16(1H, br), 3.25(1H, ddd, J=11.4, 11.4, 4.6Hz), 2.72(1H, ddd, J=17.5, 4.2, 2.3Hz), 2.55(3H, s), 2.5–2.4(1H, m), 2.3–2.2(1H, m), 2.1–1.9(1H, m) | 145.0–147.3 |
| 31 | KBr: 3304, 1672, 1618, 1608, 1369, 1232 | CDCl$_3$: 7.54(2H, d, J=8.3Hz), 7.43–7.34(3H, m), 7.06(1H, s), 6.67 (1H, s), 4.68(1H, d, J=10.8Hz), 4.3–4.2(1H, br), 3.3–3.2(1H, m), 2.75–2.65(1H, m), 2.46(1H, ddd, J=17.4, 13.8, 4.8Hz), 2.33(3H, s), 2.35–2.25(1H, m), 2.15–1.95(1H, m) | 191.3–193.4 |
| 32 | KBr: 3350, 2941, 1668, 1603, 1288, 804, 698 | CDCl$_3$: 7.58(2H, d, J=7.2Hz), 7.45–7.32(3H, m), 7.23(1H, d,J=7.9Hz), 7.02(1H, d, J=7.9Hz), 4.70(1H, d, J=11.2Hz), 4.2–4.1(1H, br), 3.30 (1H, ddd, J=11.6, 11.6, 4.8Hz), 2.71 (1H, ddd, J=17.4, 3.9, 2.5Hz), 2.47 (1H, ddd, J=17.4, 13.8, 4.8Hz), 2.34–2.26(1H, m), 2.23(3H, s), 2.14–2.00(1H, m) | 160.8–162.3 |
| 33 | KBr: 3329, 1688, 1599, 1475, 1257, 1232 | CDCl$_3$: 7.55(2H, d, J=8.0Hz), 7.48–7.32(3H, m), 6.83(1H, d, J=8.4Hz), 6.68(1H, d, J=8.4Hz), 4.65(1H, d, J=11.2Hz), 4.07(1H, brs), 3.87(3H, s), 3.24(1H, ddd, J=11.6, 11.6, 4.8Hz), 2.73(1H, ddd, J=17.6, 4.2, 2.4Hz), 2.47(1H, ddd, J=17.6, 13.8, 5.0Hz), 2.27–2.18(1H, m), 2.10–1.95 (1H, m) | 144.0–147.3 |
| 34 | KBr: 1682, 1605, 1508, 1340, 1321, 1267 | CDCl$_3$: 7.54–7.50(3H, m), 7.46–7.36 (3H, m), 6.67(1H, d, J=8.3Hz), 4.83 (1H, dd, J=10.9, 2.5Hz), 4.76–4.66 (1H, br), 3.35–3.24(1H, m), 2.86–2.77(1H, m), 2.62–2.50(1H, m), 2.36–2.28(1H, m), 2.22–2.08(1H, m) | 212.2–213.6 |
| 35 | KBr: 2210, 1670, 1614, 1479, 1269 | CDCl$_3$*: 7.54–7.49(3H, m), 7.46–7.38(3H, m), 6.77(1H, d, J=8.3Hz), 4.82(1H, dd, J=10.7, 2.5Hz), 4.79–4.72(1H, br), 3.36–3.24(1H, m), 2.87–2.77(1H, m), 2.57–2.44(1H, m), 2.37–2.28(1H, m), 2.18–2.02 (1H, m) | 254.4–258.7 |
| 36 | KBr: 3321, 2218, 1687, 1599, 1479, 1452 | CDCl$_3$: 7.56–7.51(2H, m), 7.48–7.38 (3H, m), 7.30(1H, dd, J=8.3, 0.9Hz), 7.18(1H, d, J=8.3Hz), 5.05–4.95(1H, br), 4.88(1H, dd, J=10.6, 2.4Hz), 3.40–3.31(1H, m), 2.83–2.75 (1H, m), 2.55–2.32(2H, m), 2.18–2.08(1H, m) | 186.7–188.9 |
| 37 | KBr: 3336, 1670, 1599, 1466, 1410, 1275, 791 | DMSO-d$_6$: 7.57(2H, d, J=8.4Hz), 7.47(2H, d, J=8.4Hz), 7.13(1H, dd, J=7.7, 7.7Hz), 6.96(1H, d, J=7.3Hz), 6.76(1H, d, J=7.5Hz), 6.42(1H, d, J=3.3Hz), 4.67(1H, dd, J=11.0, 3.3Hz), 3.17(1H, ddd, J=11.4, 11.4, 4.9Hz), 2.6–2.4(2H, m), 2.22–1.97(2H, m) | 205.0–207.2 |
| 38 | KBr: 3315, 1668, 1603, 1473, 1253 | CDCl$_3$*: 7.60(1H, s), 7.44–7.36 (1H, m), 7.35–7.32(2H, m), 7.26 (1H, dd, J=7.9, 1.0Hz), 7.18(1H, dd, J=7.9, 7.3Hz), 6.84(1H, dd, J=7.6, 0.8Hz), 4.69(1H, dd, J=10.9, 3.3Hz), 4.33–4.28(1H, m), 3.31–3.21 (1H, m), 2.75(1H, ddd, J=17.5, 4.0, 2.3Hz), 2.49(1H, ddd, J=17.5, 13.5, 4.3Hz), 2.37–2.28(1H, m), 2.24–2.01 (1H, m) | 190.1–191.1 |
| 39 | KBr: 3353, 1672, 1599, 1471, 1290 | CDCl$_3$*: 7.99(1H, d, J=7.6Hz), 7.42–7.16(5H, m), 6.83(1H, d, J=7.3Hz), 5.34(1H, d, J=10.9Hz), 4.35–4.22(1H, br), 3.33(1H, ddd, J=11.4, 11.4, 4.5Hz), 2.79–2.70(1H, m), 2.61–2.39(2H, m), 2.28–2.12 (1H, m) | 169.3–171.8 |
| 40 | KBr: 3305, 1722, 1668, 1601, 1473, 1275 | DMSO-d$_6$*: 8.01(2H, d, J=8.2Hz), 7.69(2H, d, J=8.2Hz), 7.14(1H, dd, J=7.9, 7.6Hz), 6.97(1H, d, J=7.6Hz), 6.78(1H, d, J=7.6Hz), 6.46(1H, d, J=3.3Hz), 4.76(1H, dd, J=10.9, 3.3Hz), 3.19(1H, ddd, J=11.4, 11.4, 5.1Hz), 2.58–2.45(2H, m), 2.22–2.00(2H, m) | 155.7–158.2 |
| 41 | KBr: 3265, 1659, 1614, 1466, 1329, 1290, 1097, 692 | DMSO-d$_6$*: 11.58(1H, s), 7.79(2H, d, J=7.3Hz), 7.58(1H, d, J=7.6Hz), 7.54(2H, t, J=7.6Hz), 7.42–7.34 (2H, m), 7.24(1H, t, J=7.6Hz), 3.43 (2H, t, J=7.1Hz), 2.88(2H, t, J=7.1Hz) | 195.4–200.6 |
| 42 | KBr: 3273, 1660, 1622, 1489, 1379, 1325, 808 | CDCl$_3$: 8.28(1H, s), 7.64–7.59(2H, m), 7.54–7.48(2H, m), 7.47(1H, dd, J=8.6, 3.5Hz), 7.43–7.36(1H, m), 6.96(1H, dd, J=11.0, 8.6Hz), 3.43 (2H, t, J=7.2Hz), 2.96(2H, t, J=7.2Hz) | 240.0 (Dec.) |

TABLE 6-continued

| Example No. | IR (cm⁻¹) | NMR (ppm) (non-mark: 300 MHz, 20° C.; *: 270 MHz, 20° C.; **: 270 MHz, 80° C.) | mp (° C.) |
|---|---|---|---|
| 43 | KBr: 3358, 1657, 1626, 1383, 1340, 1117, 768 | CDCl$_3$*: 8.28(1H, s), 7.64–7.58(2H, m), 7.54–7.47(2H, m), 7.42–7.35(1H, m), 7.35(1H, dd, J=9.6, 2.0Hz), 7.26(1H, dd, J=9.6, 2.0Hz), 3.46(2H, t, J=6.9Hz), 2.98(2H, t, J=6.9Hz) | 206.4–207.9 |
| 44 | KBr: 3325, 1666, 1635, 1597, 1392, 1335, 1296, 1198 | CDCl$_3$*: 8.43(1H, s), 7.7–7.5(5H, m), 7.45–7.35(1H, m), 6.98(1H, dd, J=11.4, 8.3Hz), 3.45(2H, t, J=7.1Hz), 2.95(2H, t, J=7.1Hz) | 220.0–222.2 |
| 45 | KBr: 1670, 1471, 1321, 1097, 698 | DMSO-d$_6$: 11.77(1H, s), 7.77(2H, d, J=7.2Hz), 7.56–7.52(3H, m), 7.40(1H, t, J=7.4Hz), 7.17(1H, d, J=8.4Hz), 3.39(2H, t, J=7.1Hz), 2.89(2H, t, J=7.1Hz) | 240.0 (Dec.) |
| 46 | KBr: 3246, 1651, 1468, 1323, 1119, 692 | DMSO-d$_6$: 11.78(1H, s), 7.79(2H, d, J=8.4Hz), 7.59(1H, d, J=1.5Hz), 7.55(2H, dd, J=7.8, 7.8Hz), 7.40(1H, t, J=7.4Hz), 7.30(1H, d, J=1.5Hz), 3.43(2H, t, J=7.1Hz), 2.90(2H, t, J=7.0Hz) | 235.1–236.6 |
| 47 | KBr: 1666, 1468, 1321, 1311, 698 | CDCl$_3$*: 8.34(1H, s), 7.62(2H, d, J=7.3Hz), 7.51(2H, dd, J=7.4, 7.4Hz), 7.64–7.58(2H, m), 7.55–7.48(1H, m), 7.43–7.34(2H, m), 7.35(1H, d, J=8.2Hz), 3.42(2H, t, J=7.3Hz), 2.99(2H, t, J=7.3Hz) | 244.0 (Dec.) |
| 48 | KBr: 1662, 1616, 1290, 1113, 771, 692 | DMSO-d$_6$: 11.68(1H, s), 7.85(2H, d, J=7.9Hz), 7.54(2H, dd, J=7.5, 7.5Hz), 7.45–7.39(2H, m), 7.30(1H, d, J=7.9Hz), 3.40(2H, t, J=7.0Hz), 2.86(2H, t, J=7.1Hz) | 230.0 (Dec.) |
| 49 | KBr: 1653, 1458, 1319, 1259, 770, 694 | CDCl$_3$: 8.20(1H, s), 7.65–7.59(2H, m), 7.50(2H, dd, J=7.6, 7.6Hz), 7.41(1H, d, J=8.1Hz), 7.40–7.33(1H, m), 7.05(1H, d, J=8.3Hz), 3.42(2H, t, J=7.2Hz), 2.95(2H, t, J=7.2Hz), 2.72(3H, s) | 236.5–237.7 |
| 50 | KBr: 3321, 1670, 1653, 1622, 1329, 1120 | CDCl$_3$: 8.23(1H, s), 7.62(2H, d, J=8.3Hz), 7.52–7.45(3H, m), 7.39–7.33(2H, m), 3.45(2H, t, J=7.1Hz), 2.96(2H, t, J=7.1Hz), 2.52(3H, s) | 210.5–211.8 |
| 51 | KBr: 3350, 1653, 1618, 1331, 1294, 692 | CDCl$_3$*: 8.23.(1H, s), 7.80–7.60(2H, m), 7.56(1H, d, J=7.6Hz), 7.55–7.45(2H, m), 7.45–7.34(1H, m), 7.08(1H, d, J=7.6Hz), 3.45(2H, t, =7.1Hz), 2.94(2H, t, J=7.1Hz), 2.59(3H, s) | 221.1–221.5 |
| 52 | KBr: 3292, 1657, 1618, 1485, 1238, 1053 | CDCl$_3$*: 8.26(1H, s), 7.64–7.59(2H, m), 7.52–7.45(3H, m), 7.39–7.33(1H, m), 6.87(1H, d, J=8.8Hz), 3.97(3H, s), 3.38(2H, t, J=7.2Hz), 2.93(2H, t, J=7.2Hz) | 228.0 (Dec.) |
| 53 | KBr: 3359, 1668, 1616, 1462, 1329, 1286, 1093, 833 | DMSO-d$_6$: 11.65(1H, s), 7.80(2H, d, J=8.4Hz), 7.60(3H, d, J=8.4Hz), 7.38(1H, d, J=7.3Hz), 7.26(1H, dd, J=7.7, 7.7Hz), 3.42(2H, t, J=7.0Hz), 2.88(2H, t, J=7.0Hz) | 248.0 (Dec.) |
| 54 | KBr: 3367, 1655, 1618, 1597, 1500, 1333, 1298, 1103 | DMSO-d$_6$*: 11.68(1H, s), 7.84(1H, dd, J=2.0, 1.7Hz), 7.75(1H, d, J=8.3Hz), 7.61(1H, d, J=7.3Hz), 7.56(1H, dd, J=8.3, 7.6Hz), 7.47–7.42(1H, m), 7.39(1H, d, J=6.9Hz), 7.27(1H, dd, J=7.9, 7.3Hz), 3.44(2H, t, J=6.9Hz), 2.88(2H, t, J=6.9Hz) | 223.0 (Dec.) |
| 55 | KBr: 1660, 1616, 1456, 1331, 1308, 1288, 758 | DMSO-d$_6$*: 11.48(1H, s), 7.67–7.60(3H, m), 7.53–7.46(2H, m)7.40(1H, d, J=7.6Hz), 7.27(1H, dd, J=7.6, 7.6Hz), 3.15(2H, t, J=6.9Hz), 2.83(2H, t, J=7.1Hz) | 233.0 (Dec.) |
| 56 | KBr: 3356, 1714, 1653, 1606, 1277, 1105 | DMSO-d$_6$*: 11.76(1H, s), 8.10(2H, d, J=8.6Hz), 7.93(2H, d, J=8.3Hz), 7.63(1H, d, J=7.3Hz), 7.39(1H, d, J=6.6Hz), 7.29(1H, dd, J=7.6, 7.6Hz), 3.48(2H, t, J=6.9Hz), 2.90(2H, t, J=6.9Hz) | 248.4 (Dec.) |
| 57 | KBr: 1682, 1524, 1481, 1464, 1340, 694 | DMSO-d$_6$*: 12.15(1H, s), 7.81(2H, d, J=7.9Hz), 7.66(1H, d, J=8.6Hz), 7.60–7.54(3H, m), 7.44(1H, t, J=7.3Hz), 3.48(2H, t, J=7.1Hz), 2.99(2H, t, J=6.9Hz) | 225.0 (Dec.) |
| 58 | KBr: 3288, 3278, 2226, 1682, 1470 | DMSO-d$_6$*: 12.14(1H, s), 7.80(2H, d, J=7.6Hz), 7.71(1H, d, J=8.3Hz), 7.59–7.54(3H, m), 7.44(1H, t, J=7.3Hz), 3.45(2H, t, J=6.9Hz), 2.96(2H, t, J=6.9Hz) | 292.0 (Dec.) |
| 59 | KBr: 3203, 2222, 1672, 1496, 1292, 700 | DMSO-d$_6$: 12.41(1H, s), 7.86(2H, d, J=8.6Hz), 7.68(1H, d, J=7.7Hz), 7.55(2H, dd, J=7.9, 7.2Hz), 7.46–7.39(2H, m), 3.43(2H, t, J=7.0Hz), 2.92(2H, t, J=7.0Hz) | 227.8–231.5 |
| 60-1 | KBr: 1693, 1593, 1507, 1297, 1245 | DMSO-d$_6$*: 12.8–12.2(2H, brs), 8.59(1H, s), 8.13(1H, s), 7.84(2H, d, J=6.9Hz), 7.55–7.38(5H, m), 2.92–2.86(2H, m), 2.44–2.33(2H, m), 1.85–1.75(2H, m) | 219.9–221.5 |
| 60-2 | KBr: 1712, 1434, 1284, 1226, 1191 | DMSO-d$_6$: 13.0–11.5(2H, brs), 11.78(1H, s), 7.61–7.44(6H, m), 7.25(1H, d, J=7.9Hz), 3.15–3.10(2H, m), 2.38–2.31(2H, m) | 250.3–252.0 |
| 60-3 | KBr: 1662, 1618, 1290, 1123, 771 | DMSO-d$_6$: 11.82(1H, s), 7.85(2H, d, J=7.3Hz), 7.55(2H, dd, J=7.9, 7.3Hz), 7.45–7.40(1H, m), 7.38(1H, d, J=7.9Hz), 7.29(1H, d, J=7.9Hz), 3.41(2H, t, J=7.1Hz), 2.87(2H, t, J=6.9Hz) | 225.2–231.5 |
| 61 | KBr: 1660, 1618, 1508, 1462, 1232, 1122 | DMSO-d$_6$: 11.83(1H, s), 7.89(2H, dd, J=8.7, 5.5Hz), 7.40(1H, d, J=9.0Hz), 7.38(2H, d, J=8.7Hz), 7.29(1H, d, J=7.9Hz), 3.48–3.40(2H, m), 2.86(2H, t, J=6.9Hz) | 192.4–196.0 |
| 62 | KBr: 3325, 1660, 1618, 1591, 1491, 1462, 1290 | DMSO-d$_6$: 11.86(1H, s), 7.87(2H, d, J=8.6Hz), 7.61(2H, d, J=8.6Hz), 7.38(1H, d, J=7.9Hz), 7.39(1H, d, J=7.9Hz), 3.39(2H, t, J=6.9Hz), 2.87(2H, t, J=6.9Hz) | 231.1–232.6 |
| 63 | KBr: 3302, 1657, 1614, 1591, 1458, 1286, 1124 | DMSO-d$_6$: 11.87(1H, s), 7.81(2H, d, J=8.8Hz), 7.74(2H, d, J=8.8Hz), 7.38(1H, d, J=7.7Hz), 7.31(1H, d, J=7.9Hz), 3.39(2H, t, J=7.0Hz), 2.87(2H, t, J=7.0Hz) | 227.1–230.0 |
| 64 | KBr: 3331, 1655, 1620, 1514, 1464, 1292, 1254, 829 | DMSO-d$_6$: 11.71(1H, s), 7.79(2H, d, J=7.6Hz), 7.38–7.33(1H, m), 7.24(1H, d, J=7.7Hz), 7.11(2H, d, J=7.9Hz), 3.84(3H, s), 3.5–3.3(2H, m), 2.86(2H, t, J=6.9Hz) | 201.9–205.3 |
| 65 | KBr: 3319, 1660, 1618, 1589, 1292, 1126 | DMSO-d$_6$: 11.76(1H, s), 7.75(2H, d, J=7.5Hz), 7.39–7.33(3H, m), 7.27(1H, d, J=7.9Hz), 3.45–3.30(2H, m), 2.86(2H, t, J=7.2Hz), 2.38(3H, s) | 225.0 (Dec.) |
| 66 | KBr: 1659, 1597, 1516, 1331, 1304, 1282 | DMSO-d$_6$: 12.09(1H, s), 8.39(2H, d, J=9.2Hz), 8.13(2H, d, J=9.2Hz), 7.42(1H, d, J=7.9Hz), 7.38(1H, d, J=7.7Hz), 3.49(2H, t, J=7.1Hz), 2.91(2H, t, J=7.0Hz) | 300.0 (Dec.) |
| 67 | KBr: 3244, 1651, 1630, 1373, 1342, 1151 | CDCl$_3$: 8.14(1H, s), 7.62–7.58(2H, m), 7.49(2H, dd, J=7.9, 7.3Hz), 7.38–7.32(1H, m), 7.26(1H, d, J=1.8Hz), 7.11(1H, d, J=2.0Hz), 3.90(3H, s), 3.45(2H, t, J=7.0Hz), 2.97(2H, t, J=7.0Hz) | 220.0 (Dec.) |

TABLE 6-continued

| Example No. | IR (cm⁻¹) | NMR (ppm) (non-mark: 300 MHz, 20° C.; *: 270 MHz, 20° C.; **: 270 MHz, 80° C.) | mp (° C.) |
|---|---|---|---|
| 68 | KBr: 3190, 1651, 1618, 1595, 1466, 1294, 1049 | CDCl₃: 8.39(1H, s), 7.68–7.62(3H, m), 7.53–7.46(2H, m), 7.40–7.33 (1H, m), 6.75(1H, d, J=8.1Hz), 4.05 (3H, s), 3.44(2H, t, J=7.1Hz), 2.94 (2H, t, J=7.1Hz) | 266.5–268.8 |
| 69 | KBr: 3265, 1659, 1614, 1466, 1329, 1290, 1097, 692 | DMSO-d₆*: 11.58(1H, s), 7.79(2H, d, J=7.3Hz), 7.58(1H, d, J=7.6Hz), 7.54(2H, t, J=7.6Hz), 7.42–7.34 (2H, m), 7.24(1H, t, J=7.6Hz), 3.43 (2H, t, J=7.1Hz), 2.88(2H, t, J=7.1Hz) | 195.4–200.6 |
| 70 | KBr: 1662, 1618, 1508, 1464, 1157 | DMSO-d₆: 11.58(1H, s), 7.80(2H, dd, J=8.8, 5.6Hz), 7.58(1H, d, J=7.9Hz), 7.39(2H, d, J=9.0Hz), 7.36(1H, d, J=7.3Hz), 7.23(1H, dd, J=7.9, 7.3Hz), 3.39(2H, t, J=7.0Hz), 2.86(2H, t, J=6.9Hz) | 188.6–193.4 |
| 71 | KBr: 3253, 1664, 1610, 1281, 1250, 1176, 833 | DMSO-d₆: 11.47(1H, s), 7.73(2H, d, J=9.0Hz), 7.56(1H, d, J=7.9Hz), 7.34(1H, d, J=7.3Hz), 7.20(1H, dd, J=7.8, 7.6Hz), 7.11(1H, d, J=9.0Hz), 3.83(3H, s), 3.45–3.30 (2H, m), 2.86(2H, t, J=7.1) | 182.6–186.1 |
| 72 | KBr: 3356, 1664, 1612, 1466, 1288, 1097, 820 | DMSO-d₆: 11.53(1H, s), 7.68(2H, d, J=8.1Hz), 7.58(1H, d, J=7.9Hz), 7.38–7.32(3H, m), 7.22(1H, dd, J=7.6, 7.6Hz), 3.41(2H, t, J=7.1Hz), 2.87(2H, t, J=7.1Hz), 2.37(3H, s) | 238.5–242.4 (Dec.) |
| 73 | KBr: 1653, 1618, 1608, 1466, 1381, 1298, 1279, 1122 | DMSO-d₆: 11.46(1H, s), 7.54(2H, d, J=7.2Hz), 7.31(1H, dd, J=7.9, 1.8Hz), 7.15(1H, dd, J=7.9, 1.8Hz), 6.68(2H, d, J=7.2Hz), 5.48(2H, s), 3.32(2H, brt, J=7.2Hz), 2.82(2H, brt, J=6.7Hz) | 220.0 (Dec.) |
| 74 | KBr: 1645, 1618, 1514, 1468, 1288 | DMSO-d₆: 11.25(1H, s), 7.49(1H, dd, J=7.9, 0.7Hz), 7.47(2H, d, J=8.6Hz), 7.30(1H, dd, J=7.3, 0.7Hz), 7.12(1H, t, J=7.6Hz), 6.67 (2H, d, J=8.6Hz), 5.43(2H, s), 3.34 (2H, t, J=7.2Hz), 2.83(2H, t, J=–7.2Hz) | 212.0 (Dec.) |
| 75 | KBr: 3361, 1576, 1417, 1342, 1246, 1219 | DMSO-d₆: 11.32(1H, s), 10.58(1H, s), 7.80(1H, d, J=7.3Hz), 7.50(1H, dd, J=7.6, 7.6Hz), 7.35(1H, t, J=7.6Hz), 7.30(1H, d, J=7.9Hz), 6.64(1H, d, J=7.9Hz), 3.5–3.3(2H, m), 2.76(1H, t, J=7.3Hz) | >300 |
| 76 | KBr: 3427, 1767, 1672, 1624, 1597, 1302, 1213 | DMSO-d₆*: 11.68(1H, s), 7.83(2H, d, J=7.6Hz), 7.50(2H, dd, J=7.6, 7.6Hz), 7.40–7.32(2H, m), 6.71(1H, d, J=7.9Hz), 5.10(2H, s), 3.73(3H, s), 3.42–3.30(2H, m), 2.80(2H, t, J=6.9Hz) | 172.0 (Dec.) |
| 77 | KBr: 1668, 1358, 1321, 1309, 820 | DMSO-d₆: 7.68–7.58(4H, m), 7.39 (1H, d, J=7.9Hz), 7.31(1H, d, J=7.9Hz), 3.96(3H, s), 3.13(2H, t, J=6.9Hz), 2.81(2H, t, J=7.1Hz) | 187.9–191.0 |
| 78 | KBr: 1676, 1473, 1356, 1331, 1279, 752 | DMSO-d₆: 7.75(1H, d, J=8.0Hz), 7.63–7.53(4H, m), 7.52–7.45(1H, m), 7.41(1H, d, J=7.4Hz), 7.31(1H, dd, J=7.9, 7.3Hz), 3.77(3H, s), 3.20(2H, t, J=7.0Hz), 2.82(2H, t, J=7.0Hz) | 120.0–123.9 |
| 79 | KBr: 1749, 1670, 1464, 1367, 1217, 704 | CDCl₃*: 7.65(1H, dd, J=6.9, 1.0Hz), 7.58–7.30(7H, m), 4.83(2H, s), 3.76(3H, s), 3.25(2H, t, J=6.9Hz), 2.93(2H, t, J=6.9Hz) | 177.1–178.9 |
| 80 | KBr: 3307, 1657, 1533, 1470, 1290 | DMSO-d₆: 11.49(1H, s), 10.12(1H, s), 7.73(4H, s), 7.57(1H, d, J=7.3Hz), 7.35(1H, d, J=7.3Hz), 7.21(1H, t, J=7.6Hz), 3.41(2H, t, J=7.1Hz), 2.86(2H, t, J=7.1Hz), 2.08(3H, s) | 213.0 (Dec.) |
| 81 | KBr: 3057, 2926, 1599, 1448, 1317, 769, 752, 737, 700 | DMSO-d₆: 11.11(1H, s), 7.72(2H, d, J=7.6Hz), 7.48(2H, dd, J=7.9, 7.6Hz), 7.29(1H, t, J=7.5Hz), 7.18 (1H, d, J=7.6Hz), 7.00(1H, d, J=7.0Hz), 4.20(1H, dd, J=8.4, 3.8Hz), 3.1–3.0(2H, m), 2.3–2.2 (1H, m), 1.9–1.7(1H, m) | 208.4–212.3 |
| 82 | KBr: 1608, 1460, 1340, 1126, 914, 702 | DMSO-d₆*: 11.16(1H, s), 7.68(2H, d, J=7.3Hz), 7.47(2H, dd, J=7.6, 7.6Hz), 7.28(1H, t, J=7.3Hz), 6.92–6.82(2H, m), 4.1–4.0(1H, m), 3.1–2.95(2H, m), 2.3–2.1(1H, m), 1.95 (2H, m), 1.8–1.6(1H, m) | 208.0–210.8 |
| 83 | KBr: 2835, 1466, 1227, 914, 800, 700 | DMSO-d₆*: 11.40(1H, s), 7.76(2H, d, J=6.9Hz), 7.48(2H, dd, J=7.8, 7.8Hz), 7.32(1H, t, J=7.4Hz), 6.93 (1H, dd, J=7.6, 4.0Hz), 6.84(1H, dd, J=12.0, 7.6Hz), 4.2–4.0(1H, m), 3.1–2.9(2H, m), 2.2–1.7(4H, m) | 217.5–218.3 |
| 84 | KBr: 2922, 2827, 1448, 914, 764 | DMSO-d₆: 11.30(1H, s), 7.74(2H, d, J=8.4Hz), 7.50(2H, dd, J=7.5, 7.5Hz), 7.33(1H, t, J=7.3Hz), 7.21 (1H, d, J=8.4Hz), 7.04(1H, d, J=8.4Hz), 4.33–4.28(1H, m), 3.22–3.12(1H, m), 2.95–2.86(1H, m), 2.19–2.10(1H, m), 1.87–1.69(3H, m) | 221.5–222.8 |
| 85 | KBr: 1599, 1460, 908, 839, 766, 700 | DMSO-d₆: 11.24(1H, s), 7.70(2H, d, J=8.3Hz), 7.49(2H, dd, J=7.5, 7.5Hz), 7.31(1H, t, J=7.3Hz), 7.15 (1H, s), 7.03(1H, s), 4.10–4.05 (1H, m), 3.08–3.00(2H, m), 2.18–2.09(1H, m), 1.82–1.66(1H, m) | 226.4–229.5 |
| 86 | KBr: 1599, 1460, 1406, 1335, 906, 770, 700 | DMSO-d₆*: 11.25(1H, s), 7.79(2H, d, J=7.3Hz), 7.49(2H, dd, J=7.8, 7.8Hz), 7.33(1H, t, J=6.8Hz), 7.10 (1H, d, J=7.3Hz), 7.01(1H, d, J=7.3Hz), 4.14(1H, dd, J=8.8, 3.9Hz), 3.10–2.95(2H, m), 2.20–2.05 (1H, m), 1.85–1.70(1H, m) | 164.2–169.1 |
| 87 | KBr: 2924, 2827, 1448, 912, 762, 692 | CDCl₃: 8.20(1H, brs), 7.63–7.58 (2H, m), 7.48(2H, dd, J=7.6, 7.6Hz), 7.34(1H, t, J=7.3Hz), 7.27 (1H, d, J=8.4Hz), 7.13(1H, d, J=8.4Hz), 4.43(1H, dd, J=3.5, 2.7Hz), 3.16–2.99(2H, m), 2.33–2.25 (1H, m), 2.06–1.95(1H, m) | 209.0 (Dec.) |
| 88 | KBr: 1462, 1090, 800, 768, 694 | DMSO-d₆: 11.09(1H, s), 7.78(2H, d, J=7.3Hz), 7.49(2H, dd, J=7.7, 7.7Hz), 7.33(1H, t, J=7.3Hz), 7.24 (1H, d, J=7.7Hz), 6.96(1H, d, J=7.5Hz), 4.08(1H, dd, J=8.9, 3.9Hz), 3.04–3.00(2H, m), 2.14–2.03 (3H, m), 1.80–1.68(1H, m) | 183.6–185.1 |
| 89 | KBr: 1622, 1601, 1460, 1194, 1147, 766 | DMSO-d₆: 10.87 (1H, s), 7.65(2H, d, J=7.2Hz), 7.44(2H, dd, J=7.8, 7.5Hz), 7.23(1H, t, J=7.3Hz), 6.69 (1H, d, J=1.8Hz), 6.64(1H, d, J=1.8Hz), 4.04(1H, dd, J=9.0, 3.7Hz), 3.77(3H, s), 3.05–2.97(2H, m), 2.23–1.95(3H, m), 1.80–1.66 (1H, m) | 191.0–193.9 |
| 90 | KBr: 1589, 1468, 1327, 1306, 1284, 1141 | DMSO-d₆: 11.89(1H, s), 7.90(1H, d, J=9.0Hz), 7.78(2H, d, J=8.4Hz), 7.54(2H, dd, J=7.7, 7.7Hz), 7.41–7.34(2H, m), 4.76–4.72(1H, m), 3.28–3.15(1H, m), 2.97–2.88(1H, m), 2.25–2.15(1H, m), 2.08–2.00 (2H, br), 1.93–1.81(1H, m) | 248.0 (Dec.) |
| 91 | KBr: 2210, 1601, 1468, 924, 770 | DMSO-d₆: 11.71(1H, s), 7.76(2H, d, J=7.3Hz), 7.53(2H, dd, J=7.8, 7.8Hz), 7.40–7.32(3H, m), 4.36–4.28 (1H, m), 3.27–3.14(1H, m), 3.03–2.91(1H, m), 2.17–1.83(4H, m) | 237.0 (Dec.) |

TABLE 6-continued

| Example No. | IR (cm⁻¹) | NMR (ppm) (non-mark: 300 MHz, 20° C.; *: 270 MHz, 20° C.; **: 270 MHz, 80° C.) | mp (° C.) |
|---|---|---|---|
| 92 | KBr: 3354, 2216, 1599, 1342, 987, 696 | DMSO-$d_6$: 11.89(1H, s), 7.81(2H, d, J=8.4Hz), 7.55–7.48(3H, m), 7.35 (1H, t, J=7.3Hz), 7.19(1H, d, J=8.3Hz), 4.15(1H, dd, J=9.3, 3.8Hz), 3.09–3.03(2H, m), 2.38–2.28 (2H, br), 2.22–2.11(1H, m), 1.84–1.70(1H, m) | 240.9–242.7 |
| 93 | KBr: 1618, 1508, 1458, 1281, 1180 | DMSO-$d_6$: 10.72(1H, s), 7.39(2H, d, J=8.4Hz), 7.07(1H, d, J=7.0Hz), 6.95(1H, dd, J=7.1, 7.1Hz), 6.92 (1H, d, J=6.6Hz), 6.64(2H, d, J=8.4Hz), 5.24(2H, s), 4.09–4.04 (1H, m), 3.00–2.94(2H, m), 2.14–2.04(1H, m), 1.82–1.69(1H, m) | 96.9–100.8 |
| 94 | KBr: 3286, 1674, 1595, 1533, 1460, 1313 | DMSO-$d_6$: 10.95(1H, s), 10.04(1H, s), 7.68(2H, d, J=8.6Hz), 7.63(2H, d, J=8.8Hz), 7.13(1H, d, J=7.5Hz), 7.02(1H, dd, J=7.4, 7.4Hz), 6.96 (1H, d, J=7.3Hz), 4.14–4.06(1H, m), 3.07–2.99(2H, m), 2.15–2.04(4H, m), 1.84–1.70(1H, m) | 240.0 (Dec.) |
| 95 | KBr: 1500, 1439, 1219, 1157, 843 | DMSO-$d_6$*: 11.04(1H, s), 7.73(2H, dd, J=8.4, 5.8Hz), 7.32(2H, dd, J=8.7, 8.7Hz), 7.14(1H, d, J=7.9Hz), 7.05(1H, dd, J=7.9, 6.9Hz), 6.98(1H, d, J=6.6Hz), 4.15–4.05(1H, m), 3.09–2.98(2H, m), 2.18–2.05(1H, m), 2.05–1.87(2H, m), 1.87–1.68(1H, m) | 200.4–203.3 |
| 96 | KBr: 3342, 1489, 1466, 1336, 1317, 1090, 920, 744 | DMSO-$d_6$: 11.11(1H, s), 7.72(2H, d, J=8.6Hz), 7.54(2H, d, J=8.6Hz), 7.15(1H, d, J=7.7Hz), 7.07(1H, dd, J=8.1, 7.0Hz), 6.99(1H, d, J=7.0Hz), 4.10(1H, dd, J=8.5, 3.8Hz), 3.15–3.00(2H, m), 2.2–1.7 (4H, m) | 199.9–203.3 |
| 97 | KBr: 3149, 2943, 1597, 1456, 916 | DMSO-$d_6$*: 11.14(1H, s), 7.75(1H, s), 7.67(1H, d, J=7.9Hz), 7.50(1H, dd, J=7.9, 7.9Hz), 7.33(1H, d, J=8.1Hz), 7.16(1H, d, J=7.9Hz), 7.08(1H, dd, J=7.9, 6.9Hz), 7.00 (1H, d, J=6.9Hz), 4.09(1H, dd, J=8.7, 3.3Hz), 3.08–3.03(2H, m), 2.18–2.08(1H, m), 1.93–1.69(3H, m) | 189.0 (Dec.) |
| 98 | KBr: 2927, 1597, 1439, 908, 766 | DMSO-$d_6$*: 10.90(1H, s), 7.59(1H, dd, J=6.9, 2.0Hz), 7.55(1H, dd, J=6.9, 2.3Hz), 7.47–7.38(2H, m), 7.15(1H, d, J=7.6Hz), 7.07(1H, dd, J=7.4, 7.4Hz), 7.00(1H, d, J=6.9Hz), 4.11(1H, dd, J=8.3, 3.8Hz), 2.88–2.68(2H, m), 2.14–2.04 (1H, m), 2.03–1.92(2H, br), 1.80–1.67(1H, m) | 212.0 (Dec.) |
| 99 | KBr: 3151, 2910, 1508, 1458, 1315, 901, 824, 746 | DMSO-$d_6$: 10.98(1H, s), 7.61(2H, d, J=8.1Hz), 7.28(2H, d, J=8.1Hz), 7.14(1H, d, J=8.1Hz), 7.03(1H, dd, J=7.6, 7.1Hz), 6.97(1H, d, J=6.8Hz), 4.15–4.07(1H, m), 3.08–3.00(2H, m), 2.34(3H, s), 2.18–2.07(1H, m), 1.84–1.73(1H, m) | 188.0–191.3 (Dec.) |
| 100 | KBr: 1504, 1460, 1246, 1180, 918, 833, 754 | DMSO-$d_6$: 10.93(1H, s), 7.64(2H, d, J=8.7Hz), 7.12(1H, d, J=7.9Hz), 7.05(2H, d, J=9.0Hz), 7.02–6.93 (2H, m), 4.13–4.05(1H, m), 3.81 (3H, s), 3.05–2.97(2H, m), 2.17–2.05(1H, m), 1.83–1.70(1H, m) | 217.0–222.0 |
| 101 | KBr: 2927, 1684, 1606, 1506, 1369 | DMSO-$d_6$*: 11.53(1H, s), 8.07(2H, d, J=8.3Hz), 7.88(2H, d, J=8.3Hz), 7.35(1H, d, J=7.9Hz), 7.21(1H, dd, J=7.9, 7.6Hz), 7.11(1H, d, J=6.6Hz), 4.70–4.61(1H, m), 3.24–3.15(2H, m), 2.37–2.06(2H, m) | 194.0–197.5 |
| 102 | KBr: 1620, 1506, 1462, 1336, 1288, 11184, 1095 | DMSO-$d_6$: 10.91(1H, s), 7.47(2H, d, J=8.6Hz), 6.99(1H, d, J=7.5Hz), 6.95(1H, d, J=7.5Hz), 6.65(2H, d, J=8.6Hz), 5.31(2H, s), 4.12–4.95 (1H, m), 2.99–2.91(2H, m), 2.14–2.03(1H, m), 1.78–1.68(1H, m) | 185.9–187.1 |
| 103 | KBr: 1589, 1489, 1464, 1336, 1097, 899, 831 | DMSO-$d_6$*: 11.29(1H, s), 7.81(2H, d, J=8.8Hz), 7.54(2H, d, J=8.3Hz), 7.11(1H, d, J=7.8Hz), 7.01(1H, d, J=7.8Hz), 4.08(1H, dd, J=8.8, 3.9Hz), 3.04–2.99(2H, m), 2.22–2.00 (3H, m), 1.85–1.65(1H, m) | — |
| 104 | KBr: 3062, 2910, 1485, 1462, 1336, 1076, 897, 827 | DMSO-$d_6$: 11.29(1H, s), 7.75(2H, d, J=8.8Hz), 7.67(2H, d, J=8.8Hz), 7.11(1H, d, J=7.7Hz), 7.01(1H, d, J=7.5Hz), 4.08(1H, dd, J=8.7, 3.9Hz), 3.05–2.97(2H, m), 2.17–2.05 (1H, m), 2.02–1.88(2H, br), 1.82–1.67(1H, m) | 187.0–191.7 |
| 105 | KBr: 1593, 1506, 1333, 1311, 1111 | DMSO-$d_6$*: 11.52(1H,s), 8.33(2H, d, J=8.9Hz), 8.06(2H, d, J=8.9Hz), 7.19(1H, d, J=7.6Hz), 7.05(1H, d, J=7.6Hz), 4.15–4.05(1H, m), 3.20–3.03(2H, m), 2.22–2.08(1H, m), 2.07–1.90(2H, br), 1.88–1.70(1H, m) | 210.0 (Dec.) |
| 106 | KBr: 2927, 1489, 1450, 1092, 1070 | DMSO-$d_6$: 7.60(2H, d, J=8.6Hz), 7.53(2H, d, J=8.4Hz), 7.12(1H, d, J=7.5Hz), 7.03(1H, d, J=7.7Hz), 4.09–4.05(1H, m), 3.90(3H, s), 2.80–2.75(2H, m), 2.3–2.0(3H, m), 1.8–1.7(1H, m) | 122.1–124.3 |
| 107 | KBr: 3392, 1601, 1458, 1362, 1313 | DMSO-$d_6$: 7.57–7.48(4H, m), 7.45–7.37(1H, m), 7.24(1H, d, J=8.1Hz), 7.13(1H, dd, J=8.1, 7.0Hz), 7.04 (1H, d, J=7.2Hz), 4.10(1H, dd, J=8.4, 3.9Hz), 3.68(3H, s), 2.87–2.79(2H, m), 2.13–2.02(1H, m), 1.79–1.65(1H, m) | 95.7–100.0 |
| 108 | KBr: 1618, 1605, 1464, 1452, 733, 700 | CDCl$_3$*: 7.58–7.50(2H, m), 7.42–7.27(3H, m), 7.12–7.05(1H, m), 6.83(0.8H, d, J=7.6Hz), 6.74(0.2H, d, J=7.6Hz), 6.55(1H, d, J=7.6Hz), 4.60(0.2H, d, J=11.6Hz), 4.54 (0.8H, d, J=11.5Hz), 4.15–4.05(1H, br), 4.05–3.95(1H, m), 3.00(0.8H, ddd, J=11.6, 11.2, 4.3Hz), 2.92–2.82 (0.2H, m), 2.34–2.27(0.8H, m), 2.09–2.01(0.8H, m), 1.19–1.87 (0.8H, m), 1.73–1.62(0.8H, m), 1.51–1.25(0.8H, m) | 104.0–105.6 |
| 109 | KBr: 3151, 3113, 2916, 1587, 1450, 1203, 930 | DMSO-$d_6$*: 11.15(1H, s), 7.73(2H, d, J=7.3Hz), 7.49(2H, dd, J=7.6, 7.6Hz), 7.32(1H, t, J=7.3Hz), 7.16 (1H, dd, J=8.61, 3.6Hz), 6.85(1H, dd, J=10.6, 8.6Hz), 4.38(1H, t, J=3.8Hz), 3.14(1H, ddd, J=15.7, 11.1, 4.6Hz), 2.92(1H, ddd, J=15.7, 4.5, 4.5Hz), 2.1–1.8(4H, m) | 192.7–193.9 |
| 110 | KBr: 2914, 1493, 1454, 1232, 1051, 770 | DMSO-$d_6$; 11.03(1H, s), 7.72(2H, d, J=7.3Hz), 7.49(2H, dd, J=7.8, 7.8Hz), 7.31(1H, t, J=7.3Hz), 7.23 (1H, d, J=8.8Hz), 6.90(1H, d, J=8.8Hz), 4.62–4.42(1H, m), 3.84 (3H, s), 3.21–2.89(2H, m), 2.23–2.08(1H, m), 1.97–1.85(1H, m) | 190.0 (Dec.) |
| 111 | KBr: 3074, 2941, 1603, 1470, 1215, 914 | DMSO-$d_6$: 11.05(1H, s), 7.76(2H, d, J=7.3Hz), 7.44(2H, dd, J=7.8, 7.8Hz), 7.27(1H, t, J=7.3Hz), 6.89 (1H, d, J=7.7Hz), 6.60(1H, d, J=7.8Hz), 4.05(1H, dd, J=8.4, 3.5Hz), 3.90(3H, s), 3.1–2.9(2H, m), 2.2–2.0(1H, m), 1.9–1.6(3H, m) | 198.3–199.2 |

TABLE 6-continued

| Example No. | IR (cm$^{-1}$) | NMR (ppm) (non-mark: 300 MHz, 20° C.; *: 270 MHz, 20° C.; **: 270 MHz, 80° C.) | mp (° C.) |
|---|---|---|---|
| 112 | KBr: 3034, 2918, 1605, 1585, 1450, 1304, 914 | DMSO-d$_6$: 10.92(1H, s), 7.72(2H, d, J=7.3Hz), 7.47(2H, dd, J=7.8, 7.8Hz), 7.28(1H, t, J=7.3Hz), 7.08 (1H, d, J=8.1Hz), 6.87(1H, d, J=8.1Hz), 4.24(1H, t, J=2.9Hz), 3.16(1H, ddd, J=16.4, 12.2, 4.2Hz), 2.9–2.8(1H, m), 2.34(3H, s), 2.2–2.0(1H, m), 1.8–1.6(3H, m) | 200.8–203.1 |
| 113 | KBr: 1601, 1446, 1323, 829, 766, 700 | DMSO-d$_6$: 10.86(1H, s), 7.68(2H, d, J=7.3Hz), 7.45(2H, dd, J=7.8, 7.8Hz), 7.26(1H, t, J=7.3Hz), 6.94 (1H, s), 6.83(1H, s), 4.10–4.00 (1H, m), 3.1G–2.95(2H, m), 2.40 (3H, s), 2.20–2.10(1H, m), 2.00–1.85(1H, br), 1.81–1.67(1H, m) | 202.0–206.1 |
| 114 | KBr: 3466, 3051, 2912, 1601, 1524, 1448, 773 | CDCl$_3$: 7.95(1H, s), 7.63(2H, d, J=7.2Hz), 7.47(2H, dd, J=7.7, 7.7Hz), 7.31(1H, t, J=7.5Hz), 7.05–6.95(2H, m), 4.29(1H, dd, J=8.1, 3.7Hz), 3.17–3.11(2H, m), 2.52(3H, s), 2.3–2.2(1H, m), 2.05–1.90(1H, m) | 230.0 (Dec.) |
| 115 | KBr: 1743, 1458, 1443, 1207, 1178, 744, 706 | CDCl$_3$: 7.50–7.35(5H, m), 7.24(1H, dd, J=8.1, 7.2Hz), 7.13(1H, d, J=7.2Hz), 7.08(1H, d, J=8.1Hz), 4.78(2H, s), 4.30(1H, dd, J=3.11 4.0Hz), 3.74(3H, s), 2.93(2H, t, J=6.2Hz), 2.26–2.15(1H, m), 2.01–1.82(1H, m) | 127.4–129.4 |
| 116 | KBr: 2924, 1605, 1574, 1462, 1387, 1306 | CF$_3$CO$_2$D: 7.94–7.30(8H, m), 5.50–5.30(3H, m), 3.50–3.35(2H, m), 2.99–2.73(2H, m) | 251.0–252.0 |
| 117 | KBr: 2933, 1601, 1460, 1319, 1063, 744 | CDCl$_3$: 7.50–7.44(4H, m), 7.43–7.35 (1H, m), 7.30–7.25(1H, m), 7.21 (1H, dd, J=8.1, 6.8Hz), 7.02(1H, d, J=6.8Hz), 4.30(2H, t, J=5.8Hz), 4.15(1H, dd, J=7.6, 4.1Hz), 3.88–3.74(2H, m), 2.82(2H, t, J=6.2Hz), 2.16–2.04(1H, m), 1.88–1.75(1H, m) | 177.1–178.9 |
| 118 | KBr: 2920, 1772, 1753, 1443, 1217, 1186 | DMSO-d$_6$: 11.31(1H, s), 7.79(2H, d, J=7.3Hz), 7.47(2H, dd, J=7.6, 7.6Hz), 7.31(1H, t, J=7.3Hz), 6.93 (1H, d, J=7.9Hz), 6.56(1H, d, J=7.9Hz), 6.15(2H, br), 4.96(2H, s) 4.36(1H, dd, J=7.1, 3.5Hz), 3.72 (3H, s), 3.06(2H, t, J=5.8Hz), 2.22–2.08(1H, m), 2.05–1.90(1H, m) | 223.9–225.4 |
| 119 | KBr: 3398, 3248, 2927, 1605, 1581, 1421, 1265 | DMSO-d$_6$: 11.42(1H, s), 9.14(2H, brs), 7.77(2H, d, J=7.3Hz), 7.44 (2H, dd, J=7.8, 7.8Hz), 7.28(1H, t, J=7.4Hz), 7.10(1H, d, J=7.9Hz), 6.48(1H, d, J=7.9Hz), 4.68–4.58 (1H, m), 4.42(2H, s), 3.12–2.98 (2H, m), 2.28–1.97(2H, m) | 186.0 (Dec.) |
| 120 | KBr: 3325, 2924, 1603, 1458, 1255, 696 | CDCl$_3$*: 8.57(1H, s), 7.63(2H, d, J=7.9Hz), 7.46(2H, dd, J=7.8, 7.8Hz), 7.35–7.25(1H, m), 6.96(1H, d, J=7.6Hz), 6.66(1H, d, J=7.6Hz), 4.32–4.20(3H, m), 4.06(2H, t, J=4.5Hz), 3.20–3.10(2H, m), 2.29–2.10(1H, m), 2.05–1.88(1H, m) | 158.2–161.1 |
| 121 | KBr: 1680, 1591, 1462, 1377, 1319 | DMSO-d$_6$*: 11.01(1H, s), 7.69(2H, d, J=7.3Hz), 7.46(2H, dd, J=7.9, 7.3Hz), 7.27(1H, t, J=7.3Hz), 7.15 (1H, d, J=7.9Hz), 7.03(1H, dd, J=7.9, 6.9Hz), 6.90(1H, d, J=6.9Hz), 3.86(1H, d, J=8.6, 3.5Hz), 3.20–3.08(2H, m), 3.03–2.90(1H, m), 2.31(6H, s), 2.12–1.89(2H, m) | 60.9–64.1 |
| 122 | KBr: 3169, 3099, 2951, 1458, 1311, 768 | DMSO-d$_6$: 11.07(1H, s), 7.72(2H, d, J=8.1Hz), 7.48(2H, dd, J=7.61 7.3Hz), 7.29(1H, t, J=7.7Hz), 7.18 (1H, d, J=7.9Hz), 7.04(1H, dd, J=8.1, 7.1Hz), 6.89(1H, d, J=7.1Hz), 4.50(1H, t, J=5.3Hz), 3.97–3.89(1H, m), 3.50(2H, dt, J=5.6, 5.6Hz), 3.18–3.07(1H, m), 3.01–2.90(1H, m), 2.85–2.64(2H, m), 2.07–1.98 (2H, m), 1.87–1.75(1H, m) | 135.4–138.8 |
| 123 | KBr: 3435, 1637, 1458, 1448, 1439, 758 | DMSO-d$_6$: 11.50(1H, s), 10.00–9.85 (1H, br), 9.30–9.15(1H, br), 8.40–8.25(3H, br), 7.76(2H, d, J=7.5Hz), 7.53(2H, dd, J=7.9, 7.5Hz), 7.42(1H, dd, J=5.9, 2.9Hz), 7.35(1H, t, J=7.3Hz), 7.21–7.15 (2H, m) 4.76–4.66(1H, m), 3.50–3.37(1H, m), 3.33–3.05(5H, m), 2.68–2.57 (1H, m), 2.23–2.07(1H, m) | 191.1 (Dec.) |
| 124 | KBr: 3304, 1622, 1558, 1448, 1373, 1308, 739, 690 | DMSO-d$_6$: 11.15(1H, s), 8.23(1H, d, J=8.2Hz), 7.72(2H, d, J=7.3Hz), 7.49(2H, t, J=7.7Hz), 7.30(1H, t, J=7.4Hz), 7.21(1H, d, J=8.3Hz), 7.06(1H, dd, J=8.1, 7.2Hz), 6.79 (1H, d, J=7.2Hz), 5.27–5.17(1H, m), 3.14–3.03(2H, m), 2.17–2.04(1H, m), 1.97–1.82(1H, m) | 210.8–215.0 |
| 125 | KBr: 3429, 3292, 1633, 1529, 694 | DMSO-d$_6$*: 11.17(1H, s), 8.82(1H, d, J=–10.2Hz), 7.98(2H, d, J=8.6Hz), 7.75(2H, d, J=10.6Hz), 7.60–7.45 (5H, m), 7.31(1H, dd, J=8.5, 6.6Hz), 7.22(1H, d, J=9.2Hz), 7.07 (1H, dd, J=8.6, 6.6Hz), 6.80(1H, d, J=7.9Hz), 5.59–5.48(1H, m), 3.23–3.14(2H, m), 2.29–2.16(1H, m), 2.16–2.00(1H, m) | 228.9–233.7 |
| 126 | KBr: 3329, 2929, 1697, 1653, 1627, 1576 | DMSO-d$_6$*: 11.15(1H, s), 8.08(1H, d, J=8.9Hz), 7.73(2H, d, J=7.6Hz), 7.49(2H, dd, J=7.9, 7.6Hz), 7.30 (1H, t, J=7.4Hz), 7.21(1H, d, J=7.9Hz), 7.05(1H, dd, J=7.9, 7.3Hz), 6.98(1H, t, J=6.3Hz), 6.80 (1H, d, J=7.3Hz), 5.30–5.18(1H, m), 3.63(2H, d, J=6.3Hz), 3.15–3.05 (2H, m), 2.18–2.02(1H, m), 2.00–1.85(1H, m), 1.40(9H, s) | 140.0 (Dec.) |
| 127 | KBr: 3421, 1655, 1647, 1541, 1458 | DMSO-d$_6$: 11.18(1H, s), 8.21(1H, d, J=8.6Hz), 7.73(2H, d, J=7.9Hz), 7.49(2H, dd, J=7.7, 7.5Hz), 7.31 (1H, t, J=7.9Hz), 7.07(1H, dd, J=7.7, 7.5Hz), 6.81(1H, d, J=7.2Hz), 5.30–5.20(1H, m), 3.34(2H, s), 3.18–3.07(2H, m), 2.19–2.08(1H, m), 2.01–1.86(1H, m) | 145.2–147.3 |
| 128 | KBr: 3437, 3269, 1649, 1531, 1450, 1358, 754, 690 | DMSO-d$_6$: 11.16(1H, s), 9.09(1H, d, J=8.6Hz), 8.07(1H, d, J=7.9Hz), 7.81(1H, dd, J=7.6, 7.3Hz), 7.77–7.66(4H, m), 7.50(2H, dd, J=7.6, 7.6Hz), 7.31(1H, dd, J=7.6, 6.9Hz), 7.23(1H, d, J=8.2Hz), 7.10(1H, dd, J=7.9, 7.3Hz), 6.97(1H, d, J=6.9Hz), 5.50–5.35(1H, m), 3.22–3.11(2H, m), 2.32–2.20(1H, m) 2.12–1.95(1H, m) | 234.5–238.3 |

TABLE 6-continued

| Example No. | IR (cm⁻¹) | NMR (ppm) (non-mark: 300 MHz, 20° C.; *: 270 MHz, 20° C.; **: 270 MHz, 80° C.) | mp (° C.) |
|---|---|---|---|
| 129 | KBr: 3429, 3356, 1632, 1614, 1587, 1525, 1450, 750 | DMSO-d₆: 11.15(1H, s), 8.53(1H, d, J=8.4Hz), 7.74(2H, d, J=−7.3Hz), 7.62(1H, d, J=6.6Hz), 7.49(2H, dd, J=7.9, 7.5Hz), 7.31(1H, dd, J=7.5, 7.3Hz), 7.20(1H, d, J=7.9Hz), 7.15 (1H, d, J=7.0Hz), 7.07(1H, d, J=7.6Hz), 6.80(1H, d, J=7.2Hz), 6.73(1H, d, J=7.3Hz), 6.52(1H, dd, J=7.3, 7.0Hz), 6.44(2H, brs), 5.53–5.43(1H, m), 3.28–3.06(2H,.m), 2.30–1.99(2H, m) | 201.7–204.6 |
| 130 | KBr: 2925, 1598, 1458, 1317, 746 | DMSO-d₆*: 11.05(1H, s), 7.71(2H, d, J=7.3Hz), 7.47(2H, dd, J=7.9, 7.6Hz), 7.28(1H, t, J=7.4Hz), 7.18 (1H, d, J=7.9Hz), 7.03(1H, dd, J=7.9, 7.3Hz), 6.88(1H, d, J=6.9Hz), 3.83–3.79(1H, m), 3.25–2.96(2H, m), 2.40(3H, s), 2.05–2.00(2H, m) | 145.1–150.0 |
| 131-1 | KBr: 3344, 1689, 1439, 1230, 762, 698 | DMSO-d₆: 11.57(1H, brs), 7.62–7.40 (7H, m), 7.15(1H, dd, J=7.8, 7.8Hz), 3.23–3.12(2H, m), 2.45–2.34 (2H, m) | 237.6–239.0 |
| 131-2 | KBr: 1703, 1587, 1454, 1298, 1232, 754 | DMSO-d₆*: 12.7–11.3(2H, br), 7.6–7.1(7H, m), 6.88(1H, dd, J=6.61 2.0Hz), 4.80(1H, d, J=7.9Hz), 3.9–3.8(1H, m), 3.5–3.3(1H, m), 3.0–2.8(1H, m), 1.9–1.7(1H, m), 1.7–1.5(1H, m), 1.3–1.1(2H, m), 0.91 (3H, t, J=6.9Hz) | — |
| 131-3 | — | CDCl₃: 7.3–7.15(4H, m), 7.09(1H, d, J=7.2Hz), 7.0–6.8(2H, br), 6.52 (1H, d, J=7.3Hz), 5.02(1H, d, J=9.4Hz), 3.9–3.8(1H, m), 3.33(1H, dq, J=13.6, 7.2Hz), 2.91(1H, dq, J=13.6, 7.2Hz), 2.7–2.4(2H, m), 1.9–1.8(1H, m), 1.4–1.3(1H, m), 1.19(3H, t, J=7.2Hz) | Oil |
| 134 | KBr: 2937, 1654, 1458, 1330, 1112 | DMSO-d₆**: 7.54–7.13(10H, m), 7.06(1H, d, J=7.6Hz), 6.98(1H, dd, J=7.9, 7.6Hz), 6.43(1H, d, J=7.6Hz), 5.09(1H, d, J=9.9Hz), 3.93–3.84(1H, m), 3.62–3.52(4H, m), 3.20–3.07(1H, m), 2.53–2.47 (4H, m), 2.06–1.89(1H, m), 1.80–1.56(3H, m) | 186.6–187.6 |
| 135 | KBr: 1633, 1601, 1497, 1458, 1385, 698 | DMSO-d₆*: 7.55–7.19(11H, m), 7.17–6.97(3H, m), 6.69(2H, d, J=7.4Hz), 6.51(1H, dd, J=7.3, 7.3Hz), 5.84 (1H, d, J=9.2Hz), 5.17(1H, d, J=10.6Hz), 4.78–4.65(1H, m), 3.28–3.17(1H, m), 2.37–2.22(1H, m), 2.00–1.89(1H, m), 1.86–1.70(1H, m), 1.64–1.46(1H, m) | 208.6–210.5 |
| 136 | KBr: 2929, 1649, 1612, 1493, 1458, 698 | DMSO-d₆**: 7.51–7.14(15H, m), 7.12(1H, d, J=7.9Hz), 6.98(1H, dd, J=7.9, 7.9Hz), 6.44(1H, d, J=7.6Hz), 5.09(1H, d, J=9.9Hz), 3.86–3.70(3H, m), 3.27–3.15(1H, m), 2.25–2.15(1H, m), 2.05–1.93 (1H, m), 1.82–1.56(2H, m) | 125.5–128.5 |
| 137 | KBr: 2929, 1637, 1458, 1381, 696 | DMSO-d₆**: 7.53–7.13(10H, m), 7.05(1H, d, J=7.6Hz), 6.96(1H, dd, J=7.6, 7.6Hz), 6.40(1H, d, J=7.6Hz), 5.08(1H, d, J=10.2Hz), 3.89–3.84(1H, m), 3.16–3.05(1H, m), 2.43–2.39(4H, m), 2.02–1.87 (2H, m), 1.76–1.31(8H, m) | 169.5–171.3 |
| 138 | KBr: 2929, 1649, 1458, 1331, 700 | DMSO-d₆**: 7.54–7.13(10H, m), 7.11–6.97(2H, m), 6.51(0.5H, d, J=7.6Hz), 6.43(0.5H, d, J=7.6Hz), 5.13(0.5H, d, J=9.9Hz), 5.09(0.5H, d, J=10.9Hz), 4.00–3.92(0.5H, m), 3.89–3.84(0.5H, m), 3.47–3.33(4H, m), 3.03–2.91(1H, m), 2.52–2.40 (4H, m), 2.21–2.08(1H, m), 2.02–1.87(4H, m), 1.72–1.55(1H, m), 1.45–1.32(1H, m) | 130.4–135.3 |
| 139 | KBr: 1740, 1666, 1655, 1458, 1381, 1194 | CDCl₃*: 8.2–7.8(1H, m), 7.45–7.10 (7H, m), 4.92(0.3H, d, J=9.9Hz), 4.82(0.7H, d, J=8.9Hz), 4.22(0.6H, q, J=7.2Hz), 4.18(1.4H, d, J=7.2Hz), 4.03–3.95(0.7H, m), 3.80–3.75(0.3H, m), 3.50(0.6H, d, J=2.0Hz), 3.41(1.4H, s), 3.29–3.17 (0.7H, m), 3.11–2.99(0.3H, m), 2.25–2.14(1H, m), 2.01–1.55(7H, m), 1.31(0.9H, t, J=7.1Hz), 1.27(2.1H, t, J=7.1Hz) | 99.3–102.2 |
| 140 | — | CDCl₃*: 7.25–7.1(4H, m), 7.07(1H, dd, J=7.6, 7.6Hz), 6.9–6.75(2H, m), 6.26(1H, d, J=7.6Hz), 4.84(1H, d, J=8.9Hz), 3.8–3.65(5H, m), 3.6–3.5 (1H, m), 3.27(1H, dq, J=13.5, 7.3Hz), 2.82(1H, dq, J=13.5, 7.3Hz), 2.63(2H, dt, J=11.4, 4.6Hz), 2.49(2H, dt, J=11.4, 4.6Hz), 1.9–1.65(2H, m), 1.16(3H, t, J=7.3Hz), 0.95–0.7(1H, m) | Oil |
| 141 | KBr: 3367, 2852, 1606, 1460, 1120, 743, 706 | DMSO-d₆*: 7.52(2H, d, J=7.6Hz), 7.37(2H, dd, J=7.6, 6.9Hz), 7.28 (1H, t, J=6.9Hz), 6.94(1H, dd, J=7.6, 7.6Hz), 6.71(1H, d, J=7.6Hz), 6.39(1H, d, J=7.6Hz), 5.91(1H, d, J=3.3Hz), 4.42(1H, dd, J=11.2, 3.3Hz), 3.9–3.8(1H, m), 3.65–3.50(4H, m), 2.8–2.65(1H, m), 2.55–2.4(4H, m), 2.05–1.9(2H, m), 1.65–1.5(2H, m) | 117.2–120.2 |
| 142 | KBr: 3369, 2852, 1605, 1504, 1462, 752 | CDCl₃*: 7.56(2H, d, J=8.3Hz), 7.42–7.32(3H, m), 7.19(2H, dd, J=7.9, 7.9Hz), 7.06(1H, dd, J=7.6, 7.6Hz), 6.86(1H, d, J=7.6Hz), 6.72–6.68(3H, m), 6.58(1H, d, J=7.6Hz), 4.77–4.71(1H, m), 4.58(1H, d, J=11.6Hz), 3.10–3.00(1H, m), 2.61–2.52(1H, m), 2.14–2.05(1H, m), 1.81–1.67(1H, m), 1.57–1.43 (1H, m) | 146.3–147.1 |
| 143 | KBr: 3358, 2856, 1621, 1602, 1452, 741, 698 | CDCl₃: 7.54(2H, d, J=7.2Hz), 7.43 7.21(8H, m), 7.08(1H, dd, J=7.9, 7.5Hz), 6.88(1H, d, J=7.7Hz), 6.55 (1H, d, J=7.5Hz), 4.53(1H, d, J=11.4Hz), 4.15–4.02(1H, br), 4.03–3.95(1H, m), 3.93(1H, d, J=12.8Hz), 3.82(1H, d, J=12.8Hz), 3.04–2.98(1H, m), 2.45–2.30(1H, m), 2.07–2.03(1H, m), 1.61–1.52(2H, m) | 116.7–119.4 |
| 144 | KBr: 3369, 2931, 1603, 1460, 1045, 704 | CDCl₃: 7.54(2H, d, J=7.5Hz), 7.40–7.28(3H, m), 7.05(1H, dd, J=7.5, 7.5Hz), 6.96(1H, d, J=7.7Hz), 6.52 (1H, d, J=7.3Hz), 4.52(1H, dd, J=11.4, 3.5Hz), 4.09–4.03(1H, m), 3.97–3.88(1H, m), 2.98–2.87(1H, m), 2.62–2.42(4H, m), 2.14–1.98 (2H, m), 1.72–1.38(8H, m) | 139.2–141.9 |

TABLE 6-continued

| Example No. | IR (cm$^{-1}$) | NMR (ppm) (non-mark: 300 MHz, 20° C.; *: 270 MHz, 20° C.; **: 270 MHz, 80° C.) | mp (° C.) |
|---|---|---|---|
| 145 | KBr: 2935, 2823, 1605, 1462, 1261 | DMSO-d$_6$*: 7.50(2H, d, J=6.6Hz), 7.37(2H, dd, J=7.1, 7.1Hz), 7.29 (1H, t, J=7.1Hz), 6.95(1H, dd, J=7.6, 7.6Hz), 6.70(1H, d, J=7.6Hz), 6.41(1H, d, J=7.6Hz), 5.93(1H, d, J=3.3Hz), 4.43(1H, dd, J=11.6, 3.3Hz), 3.99–3.92(1H, m), 3.07–2.95(5H, m), 2.82–2.63(4H, m), 2.06–1.92(2H, m), 1.65–1.54 (2H, m) | 109.7–113.7 |
| 146 | KBr: 3365, 1740, 1605, 1458, 1205, 744, 702 | CDCl$_3$*: 7.55–7.51(2H, m), 7.41–7.27(3H, m), 7.10–7.04(1H, m), 6.84(1H, d, J=7.6Hz), 6.55(1H, d, J=7.6Hz), 4.53(1H, d, J=11.5Hz), 4.13–4.05(1H, m), 4.01–3.93(1H, m), 3.73(3H, s), 3.47(2H, s), 3.04–2.94(1H, m), 2.27–2.18(1H, m), 2.12–2.04(1H, m), 1.68–1.45 (2H, m) | Oil |
| 147 | Neat: 3367, 2960, 1726, 1605, 1464, 1279 | CDCl$_3$*: 7.55(2H, d, J=8.6Hz), 7.44 (1H, dd, J=9.2, 7.6Hz), 7.40–7.28 (2H, m), 7.08–6.95(2H, m), 6.58–6.50(1H, m), 4.52(1H, dd, J=11.4, 3.1Hz), 4.19–4.00(1H, br), 2.97–2.76(1H, m), 2.49–2.32(4H, m), 2.20–2.02(2H, m), 1.61–1.39(6H, m), 0.86(6H, t, J=7.3Hz) | Oil |
| 148 | KBr: 3303, 2921, 1602, 1452, 1107 | CDCl$_3$*: 8.05(1H, br.s), 7.60(2H, d, J=7.9Hz), 7.46(2H, dd, J=7.9, 7.6Hz), 7.31(1H, t, J=7.3Hz), 7.25–7.08(3H, m), 3.95(1H, dd, J=7.1, 4.8Hz), 3.77(4H, dd, J=4.6, 4.6Hz), 3.24(1H, ddd, J=15.6, 5.4, 5.4Hz), 3.01(1H, ddd, J=15.8, 7.9, 5.6Hz), 2.82(2H, dt, J=11.2, 4.6Hz), 2.61 (2H, dt, J=11.2, 4.6Hz), 2.22–2.09 (2H, m) | 191.8–195.5 |
| 149 | KBr: 3407, 1601, 1506, 1446, 1313 | CDCl$_3$*: 8.11(1H, s), 7.61(2H, d, J—7.3Hz), 7.47(2H, dd, J=7.9, 7.6Hz), 7.35–7.09(6H, m), 6.80–6.71 (3H, m), 5.1–4.9(1H, br), 4.0–3.9 (1H, m), 3.18–3.13(2H, m), 2.41–2.31(1H, m), 2.21–2.09(1H, m) | 133.3–134.4 |
| 150 | KBr: 3442, 2958, 1601, 1446, 754 | CDCl$_3$*: 8.00(1H, brs), 7.59(2H, d, J=7.9Hz), 7.46(2H, dd, J=7.9, 7.3Hz), 7.33–7.15(4H, m), 4.28(1H, dd, J=10.9, 3.3Hz), 3.21(1H, ddd, J=15.8, 3.6, 3.6Hz), 3.03(1H, ddd, J=16.1, 11.8, 4.4Hz), 2.64–2.45(4H, m), 2.31–2.25(1H, m), 1.97–1.82 (1H, m), 1.63–1.49(4H, m), 0.91 (6H, t, J=7.4Hz) | 111.3–114.2 |
| 151 | KBr: 3437, 2927, 1601, 1448, 1313 | DMSO-d$_6$*: 11.04(1H, s), 7.70(2H, d, J=8.3Hz), 7.47(2H, dd, J=7.4, 7.4Hz), 7.30(1H, t, J=7.9Hz), 7.14 (1H, d, J=7.6Hz), 7.05(1H, dd, J=7.1, 7.1Hz), 6.94(1H, dd, J=7.9Hz), 4.02–3.95(1H, m), 3.18–2.92(2H, m), 2.78–2.45(4H, m), 2.26–1.80(2H, m), 1.61–1.41(6H, m) | 145.4–149.2 |
| 152 | KBr: 2927, 2831, 1601, 1450, 1315 | CDCl$_3$*: 8.07(1H, s), 7.59(2H, d, J=8.3Hz), 7.45(2H, dd, J=7.6, 7.6Hz), 7.30(1H, t, J=7.4Hz), 7.22 (1H, dd, J=7.6, 1.7Hz), 7.17(1H, dd, J=7.3, 7.3Hz), 7.14–7.11(1H, m), 4.02(1H, dd, J=9.2, 3.6Hz), 3.23(1H, ddd, J=16.2, 5.0, 5.0Hz), 3.07–2.96(5H, m), 2.87–2.79(2H, m), 2.67–2.58(2H, m), 2.25–2.02 (2H, m) | 140.1–144.9 |
| 153 | KBr: 3419, 2920, 1601, 1493, 1450, 1317 | CDCl$_3$*: 8.08(1H, s), 7.61(2H, d, J=6.9Hz), 7.49–7.42(5H, m), 7.37–7.25(4H, m), 7.18(1H, dd, J=7.9, 6.9Hz), 7.05(1H, d, J=6.9Hz), 4.15–4.10(1H, m), 4.01(2H, d, J=5.3Hz), 3.31–3.19(1H, m), 3.12–3.02(1H, m), 2.25–2.15(2H, m) | 37.2–39.8 |
| 154 | KBr: 2980, 2796, 1599, 1452, 1317, 1111, 762, 704 | CDCl$_3$: 7.52–7.35(5H, m), 7.24–7.18 (2H, m), 7.14–7.10(1H, m), 4.15 (2H, q, J=7.2Hz), 3.98(1H, dd, J=8.6, 3.7Hz), 3.78(4H, t, J=4.6Hz), 2.97(1H, d, J=15.6, 5.1Hz), 2.85–2.75(3H, m),2.61(2H, dt, J=11.0, 4.6Hz), 2.20–1.97(2H, m), 1.29(3H, t, J=7.2Hz) | 149.2–151.1 |
| 155 | KBr: 3398, 2926, 1736, 1603, 1450, 1209, 752, 696 | CDCl$_3$*: 8.11(1H, s), 7.60(2H, d, J=7.3Hz), 7.46(2H, dd, J=7.9, 7.6Hz), 7.30(1H, t, J=7.9Hz), 7.26 (1H, d, J=7.9Hz), 7.16(1H, dd, J=8.3, 6.9Hz), 6.98(1H, d, J=6.9Hz), 4.08(1H, t, J=4.1Hz), 3.75(3H, s), 3.59(2H, d, J=3.3Hz), 3.30–3.18(1H, m), 3.09–2.99(1H, m), 2.26–2.06(2H, m) | 107.6–108.5 |
| 156 | KBr: 1635, 1579, 1460, 1381, 1325, 754 | DMSO-d$_6$*: 11.29(1H, s), 7.73(2H, d, J=7.6Hz), 7.50(2H, dd, J=7.6, 7.6Hz), 7.33(1H, t, J=7.6Hz), 7.31 (1H, d, J=7.9Hz), 7.12(1H, dd, J=7.6, 7.6Hz), 6.99(1H, d, J=7.3Hz), 4.49–4.43(1H, m), 3.30–2.97(4H, m), 2.17–2.10(1H, m), 2.09–2.02(1H, m) | 232.0 (Dec.) |
| 157 | KBr: 3305, 1738, 1647, 1448, 1209, 752 | CDCl$_3$*: 8.07(1H, s), 7.62–7.56 (2H, m),7.46(2H, dd, J=7.9, 7.6Hz), 7.31(1H, t, J=7.3Hz), 7.24 (1H, d, J=7.9Hz), 7.18(1H, dd, J=7.9, 6.9Hz), 7.10(1H, d, J=6.9Hz), 4.11(1H, dd, J=9.9, 4.0Hz), 3.87(3H, s), 3.76–3.68(2H, m), 3.49(2H, t, J=4.9Hz), 3.29–3.17 (1H, m), 3.09–2.96(1H, m), 2.95–2.81(2H, m), 2.71–2.60(2H, m), 2.24–2.13(1H, m), 2.11–1.96(1H, m) | 240.5–242.8 |
| 158 | KBr: 3429, 1618, 1450, 1377, 764 | DMSO-d$_6$*: 11.14(1H, s), 7.71(2H, d, J=7.6Hz), 7.48(2H, dd, J=7.9, 7.6Hz), 7.30(1H, t, J=7.3Hz), 7.21 (1H, d, J=7.9Hz), 7.08(1H, dd, J=7.6, 7.3Hz), 6.99(1H, d, J=6.9Hz), 4.15–4.05(1H, m), 3.60–3.23(4H, m), 3.21–2.93(2H, m), 2.85–2.73(2H, m), 2.69–2.52(2H, m), 2.17–1.90(2H, m) | 189.0 (Dec.) |
| 159 | KBr: 3398, 1647, 1450, 1274, 1248, 758 | CDCl$_3$*: 8.09(1H, s), 7.59(2H, d, J=7.3Hz), 7.46(2H, dd, J=7.6, 7.3Hz), 7.35–7.08(4H, m), 4.17(2H, s), 4.15–4.05(1H, m), 3.82–3.70 (2H, m), 3.4–2.6(8H, m), 2.25–2.10 (1H, m), 2.10–2.00(1H, m) | 159.8–161.0 |
| 160 | KBr: 3446, 2935, 1464, 1115, 750 | DMSO-d$_6$*: 7.55–7.47(4H, m), 7.43–7.36(1H, m), 7.26(1H, d, J=8.2Hz), 7.12(1H, dd, J=7.9, 7.0Hz), 6.99 (1H, d, J=7.3Hz), 3.92–3.86(1H, m), 3.67(3H, s), 3.64–3.57(4H, m), 2.94–2.60(4H, m), 2.52–2.44(2H, m), 2.10–1.86(2H, m) | 109.0–111.3 |
| 161 | KBr: 2926, 1659, 1458, 1381, 1325, 793, 702 | CDCl$_3$: 8.10–7.90(1H, m), 7.47–7.27 (5H, m), 7.25(1H, t, J=7.9Hz), 7.09 (1H, d, J=7.7Hz), 5.61–5.56(1H, m), 4.99(1H, d, J=10.3Hz), 3.24(1H, ddd, J=10.6, 10.6, 5.5Hz), 2.62–2.48 (1H, m), 2.38–2.12(1H, m), 2.12–1.95(2H, m), 1.79(3H, brs) | 119.2–121.6 |

TABLE 6-continued

| Example No. | IR (cm$^{-1}$) | NMR (ppm) (non-mark: 300 MHz, 20° C.; *: 270 MHz, 20° C.; **: 270 MHz, 80° C.) | mp (° C.) |
|---|---|---|---|
| 162 | KBr: 3030, 1657, 1456, 1381, 800 | CDCl$_3$*: 8.10–7.85(1H, m), 7.44–7.27(5H, m), 7.27–7.15(1H, m), 6.86–6.75(1H, d, J=7.6Hz), 6.57–6.45(1H, dd, J=9.7, 3.1Hz), 5.99–5.88(1H, m), 5.06–4.94(1H, d, J=8.6Hz), 3.48–3.29(1H, m), 2.62–2.42(1H, m), 2.48–2.17(1H, m), 1.81(3H, brs) | 153.5–155.4 |
| 163 | KBr: 1666, 1466, 1381, 1352, 1325, 797 | CDCl$_3$*: 8.25–7.97(1H, m), 7.47–7.15(7H, m), 4.98(1H, d, J=8.6Hz), 3.87(1H, d, J=4.0Hz), 3.71(1H, dd, J=3.6, 3.0Hz), 3.30–3.17(1H, m), 2.75–2.60(1H, m), 1.83(3H, brs), 1.71–1.50(1H, m) | 183.1–186.8 |
| 164 | KBr: 1707, 1468, 1383, 1325, 700 | CDCl$_3$: 8.2–7.9(1H, m), 7.46–7.22(6H, m), 6.92(1H, d, J=7.5Hz), 5.07(1H, d, J=7.3Hz), 3.68–3.47(1H, m), 3.52(2H, s), 2.97(1H, dd, J=16.3, 5.5Hz), 2.45(1H, dd, J=16.2, 12.6Hz), 1.87(3H, brs) | 111.7–116.3 |
| 165 | KBr: 3371, 1705, 1606, 1466, 763, 754, 700 | DMSO-d$_6$: 7.51(2H, d, J=7.3Hz), 7.39(2H, dd, J=7.5, 7.0Hz), 7.30(1H, t, J=7.2Hz), 6.99(1H, dd, J=7.7, 7.5Hz), 6.46(1H, d, J=7.5Hz), 6.45(1H, d, J=7.5Hz), 6.17(1H, d, J=3.5Hz), 4.71(1H, dd, J=10.8, 3.5Hz), 3.46(1H, d, J=20.7Hz), 3.37(1H, d, J=20.4Hz), 3.37–3.23(1H, m), 2.65(1H, dd, J=15.9, 6.7Hz), 2.58(1H, dd, J=15.9, 10.9Hz) | 129.9–131.8 |
| 166 | KBr: 3365, 2922, 1659, 1624, 1603, 1462, 756, 737, 700 | CDCl$_3$*: 7.60–7.52(2H, m), 7.44–7.25(3H, m), 7.07–6.97(1H, m), 6.60–6.49(2H, m), 4.68–4.54(1H, m), 4.10(1H, brs), 3.24–2.95(2H, m), 2.77–2.55(0.5H, m), 2.47–2.34(0.5H, m), 2.15–2.05(0.5H, m), 2.00–1.80(0.5H, m), 1.80–1.50(1H, m) | 81.3–85.0 |
| 167 | KBr: 3404, 2922, 1603, 1452, 1336, 748, 696 | DMSO-d$_6$: 11.03(1H, brs), 7.70(2H, d, J=7.3Hz), 7.48(2H, dd, J=7.7, 7.7Hz), 7.29(1H, t, J=7.4Hz), 7.11(1H, d, J=7.9Hz), 7.00(1H, dd, J=7.9, 7.2Hz), 6.70(1H, d, J=7.0Hz), 3.30–3.13(2H, m), 3.03–2.93(1H, m), 2.81–2.64(2H, m), 1.96–1.73(2H, br) | 65.8–68.9 |
| 168 | KBr: 3479, 2362, 2224, 1606, 1338 | DMSO-d$_6$: 11.44(1H, s), 7.98(2H, d, J=8.1Hz), 7.94(2H, d, J=8.4Hz), 7.17(1H, d, J=7.6Hz), 7.04(1H, d, J=7.6Hz), 4.15–4.02(1H, m), 3.15–3.00(2H, m), 2.20–2.07(1H, m), 1.96(2H, brs), 1.82–1.68(1H, m) | 213.9–216.7 |
| 169 | KBr: 3388, 3334, 3176, 1612, 1549, 1408 | DMSO-d$_6$: 11.32(1H, s), 8.04(1H, s), 7.98(2H, d, J=8.6Hz), 7.86(2H, d, J=8.4Hz), 7.41(1H, brs), 7.13(1H, d, J=7.7Hz), 7.02(1H, d, J=7.5Hz), 4.15–4.07(1H, m), 3.11–3.02(1H, m), 2.20–2.08(1H, m), 1.92–1.69(3H, m) | 166.7–170.3 |
| 170 | KBr: 3448, 1687, 1641, 1504, 1421 | CD$_3$OD*: 8.03(2H, d, J=8.3Hz), 7.76(2H, d, J=8.6Hz), 7.13(1H, d, J=7.6Hz), 6.99(1H, d, J=7.9Hz), 4.7–4.6(1H, m), 3.2–3.1(1H, m), 2.4–2.2(2H, m) | >300 |
| 171 | KBr: 3365, 1705, 1608, 1452, 1811, 1292 | DMSO-d$_6$: 11.43(1H, s), 8.06(2H, d, J=8.6Hz), 7.95(2H, d, J=8.6Hz), 7.16(1H, d, J=7.7Hz), 7.04(1H, d, J=7.7Hz), 4.19–4.11(1H, m), 3.88(3H, s), 3.20–2.90(4H, m), 2.20–2.08(1H, m), 1.87–1.72(1H, m) | 177.1–180.4 |
| 172 | KBr: 3431, 1651, 1456, 1047, 804 | DMSO-d$_6$: 11.20(1H, s), 7.75(2H, d, J=8.3Hz), 7.42(2H, d, J=8.4Hz), 7.08(1H, d, J=7.7Hz), 7.00(1H, d, J=8.3Hz), 5.25(1H, t, J=5.8Hz), 4.54(2H, d, J=5.5Hz), 4.09(1H, dd, J=8.8, 3.7Hz), 3.03(2H, t, J=6.1Hz), 2.15–2.02(3H, m), 1.81–1.74(1H, m) | 105.7–110.2 |
| 173 | KBr: 3462, 3331, 1614, 1601, 1454, 1284, 835, 759 | DMSO-d$_6$: 10.89(1H, s), 9.59(1H, brs), 7.53(2H, d, J=8.4Hz), 7.13(1H, d, J=7.6Hz), 7.04–6.93(2H, m), 6.87(2H, d, J=8.7Hz), 4.20–4.13(1H, m), 3.05–2.97(2H, m), 2.17–2.06(1H, m), 1.88–1.73(1H, m) | 208.0 (Dec.) |
| 174 | KBr: 3369, 3292, 1454, 1217, 795, 692 | DMSO-d$_6$*: 10.70(1H, s), 7.66(2H, d, J=7.6Hz), 7.45(2H, dd, J=7.9, 7.6Hz), 7.26(1H, t, J=7.5Hz), 6.99(1H, d, J=8.6Hz), 6.48(1H, d, J=8.2Hz), 4.24(1H, dd, J=9.6, 4.4Hz), 3.04–2.95(2H, m), 2.23–2.10(1H, m), 1.92–1.71(1H, m) | 150.0 (Dec.) |
| 177 | KBr: 3444, 3356, 2902, 1603, 1514, 1460 | DMSO-d$_6$: 11.37(1H, s), 8.52–8.28(3H, br), 7.74(2H, d, J=7.2Hz), 7.51(2H, d, J=7.7, 7.7Hz), 7.39–7.30(2H, m), 7.16(1H, dd, J=7.9, 7.2Hz), 7.09(1H, d, J=7.2Hz), 4.72–4.63(1H, m), 3.21–3.10(2H, m), 2.36–2.23(1H, m), 2.23–2.08(1H, m) | 228.9–232.6 |
| 178 | KBr: 3431, 2868, 1601, 1520, 1468, 1373, 748 | DMSO-d$_6$: 8.49(3H, brs), 7.59–7.41(6H, m), 7.24(1H, dd, J=7.9, 7.3Hz), 7.16(1H, d, J=6.9Hz), 4.68(1H, dd, J=6.9, 4.0Hz), 3.73(3H, s), 2.95–2.85(2H, m), 2.30–2.19(1H, m), 2.19–2.05(1H, m) | 224.0 (Dec.) |
| 179 | KBr: 2922, 1599, 1520, 1491, 1458, 1093, 833 | DMSO-d$_6$: 11.63.(1H, s), 8.40(3H, brs), 7.83(2H, d, J=8.4Hz), 7.29(2H, d, J=8.4Hz), 7.26(1H, d, J=7.6Hz), 7.11(1H, d, J=7.6Hz), 4.73–4.65(1H, m), 3.15–3.07(2H, m), 2.35–2.20(1H, m), 2.20–2.05(1H, m) | 257.6–262.8 (Dec.) |
| 180 | KBr: 2879, 1489, 1450, 1092, 1070, 1012 | DMSO-d$_6$: 8.47(3H, brs), 7.64(2H, d, J=8.4Hz), 7.55(2H, d, J=8.7Hz), 7.28(1H, d, J=7.9Hz), 7.13(1H, d, J=6.8Hz), 4.73–4.63(1H, m), 3.94(3H, s), 2.91–2.76(2H, m), 2.30–2.15(1H, m), 2.15–2.00(1H, m) | >300 |
| 181 | KBr: 3376, 2924, 1601, 1462, 1325 | DMSO-d$_6$*: 11.51(1H, s), 10.2–10.0(1H, br), 7.76(2H, d, J=7.6Hz), 7.52(2H, dd, J=7.9, 7.6Hz), 7.42(1H, d, J=6.9Hz), 7.35(1H, t, J=7.6Hz), 7.25–7.16(2H, m), 4.77–4.73(1H, m), 3.30–3.05(2H, m), 2.84(3H, d, J=4.6Hz), 2.80(3H, d, J=4.6Hz), 2.68–2.52(1H, m), 2.29–2.09(1H, m) | 208.5 (Dec.) |
| 182 | KBr: 3427, 1672, 1462, 1300, 1238, 1117, 1018, 748 | CDCl$_3$*: 9.48(1H, brs), 7.65(1H, dd, J=7.6, 1.7Hz), 7.54(1H, d, J=7.9Hz), 7.39(1H, ddd, J=8.7, 6.9, 1.8Hz), 7.23(1H, d, J=7.9Hz), 7.16–7.08(2H, m), 4.02(3H, s), 3.45(2H, t, J=6.9Hz,), 2.96(2H, t, J=7.1Hz) | 101.9–103.0 |
| 183 | KBr: 3446, 2931, 2837, 1464, 1450, 1435, 1238, 1024, 754 | DMSO-d$_6$: 10.92(1H, s), 7.47(1H, dd, J=7.5, 1.8Hz), 7.38(1H, ddd, J=8.7, 6.9, 1.8Hz), 7.14(1H, d, J=7.6Hz), 7.11.–7.02(2H, m), 6.99(1H, d, J=7.6Hz), 4.08(1H, dd, J=8.7, 3.8Hz), 3.84(3H, s), 2.89–2.68(2H, m), 2.14–1.79(3H, m), 1.79–1.51(1H, m) | 105.0–108.9 |

TABLE 6-continued

| Example No. | IR (cm⁻¹) | NMR (ppm) (non-mark: 300 MHz, 20° C.; *: 270 MHz, 20° C.; **: 270 MHz, 80° C.) | mp (° C.) |
|---|---|---|---|
| 184 | KBr: 2941, 1466, 1439, 1317, 1257, 1236, 1022, 920, 760 | DMSO-d₆: 10.66(1H, s), 7.48(1H, dd, J=7.6, 1.6Hz), 7.33(1H, ddd, J=8.6, 7.9, 1.6Hz), 7.19–7.10(2H, m), 7.08–6.94(3H, m), 4.09(1H, dd, J=8.8, 3.9Hz), 3.86(3H, s), 2.99–2.71(2H, m), 2.14–2.00(1H, m), 1.87(2H, brs), 1.82–1.64(2H, m) | 160.3–162.1 |
| 185 | KBr: 3412, 2927, 1456, 1284, 1240, 1111, 750 | DMSO-d₆: 7.45(1H, dd, J=7.6, 1.6Hz), 7.23(1H, d, J=7.7Hz), 7.16 (1H, ddd, J=8.5, 6.8, 1.7Hz), 7.07–6.96(3H, m), 6.91(1H, dd, J=7.5, 7.5Hz), 4.25(1H, dd, J=8.3, 3.9Hz), 3.05–2.83(2H, m), 2.21–2.05(1H, m), 1.93–1.76(1H, m) | 168.0 (Dec.) |
| 186 | KBr: 1697, 1653, 1591, 1462, 1385, 1327, 766 | CDCl₃*: 8.55–8.10(1H, m), 7.59 (1H, d, J=7.6Hz), 7.55–7.44(1H, m), 7.44–7.32(2H, m), 7.29–7.12(2H, m), 5.65–5.30(1H, br), 3.62–3.41(1H, m), 2.87–2.73(1H, m), 2.65–2.40 (2H, m), 2.24–2.06(1H, m) | 184.0–187.2 |
| 187 | KBr: 2926, 1659, 1458, 1381, 1325, 793, 702 | CDCl₃: 8.10–7.90(1H, br), 7.47–7.27(5H, m), 7.25(1H, dd, J=7.9, 7.9Hz), 7.09(1H, d, J=7.7Hz), 5.61–5.56(1H, m), 4.99(1H. d, J=10.3Hz), 3.24(1H, ddd, J=10.7, 10.7, 5.4Hz), 2.62–2.48(1H, m), 2.38–2.12(1H, m), 2.11–1.95(2H, m), 1.79(3H, brs) | 119.2–121.6 |
| 188 | KBr: 1655, 1458, 1383, 1319, 1034, 798, 760, 744 | CDCl₃: 8.11–7.89(1H, m), 7.60–7.04(5.6H, m), 6.81–6.66(0.4H, m), 5.99(0.4H, d, J=9.2Hz), 5.73(0.6H, d, J=9.9Hz), 5.70–5.60(0.6H, m), (0.4H, m), 3.96–3.80 (0.4H, m), 3.42–3.16(0.6H, m), 2.69–1.92(3.6H, m), 1.78(3H, brs), 0.92–0.78(0.4H, m) | 165.5–167.2 |
| 189 | KBr: 1653, 1458, 1385, 1327, 1230, 793, 768 | CDCl₃: 8.20–7.75(1H, m), 7.56–7.41(1H, m), 7.39–7.06(5H, m), 5.62–5.39(1H, m), 5.39–5.26(1H, m), 3.45–3.17(1H, m), 2.69–2.47 (1H, m), 2.42–2.00(3H, m), 1.85 (3H, brs) | 156.8–158.1 |
| 190 | KBr: 2962, 2935, 1653, 1456, 1385, 802, 750, 704 | CDCl₃*: 8.30–7.70(1H, br), 7.45–7.29(5H, m), 7.21(1H, dd, J=7.9, 7.9Hz), 7.08(1H, d, J=7.6Hz), 4.88 (1H, d, J=8.9Hz), 3.84(1H, t, J=6.6Hz), 3.26(1H, dd, J=16.0, 9.1Hz), 2.69–2.46(4H, m), 2.29–2.15 (1H, m), 1.99–1.50(10H, m) | 74.1–76.0 |
| 191 | KBr: 1664, 1456, 1389, 1350, 1313, 1113, 798 | CDCl₃: 8.18–7.83(1H, br), 7.60–6.95(6H, m), 5.59(1H, d, J=9.0Hz), 4.00–3.55(5H, m), 3.25–3.10(1H, m), 2.70–2.45(4H, m), 2.45–2.20 (2H, m), 2.15–1.40(5H, m) | 135.7–140.8 |
| 192 | KBr: 1662, 1495, 1456, 1379, 1352, 1315, 1115, 804 | CDCl₃*: 8.20–7.80(1H, br), 7.55–7.39(1H, m), 7.39–7.06(5H, m), 5.45–5.15(1H, m), 3.97–3.88(1H, m), 3.77–3.59(4H, m), 3.27–3.13 (1H, m), 2.67–2.43(4H, m), 2.36–2.13(2H, m), 2.08–1.49(5H, m) | 168.0–172.6 |
| 193 | KBr: 2937, 1653, 1637, 1458, 1383, 1352, 1051, 756, 702, | CDCl₃*: 8.10–7.80(1H, br), 7.45–7.20(7H, m), 4.85(1H, d, J=9.6Hz), 4.03–3.82(1H, m), 3.74–3.58(1H, m), 3.19–2.88(1H, m), 2.82–2.65 (2H, m), 2.58–2.41(2H, m), 2.33–1.29(11H, m) | 176.2–179.0 |
| 194 | KBr: 2935, 1732, 1653, 1458, 1385, 1188, 702 | CDCl₃*: 8.09–7.82(1H, br), 7.47–7.17(7H, m), 4.85(1H, d, J=9.5Hz), 4.12(2H, q, J=7.1Hz), 4.00–3.92 (1H, m), 3.18–3.07(1H, m), 2.88–2.78(1H, m), 2.76–2.67(1H, m), 2.48(1H, d, J=2.9, 11.1Hz), 2.30–1.52(13H, m), 1.24(3H, t, J=7.1Hz) | 111.5–113.3 |
| 195 | KBr: 3398, 2937, 2864, 1662, 1458, 1389, 1036 | CDCl₃*: 8.15–7.85(1H, m), 7.60–7.04(5.5H, m), 6.80–6.70(0.5H, m), 6.03–5.91(0.5H, m), 5.68–5.56 (0.5H, m), 4.18–3.35(7H,m), 3.22–2.88(0.5H, m), 2.84–2.64(2.5H, m), 2.64–1.40(8.5H, m), 0.91–0.71 (0.5H, m) | 79.8–84.5 |
| 196 | KBr: 3298, 2927, 1664, 1456, 1379, 1030, 806, 762 | CDCl₃*: 8.20–7.80(1H, m), 7.54–7.41(1H, m), 7.36–7.08(5H, m), 5.40–5.20(1H, m), 4.20–3.97(1H, m), 3.72–3.52(4H, m), 3.25–2.95(1H, m), 2.80–2.70(4H, m), 2.30–2.17 (2H, m), 1.95–1.60(5H,m) | 148.154.4 |
| 197 | Neat: 1747, 1666, 1458, 1381, 1190, 1039 | CDCl₃*: 8.20–7.80(1H, br), 7.52–7.17(7H, m), 4.85(1H, d, J=9.6Hz), 4.30–3.90(3H, m), 3.50–2.88(3H, m), 2.42(3H, s), 2.28–2.03(2H, m), 1.80(3H, brs), 1.70–1.55(2H, m), 1.46–1.20(3H, m) | Oil |
| 198 | KBr: 1745, 1655, 1456, 1383, 1228, 1203, 768 | CDCl₃*: 8.10–7.80(1H, m), 7.50–7.42(1H, m), 7.36–6.98(5H, m), 5.40–5.20(1H, m), 4.02–3.95(0.5H, m), 3.80–3.75(0.5H, m), 3.76 and 3.73(total 3H, s), 3.56(0.5H, d, J=17.5Hz), 3.49(0.5H, d, J=17.5Hz), 3.44(1H, s), 3.34–3.04(1H, m), 2.31–2.14(1H, m), 2.05–1.55(6H, m) | 95.8–99.6 |
| 199 | KBr: 3371, 2943, 2789, 1605, 1462, 739, 702 | CDCl₃*: 7.55(2H, d, J=7.3Hz), 7.38 (2H, dd, J=7.6, 6.6 Hz), 7.33(1H, t, J=6.9Hz), 7.04(1H, dd, J=7.6, 7.6Hz), 6.93–6.84(1H, m), 6.56(1H, d, J=7.6Hz), 4.65–4.50(1H, m), 4.15–3.73(2H, m), 3.07–2.80(1H, m), 2.78–2.58(4H, m), 2.18–1.90 (2H, m), 1.82–1.55(6H, m) | 108.0–110.0 |
| 200 | KBr: 2931, 2854, 1605, 1462, 1250, 1115, 752 | CDCl₃: 8.00–7.95(1H, m), 7.40–7.20 (2H, m), 7.17–6.90(3H, m), 6.58–6.52(1H, m), 5.18–5.11(1H, m), 4.15–3.90(2H, m), 3.80–3.50(4H, m), 3.05–2.80(1H, m), 2.69–2.47 (4H, m), 2.4–2.0(2H, m), 2.0–1.4 (2H, m) | 65.9–69.8 |
| 201 | KBr: 2929, 2854, 1489, 1458, 1228, 1115, 758 | CDCl₃*: 7.78–7.60(1H, m), 7.32–7.15(2H, m), 7.12–7.05(1H, m), 7.05(1H, d, J=8.2Hz), 6.97(1H, dd, J=7.9, 7.6Hz), 6.59–6.53(1H, m), 4.96–4.87(1H, m), 4.05–3.90(2H, m), 3.30–3.63(4H, m), 3.07–2.80 (1H, m), 2.70–2.47(4H, m), 2.40–2.00(2H, m), 1.75–1.35(2H, m) | 64.0–67.9 |
| 202 | KBr: 3365, 2933, 2854, 1605, 1462, 1055, 746, 702 | CDCl₃*: 7.54(2H, d, J=6.9Hz), 7.42–7.25(3H, m), 7.12–6.95(2H, m), 6.58–6.52(1H, m), 4.58–4.50 (1H, m), 4.15–3.60(2H, m), 2.97–1.25(13H, m) | 99.0–103.9 |
| 203 | KBr: 3338, 2935, 2864, 1605, 1460, 1443, 1034, 752 | CDCl₃*: 8.01–7.94(0.5H, m), 7.43–6.79(5.5H, m), 6.63–6.51(1H, m), 5.53–5.41(0.5H, m), 5.25–5.12 (0.5H, m), 4.24–3.82(2H, m), 3.76–3.48(6H, m), 3.42–3.32(0.5H, m), 3.08–2.66(4.5H, m), 2.55–1.44 (3.5H, m), 0.93–0.55(0.5H, m) | 61.7–63.3 |
| 204 | KBr: 3348, 2935, 2860, 1489, 1458, 1228, 1034, 760 | CDCl₃*: 7.90–7.81(1H, m), 7.33–7.00(4H, m), 6.89(1H, d, J=7.9Hz), 6.62–6.53(1H, m), 4.92(1H, d, J=11.9Hz), 4.15–3.93(2H, m), 3.75–3.48(4H, m), 3.10–2.70(5H, m), 2.35–2.10(2H, m), 1.80–1.50(2H, m) | Amorphous |

TABLE 6-continued

| Example No. | IR (cm⁻¹) | NMR (ppm) (non-mark: 300 MHz, 20° C.; *: 270 MHz, 20° C.; **: 270 MHz, 80° C.) | mp (° C.) |
|---|---|---|---|
| 205 | KBr: 1740, 1489, 1458, 1228, 1207, 760 | CDCl$_3$*: 7.84(1H, dd, J=7.6, 7.3Hz), 7.33–7.14(2H, m), 7.13–7.02 (2H, m), 6.97–6.88(1H, m), 6.59 (1H, d, J=7.6Hz), 4.98(0.5H, d, J=11.5Hz), 4.92(0.5H, d, J=11.2Hz), 4.25–3.93(1H, m), 3.90–3.71(1H, m), 3.77 and 3.74(total 3H, s), 3.61–3.50(2H, m), 3.14–2.88(1H, m), 2.50–1.89(4H, m), 1.89–1.53 (1H, m) | Oil |
| 206 | KBr: 2931, 1740, 1456, 1257, 1203, 1136, 748, 704 | CDCl$_3$*: 7.58–7.49(2H, m), 7.43–7.24(3H, m), 7.08(1H, dd, J=7.6, 7.6Hz), 6.89–6.82(1H, m), 6.56(1H, d, J=7.6Hz), 4.59(0.5H, d, J=11.9Hz), 4.53(0.5H, d, J=11.2Hz), 4.23 and 4.18(total 2H, q, J=7.1Hz), 4.02–3.92(0.5H, m), 3.76–3.71(0.5H, m), 3.52(1H, s), 3.46 (1H, s), 3.07–2.78(1H, m), 2.29–2.17(0.5H, m), 2.14–1.98(1H, m), 1.90–1.45(4.5H, m), 1.31 and 1.27 (total 3H, t, J=7.1Hz) | Oil |
| 207 | KBr: 2931, 1730, 1462, 1261, 1171, 1047, 744, 702 | CDCl$_3$: 7.58–7.50(2H, m), 7.42–7.27 (3H, m), 7.05(1H, dd, J=7.6, 6.8Hz), 6.93(1H, d, J=7.9HZ), 6.53 (1H, d, J=7.3Hz), 4.52(1H, d, J=11.4Hz), 4.12(2H, q, J=7.1Hz), 4.00–3.93(1H, m), 2.98–2.68(3H, m), 2.53(1H, ddd, J=11.1, 11.1, 2.9Hz), 2.32–1.51(11H, m), 1.25 (3H, t, J=7.1Hz) | Oil |
| 208 | Neat: 3365, 2937, 2929, 1747, 1606, 1464, 1188, 1041 | CDCl$_3$*: 7.58–7.50(2H, m), 7.44–7.24(3H, m), 7.11–7.01(1H, m), 6.97(1H, d, J=7.9Hz), 6.56(0.3H, d, J=6.9Hz), 6.54(0.7H, d, J=7.3Hz), 4.57(0.3H, d, J=9.2Hz), 4.53(0.7H, d, J=11.5Hz), 4.17 (0.6H, q, J=7.1Hz), 4.16(1.4H, q, J=7.1Hz), 4.23–4.02(0.7H, m), 3.94–3.88(0.3H, m), 3.35(0.7H, d, J=16.5 Hz), 3.28(0.3H, d, J=18.8Hz), 3.20(0.3H, d, J=16.5Hz), 3.16(0.7H, d, J=16.5Hz), 3.00–2.73 (1H, m), 2.44(1.4H, s), 2.38(0.6H, s), 2.32–1.93(3H, m), 1.67–1.32 (2H, m), 1.27(0.9H, t, J=7.3Hz), 1.25(2.1H, t, J=7.1Hz) | Oil |
| 209 | KBr: 1450, 1325, 1250, 1113, 1036, 1005, 752 | CDCl$_3$*: 8.54(1H, brs), 7.56–7.48 (2H, m), 7.38–7.11(5H, m), 3.99 (1H, dd, J=8.6, 4.0Hz), 3.78(4H, dd, J=4.6, 4.6Hz), 3.06(1H, ddd, J=15.8, 5.3, 5.3Hz), 2.94–2.79(3H, m), 2.61(2H, dt, J=11.2, 4.6Hz), 2.23–2.03(2H, m) | 163.5–167.2 |
| 210 | KBr: 3321, 2958, 2941, 1458, 1300, 1211, 1107, 1001, 758 | CDCl$_3$*: 8.54(1H, brs), 7.70–7.64 (1H, m), 7.33–7.09(6H, m), 3.95 (1H, dd, J=7.3, 4.9Hz), 3.77(4H, dd, J=4.6, 4.6Hz), 3.22(1H, ddd, J=15.8, 5.5, 5.5Hz), 3.05–2.94(1H, m), 2.82(2H, dt, J=11.5, 4.6Hz), 2.60(1H, dt, J=11.5, 4.6Hz), 2.19–2.11(2H, m) | 175.6–177.0 |
| 211 | KBr: 3367, 1711, 1450, 1196, 1138, 1047, 744 | DMSO-d$_6$: 11.06(1H, s), 7.70(2H, d, J=7.6Hz), 7.47(2H, dd, J=7.6, 7.6Hz), 7.29(1H, t, J=7.5Hz), 7.15 (1H, d, J=7.9Hz), 7.06(1H, dd, J=8.1, 7.1Hz), 6.94(1H, d, J=7.0Hz), 4.07(2H, q, J=6.8Hz), 4.04–3.98(1H, m), 3.18–3.08(1H, m), 3.05–2.93(1H, m), 2.91–2.80(2H, m), 2.69–2.57(1H, m), 2.38–2.10 (3H, m), 1.93–1.76(3H, m), 1.74–1.52(2H, m), 1.19(3H, t, J=7.2Hz) | 175.8–178.6 |
| 212 | KBr: 3446, 3304, 2926, 2864, 1448, 1026, 1016, 762 | CDCl$_3$*: 8.34(1H, brs), 7.54–7.48 (2H, m), 7.39–7.20(5H, m), 4.33 (1H, dd, J=10.7, 3.8Hz), 3.80–3.62 (4H, m), 3.05–2.81(6H, m), 2.35–2.24(1H, m), 2.12–1.95(1H, m) | 182.9–184.5 |
| 213 | — | CDCl$_3$*: 8.56(1H, brs), 7.68–7.59 (1H, m), 7.33–7.15(6H, m), 4.33 (1H, dd, J=10.2, 3.6Hz), 3.81–3.62 (4H, m), 3.26–2.82(6H, m), 2.47–2.23(3H, m), 2.15–1.97(1H, m) | — |
| 214 | KBr: 3390, 2935, 1734, 1448, 1190, 1032, 752, 694 | CDCl$_3$*: 8.06(1H, s), 7.59(2H, d, J=6.9Hz), 7.45(2H, dd, J=7.9, 7.6Hz), 7.30(1H, t, J=7.4Hz), 7.25–7.15(3H, m), 4.28(1H, dd, J=9.2, 3.6Hz), 4.21(2H, q, J=7.1Hz), 3.50 (1H, d, J=16.5Hz), 3.27(1H, d, J=16.5Hz), 3.22(1H, ddd, J=15.8, 5.1, 5.1Hz), 3.03(1H, ddd, J=15.8, 9.9, 4.5Hz), 2.61(3H, s), 2.30–2.19 (1H, m), 2.05–1.90(1H, m), 1.29 (3H, t, J=7.3Hz) | Oil |
| 215 | KBr: 2960, 2927, 2787, 1450, 1319, 750, 694 | CDCl$_3$*: 8.06(1H, brs), 7.61(2H, d, J=7.3Hz), 7.45(2H, dd, J=7.6, 7.6Hz), 7.34–7.23(2H, m), 7.13(1H, dd, J=7.9, 7.3Hz), 6.97(1H, d, J=7.3Hz), 3.70–3.55(1H, m), 3.36–3.22(1H, m), 3.07–2.40(6H, m), 2.07–1.90(1H, m), 1.90–1.72(5H, m) | 79.5–80.9 |
| 216 | KBr: 2927, 1450, 1315, 1059, 752, 694 | CDCl$_3$*: 8.03(1H, s), 7.60(2H, d, J=7.8Hz), 7.46(2H, dd, J=7.9, 7.6Hz), 7.30(1H, t, J=7.6Hz), 7.22 (1H, d, J=7.3Hz), 7.18(1H, dd, J=7.6, 6.8Hz), 7.16–7.11(1H, m), 4.12(1H, dd, J=9.7, 3.8Hz), 3.77–3.65(1H, m), 3.23(1H, ddd, J=15.8, 4.7, 4.7Hz), 3.10–2.84(3H, m), 2.75–2.65(1H, m), 2.40–2.30(1H, m), 2.28–2.17(1H, m), 2.08–1.87 (3H, m), 1.77–1.55(2H, m) | 118.5–121.3 |
| 217 | — | CDCl$_3$: 8.10(1H, brs), 7.61(2H, d, J=7.9Hz), 7.46(2H, dd, J=7.9, 7.5Hz), 7.31(1H, t, J=7.5Hz), 7.27 (1H, d, J=8.1Hz), 7.16(1H, dd, J=8.2, 7.1Hz), 6.98(1H, d, J=7.0Hz), 4.21(2H, q, J=7.1Hz), 4.08(1H, dd, J=4.0, 4.0Hz), 3.62 (1H, d, J=17.1Hz), 3.55(1H, d, J=17.1Hz), 3.25(1H, ddd, J=15.5, 10.5, 4.7Hz), 3.04(1H, ddd, J=16.1, 4.9, 4.9Hz), 2.28–2.18 (1H, m), 2.18–2.05(1H, m), 1.29 (3H, t, J=7.2Hz) | — |
| 218 | — | CDCl$_3$*: 8.61(1H, brs), 7.72–7.66 (1H, m), 7.33–7.15(5H, m), 6.98 (1H, d, J=6.9Hz), 4.08(1H, dd, J=4.6, 3.6Hz), 3.75(3H, s), 3.63 (1H, d, J=17.5Hz), 3.56(1H, d, J=17.5Hz), 3.24(1H, ddd, J=15.8, 10.3, 4.9Hz), 3.02(1H, ddd, J=15.8, 4.9, 4.9Hz), 2.29–2.06(2H, m) | — |
| 219 | KBr: 1768, 1437, 1323, 1228, 754, 689 | DMSO-d$_6$: 11.46(1H, s), 9.77–9.58 (1H, br), 9.50–9.27(1H, br), 7.75 (2H, d, J=7.3Hz), 7.52(2H, dd, J=7.7, 7.7Hz), 7.41(1H, d, J=7.7Hz), 7.35(1H, t, J=7.5Hz), 7.18(1H, dd, J=7.5, 7.2Hz), 7.14 (1H, d, J=6.6Hz), 4.75–4.67(1H, m), 4.19(1H, d, J=15.0Hz), 3.99(1H, d, J=15.0Hz), 3.28–3.04(2H, m), 2.58–2.46(1H, m), 2.26–2.12(1H, m) | 179.0 (Dec.) |

TABLE 6-continued

| Example No. | IR (cm⁻¹) | NMR (ppm) (non-mark: 300 MHz, 20° C.; *: 270 MHz, 20° C.; **: 270 MHz, 80° C.) | mp (° C.) |
|---|---|---|---|
| 220 | KBr: 2927, 2848, 1458, 1364, 1317, 1115, 750 | CDCl₃*: 7.56–7.51(1H, m), 7.42–7.34(3H, m), 7.24–7.13(3H, m), 4.02(1H, dd, J=9.1, 3.8Hz), 3.78 (4H, dd, J=4.6, 4.6Hz), 3.55(3H, s), 2.91–2.65(4H, m), 2.61(2H, dt, J=11.2, 4.6Hz), 2.23–1.97(2H, m) | 64.8–68.9 |
| 221 | KBr: 1458, 1363, 1319, 1244, 1215, 1115, 758 | CDCl₃*: 7.45–7.37(2H, m), 7.29–7.11(5H, m), 3.99(1H, dd, J=8.6, 4.0Hz), 3.77(4H, dd, J=4.6, 4.0Hz), 3.64 and 3.63(total 3H, s), 2.93 (1H, ddd, J=15.8, 5.3, 4.9Hz), 2.86–2.71(3H, m), 2.61(2H, dt, J=11.2, 4.6Hz), 2.21–2.00(2H, m) | 86.8–90.2 |
| 222 | KBr: 2927, 1757, 1471, 1375, 1223, 1211, 752 | CDCl₃*: 7.52–7.33(5H, m), 7.25–7.16(2H, m), 7.04–6.94(1H, m), 4.20 (2H, q, J=7.2Hz), 4.12–4.05(1H, m), 3.71(3H, s), 3.61(1H, d, J=17.2Hz), 3.53(1H, d, J=17.2Hz), 3.14–2.99(1H, m), 2.89–2.75(1H, m), 2.23–1.99(2H, m), 1.29(3H, t, J=7.1Hz) | 171.0 (Dec.) |
| 223 | KBr: 2937, 1741, 1470, 1429, 1365, 1205, 752, 704 | DMSO-d₆: 7.61–7.50(5H, m), 7.50–7.42(1H, m), 7.26(1H, dd, J=7.9, 7.3Hz), 7.19(1H, d, J=7.0Hz), 4.75–4.68(1H, m), 4.02(1H, d, J=16.7Hz), 3.83(1H, d, J=17.1Hz), 3.75(3H, s), 3.09–2.96(1H, m), 2.89–2.77(1H, m), 2.54–2.41(1H, m), 2.22–2.07(1H, m) | 143.5–145.2 |
| 224 | KBr: 3217, 1576, 1450, 1398, 1323, 756, 694 | DMSO-d₆*: 11.16(1H, s), 7.72(2H, d, J=7.3Hz), 7.48(2H, dd, J=7.9, 7.6Hz), 7.30(1H, t, J=7.5Hz), 7.22 (1H, d, J=7.5Hz), 7.09(1H, dd, J=7.6, 7.3Hz), 6.99(1H, d, J=7.5Hz), 4.28–4.04(1H, m), 3.60–2.86(4H, m), 2.81–1.53(9H, m) | 187.0 (Dec.) |
| 225 | KBr: 1734, 1458, 1321, 1263, 1205, 760, 696 | DMSO-d₆**: 11.30(1H, s), 10.18–9.90(1H, br), 7.76(2H, d, J=7.3Hz), 7.50(2H, dd, J=7.9, 7.3Hz), 7.42(1H, d, J=8.3Hz ), 7.33 (1H, t, J=7.5Hz), 7.28–7.12(2H, m), 4.82–4.65(1H, m), 3.62(3H, s), 3.69–2.72(8H, m), 2.72–2.56(1H, m), 2.27–1.93(4H, m) | 179.0 (Dec.) |
| 226 | KBr: 3325, 1450, 1319, 1144, 1109, 854, 758, 690 | CDCl₃*: 8.05(1H, brs), 7.60(2H, d, J=7.9Hz), 7.46(2H, dd, J=7.9, 7.6Hz), 7.31(1H, t, J=7.3Hz), 7.25–7.08(3H, m), 3.95(1H, dd, J=7.1, 4.8Hz), 3.77(4H, dd, J=4.6, 4.6Hz), 3.24(1H, ddd, J=15.6, 5.4, 5.4Hz), 3.01(1H, ddd, J=15.8, 7.9, 5.6Hz), 2.82(2H, dt, J=11.2, 4.6Hz), 2.61 (2H, d, J=11.2, 4.6Hz), 2.22–2.09 (2H, m) | 207.3–208.6 |
| 227 | KBr: 3325, 1450, 1319, 1144, 1109, 854, 758, 690 | CDCl₃*: 8.05(1H, brs), 7.60(2H, d, J=7.9Hz), 7.46(2H, dd, J=7.9, 7.6Hz), 7.31(1H, t, J=7.3Hz), 7.25–7.08(3H, m), 3.95(1H, dd, J=7.1, 4.8Hz), 3.77(4H, dd, J=4.6, 4.6Hz), 3.24(1H, ddd, J=15.6, 5.4, 5.4Hz), 3.01(1H, ddd, J=15.8, 7.9, 5.6Hz), 2.82(2H, dt, J=11.2, 4.6Hz), 2.61 (2H, d, J=11.2, 4.6Hz), 2.22–2.09 (2H, m) | 206.2–207.9 |
| 228 | KBr: 2852, 1456, 1319, 1211, 1111, 754 | CDCl₃*: 8.54(1H, brs), 7.70–7.64 (1H, m), 7.33–7.09(6H, m), 3.95 (1H, dd, J=7.3, 4.9Hz), 3.77(4H, dd, J=4.6, 4.6Hz), 3.22(1H, ddd, J=15.8, 5.5, 5.5Hz), 3.05–2.94(1H, m), 2.82(2H, dt, J=11.5, 4.6Hz), 2.60(2H, dt, J=11.5, 4.6Hz), 2.19–2.11(2H, m) | Amorphous |
| 229 | KBr: 2852, 1456, 1319, 1211, 1111, 754 | CDCl₃*: 8.54(1H, brs), 7.70–7.64 (1H, m), 7.33–7.09(6H, m), 3.95 (1H, dd, J=7.3, 4.9Hz), 3.77(4H, dd, J=4.6, 4.6Hz), 3.22(1H, ddd, J=15.8, 5.5, 5.5Hz), 3.05–2.94(1H, m), 2.82(2H, dt, J=11.5, 4.6Hz), 2.60(2H, dt, J=11.5, 4.6Hz), 2.19–2.11(2H, m) | Amorphous |
| 230 | KBr: 2927, 2848, 1464, 1115, 748, 702 | CDCl₃*: 7.52–7.34(5H, m), 7.24–7.09(3H, m), 3.97(1H, dd, J=8.1, 4.1Hz), 3.77(4H, dd, J=4.6, 4.6Hz), 3.71(3H, s), 3.03(1H, ddd, J=16.1, 5.4, 5.4Hz), 2.90–2.78(3H, m), 2.60 (2H, d, J=11.2, 4.8Hz), 2.18–2.03 (2H, m) | Amorphous |
| 231 | KBr: 2927, 2848, 1464, 1115, 748, 702 | CDCl₃*: 7.52–7.34(5H, m), 7.24–7.09(3H, m), 3.97(1H, dd, J=8.1, 4.1Hz), 3.77(4H, dd, J=4.6, 4.6Hz), 3.71(3H, s), 3.03(1H, ddd, J=16.1, 5.4, 5.4Hz), 2.90–2.78(3H, m), 2.60 (2H, dt, J=11.2, 4.8Hz), 2.18–2.03 (2H, m) | Amorphous |
| 232 | KBr: 3197, 1458, 1325, 1213, 1126, 1090, 758 | DMSO-d₆*: 11.42(1H, s), 10.10–9.80 (1H, br), 7.67(1H, dd, J=7.6, 7.3Hz), 7.53–7.31(4H, m), 7.26–7.11 (2H, m), 4.78–4.62(1H, m), 4.08–3.56(4H, m), 3.56–2.69(7H, m), 2.11–1.93(1H, m) | 161.0 (Dec.) |
| 233 | KBr: 3269, 1637, 1458, 1213, 756, 702 | DMSO-d₆*: 11.15(1H, s), 7.65(1H, dd, J=7.6, 7.6Hz), 7.48–7.27(4H, m), 7.14(1H, dd, J=7.9, 7.3Hz), 7.04(1H, d, J=6.9Hz), 4.25–4.15 (1H, m), 3.76–3.65(4H, m), 3.08–2.75(6H, m), 2.34–2.18(1H, m), 2.12–1.98(1H, m) | 135.3–137.5 |
| 234 | KBr: 3439, 2877, 1522, 1454, 1410, 1267, 793 | DMSO-d₆*: 11.38(1H, s), 8.39–8.28 (3H, br), 7.77(2H, d, J=7.9Hz), 7.48(2H, dd, J=7.9, 7.6Hz), 7.32 (1H, t, J=7.6Hz), 7.02(1H, d, J=8.1Hz), 6.73(1H, d, J=8.1Hz), 14.65–4.55(1H, m), 3.94(3H, s), 13.14–3.02(2H, m), 2.27–2.07(2H, m) | 214.0 (Dec.) |
| 235 | KBr: 3388, 2922, 1605, 1508, 1458, 1373, 750 | DMSO-d₆*: 10.90(1H, s), 10.03 (1H, s), 8.39(3H, brs), 7.45(1H, d, J=7.6Hz), 7.37(1H, d, J=7.6Hz), 7.23–6.98(5H, m), 6.93(1H, dd, J=7.6, 7.6Hz), 4.73–4.63(1H, m), 3.06–2.97(2H, m), 2.30–2.05(2H, m) | 213.0 (Dec.) |
| 236 | KBr: 3161, 1450, 1323, 1124, 1084, 758, 694 | DMSO-d₆*: 11.56(1H, s), 10.7–10.2 (1H, br), 7.76(2H, d, J=7.3Hz), 7.51(2H, dd, J=7.9, 7.6Hz), 7.45 (1H, dd, J=6.8, 1.8Hz), 7.34(1H, t, J=7.4Hz), 7.23–7.12(2H, m), 4.75–4.64(1H, m), 4.05–3.56(5H, m), 3.46–2.98(5H, m), 2.90–2.72(1H, m), 2.15–1.98(1H, m) | 202.0 (Dec.) |
| 237 | KBr: 1471, 1450, 1427, 1124, 1072, 930, 750, 702 | DMSO-d₆: 10.6–10.1(1H, br), 7.61–7.41(6H, m), 7.31–7.19(2H, m), 4.77–4.67(1H, m), 4.03–3.53(5H, m), 3.75(3H, s), 3.46–2.99(4H, m), 2.86–2.69(2H, m), 2.09–1.92(1H, m) | 209.0 (Dec.) |
| 238 | KBr: 3180, 1456, 1338, 1323, 1126, 1088, 1049, 1038, 756 | DMSO-d₆: 11.41(1H, s), 10.40–10.20 (1H, br), 7.66–7.59(2H, m), 7.52–7.45(3H, m), 7.26–7.22(2H, m), 4.77–4.68(1H, m), 4.01–3.01(9H, m), 2.85–2.69(2H, m), 2.12–1.99 (1H, m) | 165.4–167.8 |
| 239 | KBr: 1464, 1439, 1367, 1261, 1126, 1078, 891, 756 | DMSO-d₆: 10.25–10.07(1H, br), 7.75–7.65(1H, m), 7.63–7.49(4H, m), 7.35–7.23(2H, m), 4.79–4.72 (1H, m), 4.03–3.87(2H, m), 3.85–3.71(2H, m), 3.59 and 3.58(total 3H, s), 3.60–3.10(4H, m), 3.01–2.57 (3H, m), 2.14–1.98(1H, m) | 191.8–193.9 |

TABLE 6-continued

| Example No. | IR (cm$^{-1}$) | NMR (ppm) (non-mark: 300 MHz, 20° C.; *: 270 MHz, 20° C.; **: 270 MHz, 80° C.) | mp (° C.) |
|---|---|---|---|
| 240 | KBr: 3365, 2933, 1468, 1456, 1365, 1126, 760 | DMSO-d$_6$*: 10.44–10.22(1H, br), 7.63–7.51(3H, m), 7.48–7.35(2H, m), 7.33–7.23(2H, m), 4.82–4.71(1H, m), 4.05–3.72(4H, m), 3.72–3.07(4H, m), 3.64(3H, s), 3.07–2.90(1H, m), 2.85–2.62(2H, m), 2.13–1.96(1H, m) | 143.5–145.2 |
| 241 | KBr: 3230, 1456, 1338, 1323, 1066, 1053, 1036, 756 | DMSO-d$_6$*: 11.40(1H, brs), 9.5–9.3(1H, br), 7.67–7.56(2H, m), 7.53–7.44(2H, m), 7.40(1H, d, J=7.9Hz), 7.32(1H, d, J=6.9Hz), 7.22(1H, dd, J=7.9, 7.3Hz), 5.6–5.3(2H, br), 5.40–5.20(1H, m), 3.98–3.73(4H, m), 3.50–3.20(4H, m), 3.03–2.82(2H, m), 2.58–2.23(2H, m) | 118.9–121.2 |
| 242 | KBr: 3209, 1458, 1423, 1209, 1053, 758, 743 | DMSO-d$_6$*: 11.40(1H, brs), 9.7–9.5(1H, br), 7.73–7.63(1H, m), 7.51–7.30(5H, m), 7.22(1H, dd, J=7.6, 7.6Hz), 5.30–5.10(1H, m), 3.99–3.73(4H, m), 3.60–3.15(4H, m), 3.15–2.90(1H, m), 2.60–2.24(2H, m) | 118.0 (Dec.) |
| 243 | KBr: 1761, 1458, 1373, 1331, 1228, 1213, 756 | DMSO-d$_6$*: 11.36(1H, s), 9.99–9.68(1H, br), 9.68–9.39(1H, br), 7.71–7.63(1H, m), 7.52–7.33(4H, m), 7.26–7.16(2H, m), 4.82–4.67(1H, m), 4.17(1H, d, J=16.2Hz), 3.98(1H, d, J=16.2Hz), 3.76(3H, s), 3.18–3.02(1H, m), 2.98–2.83(1H, m), 2.61–2.43(1H, m), 2.18–2.08(1H, m) | 187.0 (Dec.) |
| 244 | KBr: 1751, 1433, 1367, 1217, 1209, 748 | DMSO-d$_6$: 9.99–9.74(1H, br), 9.64–9.39(1H, br), 7.70–7.40(6H, m), 7.32–7.16(2H, m), 4.80–4.68(1H, m), 4.21(2H, q, J=7.1Hz), 4.14(1H, d, J=16.3Hz), 3.94(1H, d, J=16.3Hz), 3.75(3H, s), 3.15–2.98(1H, m), 2.92–2.75(1H, m), 2.54–2.43(1H, m), 2.23–2.06(1H, m), 1.11(3H, t, J=7.2Hz) | 152.1–154.3 |
| 245 | KBr: 1757, 1745, 1379, 1228, 1215, 771, 750, 698 | DMSO-d$_6$: 11.45(1H, s), 7.75(2H, d, J=7.5Hz), 7.52(2H, dd, J=7.9, 7.5Hz), 7.42–7.36(2H, m), 7.20–7.12(2H, m), 4.72–4.65(1H, m), 4.22(2H, q, J=7.1Hz), 4.16(1H, d, J=17.4Hz), 3.94(1H, d, J=17.4Hz), 3.44–3.03(2H, m), 2.69–2.45(1H, m), 2.25–2.10(1H, m), 1.25(3H, t, J=7.1Hz) | 184.0 (Dec.) |
| 246 | KBr: 3186, 1751, 1462, 1381, 1219, 1022, 756, 696 | DMSO-d$_6$**: 11.25(1H, s), 7.75(2H, d, J=7.3Hz), 7.49(2H, dd, J=7.9, 7.6Hz), 7.39(1H, dd, J=6.3, 2.3Hz), 7.33(1H, t, J=7.5Hz), 7.25–7.10(2H, m), 4.92–4.80(1H, m), 4.20(2H, q, J=7.2Hz), 4.12(1H, d, J=16.8Hz), 3.98(1H, d, J=16.5Hz), 3.54–3.04(2H, m), 2.82(3H, s), 2.62–2.40(1H, m), 2.30–2.15(1H, m), 1.24(3H, t, J=7.1Hz) | 180.0 (Dec.) |
| 247 | KBr: 3203, 2927, 1456, 1325, 1126, 758 | DMSO-d$_6$*: 11.42(1H, s), 10.10–9.80(1H, br), 7.67(1H, dd, J=7.6, 7.3Hz), 7.53–7.31(4H, m), 7.26–7.11(2H, m), 4.78–4.62(1H, m), 4.08–3.56(4H, m), 3.56–2.69(7H, m), 2.11–1.93(1H, m) | 159.8–160.0 |
| 248 | KBr: 3203, 2927, 1456, 1325, 1126, 758 | DMSO-d$_6$*: 11.42(1H, s), 10.10–9.80(1H, br), 7.67(1H, dd, J=7.6, 7.3Hz), 7.53–7.31(4H, m), 7.26–7.11(2H, m), 4.78–4.62(1H, m), 4.08–3.56(4H, m), 3.56–2.69(7H, m), 2.11–1.93(1H, m) | 160.3–162.2 |
| 249 | KBr: 1666, 1458, 1383, 808, 764 | CDCl$_3$*: 8.12–7.85(1H, m), 7.50–7.05(5H, m), 6.83(1H, d, J=7.6Hz), 6.54(1H, dd, J=9.6, 2.6Hz), 5.98(1H, ddd, J=9.6, 6.3, 2.6Hz), 5.57–5.34(1H, m), 3.53–3.33(1H, m), 2.62(1H, dt, J=16.2, 6.6Hz), 2.34(1H, t, J=16.2Hz), 1.85(3H, brs) | 122.4–124.1 |
| 250 | KBr: 1664, 1470, 1398, 1385, 798, 783, 770 | CDCl$_3$: 8.27–8.03(1H, br), 7.46–7.06(6H, m), 5.52–5.32(1H, m), 3.88(1H, d, J=3.9Hz), 3.72(1H, t, J=3.2Hz), 3.33–3.18(1H, m), 2.79(1H, ddd, J=13.8, 6.7, 1.9Hz), 1.85(3H, brs), 1.69(1H, dd, J=13.6, 12.1Hz) | 145.7–147.1 |
| 251 | KBr: 1716, 1655, 1462, 1387, 1354, 770 | CDCl$_3$*: 8.20–7.93(1H, br), 7.48–7.08(5H, m), 6.93(1H, d, J=7.6Hz), 5.48(1H, d, J=6.6Hz), 3.68–B.55(1H, m), 3.53(2H, s), 3.07(1H, dd, J=16.5, 5.1Hz), 2.48(1H, dd, J=16.5, 12.9Hz), 1.92(3H, brs) | 172.1–174.8 |
| 252 | KBr: 3363, 1695, 1628, 1489, 1470, 758 | CDCl$_3$*: 7.82(1H, dt, J=7.4, 1.8Hz), 7.35–7.03(5H, m), 6.62(1H, t, J=6.9Hz), 5.14(1H, dd, J=10.6, 3.6Hz), 4.21–4.11(1H, m), 3.55–3.40(1H, m), 3.49(2H, s), 3.00(1H, ddd, J=15.8, 5.6, 1.7Hz), 2.57(1H, dd, J=16.0, 12.4Hz) | 149.7–151.2 |
| 253 | neat: 3354, 2978, 1632, 1606, 1493, 1119 | CDCl$_3$*: 7.85(0.5H, ddd, J=7.9, 7.6, 1.8Hz), 7.83(0.5H, ddd, J=7.9, 7.6, 1.8Hz), 7.35–6.96(4H, m), 6.62–6.49(2H, m), 4.99(0.5H, d, J=5.0Hz), 4.94(0.5H, d, J=5.3Hz), 4.03(1H, brs), 3.73(2H, t, J=4.6Hz), 3.66(2H, t, J=4.6Hz), 3.31–3.18(0.5H, m), 3.13–2.45(7.5H, m), 2.37–2.22(1H, m), 1.75(0.5H, ddd, J=14.0, 9.8, 4.4Hz), 1.67–1.50(0.5H, m) | Amorphous |
| 254 | KBr: 3319, 1454, 1111, 1005, 748 | CDCl$_3$*: 8.56–8.44(1H, m), 7.70–7.60(1H, m), 7.35–7.10(5H, m), 6.86(1H, d, J=6.3Hz), 3.79(4H, t, J=4.6Hz), 3.30–2.98(5H, m), 2.87–2.70(4H, m) | 189.8–190.9 |
| 255 | KBr: 3336, 2457, 1612, 1456, 756 | DMSO-d$_6$*: 11.24(1H, s), 10.98(1H, brs), 7.65(1H, dd, J=7.9, 7.7Hz), 7.51–7.30(3H, m), 7.23(1H, d, J=8.1Hz), 7.10(1H, dd, J=7.7, 7.2Hz), 6.84(1H, d, J=6.8Hz), 4.09–3.73(5H, m), 3.67–3.12(8H, m) | 179.6–181.0 |
| 256 | KBr: 3373, 1603, 1452, 1315, 1026, 752 | DMSO-d$_6$: 11.04(1H, s), 7.71(2H, d, J=7.3Hz), 7.47(2H, dd, J=7.9, 7.6Hz), 7.28(1H, t, J=7.5Hz), 7.17(1H, d, J=7.9Hz), 7.05(1H, dd, J=8.0, 6.9Hz), 6.93(1H, d, J=7.1Hz), 5.13(1H, d, J=5.7Hz), 4.95–4.85(1H, m), 3.14–2.98(2H, m), 2.16–2.04(2H, m), 2.00–1.87(1H, m) | 132.9–134.2 |

The structural formulae of the compounds of Examples 1 to 257 were shown in Table 8. The respective abbreviations used in the structural formulae of Table 8 represent the substituents shown in Table 7.

TABLE 7
| Abbreviation | Substituent |
|---|---|
| —Ac | —COCH$_3$ |
| —Bn | —CH$_2$–Ph (benzyl) |
| —Boc | —COOC(CH$_3$)$_3$ |
| —Bz | —CO–Ph (benzoyl) |
| —Et | —CH$_2$CH$_3$ |
| —Me | —CH$_3$ |
| —Ph | phenyl |
| —Pr | —CH$_2$CH$_2$CH$_3$ |
TABLE 8-1
Example 1 Step 1
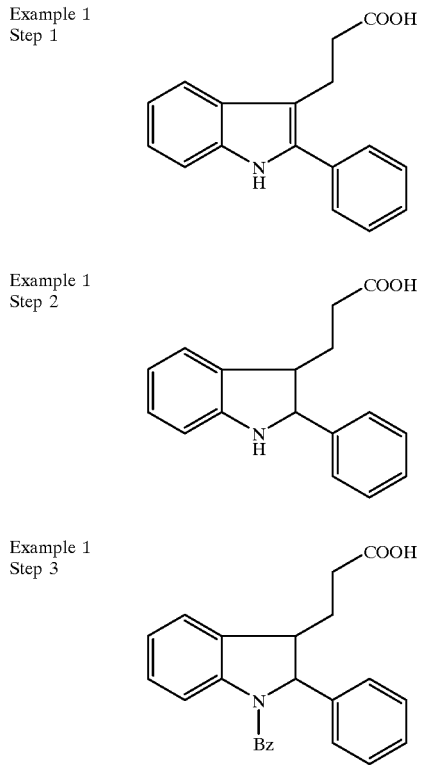
Example 1 Step 2
Example 1 Step 3
TABLE 8-1-continued
Example 1 Step 4
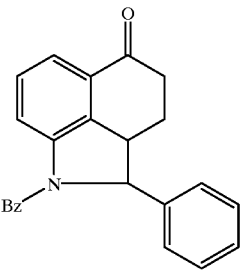
Example 2 Step 1
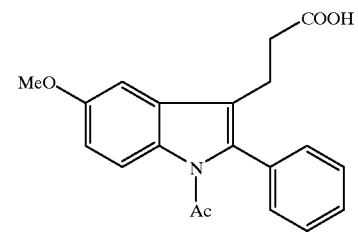
Example 2 Step 2
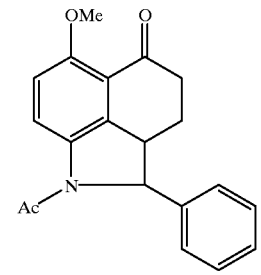
Example 3 Step 1
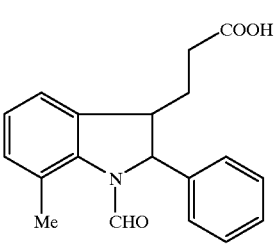
Example 3 Step 2
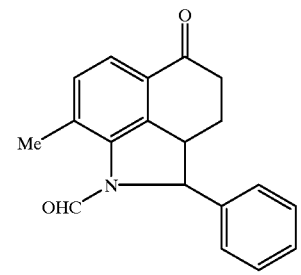
Example 4 Step 1
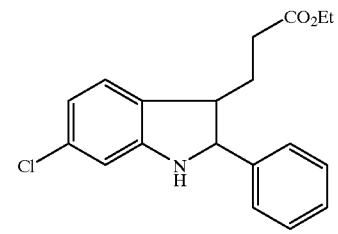

TABLE 8-1-continued
| Example 4 Step 2 | 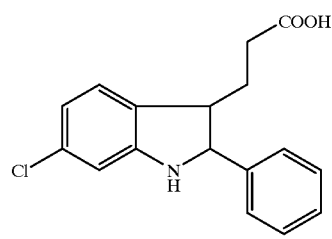 |
| --- | --- |
| Example 4 Step 3 | 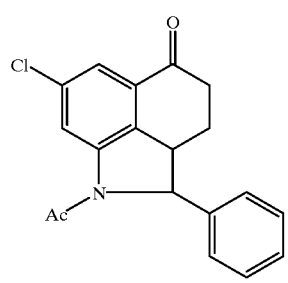 |
| Example 5 | 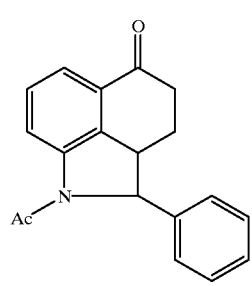 |
TABLE 8-2
| Example 6 | 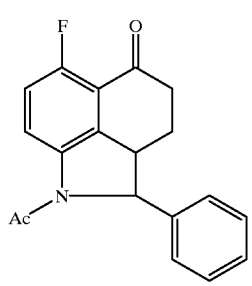 |
| --- | --- |
| Example 7 | 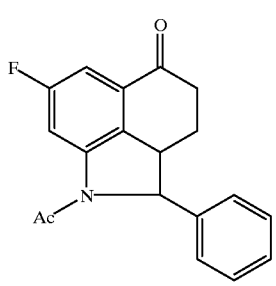 |
TABLE 8-2-continued
| Example 8 | 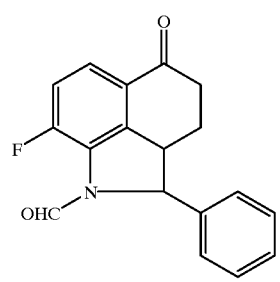 |
| --- | --- |
| Example 9 | 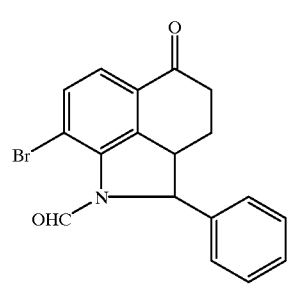 |
| Example 10 | 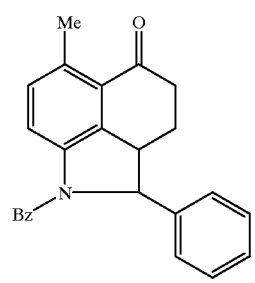 |
| Example 11 | 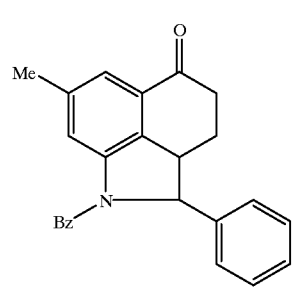 |
| Example 12 | 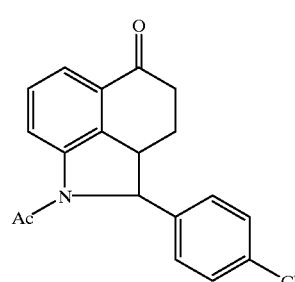 |

TABLE 8-2-continued
Example 13 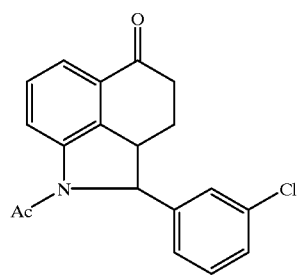
Example 14 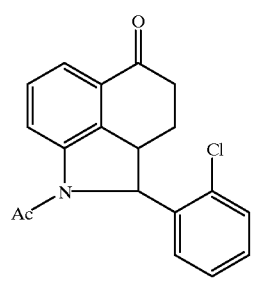
Example 15 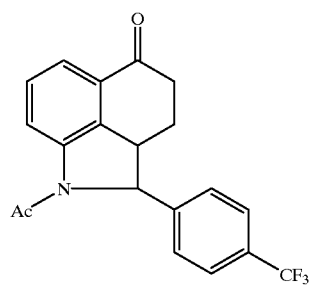
Example 16 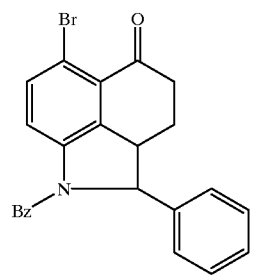
Example 17 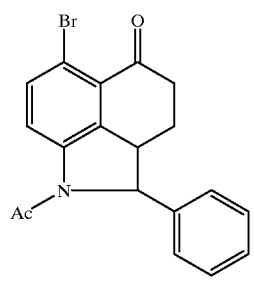
TABLE 8-3
Example 18 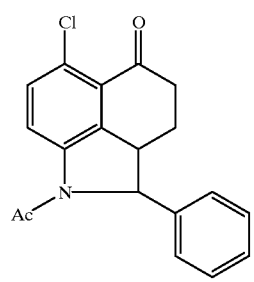
Example 19 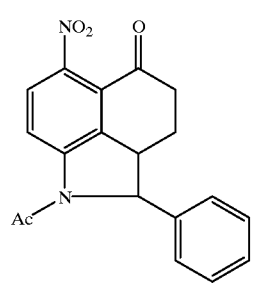
Example 20 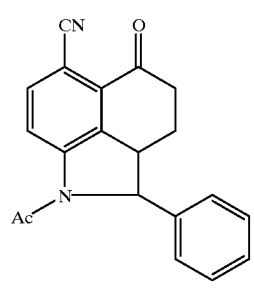
Example 21 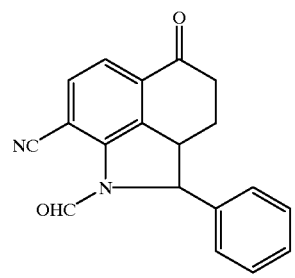
Example 22 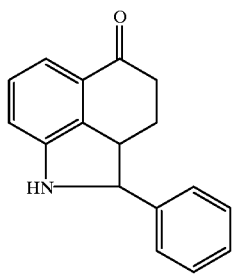

TABLE 8-3-continued
Example 23 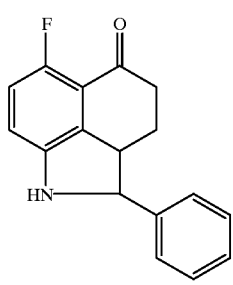
Example 24 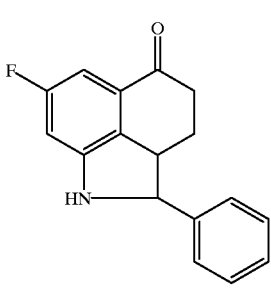
Example 25 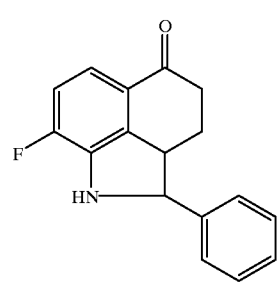
Example 26 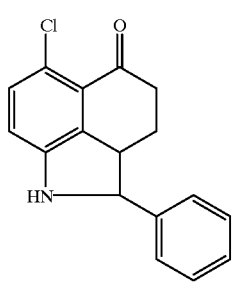
Example 27 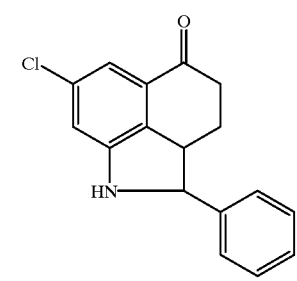
TABLE 8-3-continued
Example 28 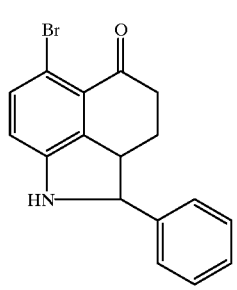
Example 29 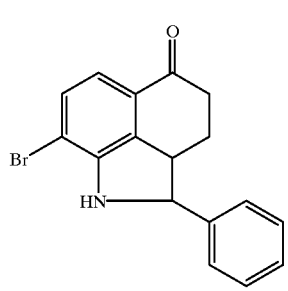
TABLE 8-4
Example 30 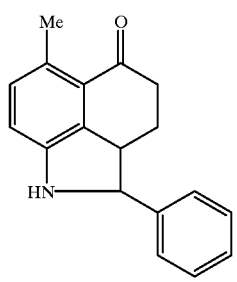
Example 31 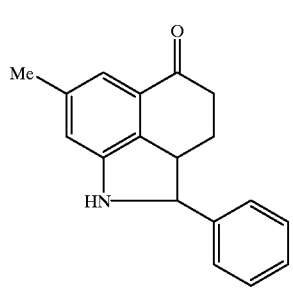
Example 32 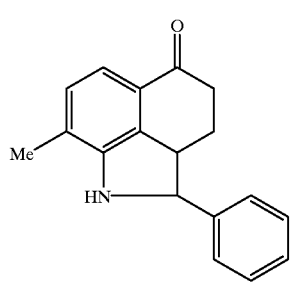

TABLE 8-4-continued
Example 33 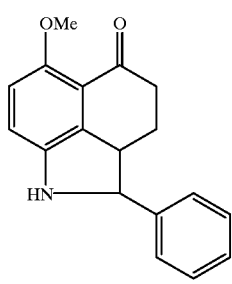
Example 34 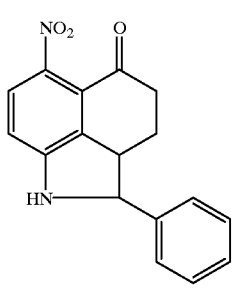
Example 35 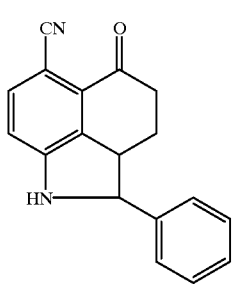
Example 36 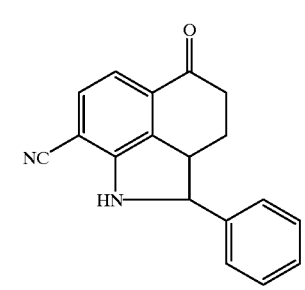
Example 37 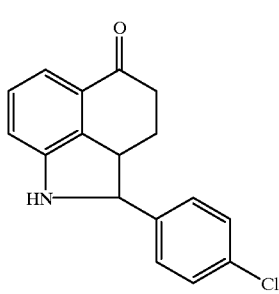
TABLE 8-4-continued
Example 38 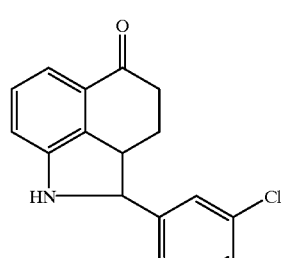
Example 39 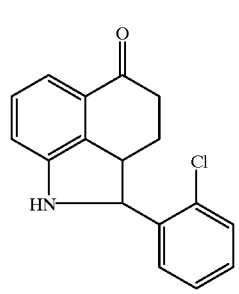
Example 40 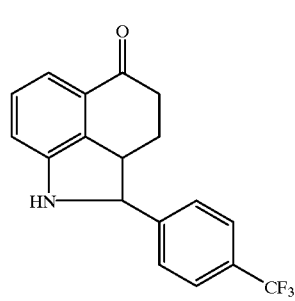
Example 41 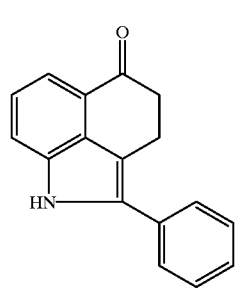
TABLE 8-5
Example 42 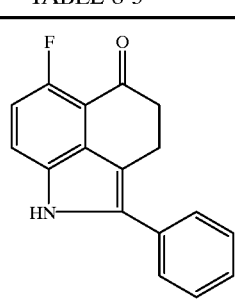

TABLE 8-5-continued
Example 43
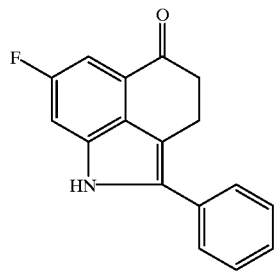
Example 44
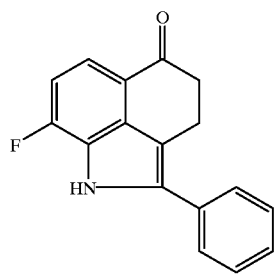
Example 45
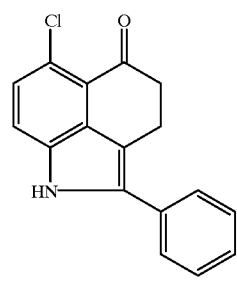
Example 46
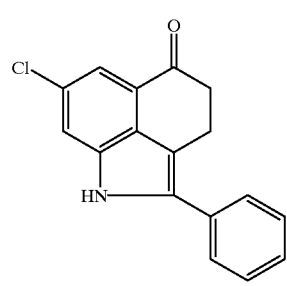
Example 47
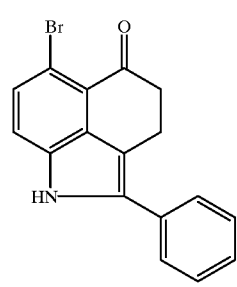
TABLE 8-5-continued
Example 48
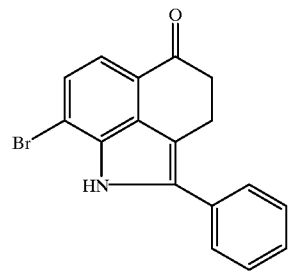
Example 49
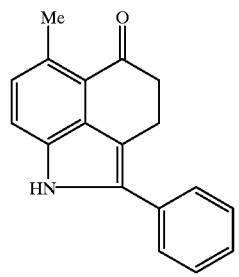
Example 50
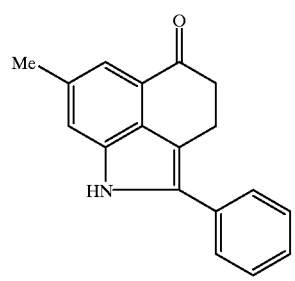
Example 51
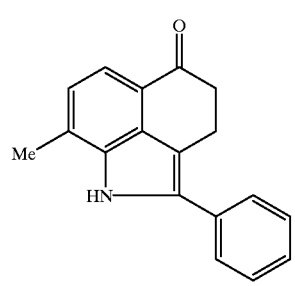
Example 52
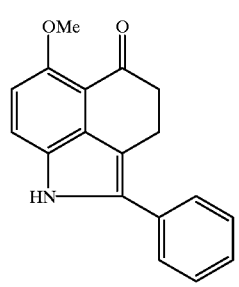

113
TABLE 8-5-continued
Example 53
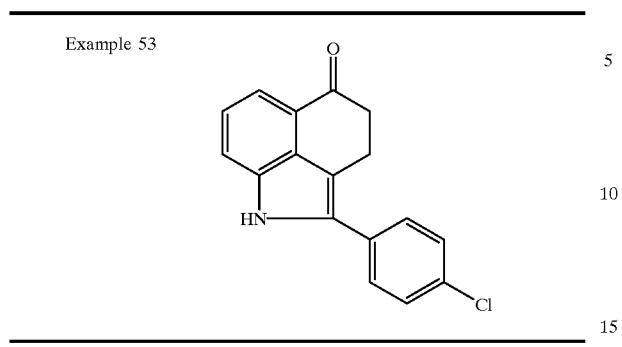
TABLE 8-6
Example 54
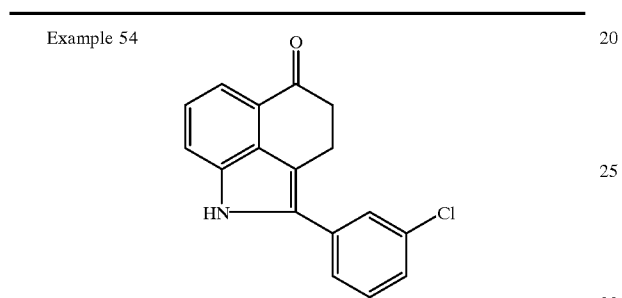
Example 55
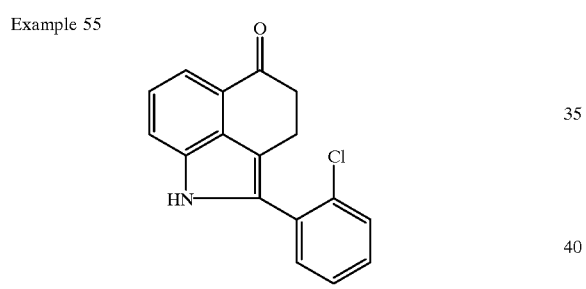
Example 56
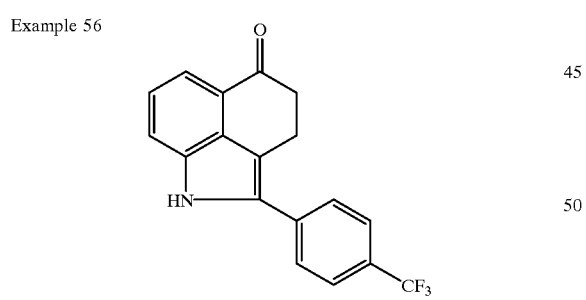
Example 57
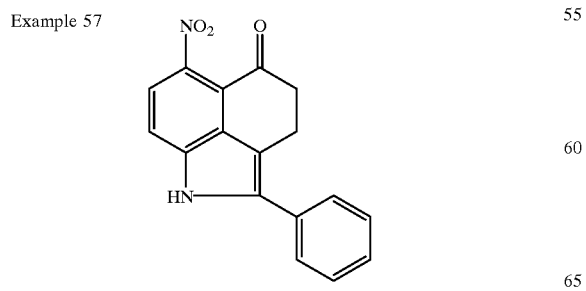
114
TABLE 8-6-continued
Example 58
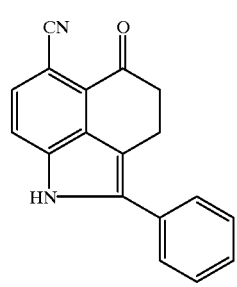
Example 59
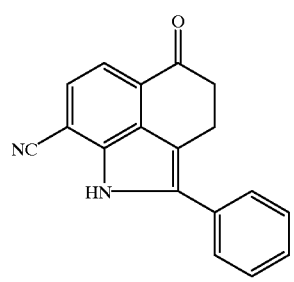
Example 60
Step 1
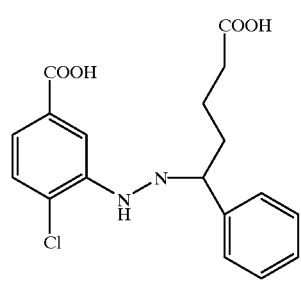
Example 60
Step 2
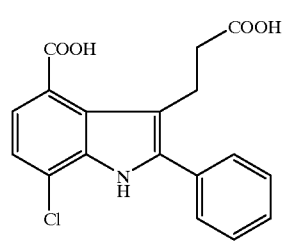
Example 60
Step 3
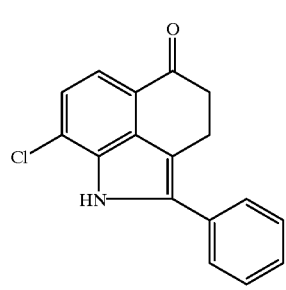

TABLE 8-6-continued
Example 61
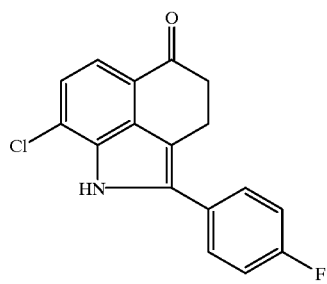
Example 62
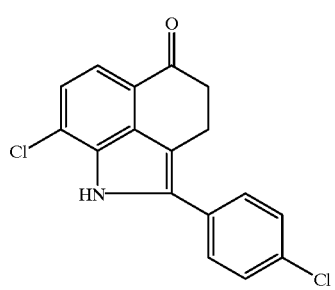
Example 63
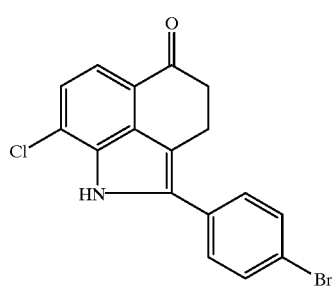
TABLE 8-7
Example 64
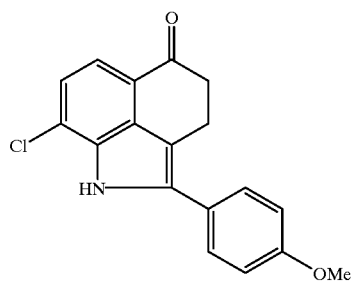
Example 65
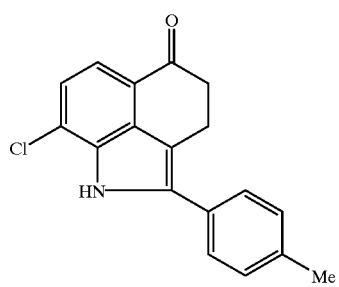
TABLE 8-7-continued
Example 66
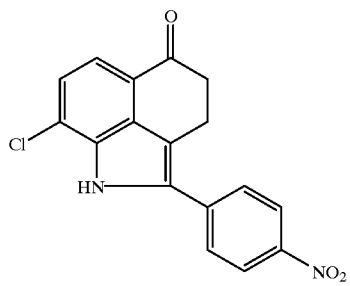
Example 67
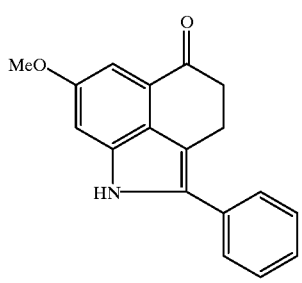
Example 68
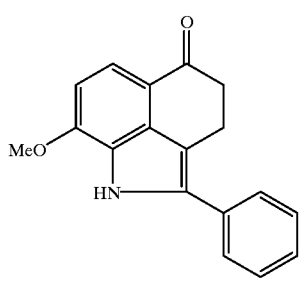
Example 69
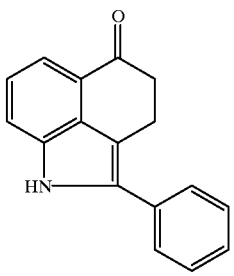
Example 70
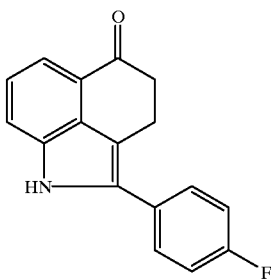

TABLE 8-7-continued
Example 71
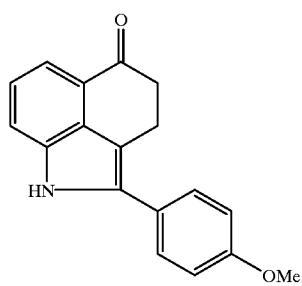
Example 72
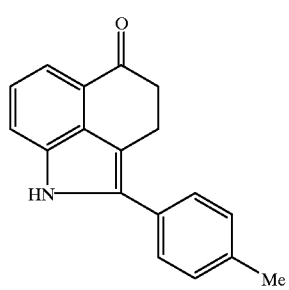
Example 73
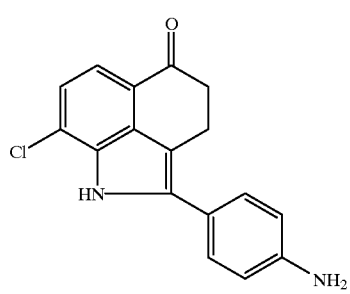
Example 74
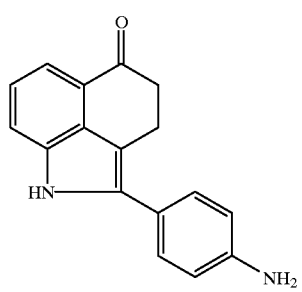
Example 75
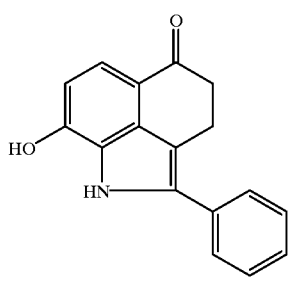
TABLE 8-8
Example 76
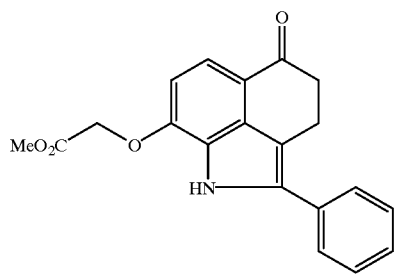
Example 77
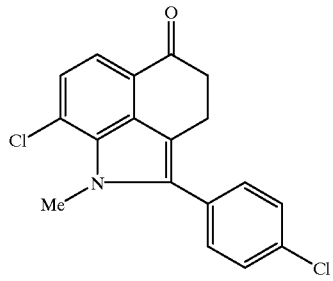
Example 78
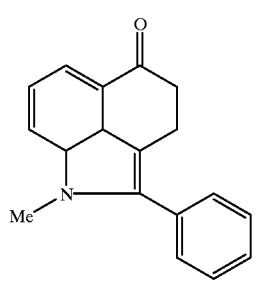
Example 79
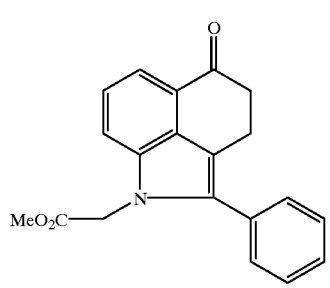
Example 80
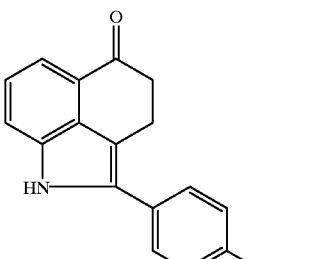

TABLE 8-8-continued
Example 81
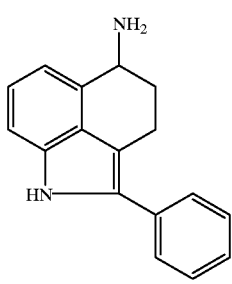
Example 82
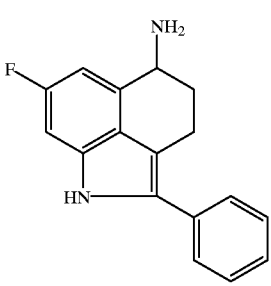
Example 83
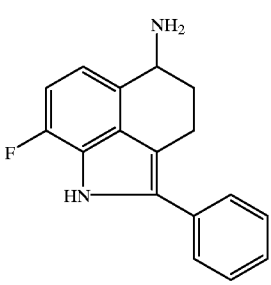
Example 84
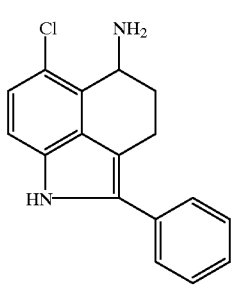
Example 85
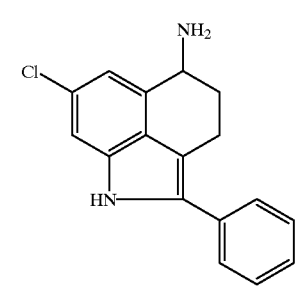
TABLE 8-8-continued
Example 86
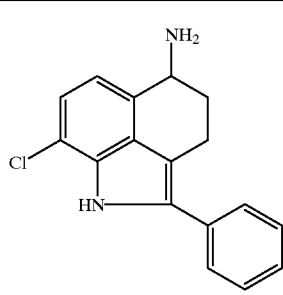
Example 87
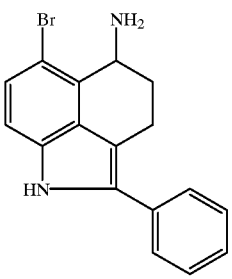
TABLE 8-9
Example 88
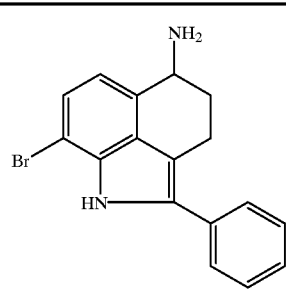
Example 89
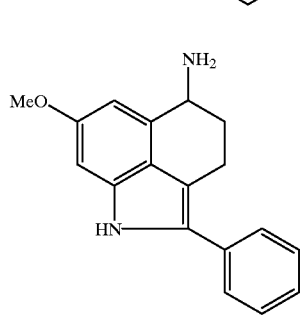
Example 90
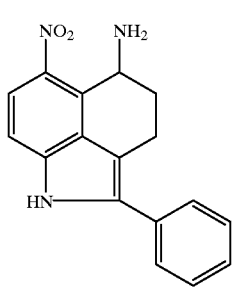

TABLE 8-9-continued
Example 91 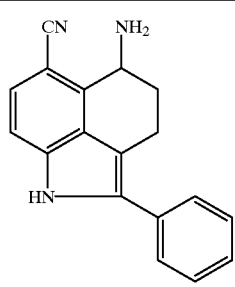
Example 92 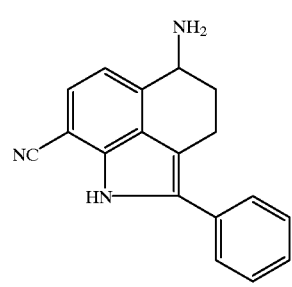
Example 93 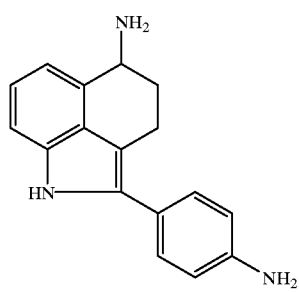
Example 94 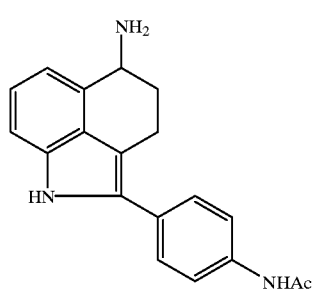
Example 95 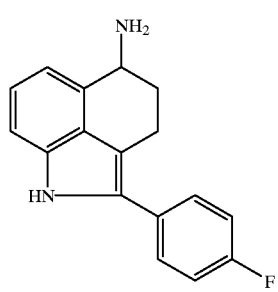
TABLE 8-9-continued
Example 96
Example 97
Example 98
Example 99
TABLE 8-10
Example 100 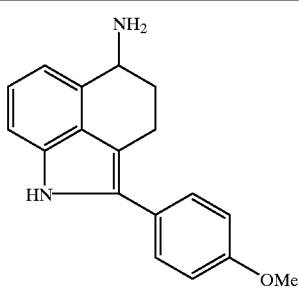

TABLE 8-10-continued
Example 101 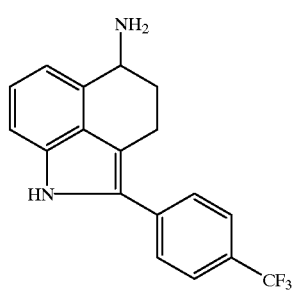
Example 102 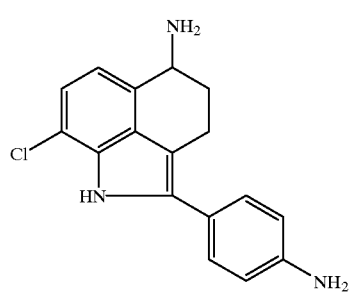
Example 103 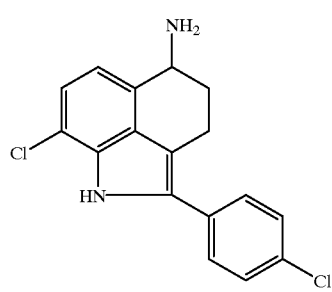
Example 104 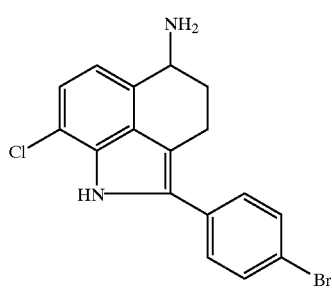
Example 105 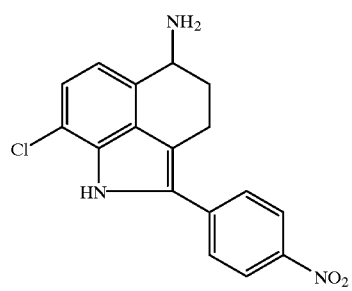
TABLE 8-10-continued
Example 106 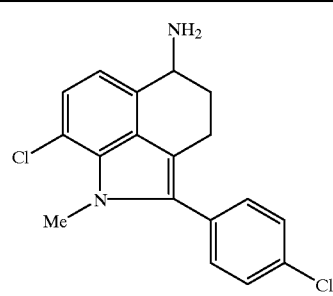
Example 107 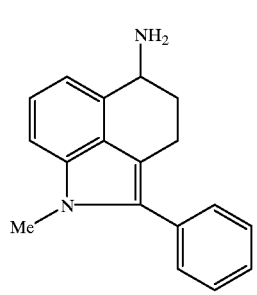
Example 108 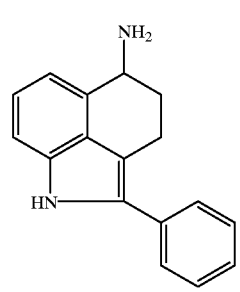
Example 109 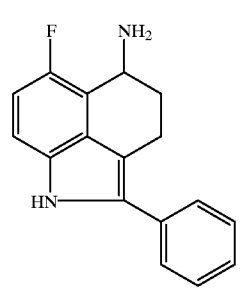
Example 110 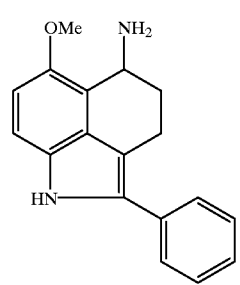

TABLE 8-10-continued
Example 111
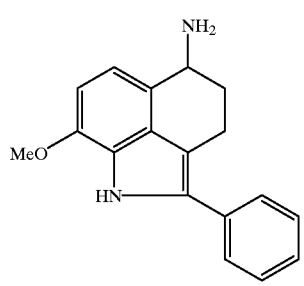
TABLE 8-11
Example 112
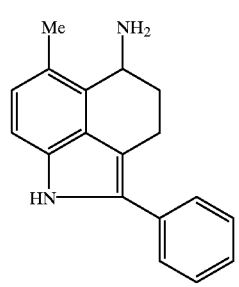
Example 113
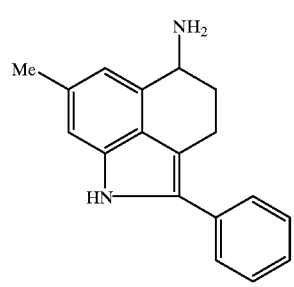
Example 114
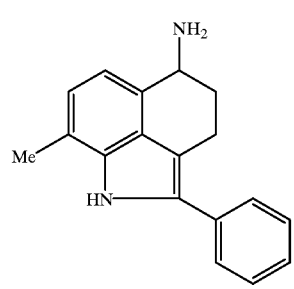
Example 115
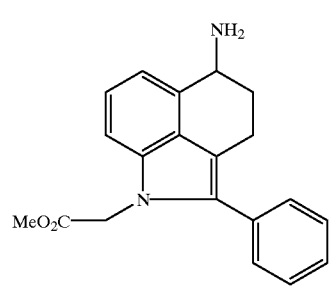
TABLE 8-11-continued
Example 116
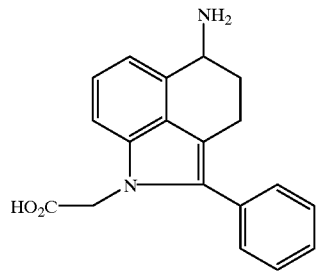
Example 117
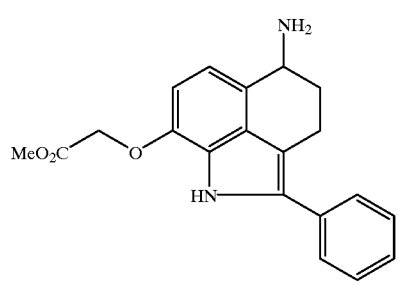
Example 118
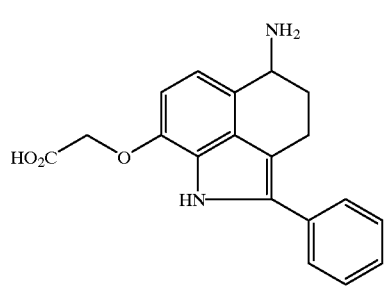
Example 119
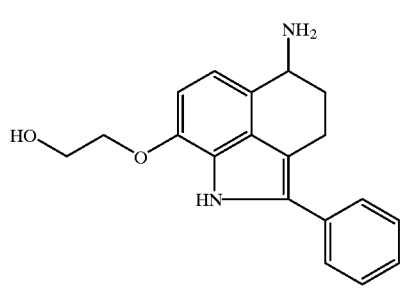
Example 120
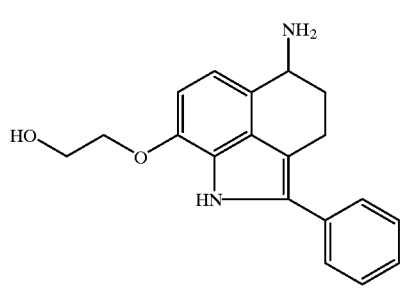

TABLE 8-11-continued
Example 121
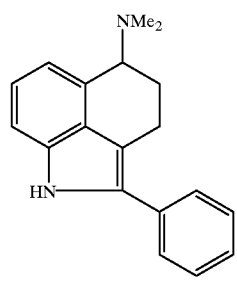
Example 122
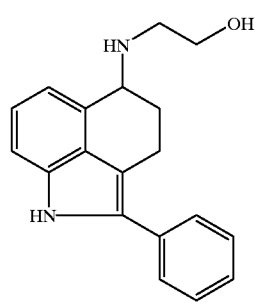
Example 123
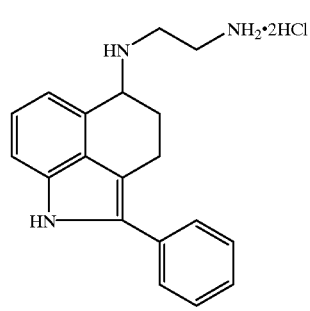
TABLE 8-12
Example 124
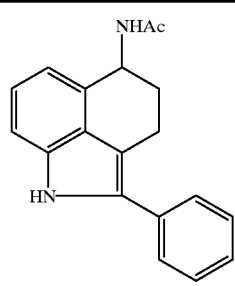
Example 125
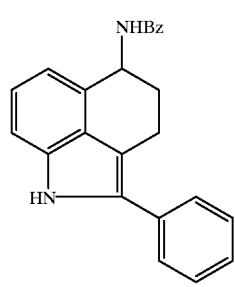
TABLE 8-12-continued
Example 126
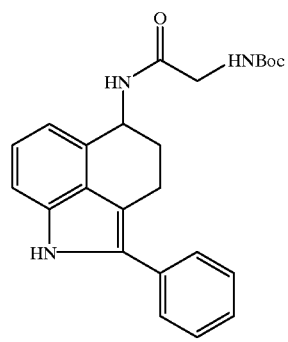
Example 127
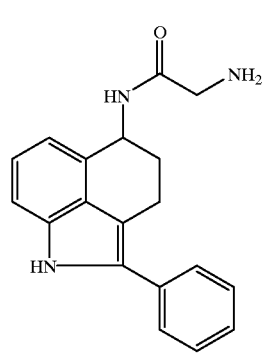
Example 128
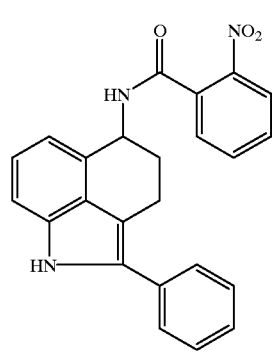
Example 129
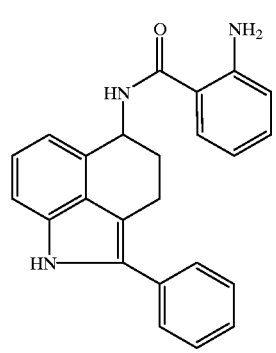

TABLE 8-12-continued
Example 130 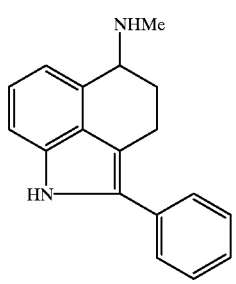
Example 131
Step 1
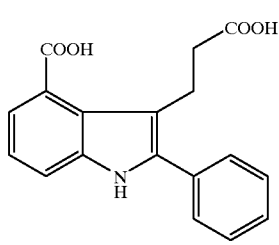
Example 131
Step 2
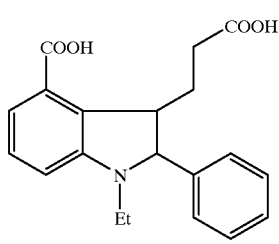
Example 131
Step 3
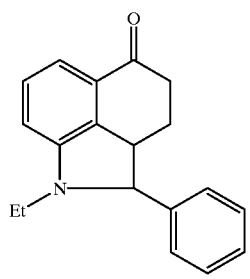
Example 132 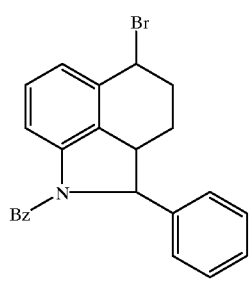
TABLE 8-12-continued
Example 133 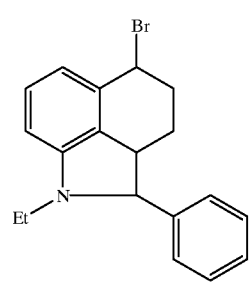
TABLE 8-13
Example 134 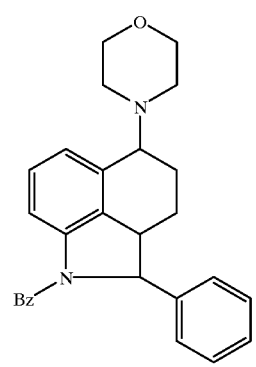
Example 135 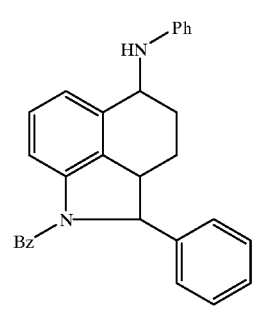
Example 136 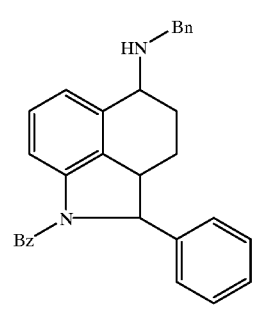

TABLE 8-13-continued
Example 137
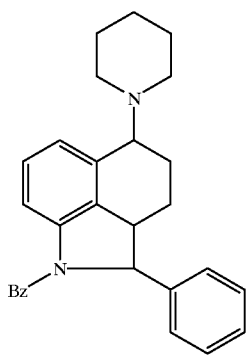
Example 138
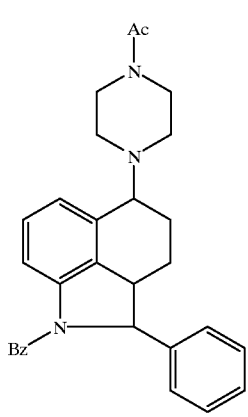
Example 139
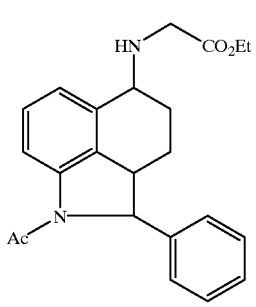
Example 140
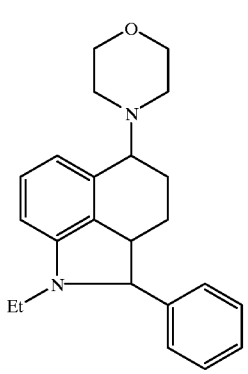
TABLE 8-13-continued
Example 141
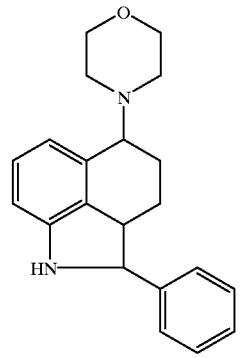
Example 142
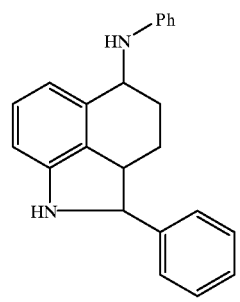
Example 143
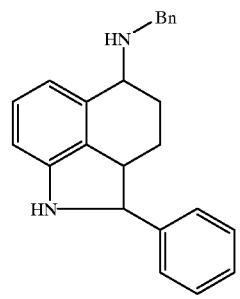
Example 144
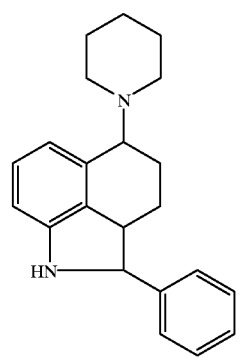

TABLE 8-13-continued
Example 145
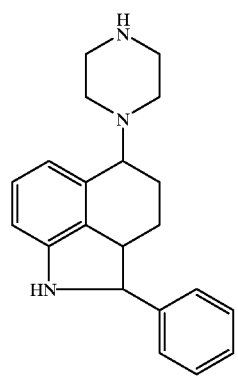
TABLE 8-14
Example 146
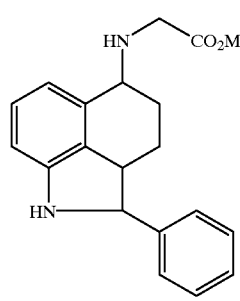
Example 147
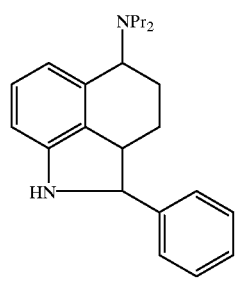
Example 148
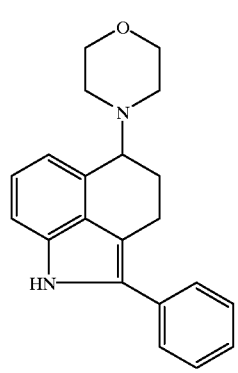
TABLE 8-14-continued
Example 149
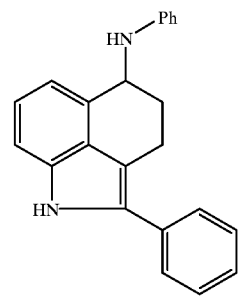
Example 150
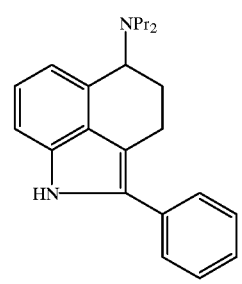
Example 151
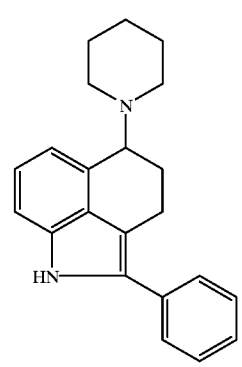
Example 152
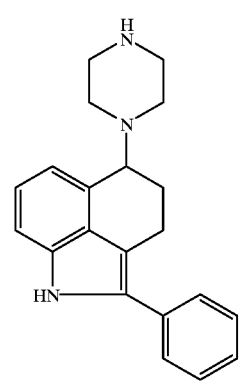

TABLE 8-14-continued
| Example 153 | 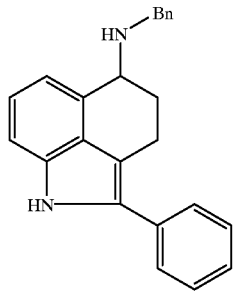 |
| Example 154 | 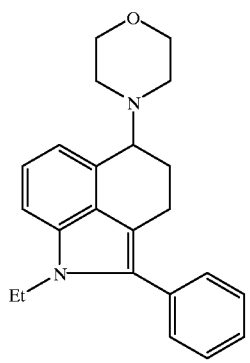 |
| Example 155 | 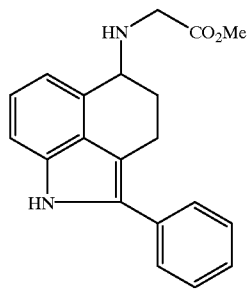 |
| Example 156 | 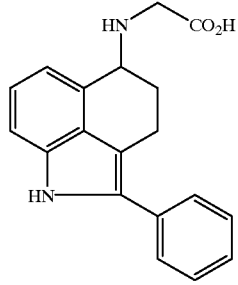 |
TABLE 8-14-continued
| Example 157 | 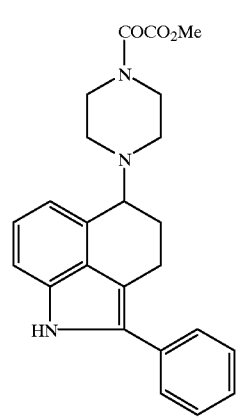 |
TABLE 8-15
| Example 158 | 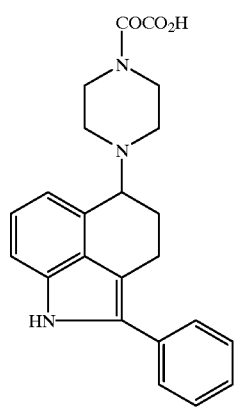 |
| Example 159 | 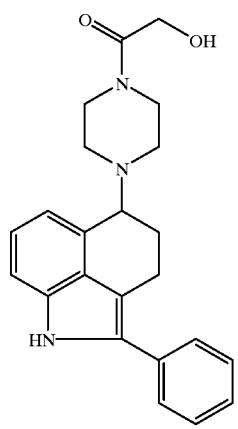 |

TABLE 8-15-continued
Example 160 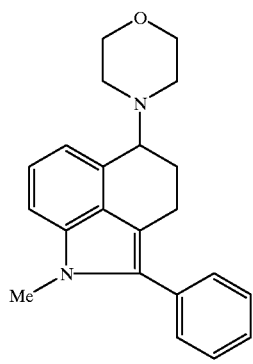
Example 161 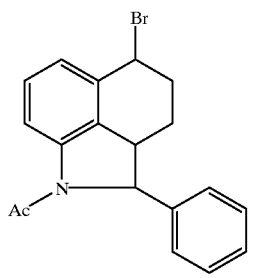
Example 162 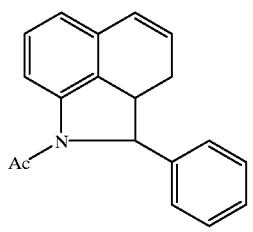
Example 163 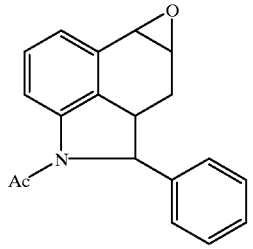
Example 164 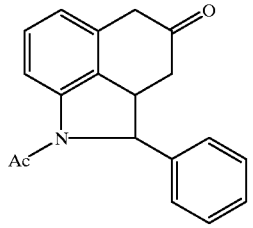
TABLE 8-15-continued
Example 165 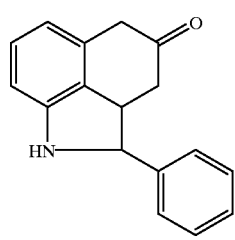
Example 166 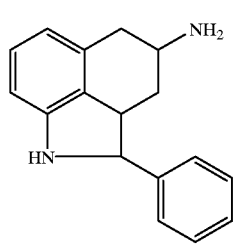
Example 167 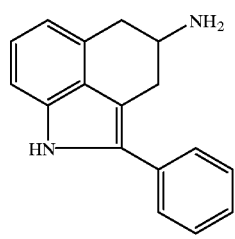
Example 168 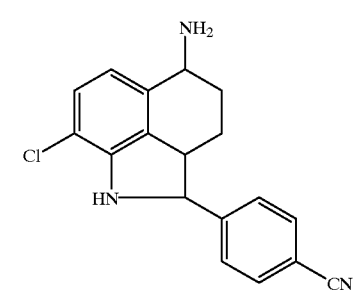
Example 169 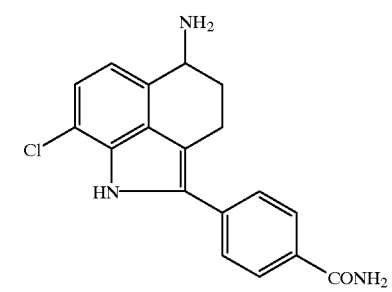

TABLE 8-16
Example 170 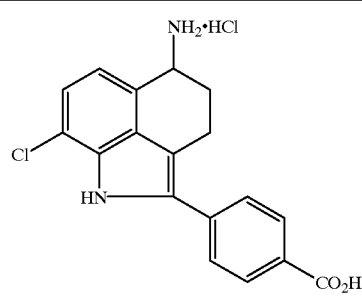
Example 171 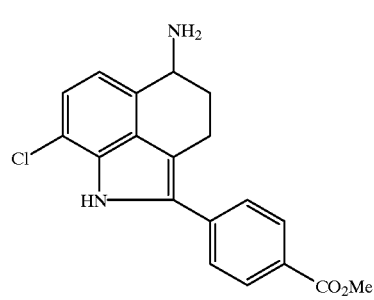
Example 172 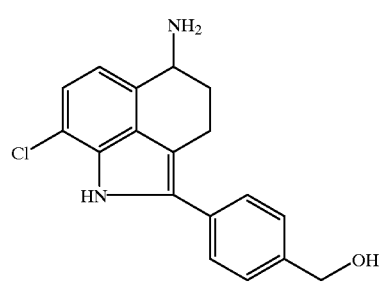
Example 173 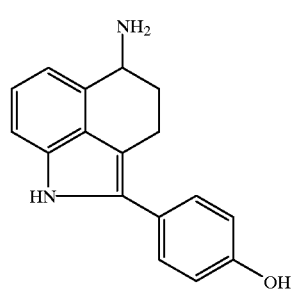
Example 174 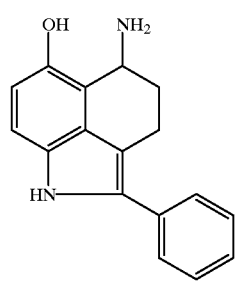
TABLE 8-16-continued
Example 175 (+) 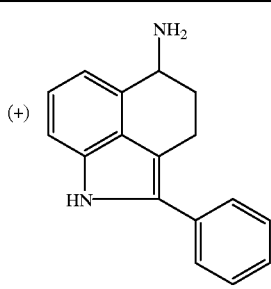
Example 176 (−) 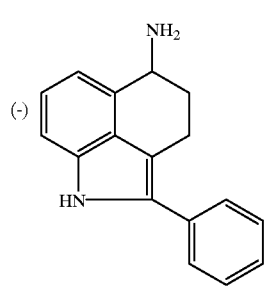
Example 177 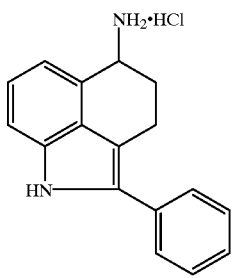
Example 178 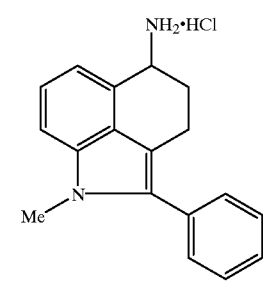
Example 179 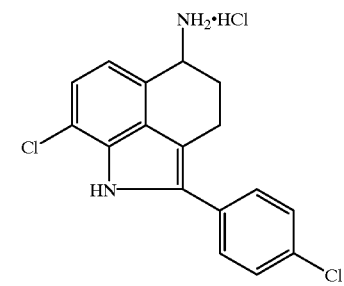

TABLE 8-16-continued
Example 180
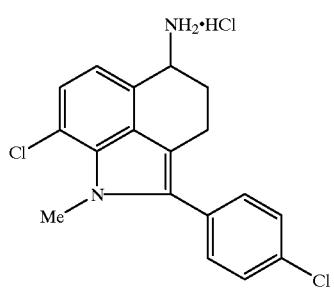
Example 181
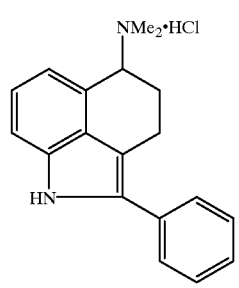
TABLE 8-17
Example 182
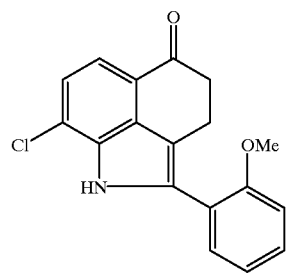
Example 183
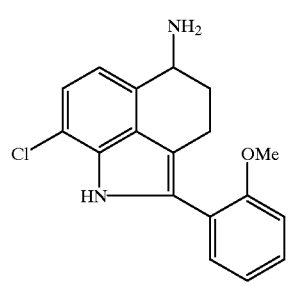
Example 184
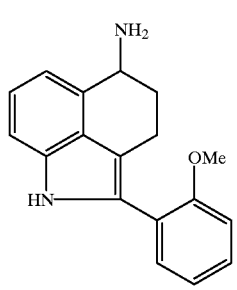
TABLE 8-17-continued
Example 185
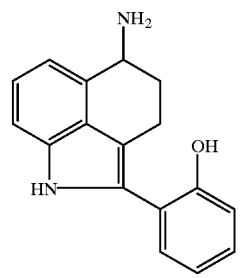
Example 186
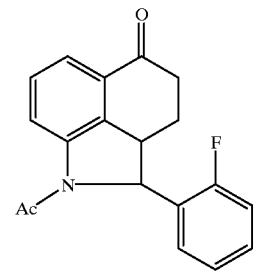
Example 187
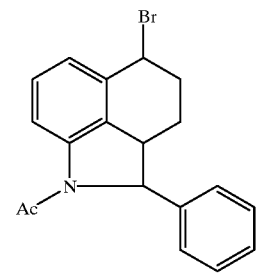
Example 188
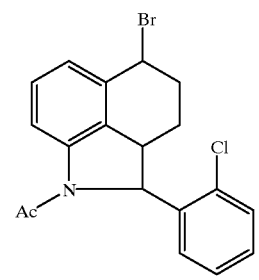
Example 189
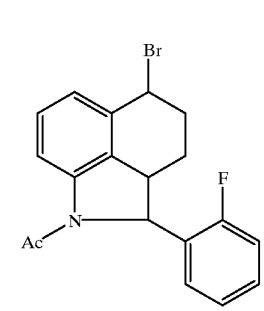

TABLE 8-17-continued
| Example 190 | 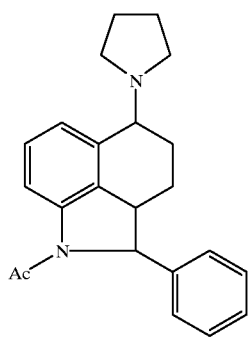 |
| Example 191 | 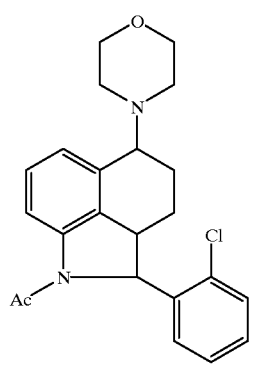 |
| Example 192 | 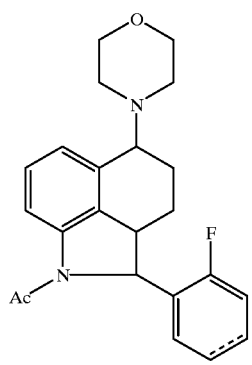 |
TABLE 8-18
| Example 193 | 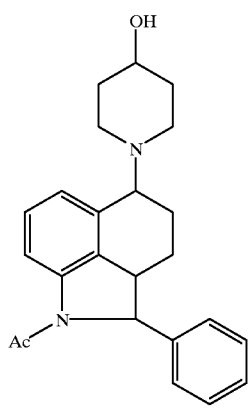 |
TABLE 8-18-continued
| Example 194 | 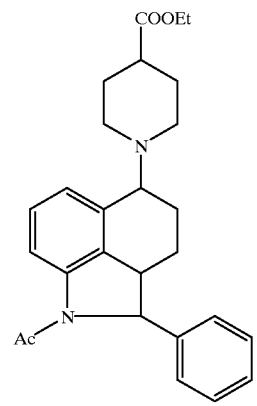 |
| Example 195 | 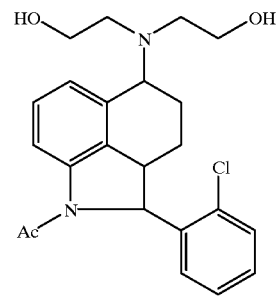 |
| Example 196 | 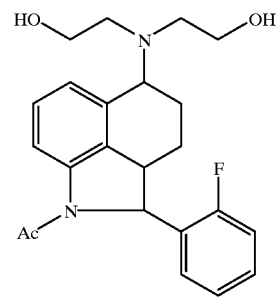 |
| Example 197 | 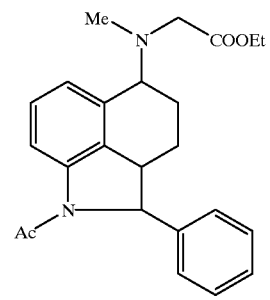 |

TABLE 8-18-continued
Example 198 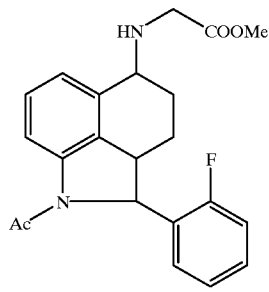
Example 199 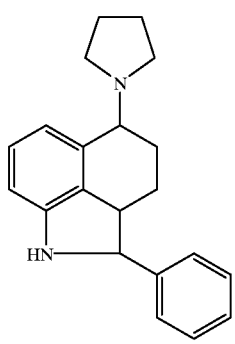
Example 200 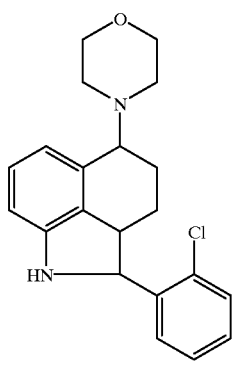
Example 201 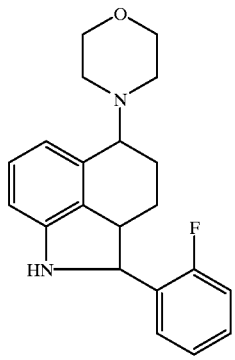
TABLE 8-18-continued
Example 202 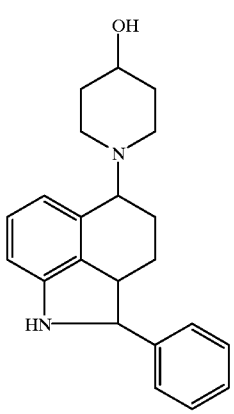
TABLE 8-19
Example 203 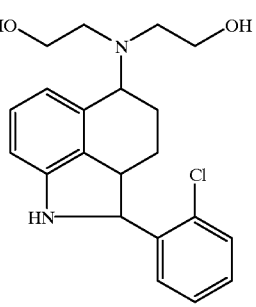
Example 204 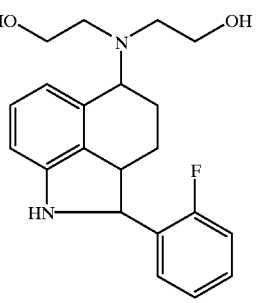
Example 205 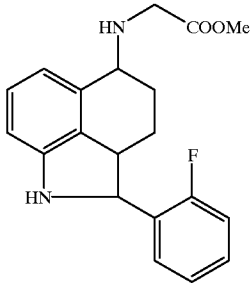

TABLE 8-19-continued

| Example 206 | (structure: tricyclic indoline with HN-CH2-COOEt substituent and phenyl group) |
| Example 207 | (structure: tricyclic indoline with N-piperidinyl-COOEt substituent and phenyl group) |
| Example 208 | (structure: tricyclic indoline with N(Me)-CH2-COOEt substituent and phenyl group) |
| Example 209 | (structure: tricyclic indole with morpholino substituent and 2-chlorophenyl group) |
| Example 210 | (structure: tricyclic indole with morpholino substituent and 2-fluorophenyl group) |
| Example 211 | (structure: tricyclic indole with N-piperidinyl-COOEt substituent and phenyl group) |
| Example 212 | (structure: tricyclic indole with N(CH2CH2OH)2 substituent and 2-chlorophenyl group) |

TABLE 8-20

| Example 213 | (structure: tricyclic indole with N(CH2CH2OH)2 substituent and 2-fluorophenyl group) |

TABLE 8-20-continued
Example 214 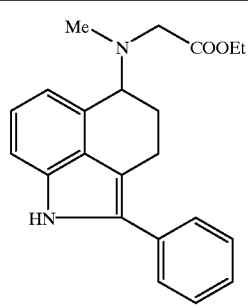
Example 215 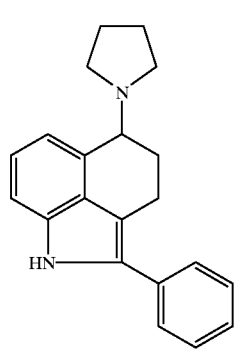
Example 216 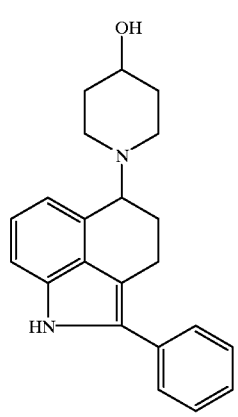
Example 217 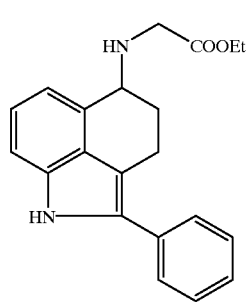
TABLE 8-20-continued
Example 218 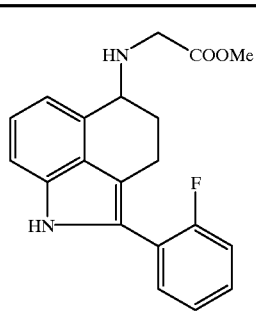
Example 219 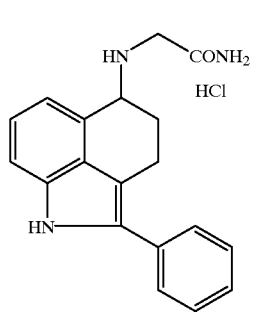
Example 220 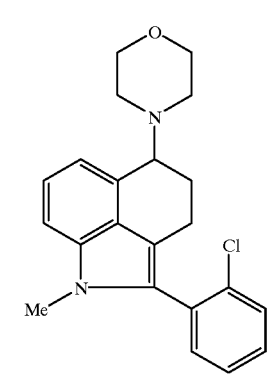
Example 221 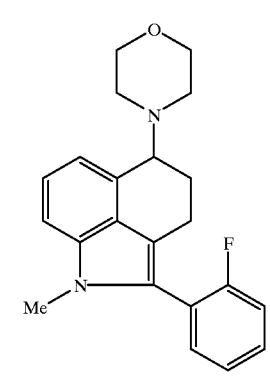

TABLE 8-20-continued
Example 222
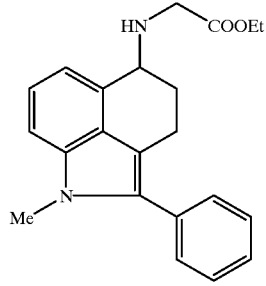
TABLE 8-21
Example 223
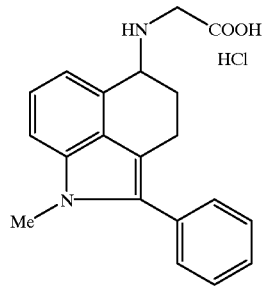
HCl
Example 224
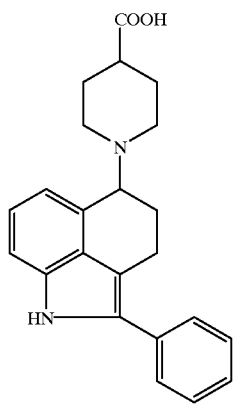
Example 225
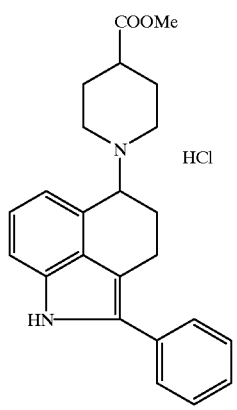
HCl
TABLE 8-21-continued
Example 226
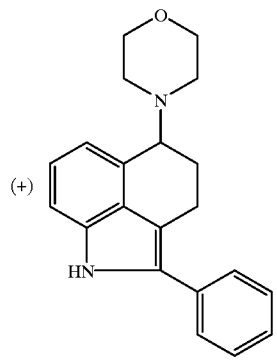
(+)
Example 227
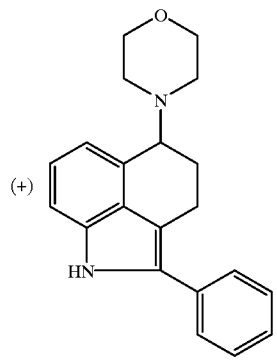
(−)
Example 228
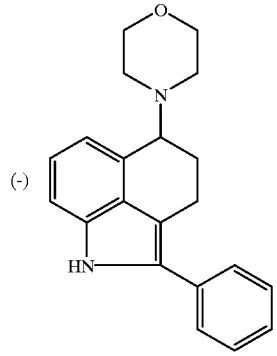
(+)
Example 229
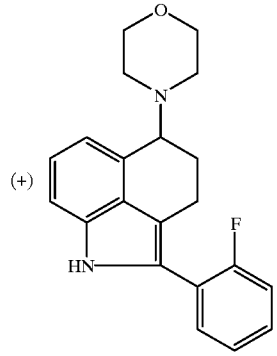
(−)

TABLE 8-21-continued

Example 230 (+) [structure: 4-morpholino-1-methyl-2-phenyl tricyclic indole]

Example 231 (−) [structure: 4-morpholino-1-methyl-2-phenyl tricyclic indole]

Example 232 [structure: 4-morpholino-2-(2-fluorophenyl) tricyclic indole · HCl]

TABLE 8-22

Example 233 [structure: 4-morpholino-2-(2-fluorophenyl) tricyclic indole · (COOH)$_2$]

TABLE 8-22-continued

Example 234 [structure: 5-amino-8-methoxy-2-phenyl tricyclic indole · HCl]

Example 235 [structure: amino-2-(2-hydroxyphenyl) tricyclic indole · HCl]

Example 236 [structure: 4-morpholino-2-phenyl tricyclic indole · HCl]

Example 237 [structure: 4-morpholino-1-methyl-2-phenyl tricyclic indole · HCl]

TABLE 8-22-continued
| Example 238 | 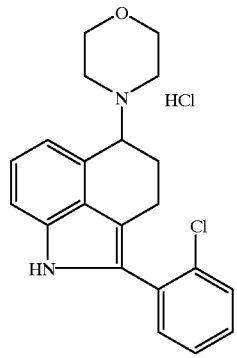 |
| Example 239 | 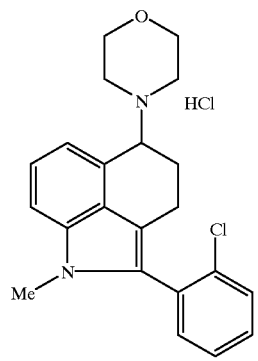 |
| Example 240 | 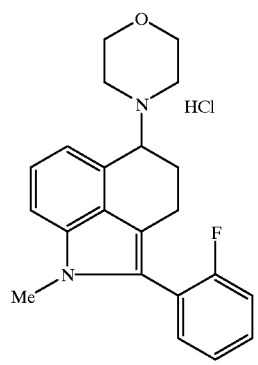 |
| Example 241 | 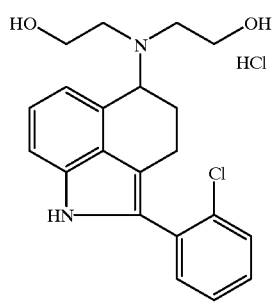 |
TABLE 8-22-continued
| Example 242 | 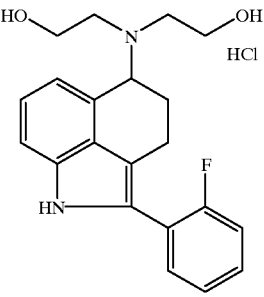 |
TABLE 8-23
| Example 243 | 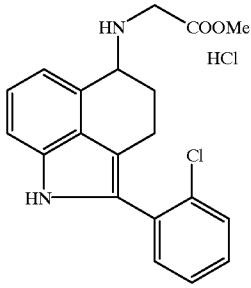 |
| Example 244 | 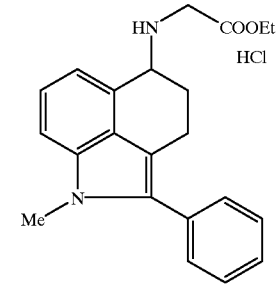 |
| Example 245 | 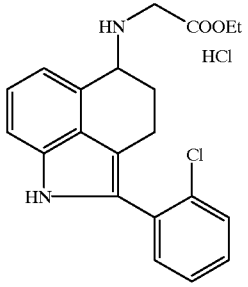 |
| Example 246 | 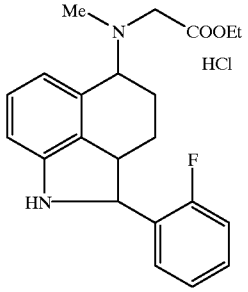 |

TABLE 8-23-continued
| Example 247 | 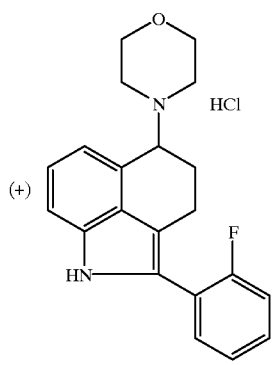 |
| Example 248 | 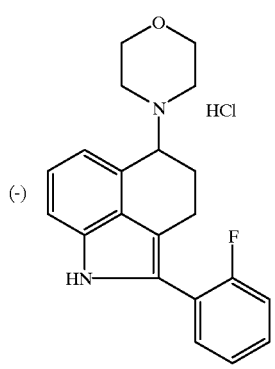 |
| Example 249 | 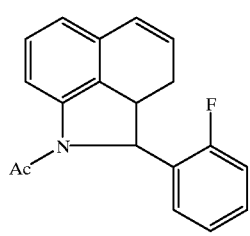 |
| Example 250 | 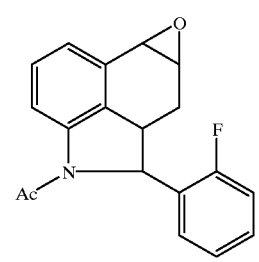 |
| Example 251 | 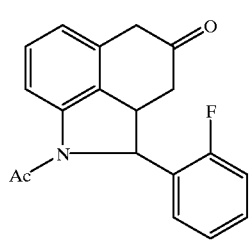 |
TABLE 8-23-continued
| Example 252 | 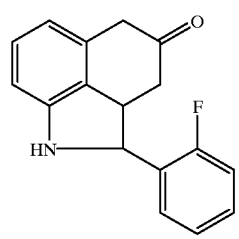 |
TABLE 8-24
| Example 253 Step 1 | 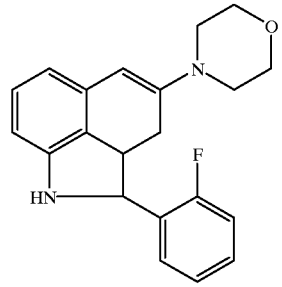 |
| Example 253 Step 2 | 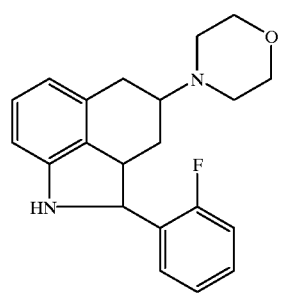 |
| Example 254 | 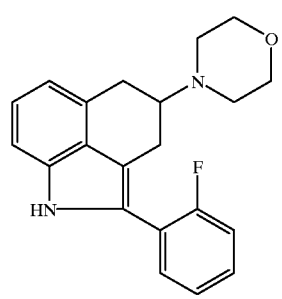 |
| Example 255 | 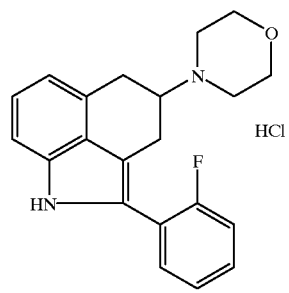 |

TABLE 8-24-continued

Example 256

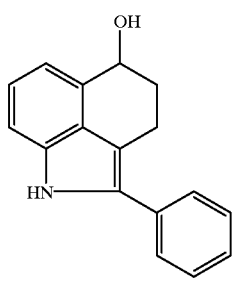

Example 257

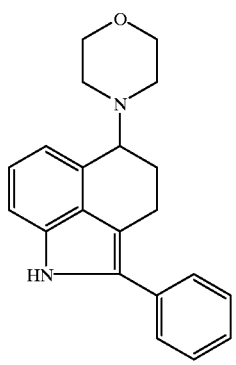

(Formulation 1: Injection)

The ingredients listed below were dissolved by mixing with 800 ml of distilled water for injection; thereafter, more distilled water for injection was added to make a total of 1,000 ml; following sterilizing filtration, the solution was dispensed as 10-ml portions into aseptic vials, which were fused and sealed.

| Compound of Example 81 | 0.5 g |
|---|---|
| 1N HCl | 10 ml |
| Glucose | 50 g |

(Formulation 2: Injection)

The ingredients listed below were dissolved by mixing with 600 ml of distilled water for injection; thereafter, more distilled water for injection was added to make a total of 1,000 ml; following sterilizing filtration, the solution was dispensed as 10-ml portions into aseptic vials, which were fused and sealed.

| Compound of Example 174 | 2 g |
|---|---|
| 1N HCl | 164 ml |
| 1N NaOH | 154 ml |

(Formulation 3: Injection)

The ingredients listed below were dissolved by mixing with 800 ml of distilled water for injection; thereafter, more distilled water for injection was added to make a total of 1,000 ml; following sterilizing filtration, the solution was dispensed as 10-ml portions into aseptic vials, which were fused and sealed.

| Compound of Example 107 | 0.1 g |
|---|---|
| 1N HCl | 10 ml |
| Glucose | 50 g |

(Formulation 4: Injection)

The ingredients listed below were dissolved by mixing with 600 ml of distilled water for injection; thereafter, more distilled water for injection was added to make a total of 1,000 ml; following sterilizing filtration, the solution was dispensed as 10-ml portions into aseptic vials, which were fused and sealed.

| Compound of Example 130 | 1 g |
|---|---|
| 1N HCl | 164 ml |
| 1N NaOH | 154 ml |

(Formulation 5: Tablet)

Ingredients listed below under (1), (2) and (3) were mixed uniformly in a fluid-bed granulator and granulated using an aqueous solution of (4) as a binding solution. The granules were dried and mixed uniformly with (5) to prepare a tableting powder mixture, which was compressed to form 200 tablets each containing 50 mg of (1).

| (1) | Compound of Example 81 | 10 g |
|---|---|---|
| (2) | Lactose | 35 g |
| (3) | Corn starch | 12 g |
| (4) | Polyvinyl alcohol | 1.5 g |
| (5) | Magnesium stearate | 1.5 g |

Industrial Applicability

The compounds of the invention having a benzindole skeleton act directly upon neurons including brain neurons and have an outstanding capability for suppressing the death of neurons, namely, an outstanding neuroprotective action. The compounds also have an analgesic action, or a capability for alleviating the pains associated with various diseases.

The compounds of the invention are low in toxicity and feature high safety; hence, they are useful as medicines both clinically and in animals and, in particular, they are expected to provide therapeutic effects against cerebrovascular disorders, neurodegenerative diseases, various other diseases that involve the degeneration, retraction or death of neurons, as well as against pains associated with various diseases.

The pharmaceutical compositions of the invention contain compounds that act directly upon neurons to be capable of directly suppressing their death; hence, unlike the heretofore used nosotropic drugs such as cerebral metabolism activators and cerebral circulation modifiers, the compositions directly prevent or otherwise control the dysfunction, degeneration or necrosis of neurons in general or specific regions due to ischemia, trauma, aging or etiology which is unknown for the cause, whereby they can be used in the treatment of cerebrovascular disorders, various neurodegenerative diseases or various other diseases that involve the degeneration, retraction or death of neurons. Specifically, cerebrovascular disorders include various diseases accompanying cerebrovascular disorders such as cerebral infarctions such as cerebral thrombosis and embolism, cerebral hemorrhages such as hypertensive intracerebral hemorrhage and subarachnoid hemorrhage, transient cerebral ischemic attacks, cerebroarteriosclerosis and their sequela; neurodegenerative diseases include dementia of Alzheimer's type, Parkinson's disease, amyotrophic lateral sclerosis (ALS), Down's syndrome, Huntington chorea and spinal cerebellar degeneration; and various other diseases that involve the degeneration, retraction or death of the neurons include brain damages at the time of revivification after cardiac arrest, brain dysfunction prior to or after brain surgery, disorders of the nervous system due to hypoxia, hypoglycemia, brain or spinal damage, introxication with drugs or gases, diabetes mellitus, administration of anti-cancer agents, alcohol and the like, senile dementia and hysmnesia. In addition, the pharmaceutical compositions contain compounds having the action of centrally alleviating the pains from various diseases and, hence, can be used as therapeutics effective against pains from various diseases of the nervous system caused by various physical or mental abnormalities. Specific examples of such pains include those associated with cancers, diabetic neuropathy, herpes zoster, arthritis, rheumatism, as well as medical or dental surgery.

Further in addition, the pharmaceutical compositions of the invention can also be used against neuropathy associated with epilepsy, schizophrenia, depression, anxiety syndrome, AIDS, rabies, measles, Japanese B encephalitis, subacute sclerosing panencephalitis and infections such as tetanus, as well as diseases including mitochondrial myopathy, Leber's syndrome, Wernicke's syndrome, Rett's syndrome, homocysteinemia, hyperprolinemia, hydroxybutylamino acidouria, lead encephalopathy and insufficiency of sulfite oxidase.

Using the processes of the invention, one can produce benzindole derivatives having an outstanding neuroprotective or analgesic action.

We claim:

1. A compound represented by the following formula (I) or a salt thereof:

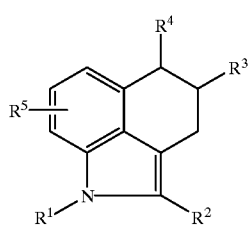

(I)

where $R^1$ represents a hydrogen atom or a straight-chained, branched or cyclic alkyl group having 1–4 carbon atoms which may be substituted by any group selected from the group consisting of one carboxyl group, one alkoxycarbonyl group having 1–4 carbon atoms and one hydroxyl group; R represents a phenyl group which may be mono- or disubstituted by any group selected from the group consisting of a halogen atom, an alkyl group having 1–4 carbon atoms which may be substituted by one hydroxyl group, an alkoxyl group having 1–4 carbon atoms which may be substituted by one hydroxyl group, an optionally protected hydroxyl group, a nitro group, an optionally protected amino group, an acetylamino group, a cyano group, an optionally protected carboxyl group, an alkoxycarbonyl group having 1–4 carbon atoms, a carbamoyl group and a trifluoromethyl group; either one of $R^3$ and $R^4$ represents a hydrogen atom and the other represents a group represented by the following formula (II):

—NR⁶R⁷ (II)

(where $R^6$ and $R^7$ each represent a hydrogen atom, a phenyl group, a benzyl group, an alkyl group having 1–4 carbon atoms which may be monosubstituted by any group selected from the group consisting of one hydroxyl group, one amino group, one carboxyl group and one alkoxycarbonyl group having 1–4 carbon atoms, a formyl group, an alkanoyl group having 1–4 carbon atoms which may be monosubstituted by an amino group, or a benzoyl group which may be monosubstituted by an amino group; $R^6$ and $R^7$ may form a pyrrolidine, piperidine, morpholine, or piperazine ring together with the nitrogen atom to which they are bound, provided that the nitrogen atom at the 4-position of the piperazine ring where a hydrogen atom is substituted may be substituted by any group selected from the group consisting of an oxalo group, and alkoxyoxalyl group having 1–4 carbon atoms, an alkanoyl group having 1–4 carbon atoms which may be substituted by one hydroxyl group and an alkyl group having 1–4 carbon atoms); $R^5$ represents a hydrogen atom, a halogen atom, an alkyl group having 1–4 carbon atoms, an optionally protected hydroxyl group, a cyano group, a nitro group or an alkoxyl group having 1–4 carbon atoms which may be monosubstituted by a group selected from the group consisting of one carboxyl group, one alkoxycarbonyl group having 1–4 carbon atoms and one hydroxyl group; when $R^4$ is a hydrogen atom, $R^6$ and $R^7$ is not a formyl group, an alkanoyl group having 1–4 carbon atoms which may be monosubstituted by an amino group, or a benzoyl group which may be monosubstituted by an amino group; and a pharmaceutically acceptable carrier thereof.

2. The compound according to claim 1 or a salt thereof, wherein $R^3$ is a hydrogen atom and $R^4$ is represented by the formula (II) as defined in claim 1.

3. The compound according to claim 1 or 2 or a salt thereof, wherein $R^1$ is a hydrogen atom or a straight-chained alkyl group having 1–4 carbon atoms and $R^5$ is a hydrogen atom, a halogen atom, an alkyl group having 1–4 carbon atoms or an optionally protected hydroxy group.

4. The compound according to claim 1 or a salt thereof, wherein $R^6$ in the formula (II) as defined in claim 1 is a hydrogen atom, a phenyl group, a benzyl group or an alkyl group having 1–4 carbon atoms which may be substituted by one hydroxyl group and $R^7$ is a hydrogen atom or an alkyl group having 1–4 carbon atoms, provided that $R^6$ and $R^7$ may form a pyrrolidine, piperidine, morpholine or piperazine ring together with the nitrogen atom to which they are bound.

5. The compound according to claim 1 or a salt thereof, wherein $R^2$ is a phenyl group which may be monosubstituted by a halogen atom, $R^3$ is a hydrogen atom, $R^4$ is represented by the formula (II) as defined in claim 1, in which $R^6$ is a hydrogen atom or an alkyl group having 1–4 carbon atoms which may be substituted by one hydroxyl group and $R^7$ is a hydrogen atom or an alkyl group having 1–4 carbon atoms, provided that $R^6$ and $R^7$ may form a morpholine ring together with the nitrogen atom to which they are bound.

6. A compound or a salt thereof which are useful for the synthesis of the compound of the formula (I) as defined in claim 1 or a salt thereof and which are represented by the following formula (III):

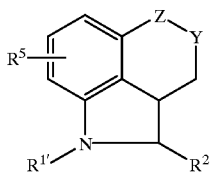

(III)

where $R^1$ represents a hydrogen atom, a formyl group, an alkanoyl group having 1–4 carbon atoms, a benzoyl group or a straight-chained, branched or cyclic alkyl group having 1–4 carbon atoms which may be substituted by any group selected from the group consisting of one carboxyl group, one alkoxycarbonyl group having 1–4 carbon atoms and one hydroxyl group; $R^2$ represents a phenyl group which may be mono- or disubstituted by any group selected from the group consisting of a halogen atom, an alkyl group having 1–4 carbon atoms which may be substituted by one hydroxyl group, an alkoxyl group having 1–4 carbon atoms which may be substituted by one hydroxyl group, an optionally protected hydroxyl group, an alkylthio group having 1–4 carbon atoms, an alkylsulfinyl group having 1–4 carbon atoms, an alkylsulfonyl group having 1–4 carbon atoms, a nitro group, an optionally protected amino group, an acetylamino group, a cyano group, an optionally protected carboxyl group, an alkoxycarbonyl group having 1–4 carbon atoms, a carbamoyl group and a trifluoromethyl group; $R^5$ represents a hydrogen atom, a halogen atom, an alkyl group having 1–4 carbon atoms, an optionally protected hydroxyl group, an alkylthio group having 1–4 carbon atoms, an alkylsulfinyl group having 1–4 carbon atoms, an alkylsulfonyl group having 1–4 carbon atoms, a cyano group, a nitro group or an alkoxyl group having 1–4 carbon atoms which may be substituted by a group selected from the group consisting of one carboxyl group, one alkoxycarbonyl group having 1–4 carbon atoms and one hydroxyl group; Y and Z each represent a methylene group or a carbonyl group, provided that they are not the same.

7. A process in which a compound represented by the following formula (III) or a salt thereof:

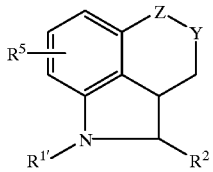

(III)

(where $R^1$ represents a hydrogen atom, a formyl group, an alkanoyl group having 1–4 carbon atoms, a benzoyl group or a straight-chained, branched or cyclic alkyl group having 1–4 carbon atoms which may be substituted by any group selected from the group consisting of one carboxyl group, one alkoxycarbonyl group having 1–4 carbon atoms and one hydroxyl group; $R^2$ represents a phenyl group which may be mono- or disubstituted by any group selected from the group consisting of a halogen atom, an alkyl group having 1–4 carbon atoms which may be substituted by one hydroxyl group, an alkoxyl group having 1–4 carbon atoms which may be substituted by one hydroxyl group, an optionally protected hydroxyl group, a nitro group, an optionally protected amino group, an acetylamino group, a cyano group, an optionally protected carboxyl group, an alkoxycarbonyl group having 1–4 carbon atoms, a carbamoyl group and a trifluoromethyl group; $R^5$ represents a hydrogen atom, a halogen atom, an alkyl group having 1–4 carbon atoms, an optionally protected hydroxyl group, a cyano group, a nitro group or an alkoxyl group having 1–4 carbon atoms which may be substituted by a group selected from the group consisting of one carboxyl group, one alkoxycarbonyl group having 1–4 carbon atoms and one hydroxyl group; Y and Z each represent a methylene group or a carbonyl group, provided that they are not the same) after removing the acyl group at 1-position as required, is dehydrogenated with a suitable oxidizing reagent to prepare a compound represented by the following formula (IV) or a salt thereof:

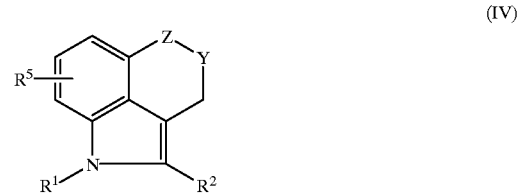

(IV)

(where $R^1$, $R^2$, $R^5$, Y and Z have the same meanings as defined in claim 1) and said compound or salt thereof is reacted under reducing conditions with an amine derivative represented by the following formula (V) of a salt thereof:

$$HNR^6R^7 \qquad (V)$$

(where $R^5$ and $R^7$ have the same meanings as defined in claim 1) so as to prepare a compound represented by the following formula (I) or a salt thereof:

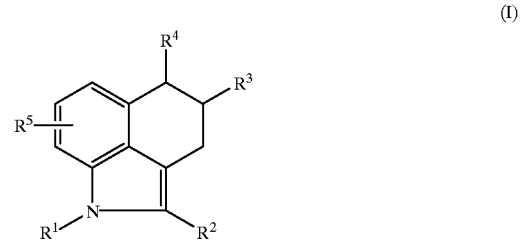

(I)

(where $R^{1'}$, $R^2$, $R^3$, $R^4$, $R^5$ and $R^6$ or $R^7$ in the formula (II) set forth in the definitions of $R^3$ and $R^4$ have the same meanings as defined in claim 1).

8. A process in which a compound represented by the following formula (III) or a salt thereof:

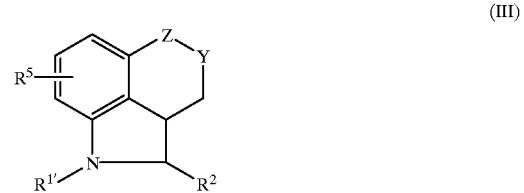

(III)

(where $R^{1'}$ represents a hydrogen atom, a formyl group, an alkanoyl group having 1–4 carbon atoms, a benzoyl group or a straight-chained, branched or cyclic alkyl group having 1–4 carbon atoms which may be substituted by any group selected from the group consisting of one carboxyl group, one alkoxycarbonyl group having 1–4 carbon atoms and one hydroxyl group; $R^2$ represents a phenyl group which may be mono- or disubstituted by any group selected from the group consisting of a halogen atom, an alkyl group having 1–4 carbon atoms which may be substituted by one hydroxyl group, an alkoxyl group having 1–4 carbon atoms which may be substituted by one hydroxyl group, an optionally protected hydroxyl group, a nitro group, an optionally protected amino group, an acetylamino group, a cyano group, an optionally, protected carboxyl group, an alkoxycarbonyl group having 1–4 carbon atoms, a carbamoyl group and a trifluoromethyl group; $R^5$ represents a hydrogen atom, a halogen atom, an alkyl group having 1–4 carbon atoms, an optionally protected hydroxyl group, a cyano group, a nitro group or an alkoxyl group having 1–4 carbon atoms which may be substituted by a group selected from the group consisting of one carboxyl group, one alkoxycarbonyl group having 1–4 carbon atoms and one hydroxyl group; Y and Z each represent a methylene group or a carbonyl group, provided that they are not the same) is reduced to prepare a hydroxy form, which is reacted with a halogenating agent to prepare a compound represented by the following formula (VI) or a salt thereof:

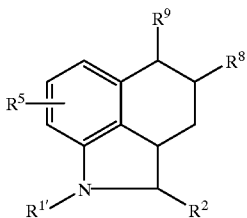

(VI)

(where $R^{1'}$, $R^2$ and $R^5$ have the same meanings as defined above; $R^8$ and $R^9$ each represent a hydrogen atom or a halogen atom, provided that they are not the same) and said compound or salt thereof is reacted with an amine derivative represented by the following formula (V) or a salt thereof:

$HNR^6R^7$ (V)

(where $R^6$ and $R^7$ have the same meanings as defined in claim 1) so as to prepare a compound represented by the following formula (VII) or a salt thereof:

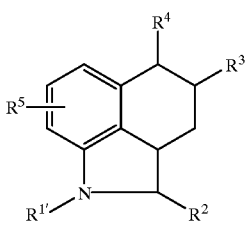

(VII)

(where $R^{1'}$, $R^2$, $R^3$, $R^4$, $R^5$ and $R^6$ or $R^7$ in the formula (II) set forth in the definitions of $R^3$ and $R^4$ have the same meanings as defined in claim 1) and, after removing the acyl group at 1-position as required, said compound or salt thereof is dehydrogenated with a suitable oxidizing reagent to produce a compound represented by the following formula (I) or a salt thereof:

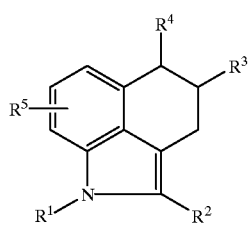

(I)

(where $R^1$, $R^2$ $R^3$, $R^4$, $R^5$ and $R^6$ or $R^7$ in the formula (II) set forth in the definitions of $R^3$ and $R^4$ have the same meanings as defined in claim 1).

9. A medicine containing the compound according to claim 1 or a salt thereof as an active ingredient.

10. A composition for treating cerebrovascular disorders or disease accompanying cerebrovascular disorders or neuroprotection or analgesia, comprising:

an effective amount of a compound according to claim 1 or a pharmaceutically acceptable salt thereof as an active ingredient; and a pharmaceutically acceptable carrier therefor.

11. A method for neuroprotection, said method comprising:

administering to a person in need thereof, an effective amount of a compound according to claim 1 or pharmaceutically acceptable salts thereof as an active ingredient, and a pharmaceutically acceptable carrier thereof.

12. A method for analgesia, said method comprising:

administering to a person in need thereof, an effective amount of a compound according to claim 1 or pharmaceutically acceptable salts thereof as an active ingredient, and a pharmaceutically acceptable carrier thereof.

13. A method for treating cerebrovascular disorders or diseases accompanying cerebrovascular disorders, said method comprising:

administering to a person in need thereof, an effective amount of a compound according to claim 1 or pharmaceutically acceptable salts thereof as an active ingredient, and a pharmaceutically acceptable carrier thereof.

* * * * *